United States Patent
Cohen et al.

(10) Patent No.: US 9,040,706 B2
(45) Date of Patent: May 26, 2015

(54) PYRROLIDINE INHIBITORS OF IAP

(71) Applicant: Genentech, Inc., South San Francisco, CA (US)

(72) Inventors: Frederick Cohen, San Francisco, CA (US); Vickie Hsiao-Wei Tsui, Burlingame, CA (US); Cuong Ly, Daly City, CA (US); John A. Flygare, Burlingame, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/088,110

(22) Filed: Nov. 22, 2013

(65) Prior Publication Data

US 2014/0080805 A1    Mar. 20, 2014

Related U.S. Application Data

(60) Division of application No. 12/538,794, filed on Aug. 10, 2009, now Pat. No. 8,609,845, which is a continuation of application No. 12/105,109, filed on Apr. 17, 2008, now abandoned, which is a continuation of application No. 11/312,063, filed on Dec. 19, 2005, now abandoned.

(60) Provisional application No. 60/638,202, filed on Dec. 20, 2004.

(51) Int. Cl.
| | | |
|---|---|---|
| C07D 277/20 | (2006.01) |
| C07D 453/02 | (2006.01) |
| C07D 471/14 | (2006.01) |
| C07D 471/04 | (2006.01) |
| C07D 417/04 | (2006.01) |
| C07D 417/14 | (2006.01) |

(52) U.S. Cl.
CPC ............ *C07D 471/04* (2013.01); *C07D 417/04* (2013.01); *C07D 417/14* (2013.01)

(58) Field of Classification Search
CPC ... C07D 471/04; C07D 417/04; C07D 417/14
USPC .............................. 548/204; 546/82, 121, 135
See application file for complete search history.

(56) References Cited

U.S. PATENT DOCUMENTS

| | | | |
|---|---|---|---|
| 4,149,003 A | 4/1979 | Carlsson et al. |
| 4,278,793 A | 7/1981 | Dürckheimer et al. |
| 4,720,484 A | 1/1988 | Vincent et al. |
| 4,837,165 A | 6/1989 | Hawke |
| 4,935,494 A | 6/1990 | Miller |
| 5,278,148 A | 1/1994 | Branca et al. |
| 5,411,942 A | 5/1995 | Widmer et al. |
| 5,559,209 A | 9/1996 | Nishimoto |
| 5,998,470 A | 12/1999 | Halbert et al. |
| 6,472,172 B1 | 10/2002 | Deng et al. |
| 6,608,026 B1 | 8/2003 | Wang et al. |
| 6,992,063 B2 | 1/2006 | Shi |
| 7,041,784 B2 | 5/2006 | Wang et al. |
| 7,067,274 B2 | 6/2006 | Fairbrother et al. |
| 7,244,851 B2 | 7/2007 | Cohen et al. |
| 8,110,568 B2 | 2/2012 | Cohen et al. |
| 8,247,557 B2 | 8/2012 | Koehler et al. |
| 8,609,845 B2 | 12/2013 | Cohen et al. |
| 2002/0177557 A1 | 11/2002 | Shi |
| 2003/0157522 A1 | 8/2003 | Boudreault et al. |
| 2004/0171554 A1 | 9/2004 | Deshayes et al. |
| 2005/0197403 A1 | 9/2005 | Harran et al. |
| 2005/0214802 A1 | 9/2005 | Fairbrother et al. |
| 2005/0234042 A1 | 10/2005 | Palermo et al. |
| 2006/0014700 A1 | 1/2006 | Cohen et al. |
| 2006/0052311 A1 | 3/2006 | Sharma et al. |
| 2006/0194741 A1 | 8/2006 | Condon et al. |
| 2007/0093428 A1 | 4/2007 | Laurent |
| 2007/0299052 A1 | 12/2007 | Cohen et al. |
| 2008/0050336 A1 | 2/2008 | Bachand et al. |

(Continued)

FOREIGN PATENT DOCUMENTS

| | | |
|---|---|---|
| EP | 1 836 201 B1 | 9/2007 |
| JP | 2006-501181 A | 1/2006 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Anonymous. (Oct. 11, 2011). Compendium of Chemical Terminology Gold Book, Version 2.3, International Union of Pure and Applied Chemistry, four pages, pp. 57, 212, and 1052.
Anonymous. (Date Unknown). "Representation of Non-Exemplified Groups Q," one page.
Arnt, C.R. et al. (Nov. 15, 2002). "Synthetic Smac/DIABLO Peptides Enhance the Effects of Chemotherapeutic Agents by Binding XIAP and cIAP1 in Situ," *Journal of Biological Chemistry* 277(46):44236-44243.
Bajaj, K. et al. (Dec. 2007). "Stereochemical Criteria for Prediction of the Effects of Proline Mutations on Protein Stability," *PLOS Computational Biology* 3(12)(e241):2465-2475.

(Continued)

*Primary Examiner* — Shawquia Jackson
(74) *Attorney, Agent, or Firm* — Morrison & Foerster LLP

(57) ABSTRACT

The invention provides novel inhibitors of IAP that are useful as therapeutic agents for treating malignancies where the compounds have the general formula I:

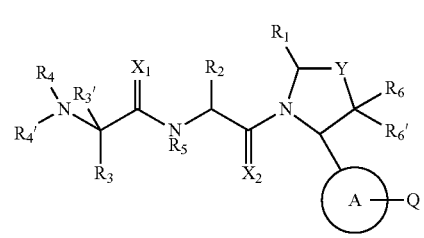

wherein A, Q, $X_1$, $X_2$, Y, $R_1$, $R_2$, $R_3$, $R_4$, $R_4'$, $R_5$, $R_6$ and $R_6'$ are as described herein.

4 Claims, No Drawings

(56) References Cited

U.S. PATENT DOCUMENTS

| | | |
|---|---|---|
| 2009/0318409 A1 | 12/2009 | Cohen et al. |
| 2011/0046066 A1 | 2/2011 | Ndubaku et al. |
| 2011/0077265 A1 | 3/2011 | Flygare et al. |
| 2011/0218211 A1 | 9/2011 | Bergeron et al. |
| 2011/0269696 A1 | 11/2011 | Dudley et al. |
| 2012/0015974 A1 | 1/2012 | Koehler |
| 2012/0202750 A1 | 8/2012 | Cohen et al. |
| 2012/0270886 A1 | 10/2012 | Koehler et al. |
| 2014/0080805 A1 | 3/2014 | Cohen et al. |

FOREIGN PATENT DOCUMENTS

| | | |
|---|---|---|
| JP | 2007-522116 A | 8/2007 |
| JP | 2007-523061 A | 8/2007 |
| JP | 2008-505904 A | 2/2008 |
| JP | 2008-505976 A | 2/2008 |
| JP | 2009-545613 A | 12/2009 |
| JP | 2010-506847 A | 3/2010 |
| JP | 5368428 B2 | 12/2013 |
| RU | 2291154 C2 | 1/2007 |
| WO | WO-92/01938 A1 | 2/1992 |
| WO | WO-94/11026 A2 | 5/1994 |
| WO | WO-94/11026 A3 | 5/1994 |
| WO | WO-94/11026 C1 | 5/1994 |
| WO | WO-98/46597 A1 | 10/1998 |
| WO | WO-00/00823 A1 | 1/2000 |
| WO | WO-00/39585 A1 | 7/2000 |
| WO | WO-02/16402 A2 | 2/2002 |
| WO | WO-02/16402 A3 | 2/2002 |
| WO | WO-02/16418 A2 | 2/2002 |
| WO | WO-02/16418 A3 | 2/2002 |
| WO | WO-02/26775 A2 | 4/2002 |
| WO | WO-02/26775 A3 | 4/2002 |
| WO | WO-02/30959 A2 | 4/2002 |
| WO | WO-02/30959 A3 | 4/2002 |
| WO | WO-02/085897 A1 | 10/2002 |
| WO | WO-02/096930 A2 | 12/2002 |
| WO | WO-02/096930 A3 | 12/2002 |
| WO | WO-03/010184 A2 | 2/2003 |
| WO | WO-03/010184 A3 | 2/2003 |
| WO | WO-03/086470 A2 | 10/2003 |
| WO | WO-03/086470 A3 | 10/2003 |
| WO | WO-2004/005248 A1 | 1/2004 |
| WO | WO-2004/007529 A2 | 1/2004 |
| WO | WO-2004/007529 A3 | 1/2004 |
| WO | WO-2004/017991 A1 | 3/2004 |
| WO | WO-2004/072641 A1 | 8/2004 |
| WO | WO-2004/106371 A1 | 12/2004 |
| WO | WO-2005/049853 A2 | 6/2005 |
| WO | WO-2005/049853 A3 | 6/2005 |
| WO | WO-2005/069888 A2 | 8/2005 |
| WO | WO-2005/069888 A3 | 8/2005 |
| WO | WO-2005/069894 A2 | 8/2005 |
| WO | WO-2005/069894 A3 | 8/2005 |
| WO | WO-2005/069894 C1 | 8/2005 |
| WO | WO-2005/084317 A2 | 9/2005 |
| WO | WO-2005/084317 A3 | 9/2005 |
| WO | WO-2005/094818 A1 | 10/2005 |
| WO | WO-2005/097791 A1 | 10/2005 |
| WO | WO-2006/014361 A1 | 2/2006 |
| WO | WO-2006/017295 A2 | 2/2006 |
| WO | WO-2006/017295 A3 | 2/2006 |
| WO | WO-2006/020060 A2 | 2/2006 |
| WO | WO-2006/020060 A3 | 2/2006 |
| WO | WO-2006/069063 A1 | 6/2006 |
| WO | WO-2006/091972 A2 | 8/2006 |
| WO | WO-2006/091972 A3 | 8/2006 |
| WO | WO-2006/122408 A2 | 11/2006 |
| WO | WO-2006/122408 C1 | 11/2006 |
| WO | WO-2007/048224 A1 | 5/2007 |
| WO | WO-2007/104162 A1 | 9/2007 |
| WO | WO-2007/106192 A2 | 9/2007 |
| WO | WO-2007/106192 A3 | 9/2007 |
| WO | WO-2007/136921 A2 | 11/2007 |
| WO | WO-2007/136921 A3 | 11/2007 |
| WO | WO-2007/136921 C1 | 11/2007 |
| WO | WO-2008/014238 A2 | 1/2008 |
| WO | WO-2008/014238 A3 | 1/2008 |
| WO | WO-2008/016893 A1 | 2/2008 |
| WO | WO-2008/045905 A1 | 4/2008 |
| WO | WO-2008/134679 A1 | 11/2008 |

OTHER PUBLICATIONS

Bakhtiar, C. et al. (Jan. 1994). "Transfer of Alkoxycarbonyl From Alkyl imidazolium-2-Carboxylates to Benzyl Alcohol, a Cyclohexanone Enamine and Diethylamine," *J. Chem. Soc. Perkin. Trans.* 1 3:329-243.

Blass, B.E. et al. (2000). "Parallel Synthesis and Evaluation of N-(1-Phenylethyl)-5-phenyl-imidazole-2-amines as $Na^+/K^+$ ATPase inhibitors," *Bioorganic & Medicinal Chemistry Letters* 10:1543-1545.

Boatright, K.M. et al. (Feb. 2003). "A Unified Model for Apical Caspase Activation," *Molecular Cell* 11:529-541.

Boden, C.D.J. et al. (Dec. 9, 1996). "Total Synthesis of the Thiazoline-Based Cyclopeptide Cyclodidemnamide," *Tetrahedron Letters* 37(50):9111-9114.

Chai, J. et al. (Aug. 24, 2000). "Structural and Biochemical Basis of Apoptotic Activation by SMAC/DIABLO;" *Nature* 406(6798):855-862.

Chari, R.V.J. et al. (Jan. 1, 1992). "Immunoconjugates Containing Novel Maytansinoids: Promising Anticancer Drugs," *Cancer Research* 52:127-131.

Chen, P. et al. (1996). "*grim*, a novel cell death gene in *Drosophila*," *Genes & Development* 10:1773-1782.

Christich, A. et al. (Jan. 22, 2002). "The Damage-Responsive *Drosophila* Gene *sickle* Encodes a Novel IAP Binding Protein Similar to but Distinct from *reaper, grim*, and *hid*," *Current Biology* 12:137-140.

Ciufolini, M.A. et al. (1997). "Studies Toward Thiostrepton Antibiotics: Assembly of the Central Pyridine-Thiazole Cluster of Micrococcins," *J. Org. Chem.* 62:3804-3805.

Communication of Further Notices of Opposition mailed Jun. 16, 2011, for European Patent Application No. 05854815.7, filed on Dec. 19, 2005, two pages.

Communication Letter to the European Patent Office from Jan Robert Naefe, Grafelfing, Germany, mailed Aug. 16, 2012, for European Patent Application No. 05854815.7, twenty-one pages.

Eurasian Patent Office Search Report for Eurasian Patent Application No. 201170344, filed on Aug. 14, 2009, one page. (Russian Only.).

Corey, E.J. et al. (1989). "(+)-1(S), 5(R), 8(S)-8-Phenyl-2-Azabicyclo[3.3.0]octan-8-ol N,O-Methylboronate (2) and Its Enantiomer, Chiral Chemzymes Which Serve as Catalysts for Their Own Enantioselective Synthesis," *Tetrahedron Letters* 30(41):5547-5550.

Crook, N.E. et al. (Apr. 1993). "An Apoptosis-Inhibiting Baculovirus Gene with a Zinc Finger-Like Motif," *Journal of Virology* 67(4):2168-2174.

Derossi, D. et al. (Feb. 1998). "Trojan Peptides: The Penetratin System for Intracellular Delivery," *Trends in Cell Biology* 8:84-87.

Deveraux, Q.L. et al. (1999). "Endogenous Inhibitors of Caspases," *Journal of Clinical Immunology* 19(6):388-398.

Deveraux, Q.L. et al. (1998). "IAPs Block Apoptotic Events Induced by Caspase-8 and Cytochrome *c* by Direct Inhibition of Distinct Caspases," *The EMBO Journal* 17(8):2215-2223.

Deveraux, Q.L. et al. (1999). "IAP Family Proteins-Suppressors of Apoptosis," *Genes & Development* 13:239-252.

Duckett, C.S. et al. (1996). "A Conserved Family of Cellular Genes Related to the Baculovirus *iap* Gene and Encoding Apoptosis Inhibitors," *The EMBO Journal* 15(11):2685-2694.

E-mail dated Apr. 28, 2011, Relating to the Date of Publication of D16 (Maybridge Medchem vol. 1: Bioisosteres brochure, one page.

Extended European Search Report mailed Dec. 28, 2010, for EP Application No. 08747109.0, filed on Apr. 29, 2008, nine pages.

European Communication mailed May 8, 2014, for EP Application No. 09805348.1, filed on Feb. 15, 2011, four pages.

Fastner, J. et al. "Determination of Oligopeptide Diversity Within a Natural Population of *Microcystis* spp. (cyanobacteria),by Typing

(56) References Cited

OTHER PUBLICATIONS

Single Colonies by Matrix-Associated Laser Desorption Ionization-Time of Flight Mass Spectrometry," Document No. 136:114054, retrieved from CAPLUS, Nov. 15, 2001, 2 pages.
Fojo, T. et al. (2003). "Strategies for Reversing Drug Resistance," *Oncogene* 22:7512-7523.
Fong, W.G. et al. (2000). "Expression and Genetic Analysis of XIAP-Associated Factor 1 (XAF1) in Cancer Cell Lines," *Genomics* 70:113-122.
Franklin, M.C. et al. (2003). "Structure and Function Analysis of Peptide Antagonists of Melanoma Inhibitor of Apoptosis (ML-IAP)," *Biochemistry* 42:8223-8231.
Freshney, R.I. (1983). *Culture of Animal Cells, A Manual of Basic Technique*, Alan R. Liss, Inc., New York, New York, p. 4.
Fulda, S. et al. (Aug. 2002). "Smac Agonists Sensitize for Apo2L/TRAIL- or Anticancer Drug-Induced Apoptosis and Induce Regression of Malignant Glioma in vivo," *Nature Medicine* 8(8):808-815.
Giménez-Bonafé, P. et al. (2009). "Overcoming Drug Resistance by Enhancing Apoptosis of Tumor Cells," *Current Cancer Drug Targets* 9:320-340.
Gordon, T. et al. (1993). "Peptide Azoles: A New Class of Biologically-Active Dipeptide Mimetics," *Bioorganic & Medicinal Chemistry Letters* 3(5):915-920.
Goyal, L. et al. (2000). "Induction of Apoptosis by *Drosophila reaper, hid* and *grim* through Inhibition of IAP Function," *The EMBO Journal* 19(4):589-597.
Grether, M.E. et al. (1995). "The Head Involution Defective Gene of *Drosophila* Melanogaster Functions in Programmed Cell Death," *Genes & Developmment* 9:1694-1708.
Guo, F. et al. (2002). "Ectopic Overexpression of Second Mitochondria-Derived Activator of Caspases (Smac/DIABLO) or Cotreatment with N-Terminus of Smac/DIABLO Peptide Potentiates Epothilone B Derivative-(BMS 247550) and Apo-2L/TRAIL-Induced Apoptosis" *Blood* 99:3419-3426.
Hamada, Y. et al. (1985). "New Methods and Reagents in Organic Synthesis. 58. A Synthesis of Patellamide A, a Cytotoxic Cyclic Peptide from a Tunicate. Revision of its Proposed Structure," *Tetrahedron Letters* 26(52):6501-6504.
Hamada, Y. et al. (1985). "New Methods and Reagents in Organic Synthesis. 56. Total Syntheses of Patellamides B and C, Cytotoxic Cyclic Peptides From a Tunicate 2. Their Real Structures Have Been Determined by Their Syntheses," *Tetrahedron Letters* 26(42):5159-5162.
Hinds, M.G. et al. (Jul. 1999). "Solution Structure of a Baculoviral Inhibitor of Apoptosis (IAP) Repeat," *Nature Structural Biology* 6(7):648-651.
Holder, J.R. et al. (Dec. 19, 2002, e-pub. Nov. 23, 2002). "Structure-Activity Relationships of the Melanocortin Tetrapeptide Ac-His-D-Phe-Arg-Trp-NH$_2$ at the Mouse Melanocortin Receptors. 4. Modifications at the Trp Position," *Journal of Medicinal Chemistry* 45(26):5736-5744.
Hu, Y. et al. (Jul. 2003). "Antisense Oligonucleotides Targeting XIAP Induce Apoptosis and Enhance Chemotherapeutic Activity Against Human Lung Cancer Cells in Vitro and in Vivo," *Clinical Cancer Research* 9(7):2826-2836.
International Preliminary Report on Patentability mailed on Feb. 8, 2011, for PCT Patent Application No. PCT/US2009/051522, filed on Jul. 23, 2009, six pages.
International Search Report and Written Opinion mailed on Apr. 5, 2010, for PCT Patent Application No. PCT/US2009/053889, filed on Aug. 14, 2009, nine pages.
International Search Report and Written Opinion mailed on May 7, 2009, for PCT Patent Application No. PCT/US2009/030674, filed on Jan. 9, 2009, twenty-one pages.
Ireland, C.M. et al. (1982). "Antineoplastic Cyclic Peptides From the Marine Tunicate *Lissoclinum patella*," *J. Org. Chem.* 47(10):1807-1811.
Jones, T.A. et al. (1991). "Improved Methods for Building Protein Models in Electron Density Maps and the Location of Errors in These Models," *Acta Cryst.* A47:110-119.

Joyeau, R. et al. (2000). "Synthesis and Activity of Pyrrolidinyl- and Thiazolidinyl-Dipeptide Derivatives as Inhibitors of the Tc80 Prolyl Oligopeptidase From *Trypanosoma cruzi*," *Eur. J. Med. Chem.* 35(2):257-266.
Keating, S. et al. (2000). "Putting the Pieces Together: Contribution of Fluorescence Polarization Assays to Small Molecule Lead Optimization," *Proceedings of SPIE: In-Vitro Diagnostic Instrumentation*, Cohn, G.E. ed. 3913:128-137.
Kipp, R.A. et al. (2002). "Molecular Targeting of Inhibitor of Apoptosis Proteins Based on Small Molecule Mimics of Natural Binding Partners," *Biochemistry* 41(23):7344-7349.
Kolb, J.M. et al. (1996). "Use of a Novel Homogeneous Fluorescent Technology in High Throughput Screening," *Journal of Biomolecular Screening* 1(4):203-210.
Lacasse, E.C. et al. (1998). "The Inhibitors of Apoptosis (IAPs) and Their Emerging Role in Cancer," *Oncogene* 17(25):3247-3259.
Lawton, L.A. et al. (1999, e-pub. Jun. 24, 1999). "A Bioactive Modified Peptide, Aeruginosamide, Isolated from the Cyanobacterium *Microcystis aeruginosa*," *J. Org. Chem.* 64(14):5329-5332.
Li, L. et al. (Sep. 3, 2004). "A Small Molecule Smac Mimic Potentiates TRAIL- and TNFα-Mediated Cell Death," *Science* 305:1471-1474.
Lin, H. et al. (2001). "Resistance of Bone Marrow-Derived Macrophages to Apoptosis is Associated With the Expression of X-Linked Inhibitor of Apoptosis Protein in Primary Cultures of Bone Marrow Cells," *Biochemical Journal* 353:299-306.
Liston, P. et al. (Jan. 25, 1996). "Suppression of Apoptosis in Mammalian Cells by NAIP and a Related Family of IAP Genes," *Nature* 379:349-353.
Liu, C. et al. (Aug. 1996). "Eradication of Large Colon Tumor Xenografts by Targeted Delivery of Maytansinoids," *Proc. Natl. Acad. Sci. USA* 93:8618-8623.
Liu, Z. et al. (Dec. 2000). "Structural Basis for Binding of Smac/DIABLO to the XIAP BIR3 Domain," *Nature* 408:1004-1008.
MacArthur, M.W. et al. (Mar. 20, 1991). "Influence of Proline Residues on Protein Conformation," *J. Mol. Biol.* 218(2):397-412.
Masuda, K. et al. (1981). "Studies on Mesoionic Compounds. Part 11. Alkylation of 5-Acylamino-1,2,3-Thiadiazoles," *J. Chem. Soc. Perkin Trans. 1* 5:1591-1595.
Maybridge Medchem. (Oct. 24, 2005). "Maybridge Medchem, Bioisosteres in Medicinal Chemistry and references cited therein," twenty-two pages.
Moody, C.J. et al. (1999, e-pub. Oct. 23, 1999). "Synthesis of Virenamide B, a Cytotoxic Thiazole-Containing Peptide," *J. Org. Chem.* 64:8715-8717.
Morriello, G. J. et al. "2-Substituted Piperidines, Pyrrolidines and Hexahydro-1H-Azepines Which Promote Release of Growth Hormone," Document No. 124:343117, retrieve from CAPLUS, Apr. 4, 1996, 4 pages.
Murray, E.D. et al. (Sep. 10, 1984). "Synthetic Peptide Substrates for the Erythrocyte Protein Carboxyl Methyltransferase," *The Journal of Biological Chemistry* 259(17):10722-10732.
Murshudov, G.N. et al. (1997). "Refinement of Macromolecular Structures by the Maximum-Likelihood Method," *Acta Cryst.* D53:240-255.
Nakamura et al. (Jul. 10, 1995). "Stereochemistry and Total Synthesis of Dolastatin E," *Tetrahedron Letters* 36(28):5059-5062.
Ndubaku, C. et al. (2009, e-pub. Jun. 3, 2009). "Antagonism of c-IAP and XIAP Proteins Is Required for Efficient Induction of Cell Death by Small-Molecule IAP Antagonists," *ACS Chemical Biology* 4(7):557-566.
Ng, C-P. et al. (Oct. 2002). "X-Linked Inhibition of Apoptosis (XIAP) Blocks Apo2 Ligand/Tumor Necrosis Factor-Related Apoptosis-Inducing Ligand-Mediated Apoptosis of Prostate Cancer Cells in the Presence of Mitochondrial Activation: Sensitization by Overexpression of Second Mitochondria-Derived Activator of Caspase/Direct IAP-Binding Protein With Low pl (Smac/DIABLO)," *Molecular Cancer Therapeutics* 1:1051-1058.
Norley, M.C. et al. (1998). "Total Synthesis and Revision of Stereochemistry of Cyclodidemnamide, a Novel Cyclopeptide from the Marine Ascidian *Didemnum molle*," *Tetrahedron Letters* 39:3087-3090.

(56) References Cited

OTHER PUBLICATIONS

Notice of Opposition to European Patent No. 1 836 201, mailed on May 11, 2010, application filed on Dec. 19, 2005, forty-seven pages.
Ösz, K. et al. (2003, e-pub. Apr. 23, 2003). "Transition Metal Complexes of Bis(imidazol-2-yl) Derivatives of Dipeptides," *Dalton Transactions* pp. 2009-2016.
Palermo, M.G. et al. "Preparation of peptides as Inhibitors of IAP," Accession No. 2005:1130635, Document No. 143:406150, retrived from CAPLUS, 20051020, 11 pages.
Pan, G. et al. (Aug. 8, 1997). "An Antagonist Decoy Receptor and a Death-Domain Containing Receptor for TRAIL," *Science* 277:815-818.
Perrakis, A. et al. (2001). "*ARP/wARP* and Molecular Replacement," *Acta Crystallographica* D57:1445-1450.
Pichon-Pesme, V. et al. (1995). "On Building a Data Bank of Transferable Experimental Electron: Density Parameters: Application to Polypeptides," *J. Phys. Chem.* 99(16):6242-6250.
Prochiantz, A. (1996). "Getting Hydrophilic Compounds into Cells: Lessons from Homeopeptides," *Current Opinion in Neurobiology* 6(5):629-634.
Response to Notice of Opposition mailed on Dec. 22, 2011, for European Patent Application No. 05854815.7, filed on Dec. 19, 2005, nineteen pages.
Riedl, S.J. et al. (Mar. 9, 2001). "Structural Basis for the Inhibition of Caspase-3 by XIAP," *Cell* 104:791-800.
Salvesen et al. (1989). "Determination of Protease Mechanism," in *Proteolytic Enzymes: A Pratical Approach*, R.J. Beynon and J.S. Bond, Oxford, IRL Press, pp. 83-104.
Sanna, M.G. et al. (Mar. 2002). "IAP Suppression of Apoptosis Involves Distinct Mechanisms: the TAK1/JNK1 Signaling Cascade and Caspase Inhibition," *Molecular and Cell Biology* 22(6):1754-1766.
Sasaki, H. et al. (Oct. 15, 2000). "Down-Regulation of X-Linked Inhibitor of Apoptosis Protein Induces Apoptosis in Chemoresistant Human Ovarian Cancer Cells," *Cancer Research* 60(20):5659-5666.
Schimmer, A.D. et al. (2005). "Targeting the IAP Family of Caspase Inhibitors as an Emerging Therapeutic Strategy," *Hematology* pp. 215-219.
SciFinder® Explore Reactions by Substructure (ID 6), Task Began Aug. 8, 2012, one page.
SciFinder® Explore Reactions by Substructure (ID 4), Task Began Aug. 8, 2012, one page.
Sharma, S.K. et al. (Mar. 2006). "Development of Peptidomimetics Targeting IAPs," *International Journal of Peptide Research and Therapeutics* 12(1):21-32.
Shiozaki, E.N. et al. (Feb. 2003). "Mechanism of XIAP-Mediated Inhibition of Caspase-9," *Molecular Cell* 11:519-527.
Shuker, S.B. et al. (Nov. 29, 1996). "Discovering High-Affinity Ligands for Proteins: SAR by NMR," *Science* 274:1531-1534.
Sidhu, S.S. et al (2000). "Phage Display for Selection of Novel Binding Peptides," *Methods in Enzymology* 328:333-363.
Srinivasula, S.M. et al. (Mar. 1, 2001). "A Conserved XIAP-Interaction Motif in Caspase-9 and SMAC/DIABLO Regulates Caspase Activity and Apoptosis," *Nature* 410:112-116.
Srinivasula, S.M. et al. (Jan. 22, 2002). "Sickle, A Novel *Drosophila* Death Gene in the *Reaper/Hid/Grim* Region, Encodes an IAP-Inhibitory Protein," *Current Biology* 12:125-130.
STN International. (Apr. 15, 2009). "STN-11739030A," last visited on Sep. 15, 2009, thirty-seven pages.
Stark, G.R. (May 1968). "Sequential Degradation of Peptides From Their Carboxyl Termini With Ammonium Thiocyanate and Acetic Anhydride," *Biochemistry* 7(5):1796-1807.
Sun, C. et al. (Oct. 21, 1999). "NMR Structure and Mutagenesis of the Inhibitor-of-Apoptosis Protein XIAP," *Nature* 401:818-822.

Sun, C. et al. (Oct. 27, 2000). "NMR Structure and Mutagenesis of the Third Bir Domain of the Inhibitor of Apoptosis Protein XIAP," *The Journal of Biological Chemistry* 275(43):33777-33781.
Supplementary European Search Report mailed Sep. 23, 2011, for EP Application No. 09805348.1, filed on Jul. 23, 2009, eight pages.
Supplementary European Search Report mailed Sep. 20, 2010, for EP Application No. 06850324.2, six pages.
Takahashi, R. et al. (Apr. 3, 1998). "A Single BIR Domain of XIAP Sufficient for Inhibiting Caspases," *The Journal of Biological Chemistry* 273(14):7787-7790.
Tamm, I. et al. (May 2000). "Expression and Prognostic Significance of IAP-Family Genes in Human Cancers and Myeloid Leukemias," *Clinical Cancer Research* 6(5):1796-1803.
Tenev, T. et al. (2002). "Jafrac2 is an IAP Antagonist that Promotes Cell Death by Liberating Dronc From DIAP1," *The EMBO Journal* 21(19):5118-5129.
Thompson, C.B. (Mar. 10, 1995). "Apoptosis in the Pathogenesis and Treatment of Disease," *Science* 267:1456-1462.
Thompson, S.K. et al. (Dec. 1997). "Design of Potent and Selective Human Cathepsin K Inhibitors that Span the Active Site," *Proc. Natl. Acad. Sci. USA* 94:14249-14254.
Thompson, S.K. et al. (1994, e-pub. Aug. 1, 1994). "Rational Design, Synthesis, and Crystallographic Analysis of a Hydroxyethylene-Based HIV-1 Protease Inhibitor Containing a Heterocyclic $P_1$'-$P_2$' Amide Bond Isostere," *J. Med. Chem.* 37(19):3100-3107.
Thompson, S.K. et al. (1994). "Synthesis and Antiviral Activity of a Novel Class of HIV-1 Protease Inhibitors Containing a Heterocyclic $P_1$'-$P_2$' Amide Bond Isostere," *Bioorganic and Medicinal Chemistry Letters* 4(20):2441-2446.
U.S. Appl. No. 60/560,186, filed Apr. 7, 2004, by Palermo et al. seventy-four pages.
Vippagunta, S.R. et al. (2001). "Crystalline Solids," *Advanced Drug Delivery Reviews* 48:3-26.
Vucic, D. et al. (Oct. 17, 2000). "ML-IAP, A Novel Inhibitor of Apoptosis that is Preferentially Expressed in Human Melanomas," *Current Biology* 10:1359-1366.
Vucic, D. et al. (Apr. 5, 2002). "SMAC Negatively Regulates the Anti-Apoptotic Activity of Melanoma Inhibitor of Apoptosis (ML-IAP)," *The Journal of Biological Chemistry* 277(14):12275-12279.
Vucic, D. et al. (Jan. 2005). "Engineering ML-IAP to Produce an Extraordinarily Potent Caspase 9 Inhibitor: Implications for SMAC-Dependent Anti-Apoptotic Activity of ML-IAP," *Biochemical Journal* 385(Part 1):11-20.
West, A.R. (1984). "Solid Solutions," Chapter 10 in *Solid State Chemistry and Its Applications*, John Wiley and Sons, New York, pp. 358 and 365.
White, K. et al. (Apr. 29, 1994). "Genetic Control of Programmed Cell Death in *Drosophila*," *Science* 264:677-683.
Wing, J.P. et al. (Jan. 22, 2002). "*Drosophila sickle* is a Novel *grim-reaper* Cell Death Activator," *Current Biology* 12:131-135.
Wu, G. et al. (Dec. 2000). "Structural Basis of IAP Recognition by Smac/DIABLO," *Nature* 408:1008-1012.
Wu, J-W. et al (Jul. 2001). "Structural Analysis of a Functional DIAP1 Fragment Bound to Grim and Hid Peptides," *Molecular Cell* 8:95-104.
Yang, L. et al. (Feb. 15, 2003). "Predominant Suppression of Apoptosome by Inhibitor of Apoptosis Protein in Non-Small Cell Lung Cancer H460 Cells: Therapeutic Effect of a Novel Polyarginine-Conjugated Smac Peptide," *Cancer Research* 63(4):831-837.
Yokokawa, F. et al. (2001). "Total Synthesis of *cis,cis*-Ceratospongamide, a Bioactive Thiazole-Containing Cyclic Peptide from Marine Origin," *Synlett* SI:986-988.
Yokokawa, F. et al. (2002). "Total Synthesis and Conformational Studies of Ceratospongamide, a Bioactive Cyclic Heptapeptide From Marine Origin," *Tetrahedron* 58:8127-8143.

\* cited by examiner

SEQUENCE LISTING

```
<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

Met Gly Ser Ser His His His His His His Ser Ser Gly Leu Val Pro
1               5                   10                  15

Arg Gly Ser His Met Leu Glu Thr Glu Glu Glu Glu Glu Gly Ala
            20                  25                  30

Gly Ala Thr Leu Ser Arg Gly Pro Ala Phe Pro Gly Met Gly Ser Glu
        35                  40                  45

Glu Leu Arg Leu Ala Ser Phe Tyr Asp Trp Pro Leu Thr Ala Glu Val
    50                  55                  60

Pro Pro Glu Leu Leu Ala Ala Ala Gly Phe Phe His Thr Gly His Gln
65                  70                  75                  80

Asp Lys Val Arg Cys Phe Phe Cys Tyr Gly Gly Leu Gln Ser Trp Lys
                85                  90                  95

Arg Gly Asp Asp Pro Trp Thr Glu His Ala Lys Trp Phe Pro Gly Cys
            100                 105                 110

Gln Phe Leu Leu Arg Ser Lys Gly Gln Glu Tyr Ile Asn Asn Ile His
        115                 120                 125

Leu Thr His Ser Leu
    130
```

PYRROLIDINE INHIBITORS OF IAP

RELATED APPLICATIONS

This application is a divisional of U.S. application Ser. No. 12/538,794, filed Aug. 10, 2009, which is a continuation application of U.S. application Ser. No. 12/105,109, filed Apr. 17, 2008, which is a continuation application of U.S. application Ser. No. 11/312,063, filed Dec. 19, 2005, which claims priority under 35 U.S.C. §119(e)(1) to U.S. provisional application 60/638,202, filed on Dec. 20, 2004, the content of each of which is incorporated herein by reference in its entirety.

FIELD OF THE INVENTION

The present invention relates to organic compounds useful for therapy and/or prophylaxis in a mammal, and in particular to inhibitors of IAP proteins useful for treating cancers.

BACKGROUND OF THE INVENTION

Apoptosis or programmed cell death is a genetically and biochemically regulated mechanism that plays an important role in development and homeostasis in invertebrates as well as vertebrates. Aberrancies in apoptosis that lead to premature cell death have been linked to a variety of developmental disorders. Deficiencies in apoptosis that result in the lack of cell death have been linked to cancer and chronic viral infections (Thompson et al., (1995) Science 267, 1456-1462).

One of the key effector molecules in apoptosis are the caspases (cysteine containing aspartate specific proteases). Caspases are strong proteases, cleaving after aspartic acid residues and once activated, digest vital cell proteins from within the cell. Since caspases are such strong proteases, tight control of this family of proteins is necessary to prevent premature cell death. In general, caspases are synthesized as largely inactive zymogens that require proteolytic processing in order to be active. This proteolytic processing is only one of the ways in which caspases are regulated. The second mechanism is through a family of proteins that bind and inhibit caspases.

A family of molecules that inhibit caspases are the Inhibitors of Apoptosis (IAP) (Deveraux et al., J Clin Immunol (1999), 19:388-398). IAPs were originally discovered in baculovirus by their functional ability to substitute for P35 protein, an anti-apoptotic gene (Crook et al. (1993) J Virology 67, 2168-2174). IAPs have been described in organisms ranging from Drosophila to human. Regardless of their origin, structurally, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion (Hinds et al., (1999) Nat. Struct. Biol. 6, 648-651). It is the BIR domain that is believed to cause the anti-apoptotic effect by inhibiting the caspases and thus inhibiting apoptosis. As an example, human X-chromosome linked IAP (XIAP) inhibits caspase 3, caspase 7 and the Apaf-1-cytochrome C mediated activation of caspase 9 (Deveraux et al., (1998) EMBO J. 17, 2215-2223). Caspases 3 and 7 are inhibited by the BIR2 domain of XIAP, while the BIR3 domain of XIAP is responsible for the inhibition of caspase 9 activity. XIAP is expressed ubiquitously in most adult and fetal tissues (Liston et al, Nature, 1996, 379(6563): 349), and is overexpressed in a number of tumor cell lines of the NCI 60 cell line panel (Fong et al, Genomics, 2000, 70:113; Tamm et al, Clin. Cancer Res. 2000, 6(5):1796). Overexpression of XIAP in tumor cells has been demonstrated to confer protection against a variety of pro-apoptotic stimuli and promotes resistance to chemotherapy (LaCasse et al, Oncogene, 1998, 17(25):3247). Consistent with this, a strong correlation between XIAP protein levels and survival has been demonstrated for patients with acute myelogenous leukemia (Tamm et al, supra). Down-regulation of XIAP expression by antisense oligonucleotides has been shown to sensitize tumor cells to death induced by a wide range of pro-apoptotic agents, both in vitro and in vivo (Sasaki et al, Cancer Res., 2000, 60(20):5659; Lin et al, Biochem J., 2001, 353:299; Hu et al, Clin. Cancer Res., 2003, 9(7):2826). Smac/DIABLO-derived peptides have also been demonstrated to sensitize a number of different tumor cell lines to apoptosis induced by a variety of pro-apoptotic drugs (Arnt et al, J. Biol. Chem., 2002, 277(46):44236; Fulda et al, Nature Med., 2002, 8(8):808; Guo et al, Blood, 2002, 99(9):3419; Vucic et al, J. Biol. Chem., 2002, 277(14):12275; Yang et al, Cancer Res., 2003, 63(4):831).

Melanoma IAP (ML-IAP) is an IAP not detectable in most normal adult tissues but is strongly upregulated in melanoma (Vucic et al., (2000) Current Bio 10:1359-1366). Determination of protein structure demonstrated significant homology of the ML-IAP BIR and RING finger domains to corresponding domains present in human XIAP, C-IAP1 and C-IAP2. The BIR domain of ML-IAP appears to have the most similarities to the BIR2 and BIR3 of XIAP, C-IAP1 and C-IAP2, and appears to be responsible for the inhibition of apoptosis, as determined by deletional analysis. Furthermore, Vucic et al., demonstrated that ML-IAP could inhibit chemotherapeutic agent induced apoptosis. Agents such as adriamycin and 4-tertiary butylphenol (4-TBP) were tested in a cell culture system of melanomas overexpressing ML-IAP and the chemotherapeutic agents were significantly less effective in killing the cells when compared to a normal melanocyte control. The mechanism by which ML-IAP produces an anti-apoptotic activity is in part through inhibition of caspase 3 and 9. ML-IAP did not effectively inhibit caspases 1, 2, 6, or 8.

Since apoptosis is a strictly controlled pathway with multiple interacting factors, the discovery that IAPs themselves are regulated was not unusual. In the fruit fly Drosophila, the Reaper (rpr), Head Involution Defective (hid) and GRIM proteins physically interact with and inhibit the anti-apoptotic activity of the Drosophila family of IAPs. In the mammal, the proteins SMAC/DIABLO act to block the IAPs and allow apoptosis to proceed. It was shown that during normal apoptosis, SMAC is processed into an active form and is released from the mitochondria into the cytoplasm where it physically binds to IAPs and prevents the IAP from binding to a caspase. This inhibition of the IAP allows the caspase to remain active and thus proceed with apoptosis. Interestingly, sequence homology between the IAP inhibitors shows that there is a four amino acid motif in the N-terminus of the processed, active proteins. This tetrapeptide appears to bind into a hydrophobic pocket in the BIR domain and disrupts the BIR domain binding to caspases (Chai et al., (2000) Nature 406: 855-862, Liu et al., (2000) Nature 408:1004-1008, Wu et al., (2000) Nature 408:1008-1012).

SUMMARY OF THE INVENTION

In one aspect of the present invention there is provided novel inhibitors of IAP proteins having the general formula I:

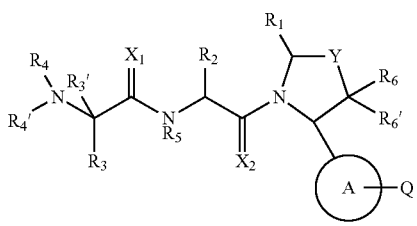

wherein
A is a 5-member aromatic heterocycle incorporating 1 to 4 heteroatoms N, O or S and is optionally substituted with one or more $R_7$ and $R_8$ groups;
Q is H, alkyl, a carbocycle, a heterocycle; wherein one or more $CH_2$ or CH groups of an alkyl is optionally replaced with —O—, —S—, —S(O)—, —S(O)$_2$, —N($R_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)—NR$_8$—, —NR$_8$—C(NH)—, —C(O)—O— or —O—C(O)—; and an alkyl, carbocycle and heterocycle is optionally substituted with one or more hydroxyl, alkoxy, acyl, halogen, mercapto, oxo, carboxyl, halo-substituted alkyl, amino, cyano, nitro, amidino, guanidino an optionally substituted carbocycle or an optionally substituted heterocycle;
$X_1$ and $X_2$ are each independently O or S;
Y is a bond, $(CR_7R_7)_n$, O or S; wherein n is 1 or 2 and $R_7$ is H, halogen, alkyl, aryl, aralkyl, amino, arylamino, alkylamino, aralkylamino, alkoxy, aryloxy or aralkyloxy;
$R_1$ is H or $R_1$ and $R_2$ together form a 5-8 member heterocycle;
$R_2$ is alkyl, a carbocycle, carbocyclylalkyl, a heterocycle or heterocyclylalkyl each optionally substituted with halogen, hydroxyl, oxo, thione, mercapto, carboxyl, alkyl, haloalkyl, alkoxy, alkylthio, sulfonyl, amino and nitro;
$R_3$ is H or alkyl optionally substituted with halogen or hydroxyl; or $R_3$ and $R_4$ together form a 3-6 heterocycle;
$R_3'$ is H, or $R_3$ and $R_3'$ together form a 3-6 carbocycle;
$R_4$ and $R_4'$ are independently H, hydroxyl, amino, alkyl, carbocycle, carbocycloalkyl, carbocycloalkyloxy, carbocycloalkyloxycarbonyl, heterocycle, heterocycloalkyl, heterocycloalkyloxy or heterocycloalkyloxycarbonyl; wherein each alkyl, carbocycloalkyl, carbocycloalkyloxy, carbocycloalkyloxycarbonyl, heterocycle, heterocycloalkyl, heterocycloalkyloxy and heterocycloalkyloxycarbonyl is optionally substituted with halogen, hydroxyl, mercapto, carboxyl, alkyl, alkoxy, amino, imino and nitro; or $R_4$ and $R_4'$ together form a heterocycle;
$R_5$ is H or alkyl;
$R_6$, and $R_6'$ are each independently H, alkyl, aryl or aralkyl;
$R_7$ is H, cyano, hydroxyl, mercapto, halogen, nitro, carboxyl, amidino, guanidino, alkyl, a carbocycle, a heterocycle or —U—V; wherein U is —O—, —S, —S(O)—, —S(O)$_2$, —N($R_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)—NR$_8$—, —NR$_8$—C(NH)—, —C(O)—O— or —O—C(O)— and V is alkyl, a carbocycle or a heterocycle; and wherein one or more $CH_2$ or CH groups of an alkyl is optionally replaced with —O—, —S—, —S(O)—, S(O)$_2$, —N($R_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —C(O)—O— or —O—C(O)—; and an alkyl, carbocycle and heterocycle is optionally substituted with hydroxyl, alkoxy, acyl, halogen, mercapto, oxo, carboxyl, acyl, halo-substituted alkyl, amino, cyano nitro, amidino, guanidino an optionally substituted carbocycle or an optionally substituted heterocycle;
$R_8$ is H, alkyl, a carbocycle or a heterocycle wherein one or more $CH_2$ or CH groups of said alkyl is optionally replaced with —O—, —S—, —S(O)—, S(O)$_2$, —N($R_8$), or —C(O)—; and said alkyl, carbocycle and heterocycle is optionally substituted with hydroxyl, alkoxy, acyl, halogen, mercapto, oxo (=O), carboxyl, acyl, halo-substituted alkyl, amino, cyano nitro, amidino, guanidino an optionally substituted carbocycle or an optionally substituted heterocycle;
and salts and solvates thereof.

In another aspect of the invention, there are provided compositions comprising compounds of formula I and a carrier, diluent or excipient.

In another aspect of the invention, there is provided a method of inducing apoptosis in a cell comprising introducing into said cell a compound of formula I.

In another aspect of the invention, there is provided a method of sensitizing a cell to an apoptotic signal comprising introducing into said cell a compound of formula I.

In another aspect of the invention, there is provided a method for inhibiting the binding of an IAP protein to a caspase protein comprising contacting said IAP protein with a compound of formula I.

In another aspect of the invention, there is provided a method for treating a disease or condition associated with the overexpression of an IAP protein in a mammal, comprising administering to said mammal an effective amount of a compound of formula I.

DETAILED DESCRIPTION OF THE PREFERRED EMBODIMENTS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion may be a saturated hydrocarbon chain, however also includes unsaturated hydrocarbon carbon chains such as "alkenylamino" and "alkynylamino. Examples of particular alkyl groups are methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted alkyl groups may contain one, for example two, three or four substituents which may be the same or different. Examples of substituents are, unless otherwise defined, halogen, amino, hydroxyl, protected hydroxyl, mercapto, carboxy, alkoxy, nitro, cyano, amidino, guanidino, urea, sulfonyl, sulfinyl, aminosulfonyl, alkylsulfonylamino, arylsulfonylamino, aminocarbonyl, acylamino, alkoxy, acyl, acyloxy, a carbocycle, a heterocycle. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Substituted alkyls include substituted methyls e.g. a methyl group substituted by the same substituents as the "substituted $C_n$-$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" means the group —C(NH)—NHR wherein R is H or alkyl or aralkyl. A particular amidine is the group —NH—C(NH)—NH$_2$.

"Amino" means primary (i.e. —NH$_2$), secondary (i.e. —NRH) and tertiary (i.e. —NRR) amines Particular secondary and tertiary amines are alkylamine, dialkylamine, arylamine, diarylamine, aralkylamine and diaralkylamine wherein the alkyl is as herein defined and optionally substituted. Particular secondary and tertiary amines are methylamine, ethylamine, propylamine, isopropylamine, phenylamine, benzylamine dimethylamine, diethylamine, dipropylamine and disopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Particular amino protecting groups are Boc, Fmoc and Cbz. Further examples of these groups are found in T. W. Greene and P. G. M. Wuts, "Protective Groups in Organic Synthesis", 2$^{nd}$ ed., John Wiley & Sans, Inc., New York, N.Y., 1991, chapter 7; E. Haslam, "Protective Groups in Organic Chemistry", J. G. W. McOmic, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Particular aryl groups are phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]). A particular aryl is phenyl. Substituted phenyl or substituted aryl means a phenyl group or aryl group substituted with one, two, three, four or five, for example 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulonylaminoalkyl, heterocyclylsulfonylamino, heterocyclylsulfonylaminoalkyl, heterocyclyl, aryl, or other groups specified. One or more methyne (CH) and/or methylene (CH$_2$) groups in these substituents may in turn be substituted with a similar group as those denoted above. Examples of the term "substituted phenyl" includes but is not limited to a mono- or di(halo) phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy) phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl) phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with any, for example 1, 2 or 3, of the substituents specified herein in the same manner as substituted alkyl groups.

"Carbocyclyl", "carbocyclylic", "carbocycle" and "carbocyclo" alone and when used as a moiety in a complex group such as a carbocycloalkyl group, refers to a mono-, bi-, or tricyclic aliphatic ring having 3 to 14 carbon atoms, for example 3 to 7 carbon atoms, which may be saturated or unsaturated, aromatic or non-aromatic. Particular saturated carbocyclic groups are cyclopropyl, cyclobutyl, cyclopentyl and cyclohexyl groups. A particular saturated carbocycle is cyclopropyl. Another particular saturated carbocycle is cyclohexyl. Particular unsaturated carbocycles are aromatic e.g. aryl groups as previously defined, for example phenyl. The terms "substituted carbocyclyl", "carbocycle" and "carbocyclo" mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as $LiAlH_4$. (Such harsh removal conditions are also to be avoided when removing amino-protecting groups and hydroxy-protecting groups, discussed below.) Particular carboxylic acid protecting groups are the alkyl (e.g. methyl, ethyl, t-butyl), allyl, benzyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Guanidine" means the group —NH—C(NH)—NHR wherein R is H or alkyl or aralkyl. A particular guanidine is the group —NH—C(NH)—$NH_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", $2^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen), for example 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Particular non-aromatic heterocycles are morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Particular 5-membered heterocycles containing a sulfur or oxygen atom and one to three nitrogen atoms are thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Particular 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a particular group. Substituents for "optionally substituted heterocycles", and further examples of the 5- and 6-membered ring systems discussed above can be found in W. Druckheimer et al., U.S. Pat. No. 4,278,793. In a particular embodiment, such optionally substituted heterocycle groups are substituted with hydroxyl, alkyl, alkoxy, acyl, halogen, mercapto, oxo, carboxyl, acyl, halo-substituted alkyl, amino, cyano, nitro, amidino and guanidino.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and in a particular embodiment at least one heteroatom is nitrogen (*Lang's Handbook of Chemistry*, supra). Included in the definition are any bicyclic groups where any of the above heteroaryl rings are fused to a benzene ring. Particular heteroaryls incorporate a nitrogen or oxygen heteroatom. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particular "heteroaryl" is: 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl- 1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl. Heteroaryl groups are optionally substituted as described for heterocycles.

"Inhibitor" means a compound which reduces or prevents the binding of IAP proteins to caspase proteins or which reduces or prevents the inhibition of apoptosis by an IAP protein. Alternatively, "inhibitor" means a compound which prevents the binding interaction of X-IAP with caspases or the binding interaction of ML-IAP with SMAC.

"Optionally substituted" unless otherwise specified means that a group may be substituted by one or more (e.g. 0, 1, 2, 3 or 4) of the substituents listed for that group in which said substituents may be the same or different. In an embodiment an optionally substituted group has 1 substituent. In another embodiment an optionally substituted group has 2 substituents. In another embodiment an optionally substituted group has 3 substituents.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, trimethamine, dicyclohexylamine, choline, and caffeine.

"Sulfonyl" means a —SO$_2$—R group wherein R is alkyl, carbocycle, heterocycle, carbocycloalkyl or heterocycloalkyl. Particular sulfonyl groups are alkylsulfonyl (i.e. —SO$_2$-alkyl), for example methylsulfonyl; arylsulfonyl, for example phenylsulfonyl; aralkylsulfonyl, for example benzylsulfonyl.

The phrase "and salts and solvates thereof" as used herein means that compounds of the inventions may exist in one or a mixture of salts and solvate forms. For example a compound of the invention may be substantially pure in one particular salt or solvate form or else may be mixtures of two or more salt or solvate forms.

The present invention provides novel compounds having the general formula I:

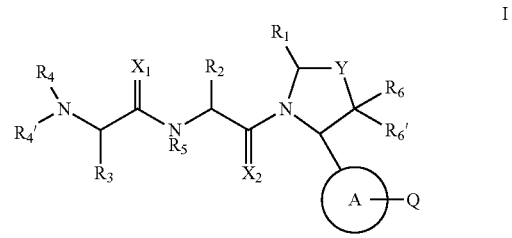

wherein A, Q, $X_1$, $X_2$, Y, $R_1$, $R_2$, $R_3$, $R_4$, $R_4'$, $R_5$, $R_6$ and $R_6'$ are as described herein.

Ring A is a 5-member aromatic heterocycle incorporating 1 to 4 heteroatoms N, O or S which is substituted with group Q and is optionally further substituted with one or more $R_7$ (for substitutions at a ring carbon atom) and one or more $R_8$ (for substitutions at a ring nitrogen).

$R_7$ in each occurrence is independently H, cyano, hydroxyl, mercapto, halogen, nitro, carboxyl, amidino, guanidino, alkyl, a carbocycle, a heterocycle or —U—V; wherein U is —O—, —S—, —S(O)—, S(O)$_2$, —N($R_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)—NR$_8$—, —NR$_8$—C(NH)—, —C(O)—O— or —O—C(O)— and V is alkyl, a carbocycle or a heterocycle;

and wherein one or more CH$_2$ or CH groups of an alkyl is optionally replaced with —O—, —S—, —S(O)—, S(O)$_2$, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)—NR$_8$—, —NR$_8$—C(NH)—, —C(O)—O— or —O—C(O)—; and an alkyl, carbocycle and heterocycle is optionally substituted with hydroxyl, alkoxy, acyl, halogen, mercapto, oxo, carboxyl, acyl, halo-substituted alkyl, amino, cyano, nitro, amidino, guanidino an optionally substituted carbocycle or an optionally substituted heterocycle. Substituents of the "optionally substituted carbocycle" and "optionally substituted heterocycle" are as defined herein. In a particular embodiment such carbocycle and heterocycle groups are substituted with hydroxyl, alkyl, alkoxy, acyl, halogen, mercapto, oxo, carboxyl, acyl, halo-substituted alkyl, amino, cyano, nitro, amidino and guanidino. In an embodiment R$_7$ is H, halogen, cyano, alkyl, hydroxyalkyl or alkoxyalkyl.

R$_8$ is H, alkyl, a carbocycle or a heterocycle wherein one or more CH$_2$ or CH groups of said alkyl is optionally replaced with —O—, —S—, —S(O)—, S(O)$_2$, —N(R$_8$), or —C(O)—; and said alkyl, carbocycle and heterocycle is optionally substituted with hydroxyl, alkoxy, acyl, halogen, mercapto, oxo (=O), carboxyl, acyl, halo-substituted alkyl, amino, cyano nitro, amidino, guanidino an optionally substituted carbocycle or an optionally substituted heterocycle. Substituents of the "optionally substituted carbocycle" and "optionally substituted heterocycle" are as defined herein. In a particular embodiment such carbocycle and heterocycle groups are substituted with hydroxyl, alkyl, alkoxy, acyl, halogen, mercapto, oxo, carboxyl, acyl, halo-substituted alkyl, amino, cyano, nitro, amidino and guanidino. In a particular embodiment R$_8$ is H, alkyl, or acyl. In an embodiment R$_8$ is methyl. In another embodiment R$_8$ is acetyl. In a particular embodiment R$_8$ is H. In an embodiment R$_7$ is H, halogen, amino, hydroxyl, carboxyl, alkyl, haloalkyl or aralkyl. In a particular embodiment R$_7$ is halogen, for example Cl or F. In a particular embodiment R$_7$ is H. It is understood that substitutions defined for R$_7$ and R$_8$ as well as all other variable groups herein are subject to permissible valency.

In a particular embodiment ring A has the general formula II:

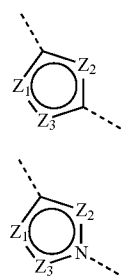

wherein Z$_1$ is NR$_8$, O or S; and Z$_2$, Z$_3$ and Z$_4$ are each independently N or CR$_7$. Group Q is attached to ring A of formula II and II' at the ring member between Z$_2$ and Z$_3$. In a particular embodiment Z$_1$ is S. In a particular embodiment Z$_1$ is O. In another particular embodiment Z$_1$ is NR$_8$ wherein R$_8$ is as defined herein. In a particular embodiment Z$_1$ is NR$_8$ wherein R$_8$ is H. In another particular embodiment Z$_1$ is NR$_8$ wherein R$_8$ is Me. In another embodiment Z$_1$ is O or S while Z$_2$ is N and Z$_3$ is N or CR$_7$. In a particular embodiment Z$_1$ is S while Z$_2$ is N and Z$_3$ is CR$_7$. In a particular embodiment Z$_1$ is S while Z$_2$ is N and Z$_3$ is CH.

In a particular embodiment, ring A is an aromatic heterocycle selected from the group consisting of IIa-IIcc:

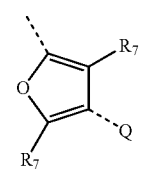

IIa

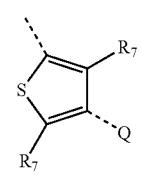

IIb

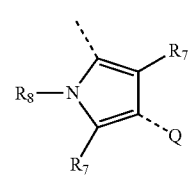

IIc

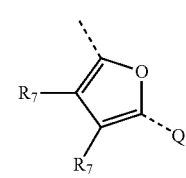

IIc

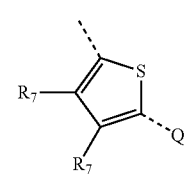

IId

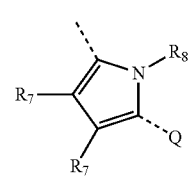

IIe

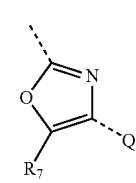

IIf

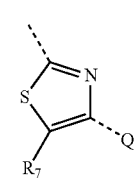

IIg

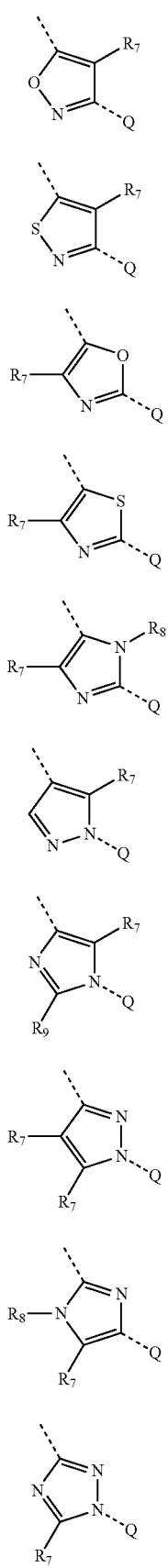
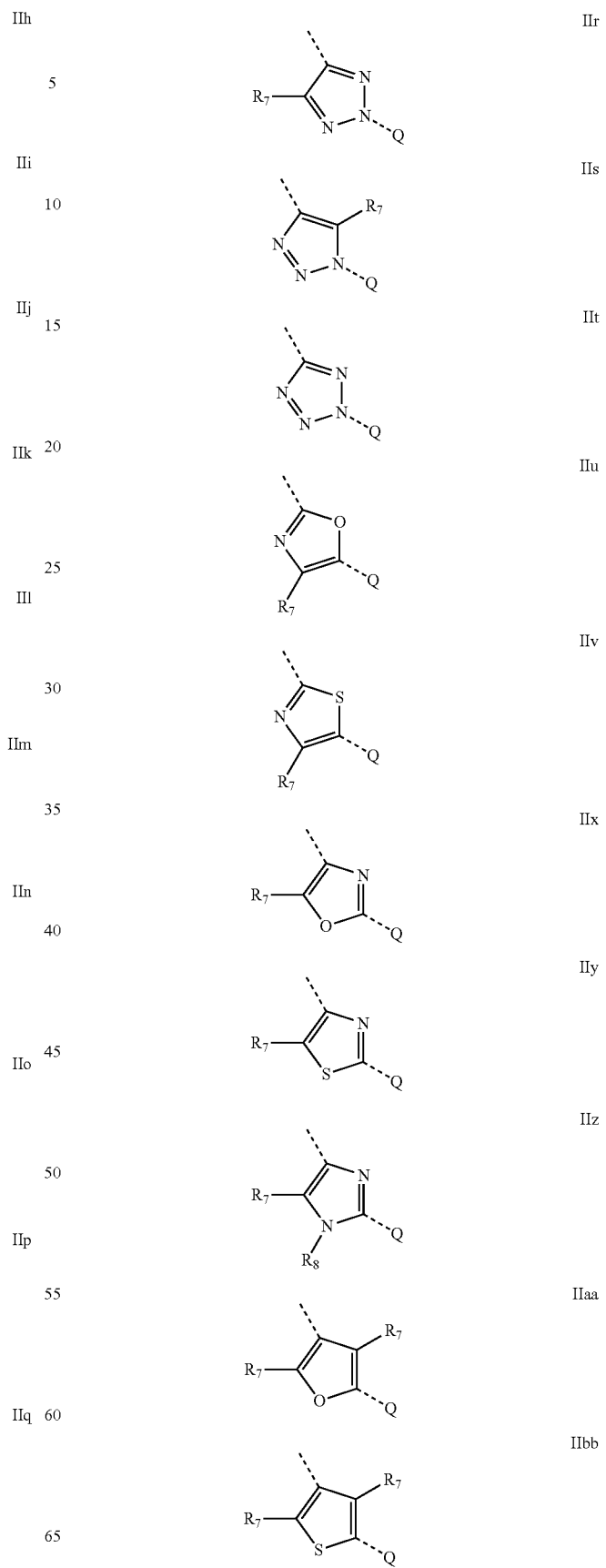

-continued

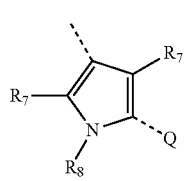

IIcc wherein $R_7$ and $R_8$ are as defined herein. Q is not part of ring A and is shown for positional purposes. In a particular embodiment, ring A is any one of the groups IIa-IIz wherein $R_8$ is H and $R_7$ is H, Cl, or hydroxypropynyl. In another particular embodiment, ring A is any one of the groups IIa-IIz wherein $R_7$ and $R_8$ are both H. In another embodiment, ring A is the IIg. In another embodiment, ring A is IIg and $R_7$ is H.

Q is H, alkyl, a carbocycle, a heterocycle; wherein one or more $CH_2$ or CH groups of an alkyl is optionally replaced with —O—, —S—, —S(O)—, $S(O)_2$, —N($R_8$)—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—; and wherein any of the foregoing alkyl, carbocycle and heterocycle is optionally substituted with one or more hydroxyl, alkoxy, acyl, halogen, mercapto, oxo, carboxyl, acyl, halo-substituted alkyl, amino, cyano nitro, amidino, guanidino an optionally substituted carbocycle or an optionally substituted heterocycle. Substituents of the "optionally substituted carbocycle" and "optionally substituted heterocycle" are as defined herein. In a particular embodiment such carbocycle and heterocycle groups are substituted with hydroxyl, alkyl, alkoxy, acyl, halogen, mercapto, oxo, carboxyl, acyl, halo-substituted alkyl, amino, cyano, nitro, amidino and guanidino. In a particular embodiment Q is a carbocycle or heterocycle optionally substituted with halogen, amino, oxo, alkyl, a carbocycle or a heterocycle; wherein one or more $CH_2$ or CH groups of an alkyl is optionally replaced with —O—, —S—, —S(O)—, $S(O)_2$, —N($R_8$)—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—; and wherein said alkyl, carbocycle or heterocycle is optionally substituted with halogen, amino, hydroxyl, mercapto, carboxyl, alkoxy, alkoxyalkoxy, hydroxyalkoxy, alkylthio, acyloxy, acyloxyalkoxy, alkylsulfonyl, alkylsulfonylalkyl, alkylsulfinyl, and alkylsulfinylalkyl.

In a particular embodiment, Q is a carbocycle or heterocycle selected from the group consisting of IIIa-IIIs:

IIIa

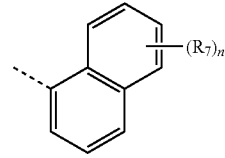

IIIb

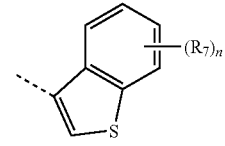

IIIc

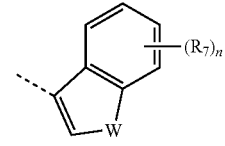

IIId

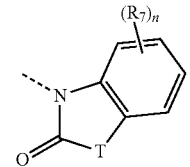

IIIe

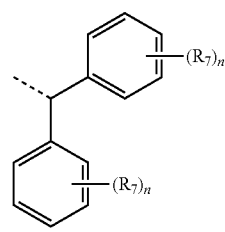

IIIf

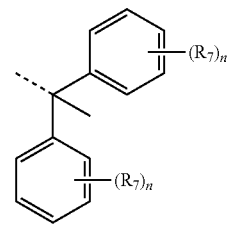

IIIg

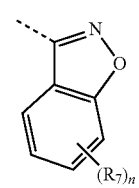

IIIh

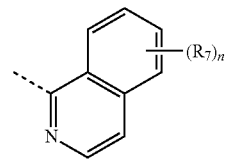

IIIi

IIIj

IIIk

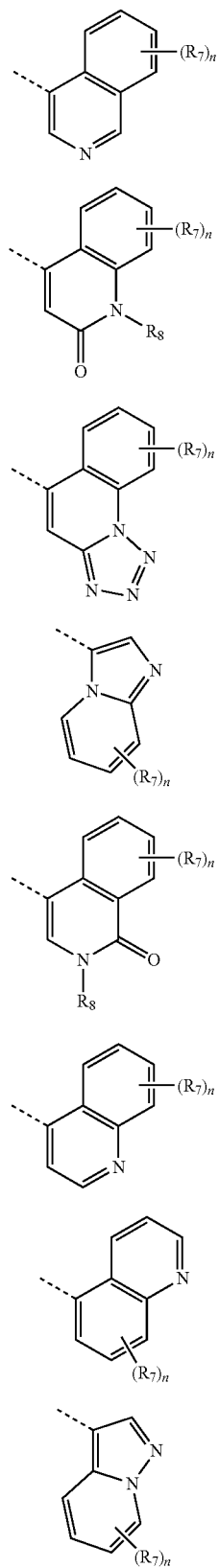

wherein n is 1-4, for example 1-3, for example 1-2, for example 1; T is O, S, NR$_8$ or CR$_7$R$_7$; W is O, NR$_8$ or CR$_7$R$_7$; and R$_7$ and R$_8$ are as defined herein. In a particular embodiment Q is any one of IIIa-IIIi wherein R$_8$ is H and R$_7$ is selected from the group consisting of H, F, Cl, Me, methoxy, hydroxyethoxy, methoxyethoxy, acetoxyethoxy, methylsulfonyl methylsulfonylmethyl, phenyl and morpholin-4-yl. In another particular embodiment Q is IIId. In a particular embodiment Q is IIId which is substituted at the 4-position with R$_7$. In another particular embodiment Q is IIId which is substituted at the 5-position with R$_7$.

X$_1$ and X$_2$ are each independently O or S. In a particular embodiment, X$_1$ and X$_2$ are both O. In another particular embodiment X$_1$ and X$_2$ are both S. In another particular embodiment, X$_1$ is S while X$_2$ is O. In another particular embodiment, X$_1$ is O while X$_2$ is S.

Y is a bond, (CR$_7$R$_7$)$_n$, O or S; wherein n is 1 or 2 and R$_7$ is H, halogen, alkyl, aryl, aralkyl, amino, arylamino, alkylamino, aralkylamino, alkoxy, aryloxy or aralkyloxy. In a particular embodiment, Y is (CHR$_7$)$_n$, O or S; wherein n is 1 or 2 and R$_7$ is H, halogen, alkyl, aryl, aralkyl, amino, arylamino, alkylamino, aralkylamino, alkoxy, aryloxy or aralkyloxy. In a particular embodiment, Y is CH$_2$. In a particular embodiment n is 1. In a particular embodiment Y is a bond. In a particular embodiment n is 1 and Y is CHR$_7$ wherein R$_7$ is aralkyloxy, for example benzyloxy. In a particular embodiment n is 1 and Y is CHR$_7$ wherein R$_7$ is F. In a particular embodiment n is 1 and Y is CHR$_7$ wherein R$_7$ is aralkylamino, for example benzylamino. In another particular embodiment Y is O. In another particular embodiment Y is S.

R$_1$ is H or R$_1$ and R$_2$ together form a 5-8 member ring. In a particular embodiment, R$_1$ is H. In a particular embodiment, R$_1$ and R$_2$ together form a 6-member ring. In a particular embodiment, R$_1$ and R$_2$ together form a 7-member ring. In another particular embodiment, R$_1$ and R$_2$ together form an 8-member ring. In another particular embodiment, R$_1$ and R$_2$ together form a 7-member ring while Y is S. In another particular embodiment, R$_1$ is H, while Y is CH$_2$. In another particular embodiment, R$_1$ is H, while Y is S. In another particular embodiment, R$_1$ is H, while Y is O.

R$_2$ is alkyl, a carbocycle, carbocyclylalkyl, a heterocycle or heterocyclylalkyl each optionally substituted with halogen, hydroxyl, oxo, thione, mercapto, carboxyl, alkyl, haloalkyl, alkoxy, alkylthio, sulfonyl, amino and nitro. In a particular embodiment R$_2$ is alkyl, a carbocycle, carbocyclylalkyl, a heterocycle or heterocyclylalkyl each optionally substituted with halogen, hydroxyl, oxo, mercapto, thione, carboxyl, alkyl, haloalkyl, alkoxy, alkylthio, sulfonyl, amino and nitro. In an embodiment R$_2$ is alkyl, a carbocycle, carbocyclylalkyl, a heterocycle or heterocyclylalkyl each optionally substituted with halogen, hydroxyl, mercapto, carboxyl, alkyl, alkoxy, amino and nitro. In a particular embodiment R$_2$ is alkyl, cycloalkyl, cycloalkylalkyl, aryl, aralkyl, a heterocycle or heterocyclylalkyl. In a particular embodiment R$_2$ is alkyl, cycloalkyl or a heterocycle. In a particular embodiment R$_2$ is selected from the group consisting of t-butyl, isopropyl, cyclohexyl, tetrahydropyran-4-yl, N-methylsulfonylpiperidin-4-yl, tetrahydrothiopyran-4-yl, tetrahydrothiopyran-4-yl (in which the S is in oxidized form SO or SO$_2$), cyclohexan-4-one, 4-hydroxycyclohexane, 4-hydroxy-4-methylcyclohexane, 1-methyl-tetrahydropyran-4-yl, 2-hydroxyprop-2-yl, but-2-yl, phenyl and 1-hydoxyeth-1-yl. In an embodiment of the invention R$_2$ is t-butyl, isopropyl, cyclohexyl, cyclopentyl, phenyl or tetrahydropyran-4-yl. In a particular embodiment, R$_2$ is phenyl. In a particular embodiment, R$_2$ is cyclohexyl. In another embodiment R$_2$ is tetrahydropyran-4-yl. In another particular embodiment, R$_2$ is isopropyl (i.e. the valine amino acid side chain). In another particular embodiment, R$_2$ is t-butyl. In a particular embodiment R$_2$ is oriented such that the amino acid, or amino acid analogue, which it comprises is in the L-configuration.

$R_3$ is H or alkyl optionally substituted with halogen or hydroxyl; or $R_3$ and $R_4$ together form a 3-6 heterocycle. In an embodiment $R_3$ is H or alkyl; or $R_3$ and $R_4$ together form a 3-6 heterocycle. In an embodiment $R_3$ is H or methyl, ethyl, propyl or isopropyl. In a particularly particular embodiment $R_3$ is H or methyl. In a another particular embodiment $R_3$ is methyl. In another particular embodiment, $R_3$ is ethyl. In a particular embodiment $R_3$ is fluoromethyl. In a particular embodiment $R_3$ is hydroxyethyl. In another embodiment $R_3$ is oriented such that the amino acid, or amino acid analogue, which it comprises is in the L-configuration. In a particular embodiment $R_3$ and $R_4$ together with the atoms from which they depend form a 3-6 heterocycle. In a particular embodiment $R_3$ and $R_4$ together form an azetidine ring. In a particular embodiment $R_3$ and $R_4$ together form a pyrrolidine.

$R_3'$ is H, or $R_3$ and $R_3'$ together form a 3-6 carbocycle. In an embodiment, $R_3'$ is H. In another embodiment $R_3$ and $R_3'$ together form a 3-6 carbocycle, for example a cyclopropyl ring. In a particular embodiment $R_3$ and $R_3'$ are both methyl.

$R_4$ and $R_4'$ are independently H, hydroxyl, amino, alkyl, carbocycle, carbocycloalkyl, carbocycloalkyloxy, carbocycloalkyloxycarbonyl, heterocycle, heterocycloalkyl, heterocycloalkyloxy or heterocycloalkyloxycarbonyl; wherein each alkyl, carbocycloalkyl, carbocycloalkyloxy, carbocycloalkyloxycarbonyl, heterocycle, heterocycloalkyl, heterocycloalkyloxy and heterocycloalkyloxycarbonyl is optionally substituted with halogen, hydroxyl, mercapto, carboxyl, alkyl, alkoxy, amino, imino and nitro; or $R_4$ and $R_4'$ together form a heterocycle. In an embodiment $R_4$ and $R_4'$ are independently H, hydroxyl, amino, alkyl, aryl, aralkyl, cycloalkyl, cycloalkylalkyl, heteroaryl, or heteroarylalkyl wherein each alkyl, aryl, aralkyl, cycloalkyl, cycloalkylalkyl, heteroaryl and heteroarylalkyl is optionally substituted with halogen, hydroxyl, mercapto, carboxyl, alkyl, alkoxy, amino and nitro; or $R_4$ and $R_4'$ together form a heterocycle. In a particular embodiment $R_4$ and $R_4'$ together form a heterocycle, for example an azetidine ring, or a pyrrolidine ring. In a particular embodiment $R_4$ and $R_4'$ are both H. In another particular embodiment $R_4$ is methyl and $R_4'$ is H. In a particular embodiment one of $R_4$ and $R_4'$ is hydroxyl (OH) while the other is H. In another embodiment, one of $R_4$ and $R_4'$ is amino, such as $NH_2$, NHMe and NHEt, while the other is H. In a particular embodiment, $R_4'$ is H and $R_4$ is H, alkyl, aryl, aralkyl, cycloalkyl, cycloalkylalkyl, heteroaryl or heteroarylalkyl. In a particular embodiment $R_4$ is a group selected from the group consisting of:

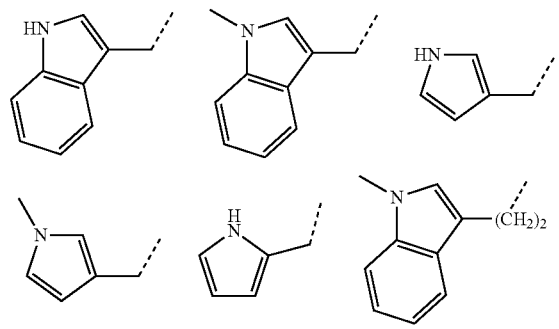

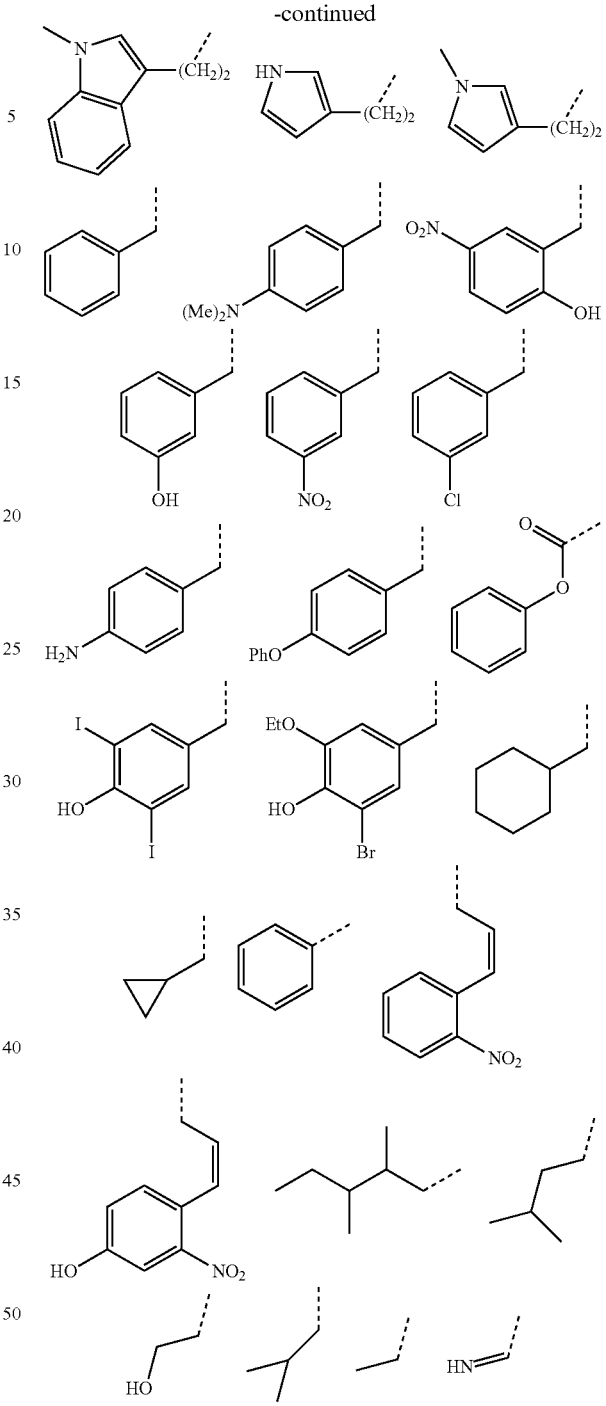

$R_5$ is H or alkyl. In a particular embodiment, $R_5$ is H or methyl. In a particular embodiment, $R_5$ is H. In another particular embodiment, $R_5$ is methyl.

$R_6$, and $R_6'$ are each independently H, alkyl, aryl or aralkyl. In a particular embodiment, $R_6$ is alkyl, for example methyl. In another particular embodiment $R_6$ is aryl, for example phenyl. In another particular embodiment $R_6$ is aralkyl, for example benzyl. In a particular embodiment $R_6$ and $R_6'$ are the same, for example both alkyl, e.g. both methyl. In another particular embodiment $R_6$ is methyl and $R_6'$ is H. In another embodiment $R_6$ and $R_6'$ are both H.

Compounds of the invention contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention. In a particular embodiment, compounds of the invention have the following stereochemical configuration of formula I'

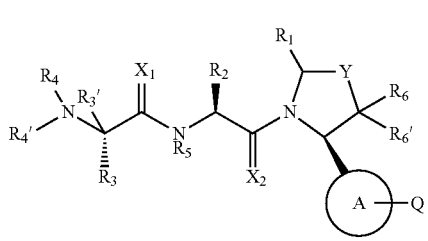

wherein ring A, Q, $X_1$, $X_2$, Y, $R_1$, $R_2$, $R_3$, $R_4$, $R_4'$, $R_5$, $R_6$ and $R_6'$ are as described herein.

In an embodiment, compounds of the invention have the general formula IV

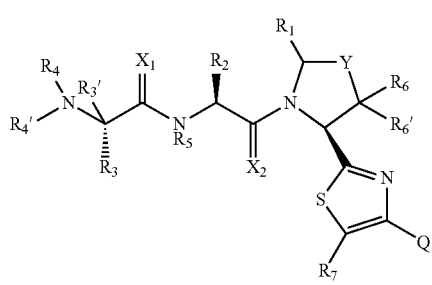

wherein Q, $X_1$, $X_2$, Y, $R_1$, $R_2$, $R_3$, $R_4$, $R_4'$, $R_5$, $R_6$, $R_6$ and $R_7$ are as described herein. In a particular embodiment Q is a carbocycle or a heterocycle optionally substituted with one or more hydroxyl, alkyl, alkoxy, acyl, halogen, mercapto, oxo, carboxyl, amino, cyano, nitro, amidino, guanidino an optionally substituted carbocycle or an optionally substituted heterocycle wherein one or more $CH_2$ or CH groups of said alkyl is optionally replaced with —O—, —S—, —S(O)—, $S(O)_2$, —N($R_8$)—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—. In a particular embodiment, Q is aryl or heteroaryl optionally substituted with one or more hydroxyl, alkyl, alkoxy, acyl, halogen, mercapto, oxo, carboxyl, amino, cyano, nitro, amidino, guanidino an optionally substituted carbocycle or an optionally substituted heterocycle wherein one or more $CH_2$ or CH groups of said alkyl is optionally replaced with —O—, —S—, —S(O)—, $S(O)_2$, —N($R_8$)—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—. In a particular embodiment Q is aryl or heteroaryl optionally substituted with one or more hydroxyl, alkyl, alkoxy, alkoxyalkoxy, acyl, halogen, mercapto, carboxyl, acyl, halo-substituted alkyl, amino, cyano, nitro, amidino, guanidino. In a particular embodiment Q is aryl or heteroaryl optionally substituted with halogen, alkyl, alkoxy, alkoxyalkoxy, cyano. In an embodiment Q is IIIa to IIIs wherein $R_7$, $R_8$ and n are as defined herein. In a particular embodiment Q is IIIq. In a particular embodiment Q is IIId. In a particular embodiment Q is IIIb, IIIc, IIIe, IIIf, IIIj, IIIk, IIIl, IIIn, IIIo, IIIq, IIIr or IIIs.

In an embodiment when compounds of the invention have the general formula IV, $R_1$ is H. In an embodiment when compounds of the invention have the general formula IV, $R_2$ is alkyl, a carbocycle, carbocyclylalkyl, a heterocycle or heterocyclylalkyl each optionally substituted with halogen, hydroxyl, mercapto, carboxyl, alkyl, alkoxy, amino and nitro. In an embodiment when compounds of the invention have the general formula IV, $R_3$ is H or methyl, ethyl, propyl or isopropyl. In an embodiment when compounds of the invention have the general formula IV, $R_4$ is methyl and $R_4'$ is H. In an embodiment when compounds of the invention have the general formula IV, $R_5$ is H. In an embodiment when compounds of the invention have the general formula TV, $R_6$ and $R_6'$, are both H. In an embodiment, when compounds of the invention have the general formula IV $R_7$ is H, halogen, cyano, alkyl, hydroxyalkyl or alkoxyalkyl. In an embodiment, when compounds of the invention have the general formula IV, $X_1$ and $X_2$ are both O. In an embodiment, when compounds of the invention have the general formula IV, Y is $CH_2$.

The invention also encompasses prodrugs of the compounds described above. Suitable prodrugs where applicable include known amino-protecting and carboxy-protecting groups which are released, for example hydrolyzed, to yield the parent compound under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. In a particular embodiment, the nitrogen atom is one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50° C. The reactions are usually also carried out in the presence of an inorganic base such as potassium carbonate or sodium bicarbonate, or an organic base such as an amine, including pyridine, triethylamine, etc. One manner of preparing prodrugs is described in U.S. Ser. No. 08/843,369 filed Apr. 15, 1997 (corresponding to PCT publication WO9846576) the contents of which are incorporated herein by reference in their entirety.

Particular compounds of formula I include the following:
1
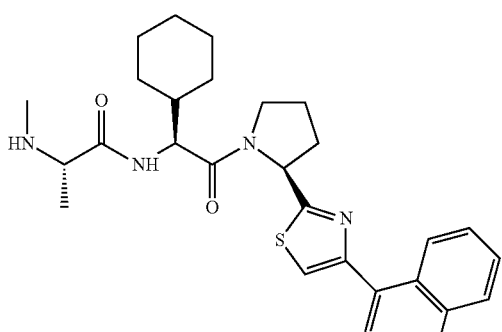
2
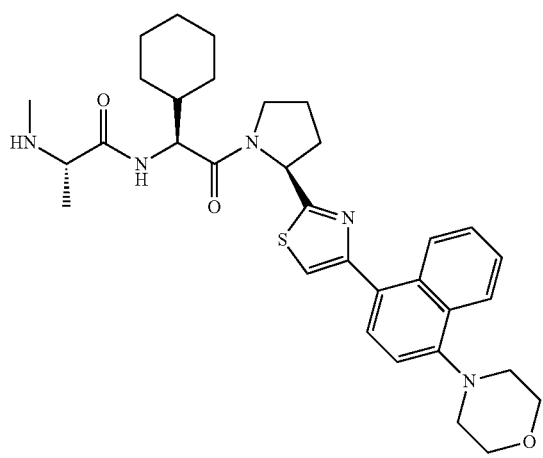
3
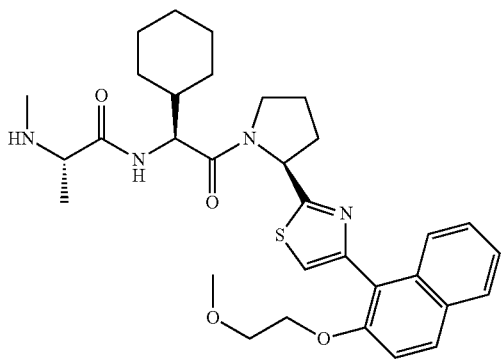
4
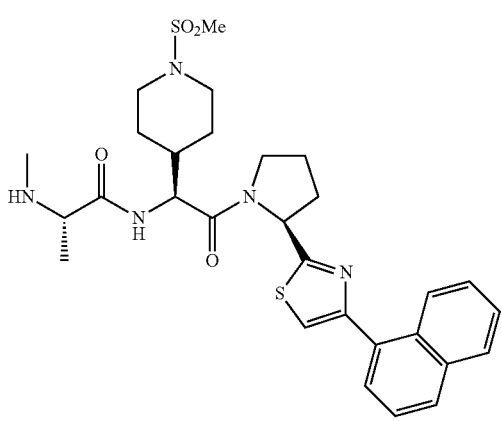
5
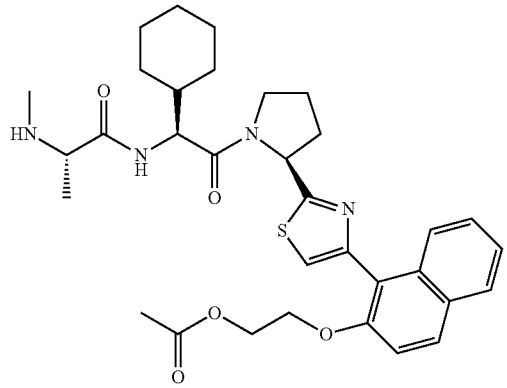
6
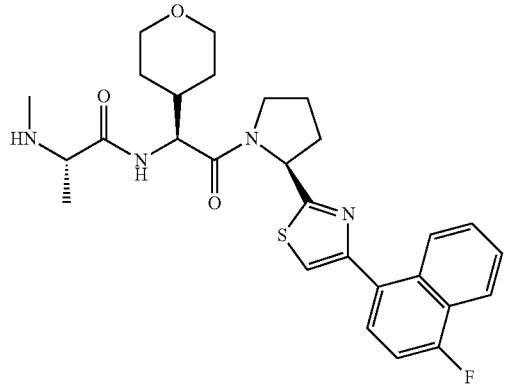
7
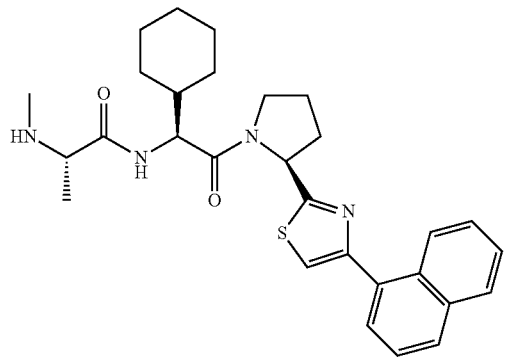
8
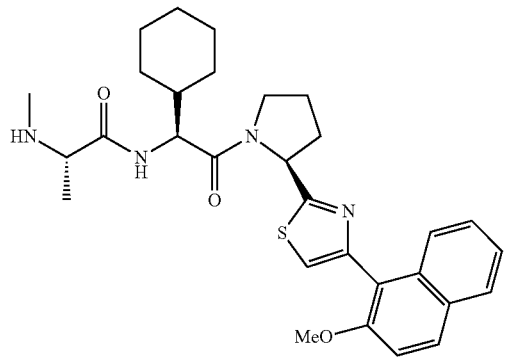

9
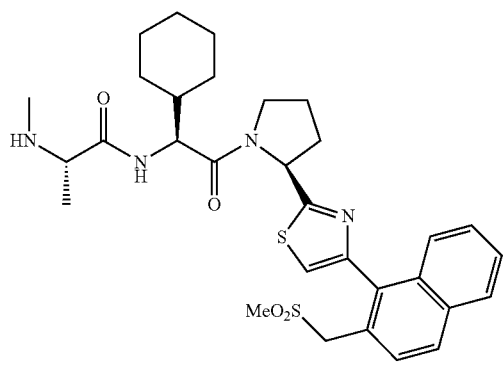
10
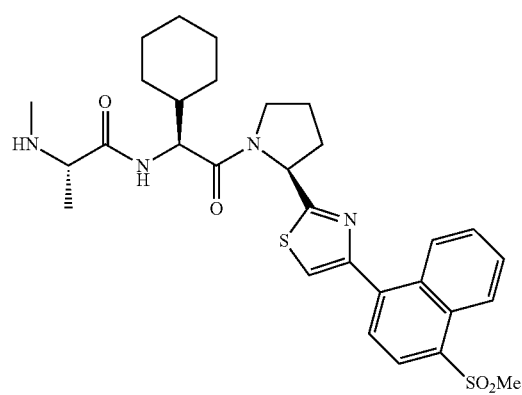
11
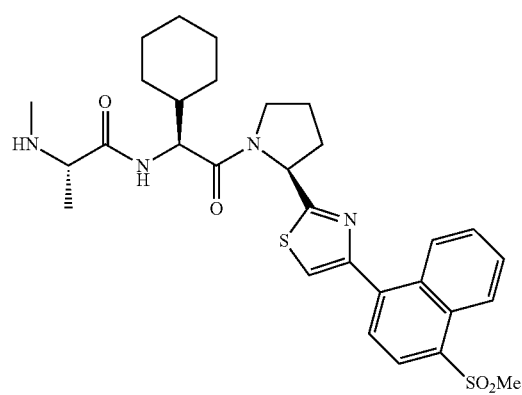
12
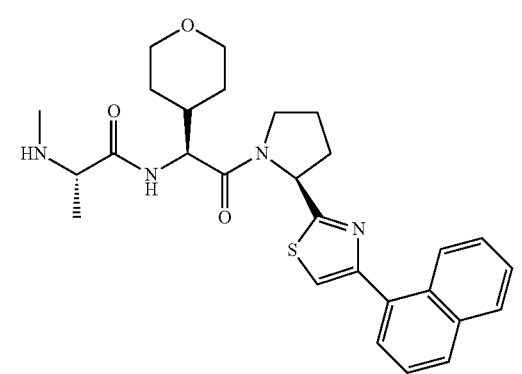
13
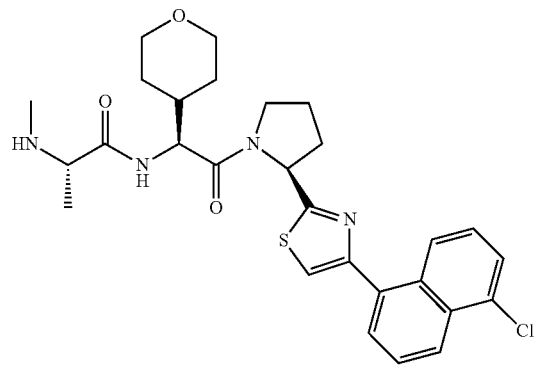
14
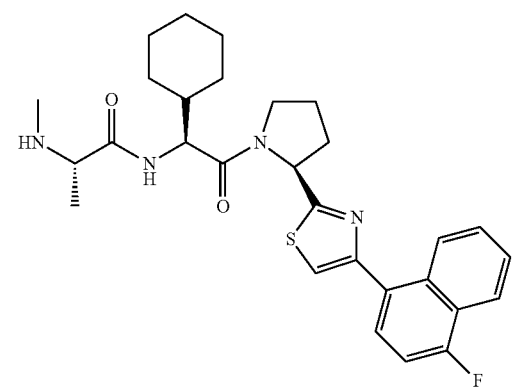
15
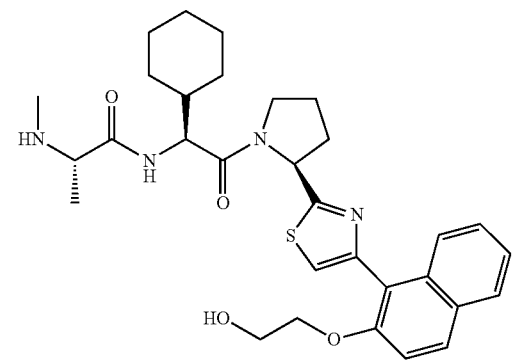
16
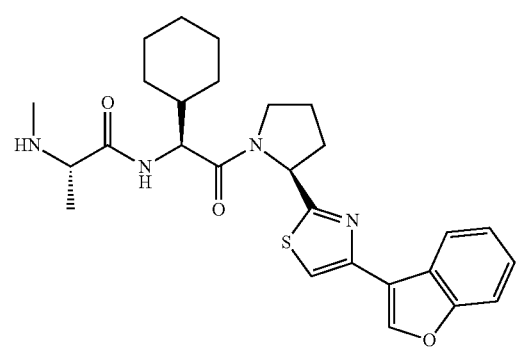

17
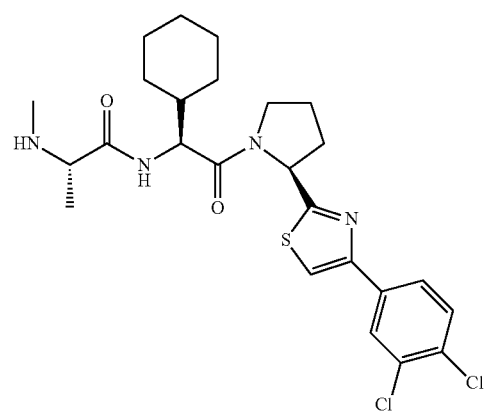
18
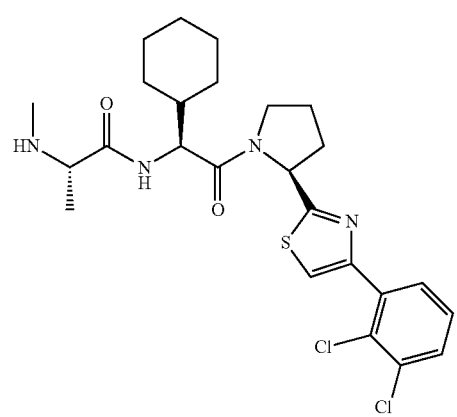
19
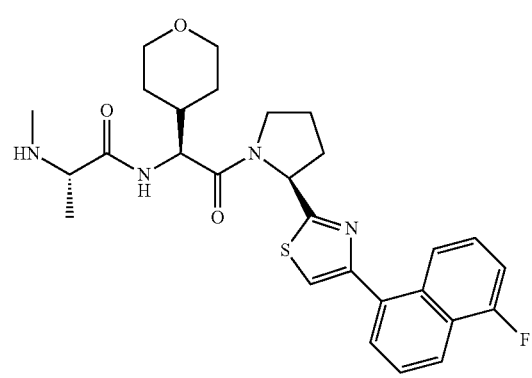
20
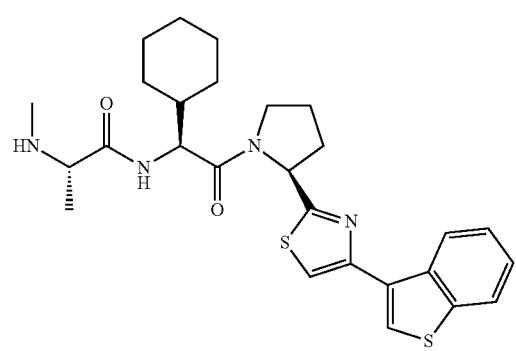
21
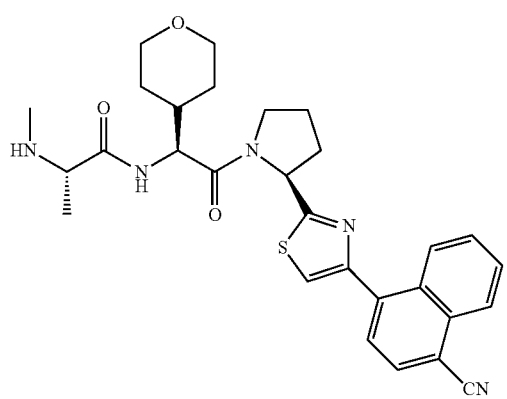
22
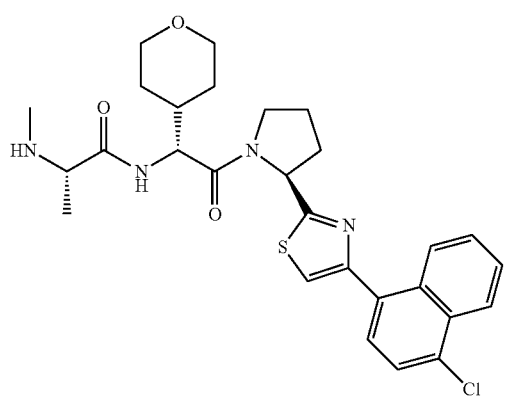
23
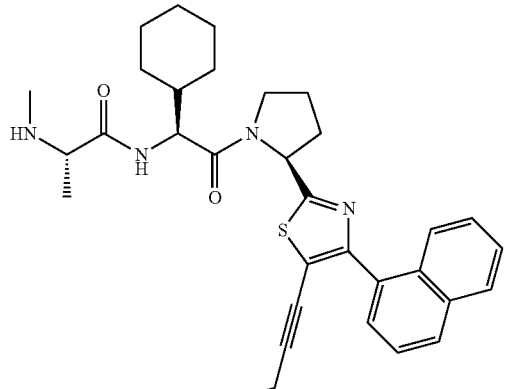
24
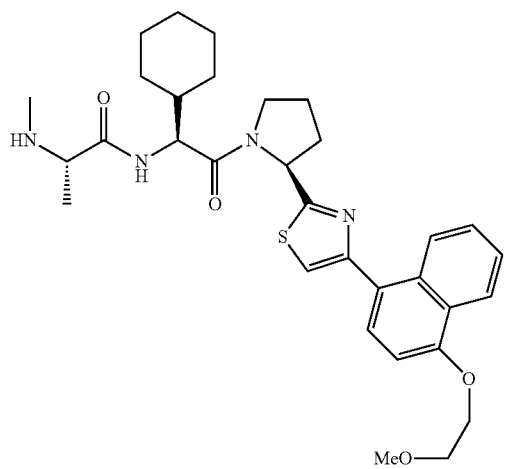

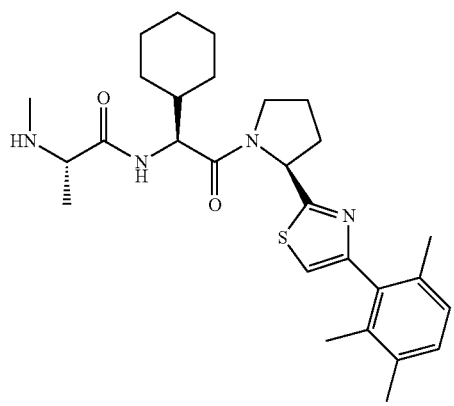
25
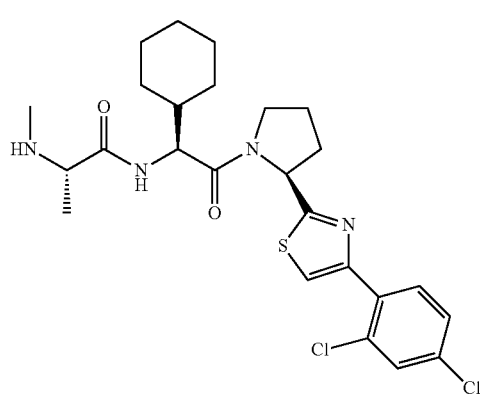
26
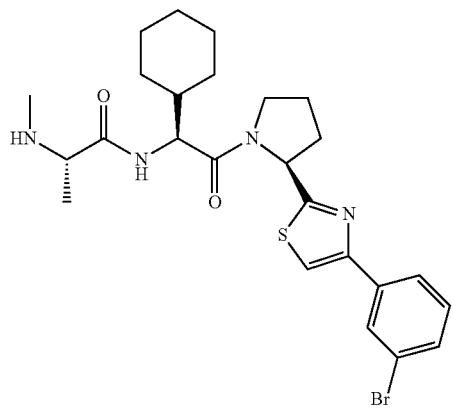
27
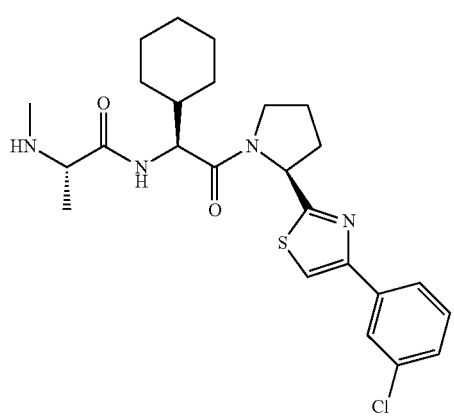
28
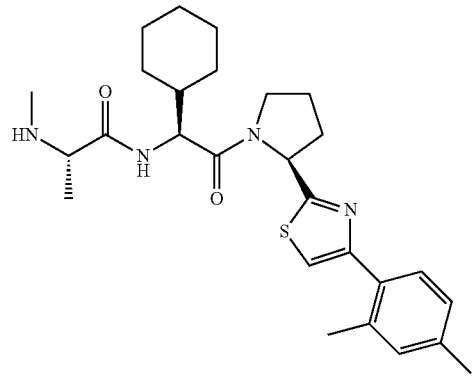
29
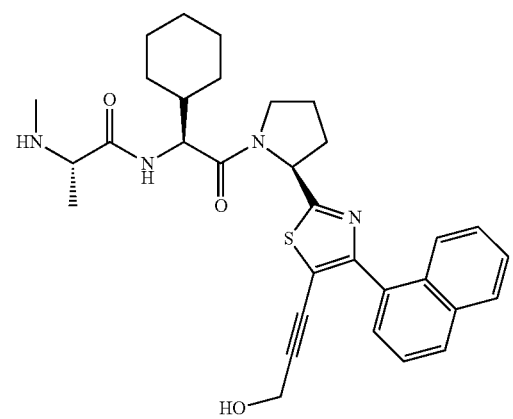
30
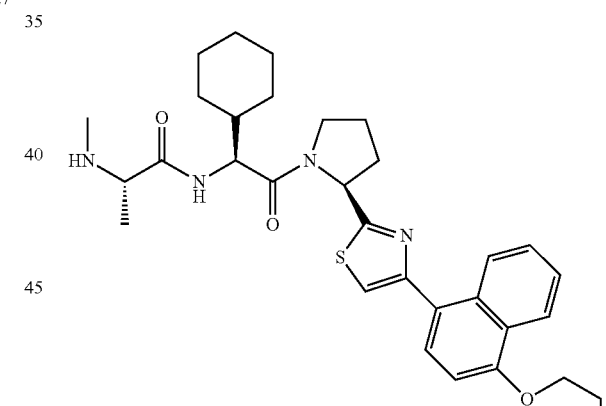
31
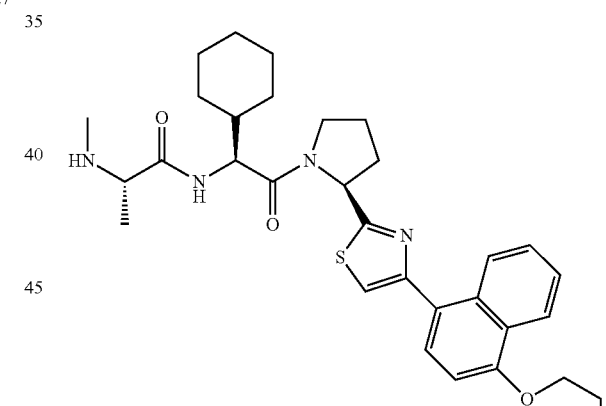
32

| 33 | 37 |
|---|---|
| 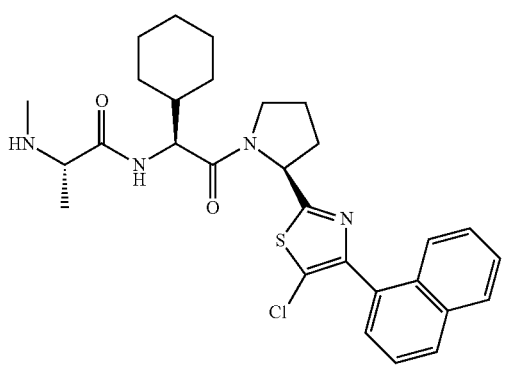 | 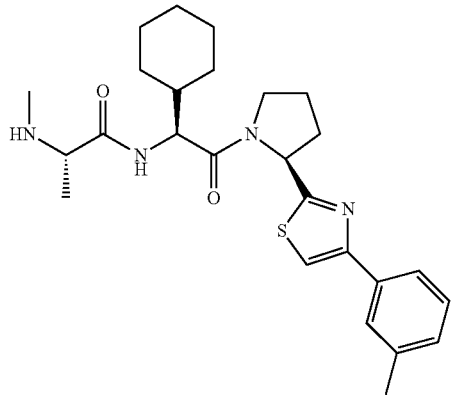 |
| 34 | 38 |
| 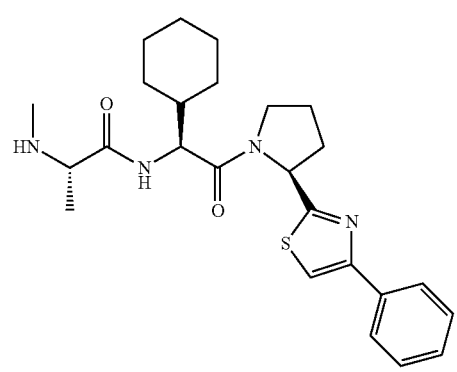 | 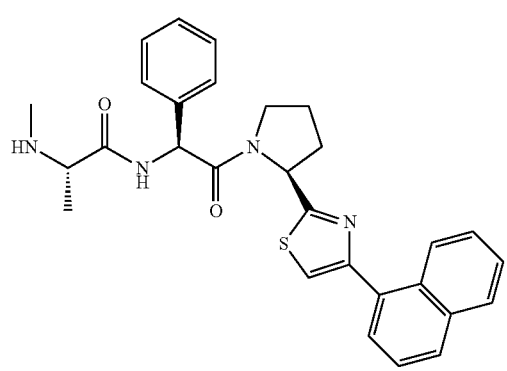 |
| 35 | 39 |
| 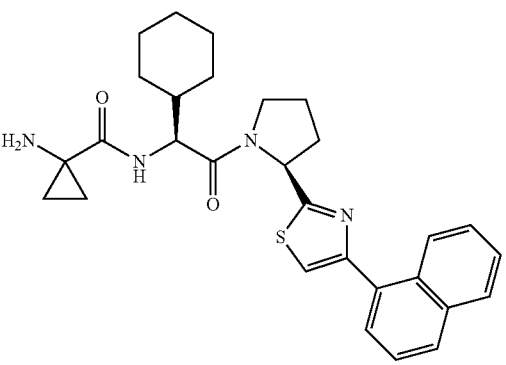 | 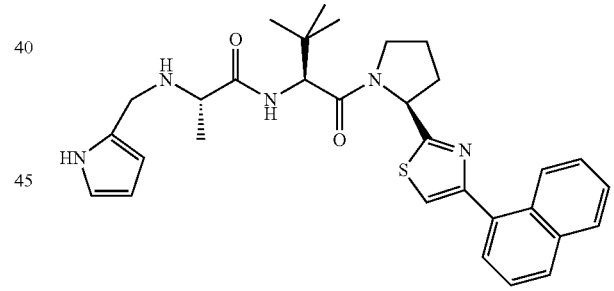 |
| 36 | 40 |
| 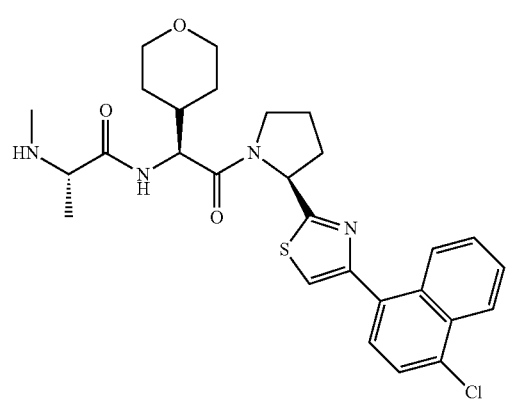 | 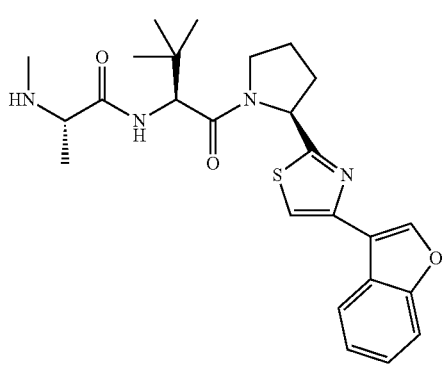 |

41 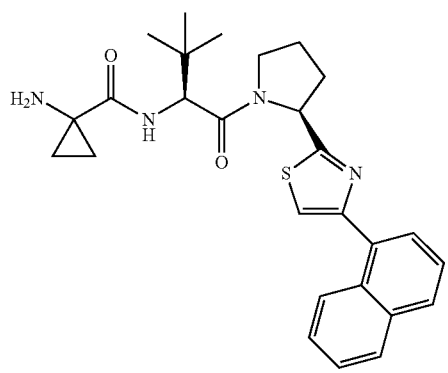
42 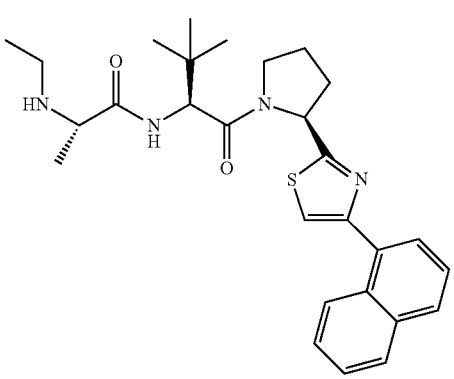
43 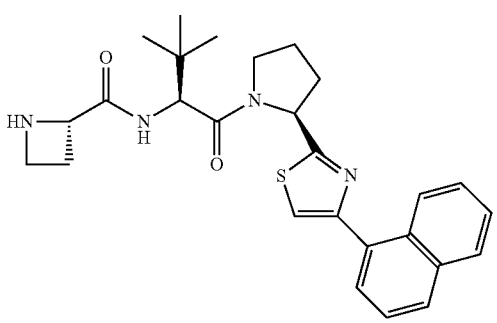
44 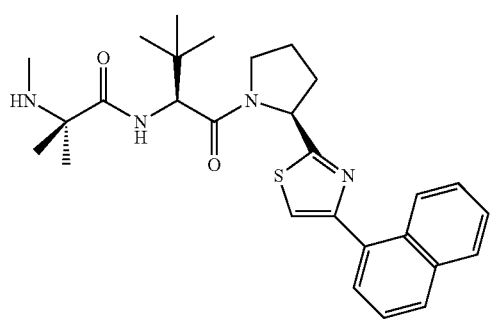
45 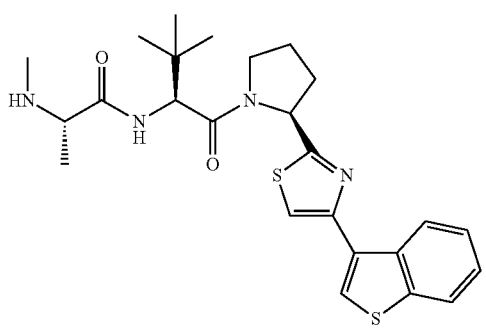
46 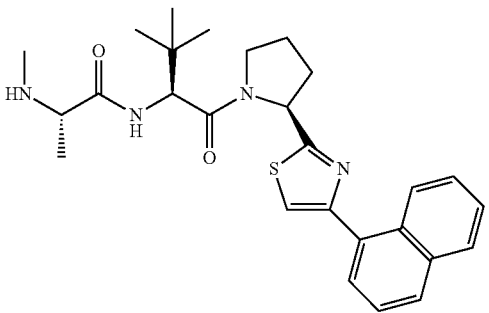
47 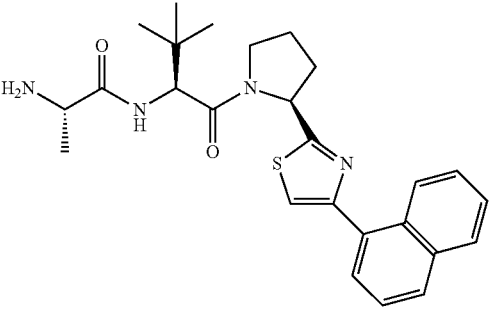
48 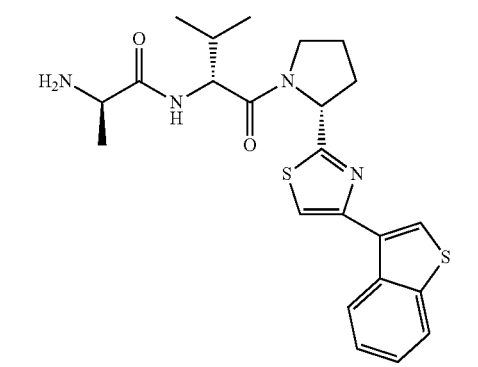
49 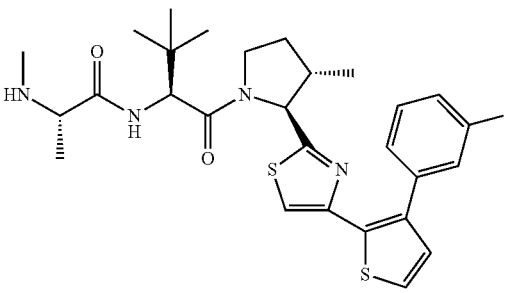

50
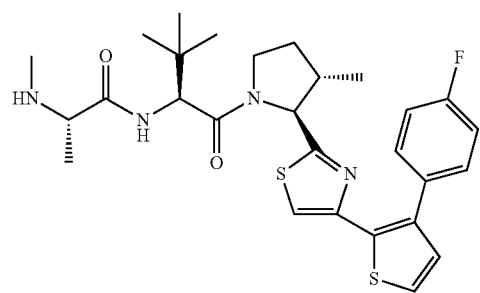
51
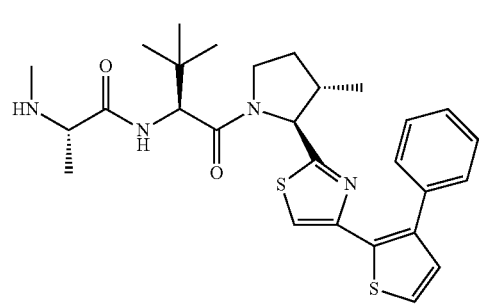
52
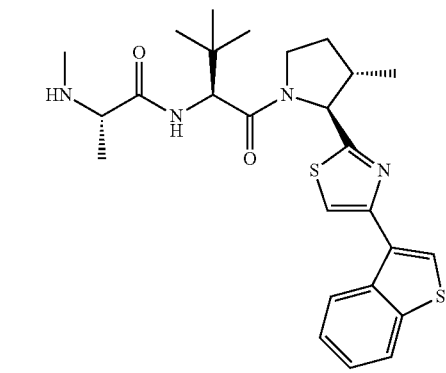
53
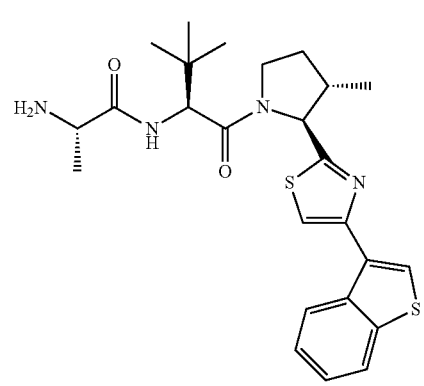
54
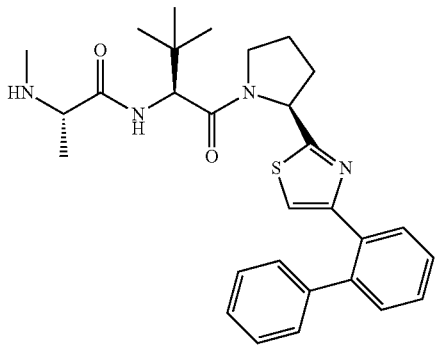
55
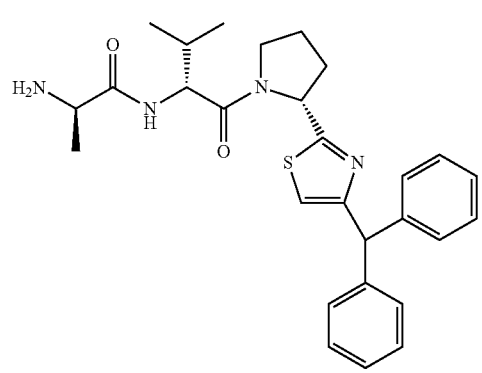
56
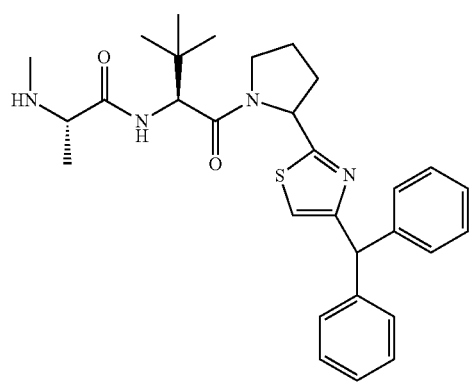
57
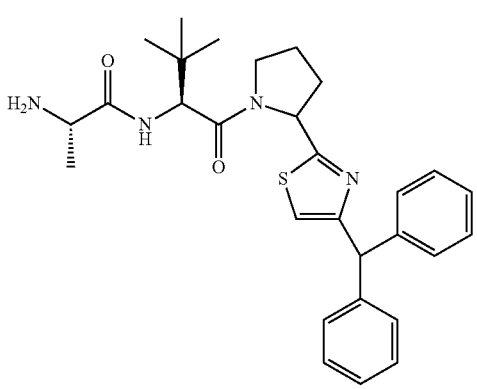

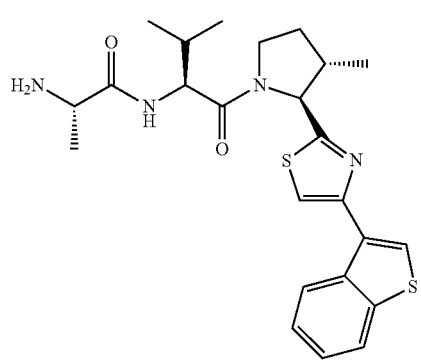
58
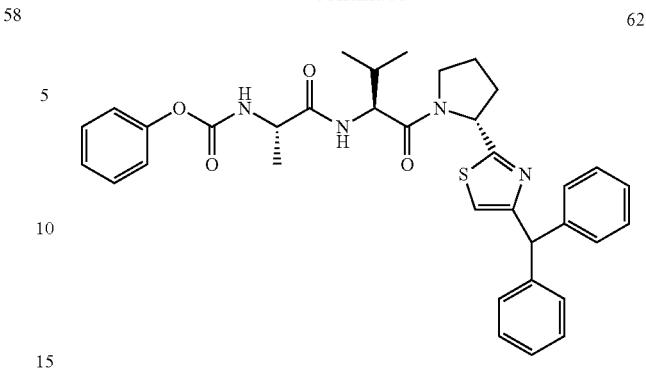
62
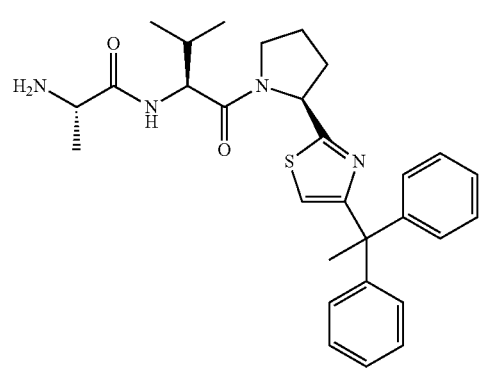
59
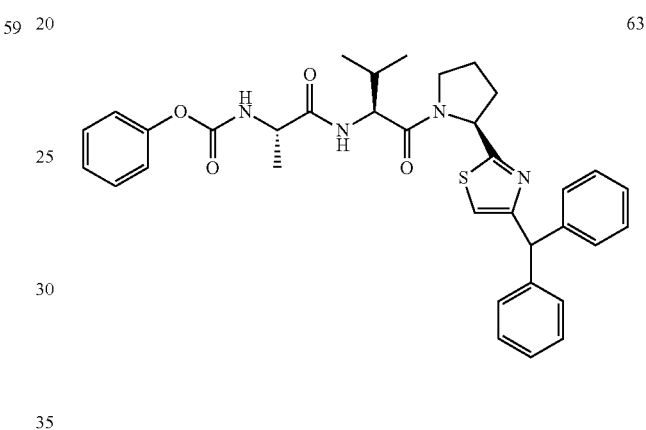
63
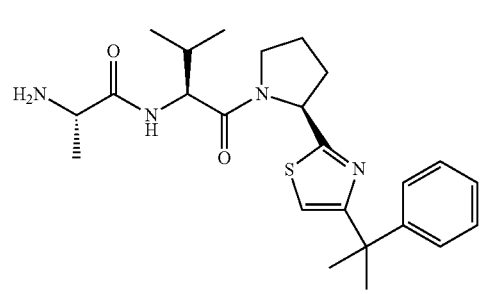
60
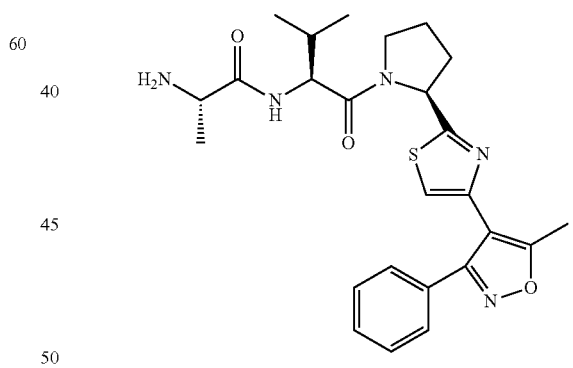
64
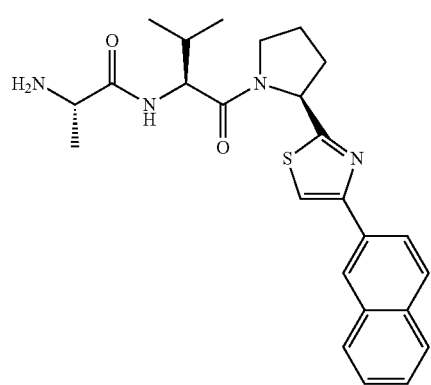
61
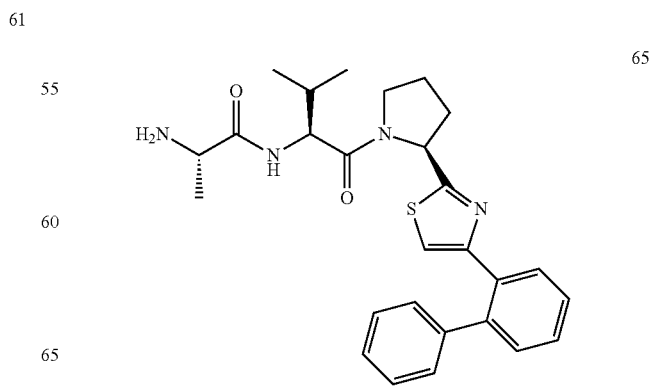
65

66
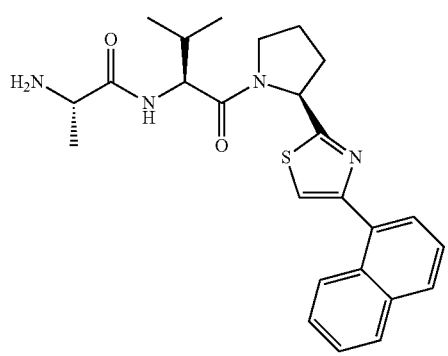
67
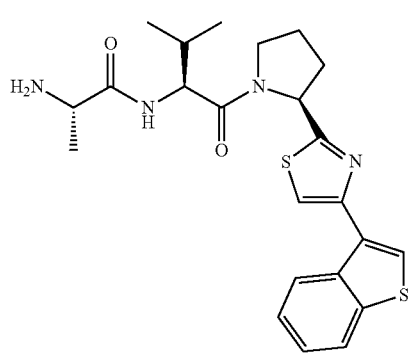
68
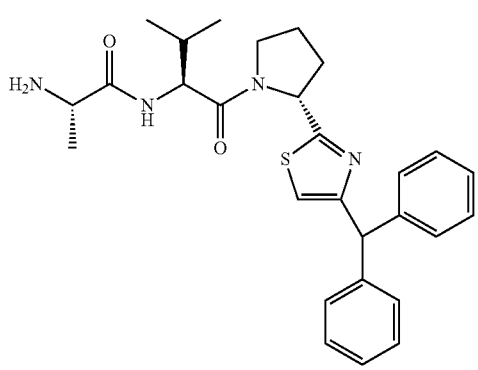
69
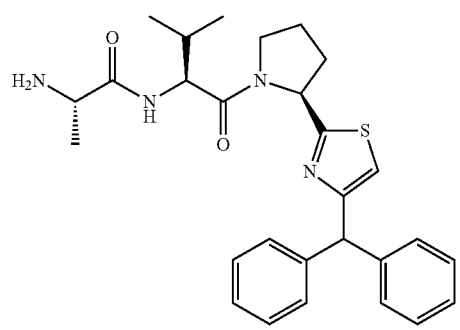
70
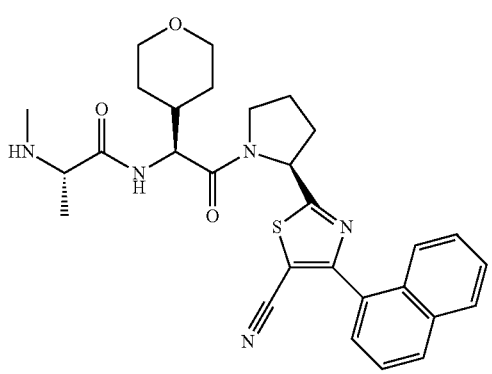
71
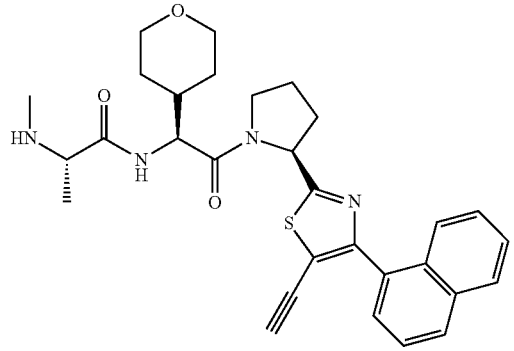
72
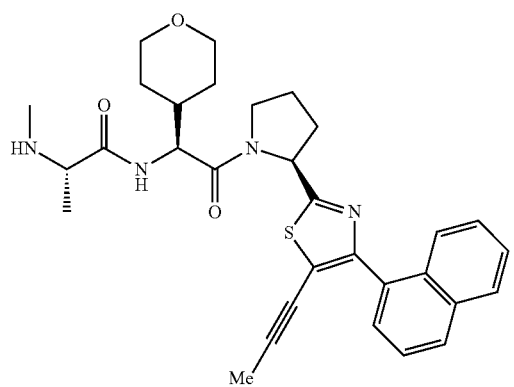
73
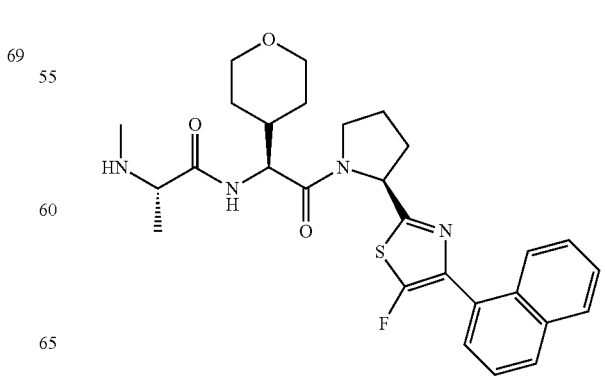

74 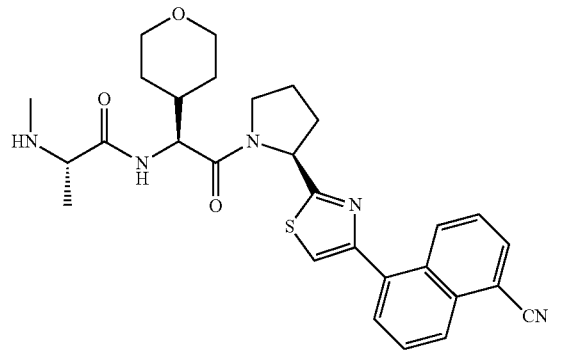
78 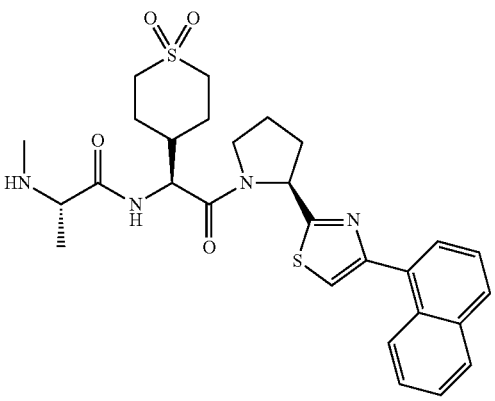
75 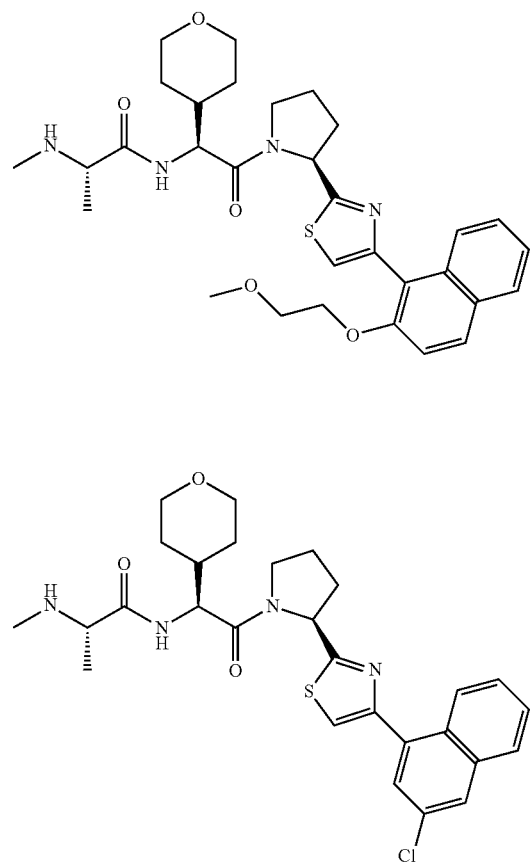
79 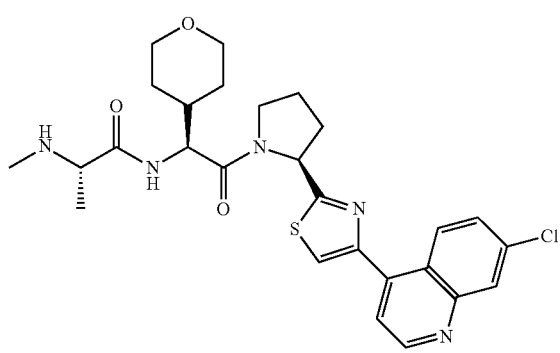
76
77
80 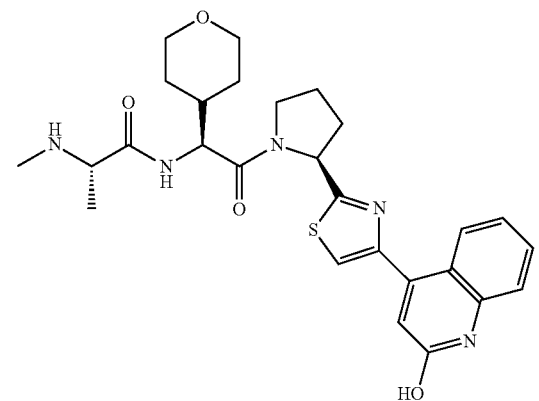
81 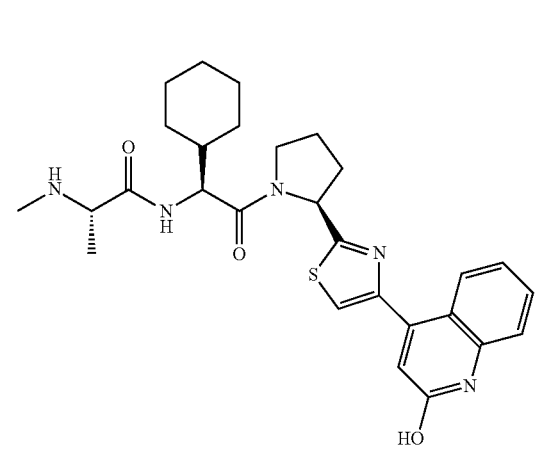

82
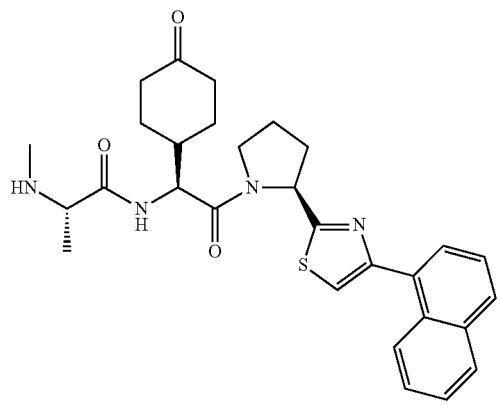
83
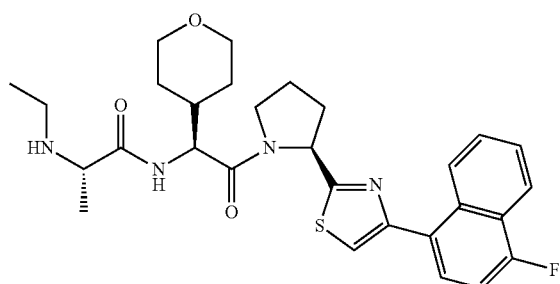
84
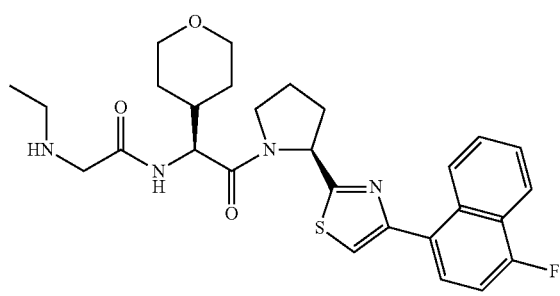
85
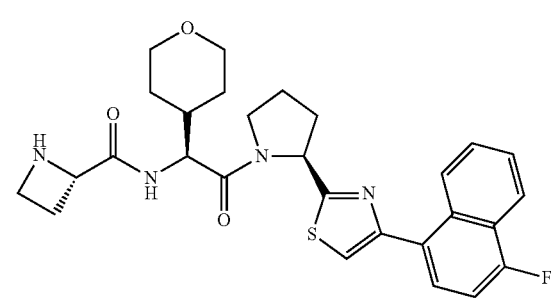
86
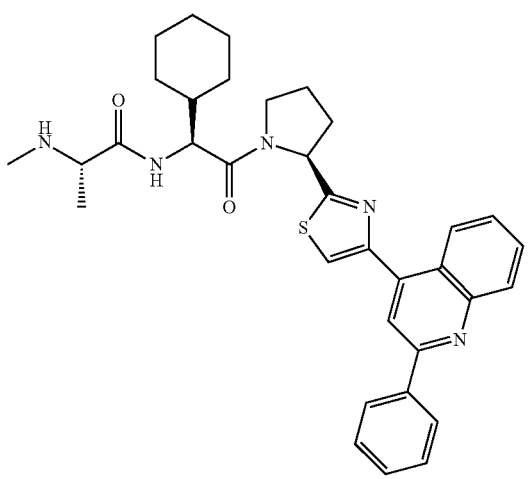
87
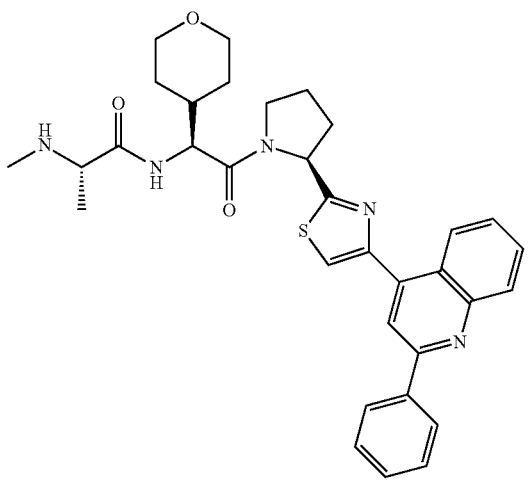
88
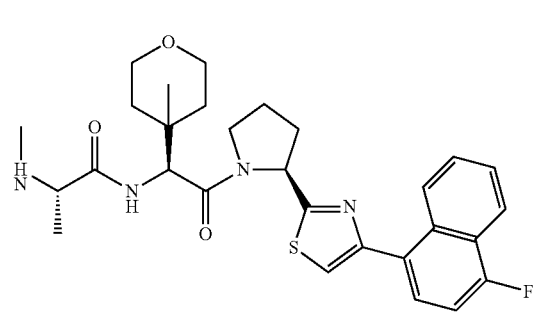
89
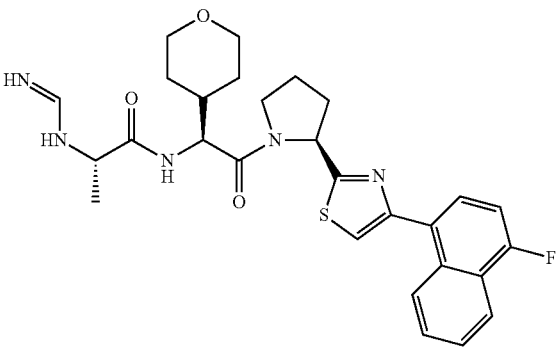

45
-continued
90
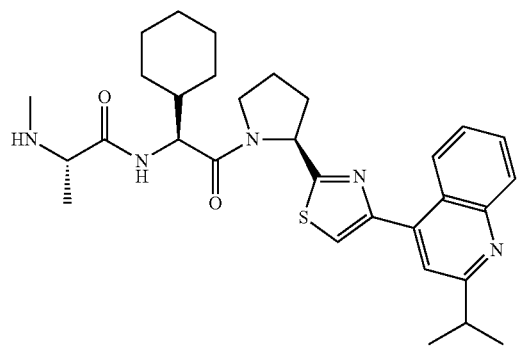
91
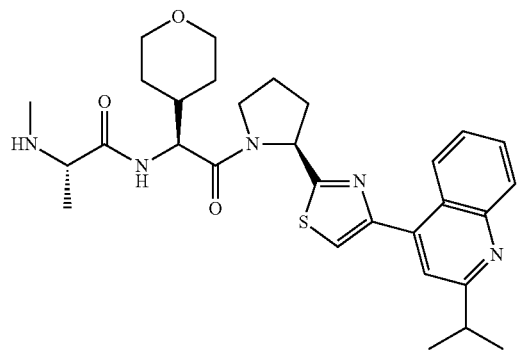
92
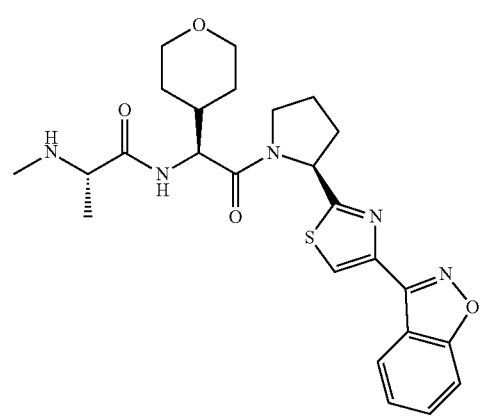
93
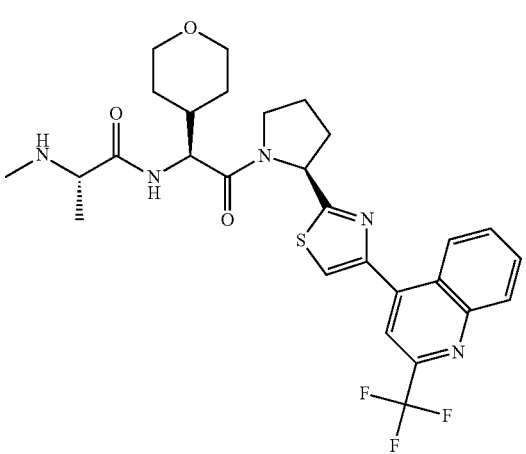
46
-continued
94
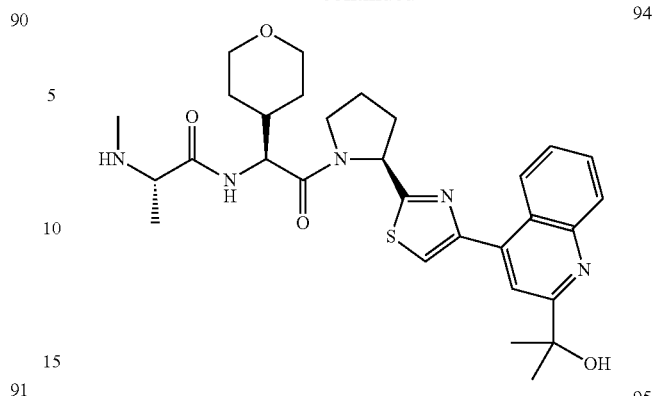
95
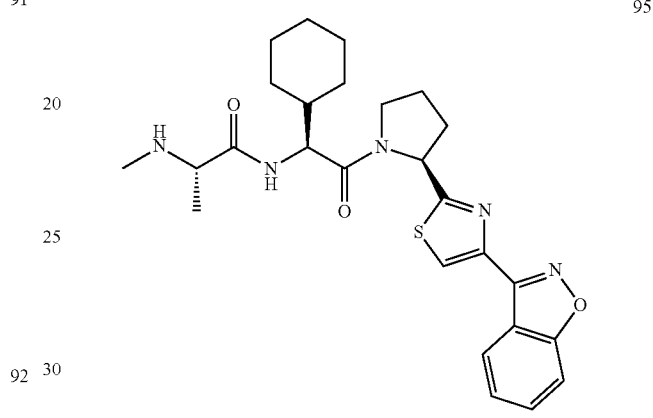
96
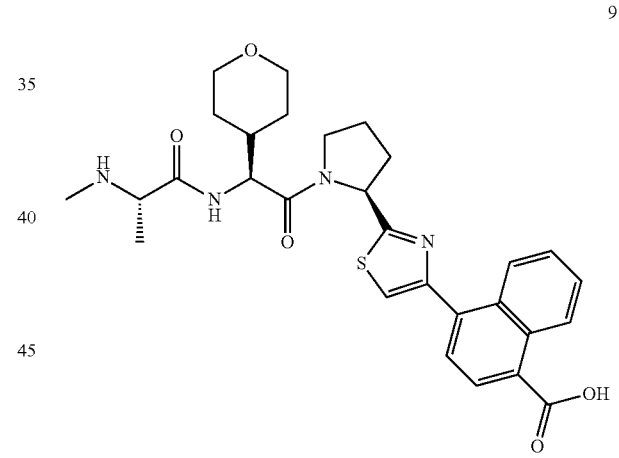
97
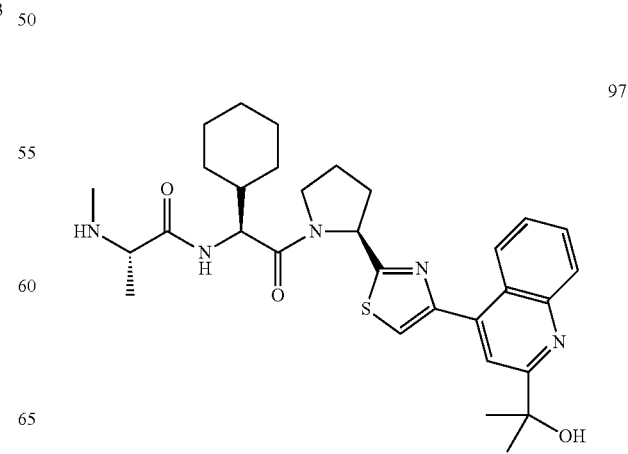

98
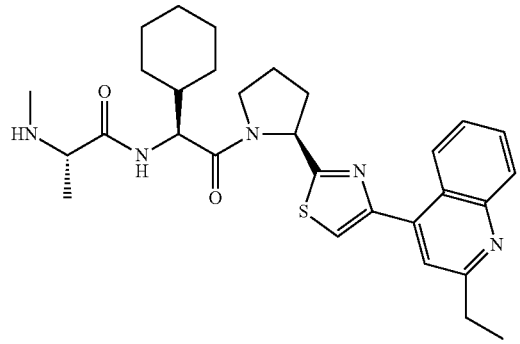
102
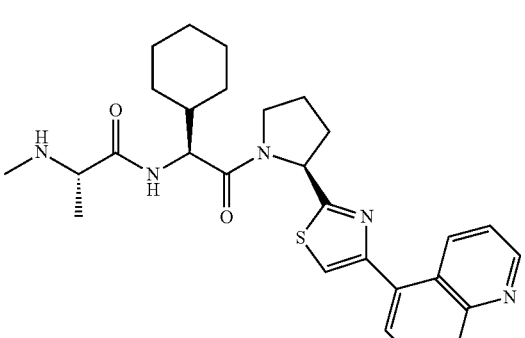
99
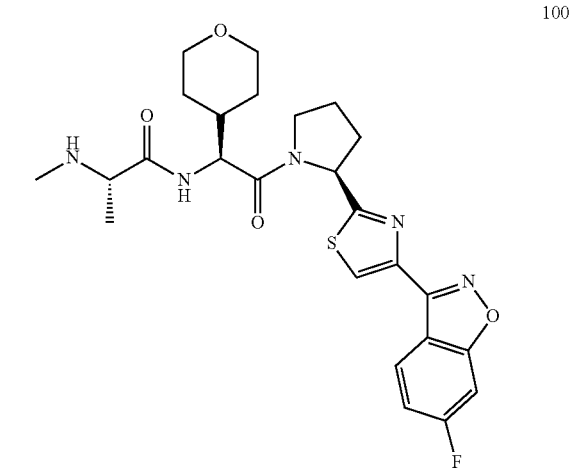
103
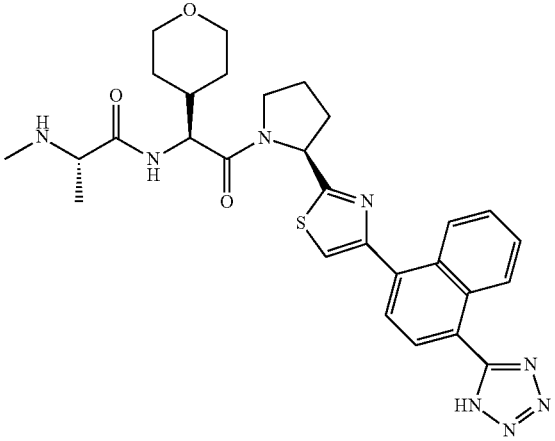
100
104
101
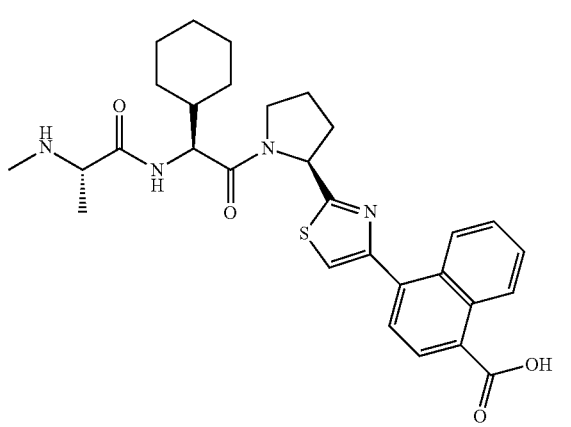
105
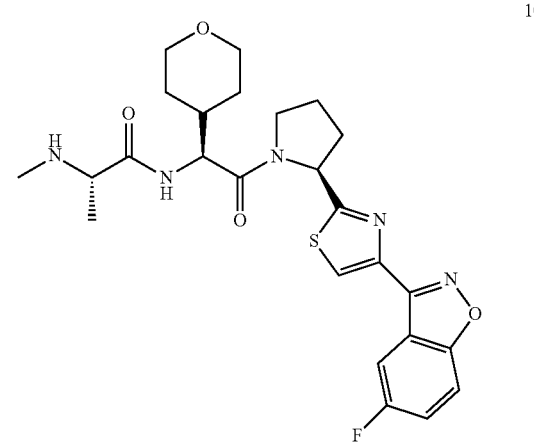

106
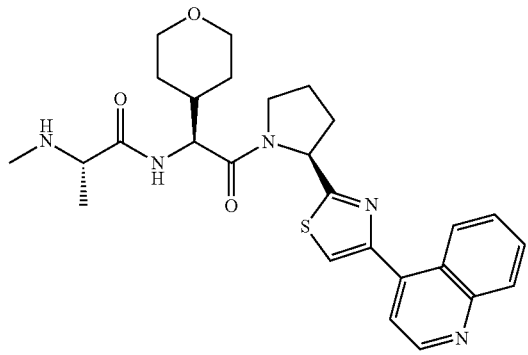
107
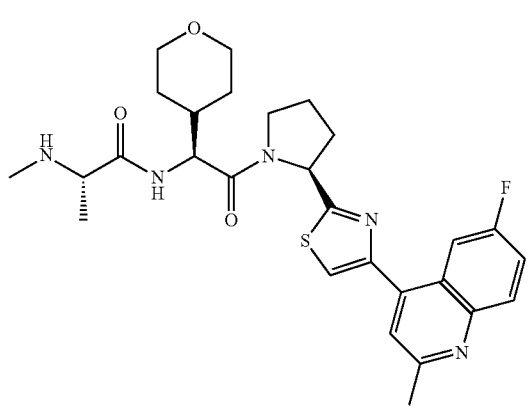
108
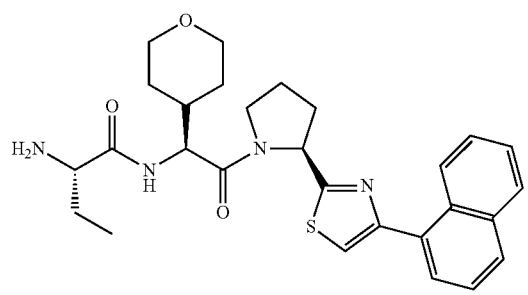
109
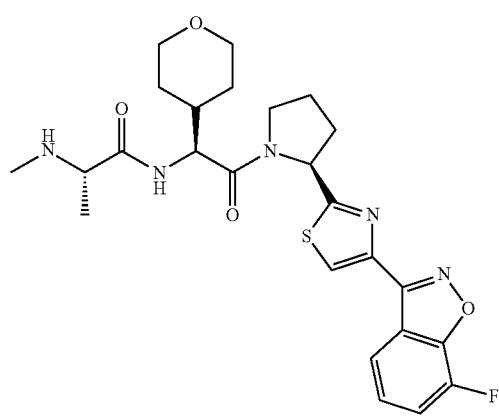
110
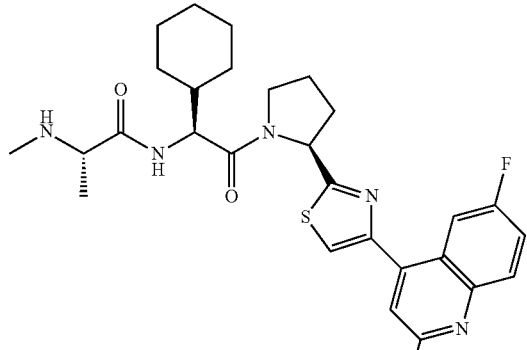
111
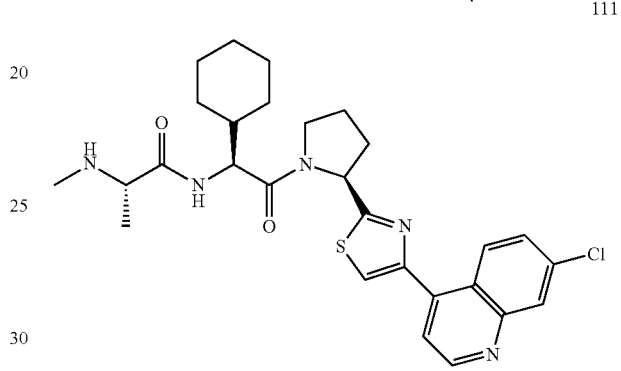
112
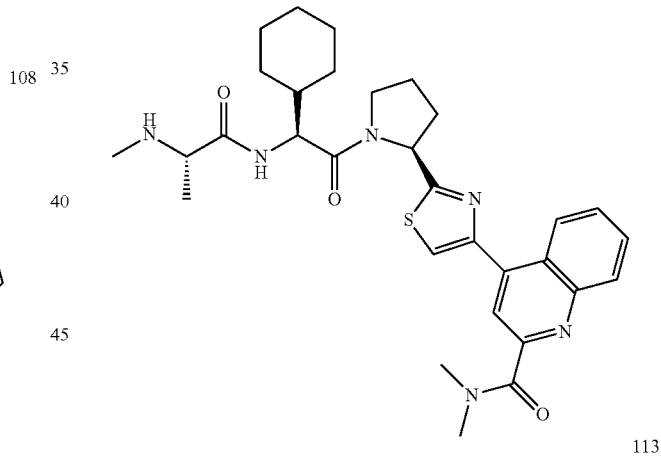
113
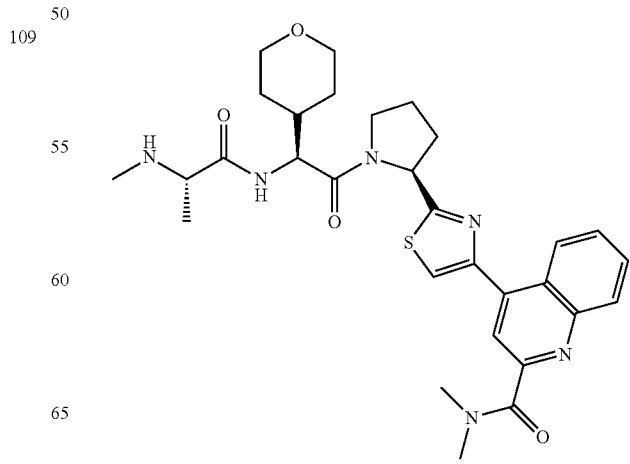

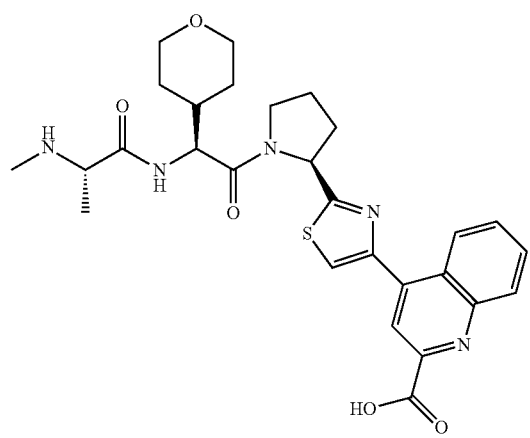
114
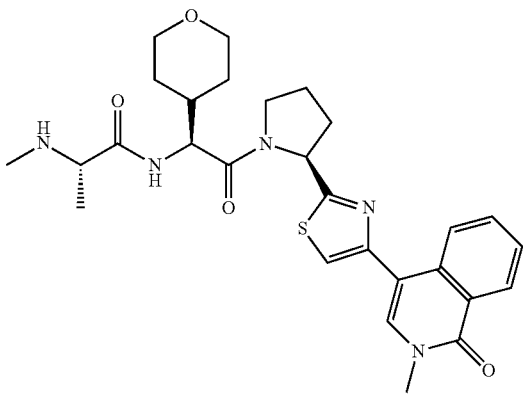
117
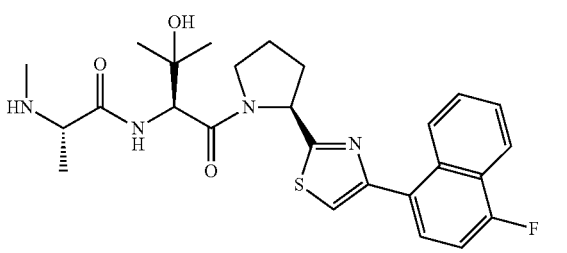
118
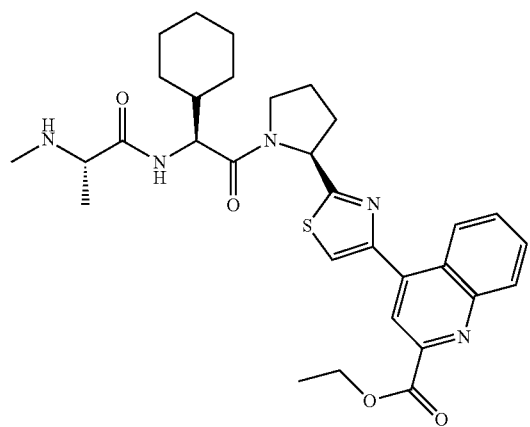
115
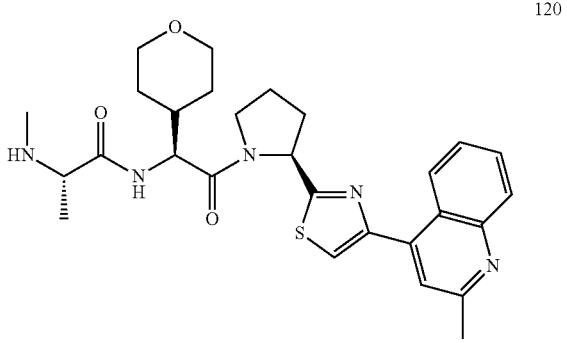
119
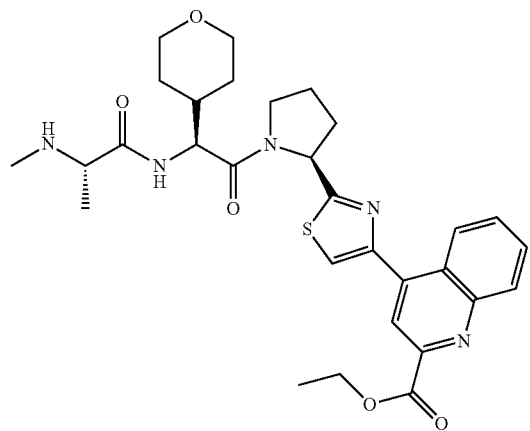
116
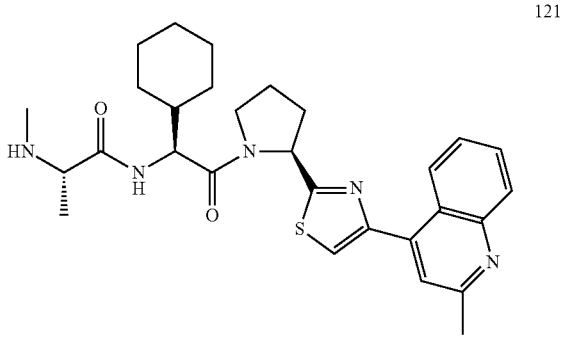
120
121

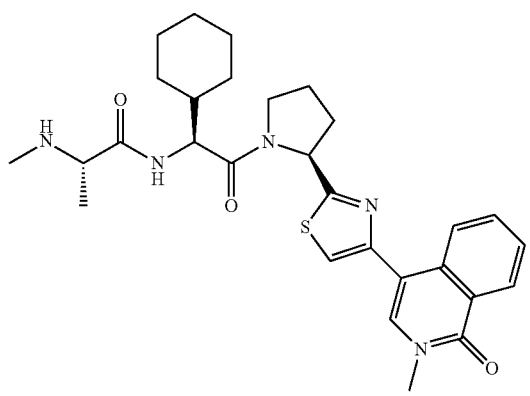
122
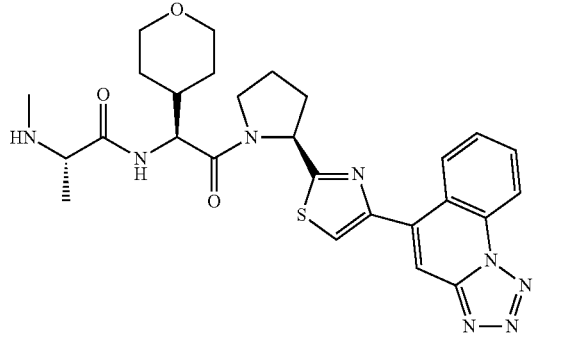
126
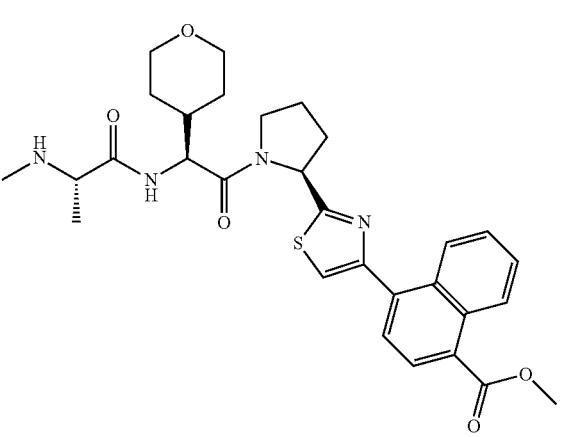
123
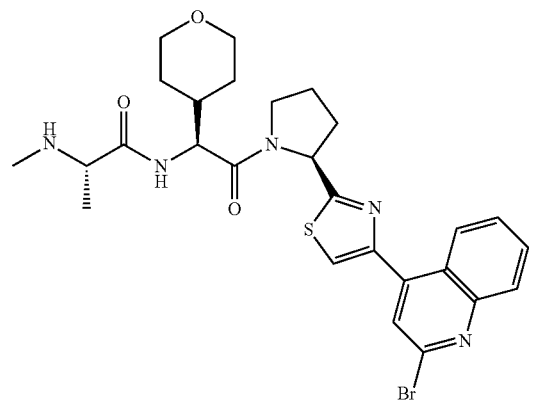
127
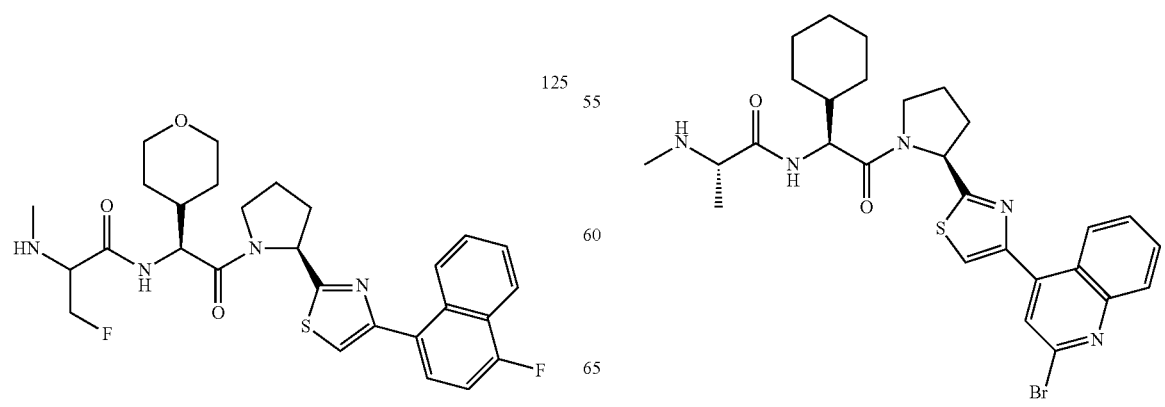

130
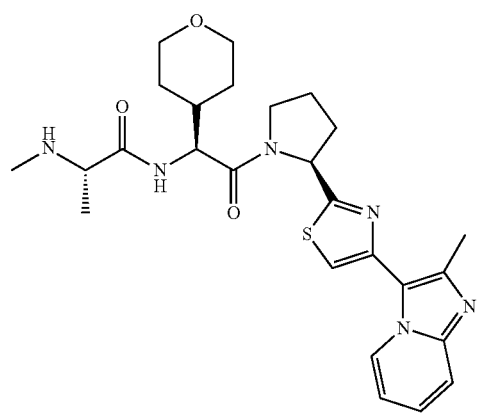
131
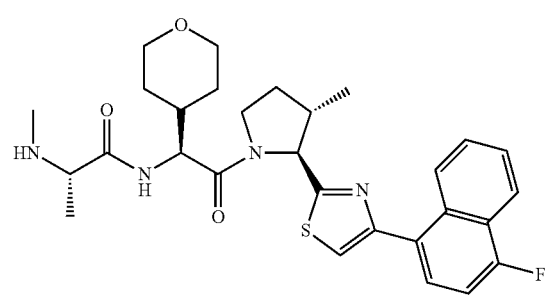
132
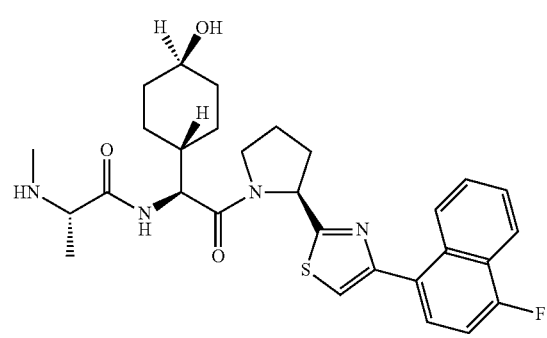
133
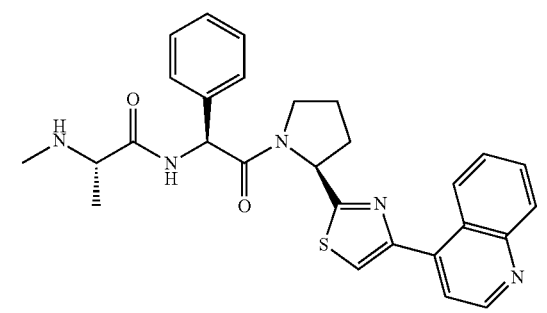
134
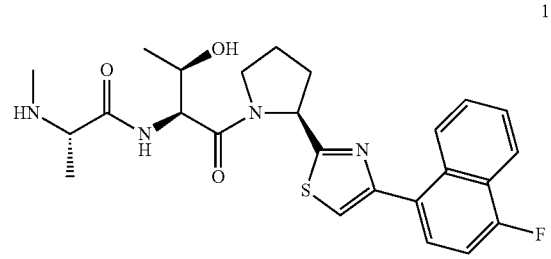
135
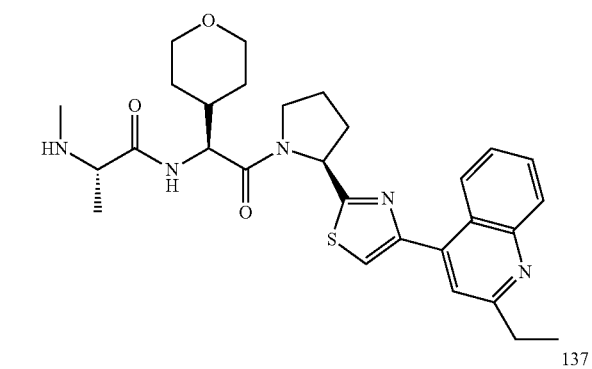
136
137
138
139
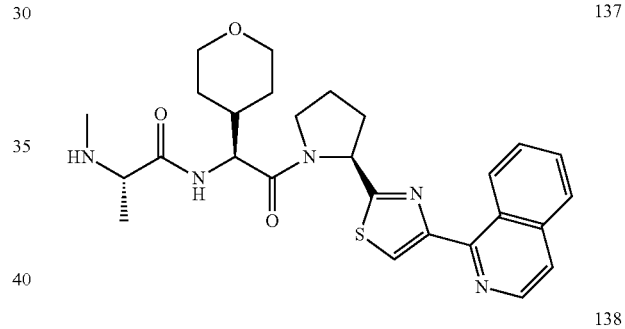
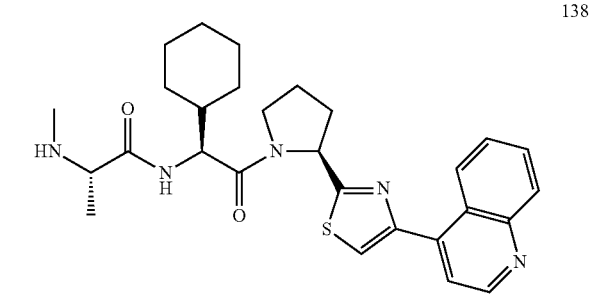
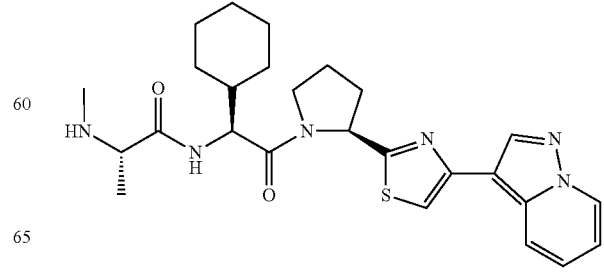

140
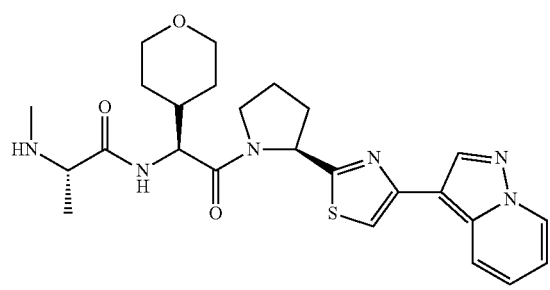

141
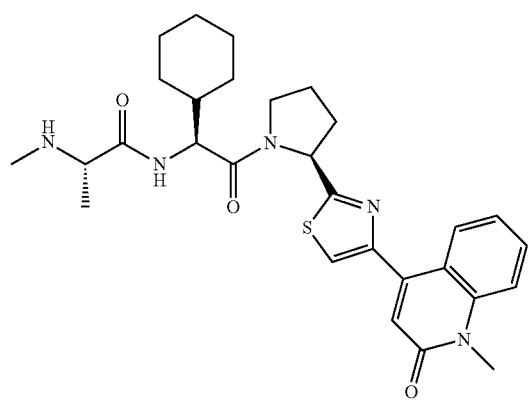

142
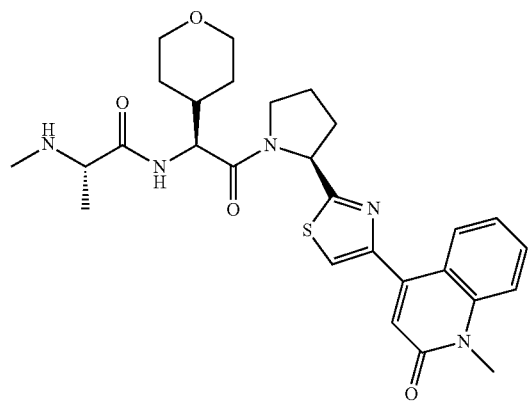

143
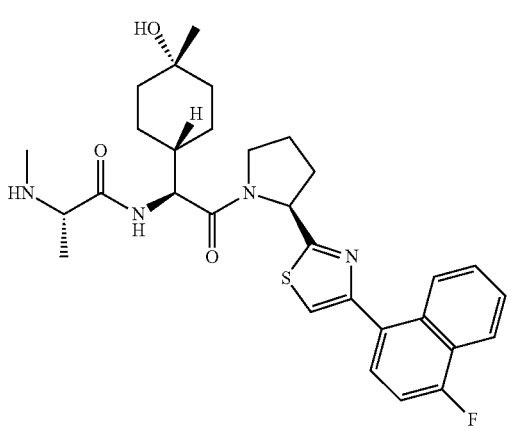

144
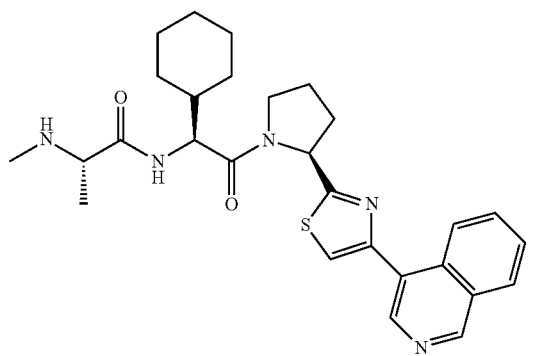

145
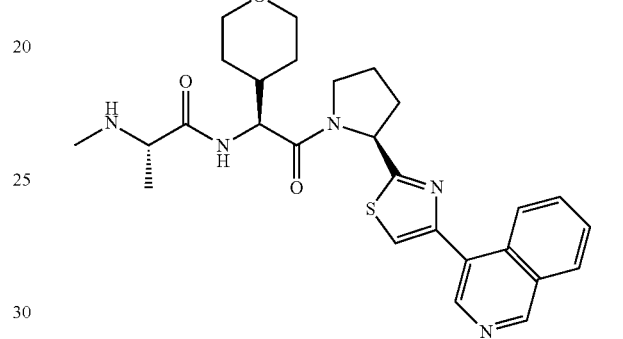

146
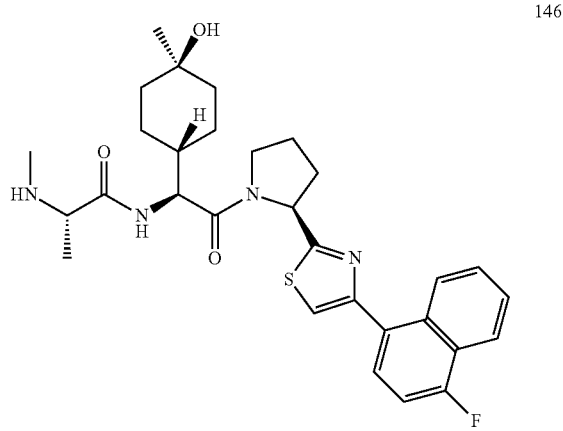

147
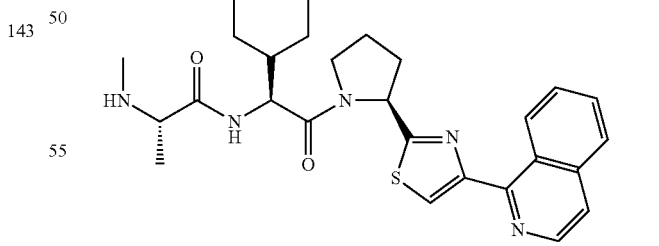

Synthesis

Compounds of the invention are prepared using standard organic synthetic techniques from commercially available starting materials and reagents. It will be appreciated that synthetic procedures employed in the preparation of compounds of the invention will depend on the particular substituents present in a compound and that various protection and deprotection steps that are standard in organic synthesis may be required but may not be illustrated in the following general schemes. In a particular general synthetic scheme compounds of the invention may be prepared using typical peptide chemistry techniques by coupling amino acid residue analogues employing typical amide coupling procedures. In scheme 1, amine-protected amino acid residue analogues are coupled and deprotected sequentially to give the final compounds.

Scheme 1

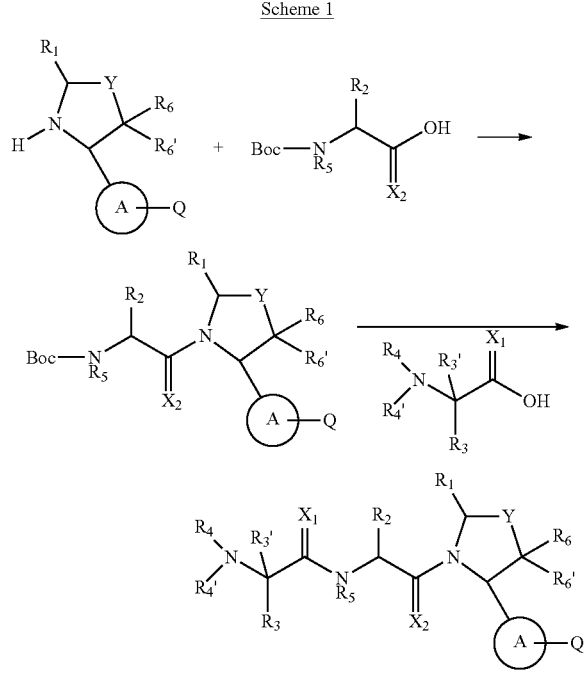

It will be appreciated that the amino acid analogs may be coupled in any order and may be prepared using solid phase support which is routine in the art. For example, Scheme2 illustrates an alternative amino acid residue analogue coupling route.

Scheme 2

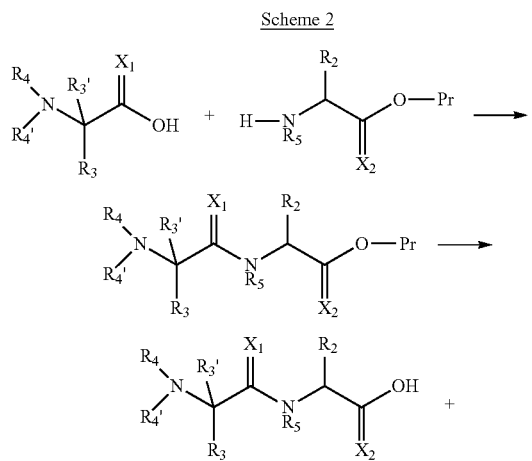

-continued

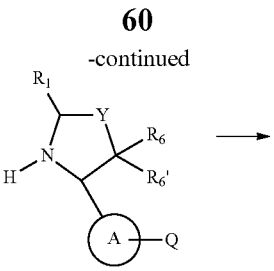

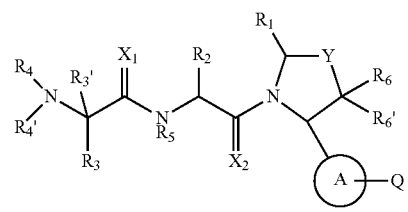

The intermediate incorporating ring A is prepared from commercially available reagents employing standard organic chemistry techniques. For example, when ring A is thiazole, the intermediate may be prepared according to scheme 3.

Scheme 3

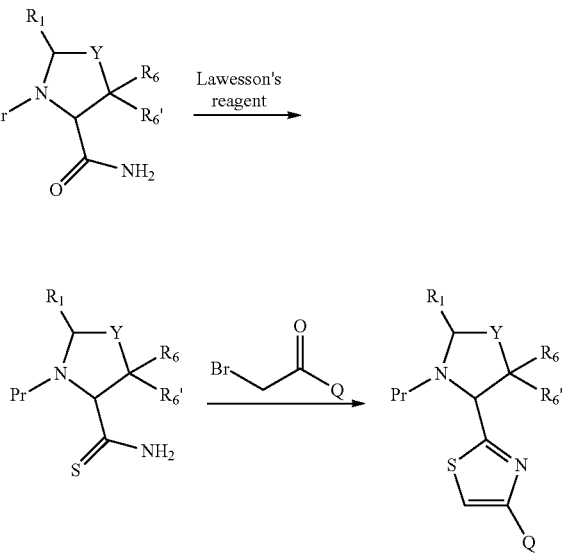

wherein Q, Y, $R_1$, $R_6$, and $R_6'$ are as defined herein and Pr is an amine protecting group. A proline analogue wherein the alpha nitrogen is protected (Pr), for example with Boc or Cbz, and amidated is converted to the corresponding thioamide, for example using Lawesson's reagent according to the procedures described in Williams et al (J. Org. Chem, 2001, 66:8463). The thiamide is then cyclized with an appropriate bromide to give the desired thiazole substituted with group Q, for example using the procedures described in Ciufolini et al, (J. Org. Chem. 1997, 62: 3804). Alternatively, the bromide in the present scheme may incorporate a functional group which may be used to couple a desired group Q to the thiazole formed from the cyclization step.

For compounds of the invention in which ring A is an oxazole, the intermediate may be prepared according to scheme 4.

Scheme 4

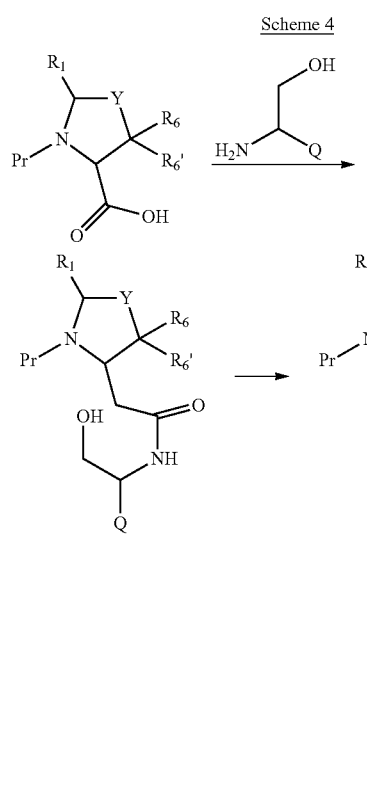

wherein Q, Y, $R_1$, $R_6$, and $R_6'$ are as defined herein and Pr is an amine protecting group. The starting proline analogue is reacted with an appropriate amine using standard amide forming procedures. The resulting amide is cyclized, for example using Burgess Reagent according to the procedures described in Pihko et al (J. Org. Chem., 1999, 64:652), to give the dihydro-oxazole. The dihydro-oxazole is then reduced to give the desired oxazole substituted with group Q. Alternatively, the amine of the first step in the present scheme may incorporate a functional group in place of Q which may be used directly or indirectly to couple a desired group Q to the thiazole formed from the cyclization step.

Compounds of the invention in which $R_4$ or $R_4'$ are other than H may be prepared according to standard organic chemistry techniques, for example by reductive amination in which a starting amino acid residue analog e.g. $NH_2$—$CH(R_3)$—$C(O)$—$OH$ is reacted with a suitable aldehyde or ketone to give the desired $R_4$ and $R_4'$ substituents. See scheme 5. The resulting $R_4/R_4'$ substituted amino acid intermediate can then be conjugated to the next amino acid intermediate or the remainder of the compound using standard peptide coupling procedures.

Scheme 5

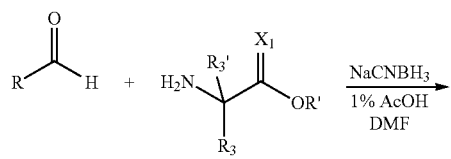

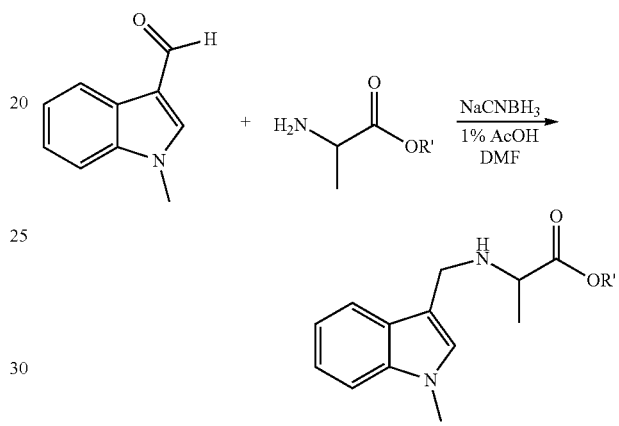

In a particular embodiment, alanine is reacted with 1-methylindole-2-carboxaldehyde and reduced with sodium cyanoborohydride dissolved in 1% HOAc/DMF to give the N-substituted alanine residue which may be used in preparing compounds of the invention. See scheme 6.

Scheme 6

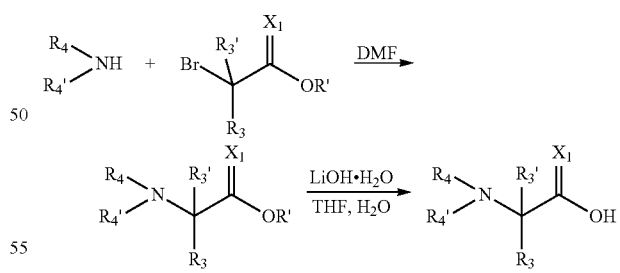

Alternatively, the reductive amination procedure to introduce $R_4/R_4'$ substituents is the final step in the preparation of the compound.

When compounds of the invention incorporate $R_4$ or $R_4'$ substituents other than H, they may also be prepared by substitution of a suitable acid intermediate which incorporates a leaving group with a desired amine. For example Br—CH($R_3$)—C(O)—OH is substituted with an amine $R_4$—$NH_2$ or $R_4$—NH—$R_4'$ according to scheme 7.

Scheme 7

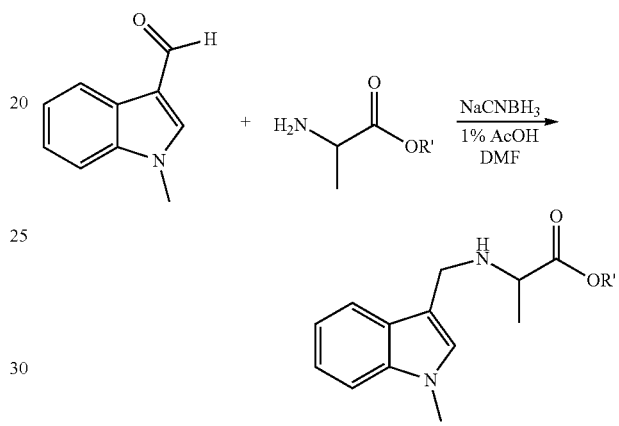

Alternatively, the substitution reaction introducing $R_4$ or $R_4'$ substituents may be performed as a final step in the preparation of the compound as illustrated in scheme 8.

Scheme 8

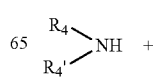

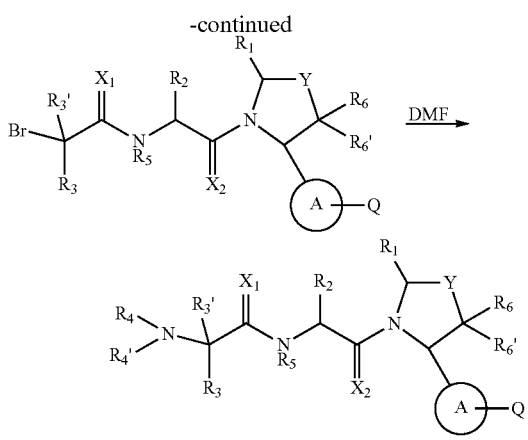

In a particular embodiment, 2-bromopropionic acid is reacted with the following amines dissolved in DMF and bubbled for until substitution is complete to form N-substituted alanine residues:

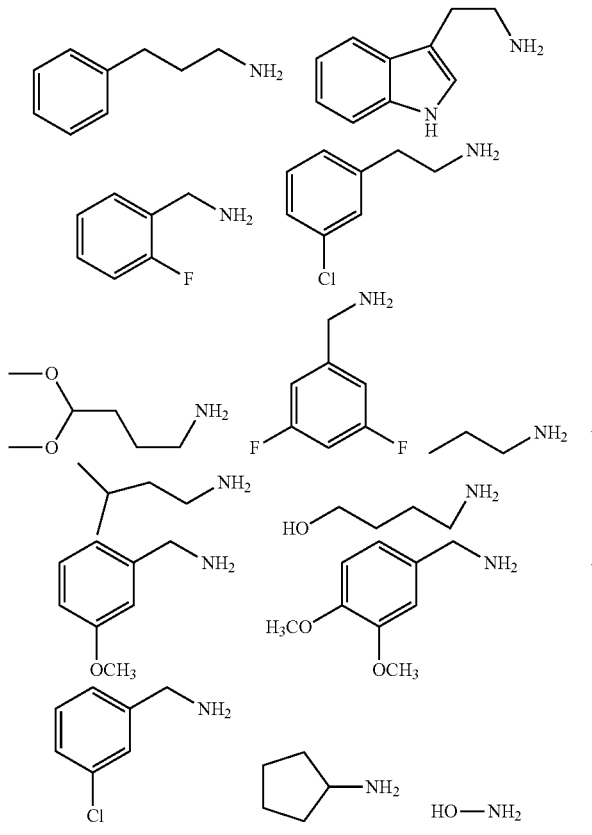

Compounds of the invention in which either $X_1$ or $X_2$ is sulfur, i.e. the compound incorporates a thioamide, may be prepared according to established organic chemistry techniques. For example, compounds in which $X_2$ is sulfur can be prepared according to scheme 9 starting from an Fmoc protected amino acid residue analog $NH_2$—$CH(R_2)$—COOH which is dissolved in THF and cooled to −25° C., with addition of DIPEA followed by addition of isobutylchloroformate. After 10 minutes, the diamine, 4-nitrobenzene-1,2-diamine, is added and the reaction mixture is continuously stirred at −25° C. for 2 hours, then at room temperature overnight. THF is vacuumed off and the mixture is then subjected to flash chromatography using 50% EtOAc/Hexane to yield the product. The Fmoc-alanine derivative, phosphorus pentasulfide and sodium carbonate are mixed in THF and stirred overnight. The solution is concentrated and direct chromatography using 80% EtOAc/Hexane yields the activated thioalanine. The activated thioalanine and sodium nitrite are then mixed in acetic acid and diluted with $H_2O$. The resulting precipitant is filtered and dried to yield the product. The thioalanine is coupled to an A ring substituted proline amino acid residue analog by dissolving both in DMF. The thioamide product may then be deprotected with 20% PIP/DMA for 15 minutes and used to conjugate to the $R_4/R_4'$—N—$C(R_3)(R_3')$—COOH. Alternatively the Fmoc-protected thioamide is first coupled to the A ring substituted proline amino acid residue analog followed by Fmoc deprotection and subsequent coupling to the $R_4/R_4'$—$R_4/R_4'$—N—$C(R_3)(R_3')$—COOH amino acid residue analog.

Scheme 9

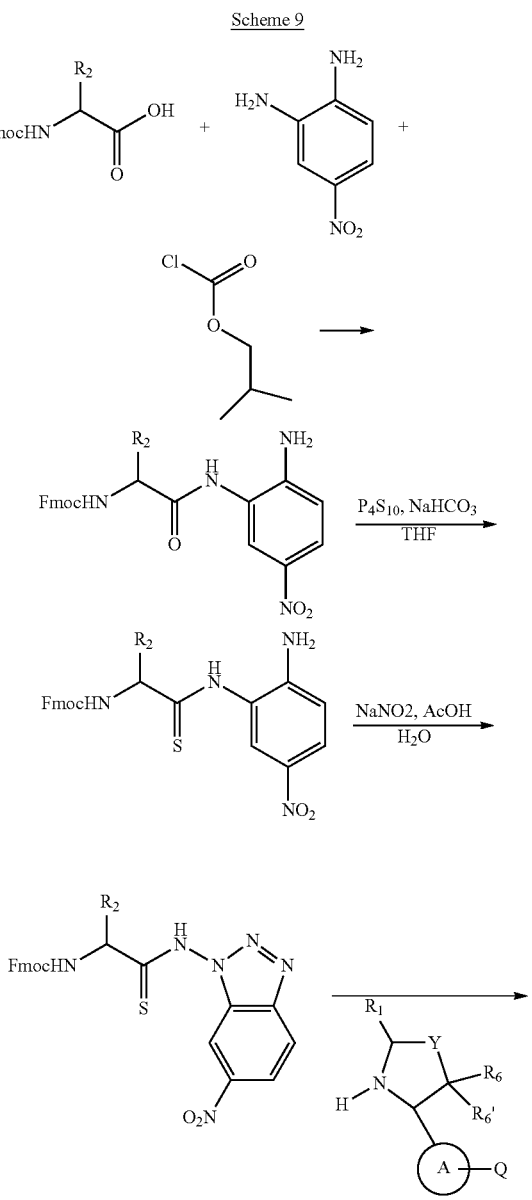

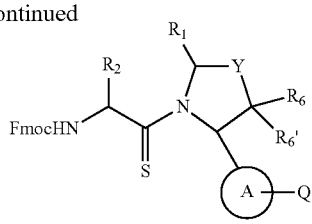

Utility

The compounds of the invention inhibit the binding of IAP proteins to caspases, in particular X-IAP binding interaction with caspases 3 and 7. The compounds also inhibit the binding of ML-IAP to Smac protein. Accordingly, the compounds of the invention are useful for inducing apoptosis in cells or sensitizing cells to apoptotic signals, in particular cancer cells. Compounds of the invention are useful for inducing apoptosis in cells that overexpress IAP proteins. Alternatively, compounds of the invention are useful for inducing apoptosis in cells in which the mitochondrial apoptotic pathway is disrupted such that release of Smac from ML-IAP proteins is inhibited, for example by up regulation of Bcl-2 or down regulation of Bax/Bak. More broadly, the compounds can be used for the treatment of all cancer types which fail to undergo apoptosis. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidca carcinoma, papillary thyroidca carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

Compounds of the invention are useful for sensitizing cells to apoptotic signals. Accordingly, the compounds may be administered prior to, concomitantly with, or following administration of radiation therapy or cytostatic or antineoplastic chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, ST1571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a particular embodiment, compounds of the present invention are coadministered with a cytostatic compound selected from the group consisting of cisplatin, doxorubicin, taxol, taxotere and mitomycin C. In a particular embodiment, the cytostatic compound is doxorubicin.

Another class of active compounds which can be used in the present invention are those which are able to sensitize for or induce apoptosis by binding to death receptors ("death receptor agonists"). Such agonists of death receptors include death receptor ligands such as tumor necrosis factor α (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. In an embodiment, the death receptor ligand is TNF-α. In a particular embodiment, the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

For the purpose of sensitizing cells for apoptosis, the compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention.

Furthermore, the present invention encompasses types of non-ionizing radiation like e.g. ultraviolet (UV) radiation, high energy visible light, microwave radiation (hyperthermia therapy), infrared (IR) radiation and lasers. In a particular embodiment of the present invention UV radiation is applied.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of formula I used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but may range anywhere from about 3 to about 8. Formulation in an acetate buffer at pH 5 is a suitable embodiment. In an embodiment, the inhibitory compound for use herein is sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit IAP interaction with caspases, induce apoptosis or sensitize a malignant cell to an apoptotic signal. Such amount is may be below the amount that is toxic to normal cells, or the mammal as a whole.

Generally, the initial pharmaceutically effective amount of the compound of the invention administered parenterally per dose will be in the range of about 0.01-100 mg/kg, for example about 0.1 to 20 mg/kg of patient body weight per day, with the typical initial range of compound used being 0.3 to 15 mg/kg/day. Oral unit dosage forms, such as tablets and capsules, may contain from about 25 to about 1000 mg of the compound of the invention.

The compound of the invention may be administered by any suitable means, including oral, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants.

EXAMPLES

The invention will be more fully understood by reference to the following examples. They should not, however, be construed as limiting the scope of the invention. Reagents and solvents were obtained from commercial sources and used as received. ISCO chromatography refers to use of a pre-packed silica gel columns on a Companion system by Teledyne-Isco, Inc. Lincoln, Nebr. The identity and purity of all compounds were checked by LCMS and $^1$H NMR analysis.

Abbreviations used herein are as follows:
ACN: acetonitrile;
Chg: cyclohexylglycine;
DCM: dichloromethane
DIPEA: diisopropylethylamine;
DMAP: 4-dimethylaminopyridine;
DME: 1,2-dimethoxyethane;
DMF: dimethylformamide;
DMSO: dimethylsulfoxide
EDC: 1-ethyl-3-(3-dimethylaminopropyl)carbodiimide;
EEDQ: 2-ethoxy-1-ethoxycarbonyl-1,2-dihydroquinoline
LCMS: liquid chromatography mass spectrometry;
HATU: O-(7-Azobenzotriazol-1-yl)-1,1,3,3-tetramethyluronium hexafluorophosphate;
HOBt: N-Hydroxybenzotriazole
HBTU: 2-(1H-Benzotriazol-1-yl)-1,1,3,3-Tetramethyl-uronium Hexafluorophosphate
HPLC: high performance liquid chromatography;
NBS: N-bromosuccinamide;
TASF: tris(dimethylamino)sulfonium difluorotrimethylsilicate;
TEA: triethylamine;
TFA: trifluoroacetate;
THF: tetrahydrofuran;

Example 1

2-[tert-Butoxycarbonyl-(1H-pyrrol-2-ylmethyl)-amino]-propionic acid

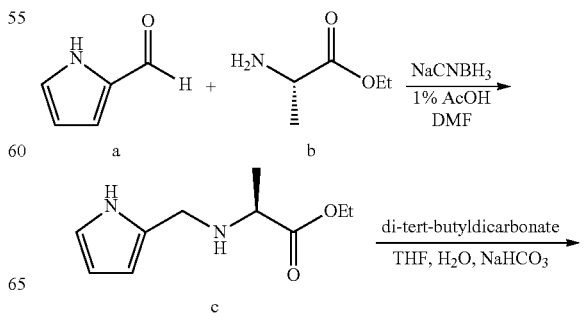

-continued

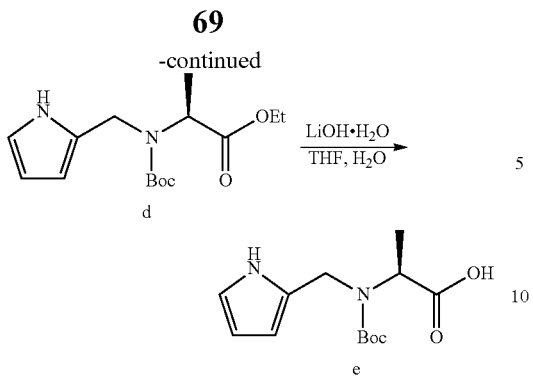

-continued

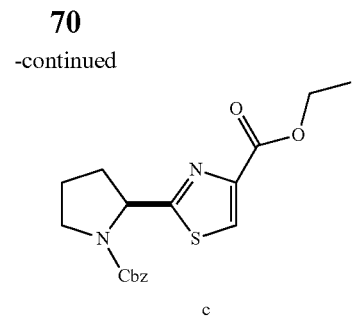

Alanine ethyl ester b (5 g, 32.5 mmol), pyrrole-2-carboxaldehyde a (3.1 g, 32.5 mmol), sodium cyanoborohydride (2.04 g, 32.5 mmol) and AcOH (1%) were mixed in DMF and stirred overnight. The reaction was quenched with H₂O, and DMF was evaporated. The mixture was diluted with EtOAc, washed by 0.1N NaOH, dried and concentrated to yield product c 2.5 g. The resulting ester c (2.5 g, 12.8 mmol), di-tert-butyldicarbonate (3.06 g, 14 mmol) were mixed in THF, H₂O with NaHCO₃ and stirred overnight. THF was evaporated, and the mixture was diluted with EtOAc, washed by 1N NaOH, sat. NH₄Cl and brine. After dried, the mixture was concentrated to yield the Boc-protected ester d 3.3 g. The Boc-protected ester d (1.67 g, 5.6 mol), lithium hydroxide mono hydrate (284 mg, 6.77 mmol) were mixed in THF and H₂O at 0° C. THF was vacuumed off, and the solution was acidified by dilute H₂SO₄, extracted by EtOAc twice. Organic layers were combined, dried and evaporated giving product 2-[tert-butoxycarbonyl-(1H-pyrrol-2-ylmethyl)-amino]-propionic acid c.

Following the general procedure of Ciufolini (Ciufolini, M. A. et al, *J. Org. Chem.* 1997, 62, 3804), ethyl bromopyruvate (200 μl, 1.43 mmol) was added to a suspension of thioamide b (378 mg, 1.43 mmol) in ethanol (5 mL), and the mixture heated at 80° C. for 5 min. The solvent was evaporated under reduced pressure, and the residue purified by flash chromatography (SiO₂, gradient elution, 30-40-50% ethyl acetate-hexanes) to afford 393 mg (74%) of thiazole c as a colorless solid.

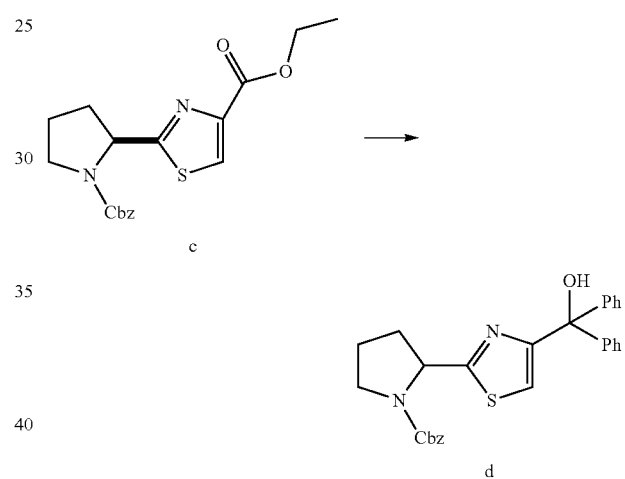

Example 2

Thiazole Substituted Pyrrolidine

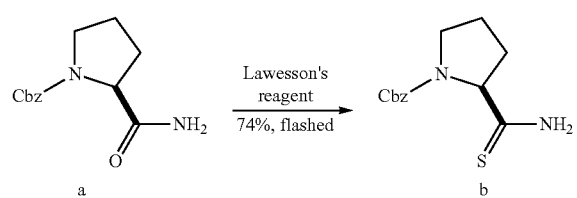 [SMILES: NC(=O)[C@@H]1CCCN1C(=O)OCc1ccccc1 ; NC(=S)[C@@H]1CCCN1C(=O)OCc1ccccc1]

Following the general procedure of Williams (Williams, D. R. et al, M. *J. Org. Chem.* 2001, 66, 8463), a mixture of N-Cbz-proline amide a (500 mg, 2.0 mmol) Lawesson's reagent (420 mg, 1.05 mmol) and toluene (5 mL) was heated at reflux for 2 h. The solution was concentrated, adsorbed onto Celite, and purified by flash chromatography (SiO₂, 40% ethyl acetate-hexanes) to afford 393 mg (74%) of compound b as a colorless solid.

Phenyl magnesium bromide (2.1 mL of 1.0 M solution in THF, 2.1 mmol) was added dropwise to a cold (−78° C.) solution of ester c (360 mg, 1.0 mmol) in THF (5 mL) over 5 min. The cooling bath was removed and the solution allowed to reach room temperature, at which time it was poured into saturated aqueous NH₄Cl (50 mL). The aqueous layer was extracted with 50% ethyl acetate-hexanes (3×10 mL). The combined organic layers were dried (Na₂SO₄), filtered, and concentrated. The residue was purified by flash chromatography (SiO₂, gradient elution, 30-40% ethyl acetate-hexanes) to afford 404 mg (84%) of thiazole d as a colorless solid.

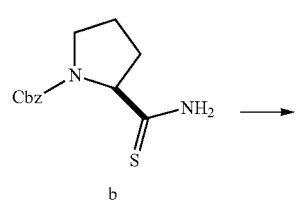

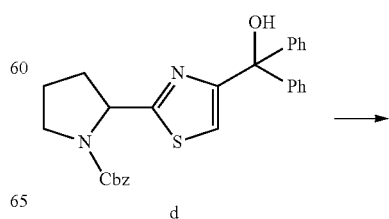

-continued

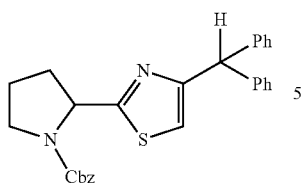

e

Triethylsilane (850 µl, 5.3 mmol) and TFA (5 mL) were added sequentially to alcohol d, and the resulting solution was allowed stand at rt for 1 h. The solvent was evaporated, and the residue purified by flash chromatography (SiO$_2$, 30% ethyl acetate-hexanes) to afford a quantitative yield of compound e as a colorless oil.

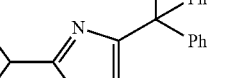

Following the general procedure of Thurston (Bose, S. D.; Thurston, D. E. *Tetrahedron Lett.* 1990, 31, 6903), BF$_3$·Et$_2$O (0.78 mL, 6.2 mmol) was added to a solution of carbamate e (280 mg, 0.62 mmol), propanethiol (560 µl, 6.2 mmol) and CH$_2$Cl$_2$ (3 mL) at rt. After 1 day at rt, the reaction was poured into 1 N NaOH (50 mL) and stirred vigorously for 1 h. The layers were separated and the organic phase was washed with 1 N NaOH (2×5 mL). The combined aqueous layers were extracted with CH$_2$Cl$_2$ (2×5 mL), and the combined organic layers were dried (K$_2$CO$_3$), filtered and concentrated. The residue was purified by flash chromatography (SiO$_2$, gradient elution, 40-50-60% ethyl acetate-hexanes, 1% TEA) to afford 122 mg (61%) of amine f as a colorless solid.

Example 3

Oxazole Substituted Pyrrolidine

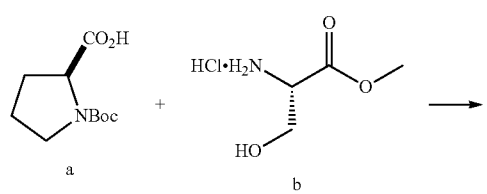

-continued

A mixture of N-Boc-proline a (5.35 g, 24.9 mmol) serine methyl ester hydrochloride b (3.50 g, 22.5 mmol), EDC (4.76 g, 24.85 mmol), DIPEA (4.0 mL, 22.5 mmol) and CH$_2$Cl$_2$ (90 mL) was maintained overnight. The mixture was diluted with CH$_2$Cl$_2$ (200 mL) and washed with 1 N HCl (3×100 mL), 0.1 N NaOH (3×100 mL) and brine (1×100 mL). The organic layer was dried (Na$_2$SO$_4$), filtered, and concentrated to afford 5.2 g (73%) of dipeptide c as a colorless foam.

To a cool (0° C.) solution of dipeptide c (4.57 g, 14.4 mmol) and THF (100 mL) was added Burgess Reagent (Pihko, P. M.; Koskinen, A. M. P.; Nissinen, M. J.; Rissanen, K. *J. Org. Chem.* 1999, 64, 652, and references therein) (3.77 g, 15.8 mmol) in 3 portions over 30 min. The cooling bath was removed and the reaction allowed to reach rt, then heated at reflux for 1 h. After cooling to rt, the THF was removed under reduced pressure and the residue was partitioned between EtOAc (200 mL) and saturated aqueous NH$_4$Cl (200 mL). The organic layer was washed with saturated aqueous NH$_4$Cl (2×50 mL). The combined aqueous phases were extracted with EtOAc (1×50 mL) and the combined organic phases were washed with brine, dried (Na$_2$SO$_4$), filtered, and concentrated. The residue was purified by flash chromatography (SiO$_2$, 50-75-100% ethyl acetate-hexanes) to afford 2.94 g (68%) of compound d as a colorless solid.

Following the general procedure of Koskinen (Pihko, P. M.; Koskinen, A. M. P.; Nissinen, M. J.; Rissanen, K. *J. Org.*

Chem. 1999, 64, 652, and references therein), to degassed CH₂Cl₂ (25 mL), was added CuBr (8.79 g, 39.3 mmol), hexamethylene tetraamine (5.51 g, 39.3 mmol) and DBU (5.9 mL, 39.3 mmol) and the resulting dark mixture stirred vigorously while it was cooled to 0° C. To this mixture was added a degassed solution of d (2.94 g, 9.83 mmol) and CH₂Cl₂ (25 mL) over 5 min. The cooling bath was removed and the mixture stirred vigorously for 2 h. The reaction was then poured into 1:1 saturated aqueous NH₄Cl:conc. NH₄OH (200 mL), stirred for 30 min, then extracted with EtOAc (3×50 mL). The combined organic phases were washed with saturated aqueous NH₄Cl (2×50 mL), brine, dried (Na₇SO₄), filtered, and concentrated. The residue was purified by flash chromatography (SiO-₂, 40-50% ethyl acetate-hexanes) to afford 1.1 g (38%) of oxazole e as a colorless solid.

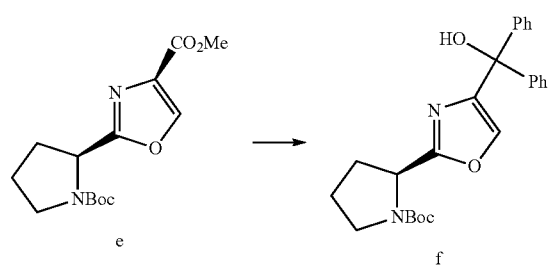

Phenylmagnesium bromide (4.4 mL of 1.0 M solution in THF, 4.4 mmol) was added dropwise to a cold (-78° C.) solution of ester e (600 mg, 2.0 mmol) in THF (10 mL) over 5 min. The cooling bath was removed and the solution allowed to reach rt, at which time it was poured into saturated aqueous NH₄Cl (50 mL). The aqueous layer was extracted with 50% ethyl acetate-hexanes (3×10 mL). The combined organic layers were dried (Na₂SO₄), filtered, and concentrated. The residue was purified by flash chromatography (SiO₂, gradient elution, 20-30-40% ethyl acetate-hexanes) to afford 443 mg (52%) of oxazole f as a colorless solid.

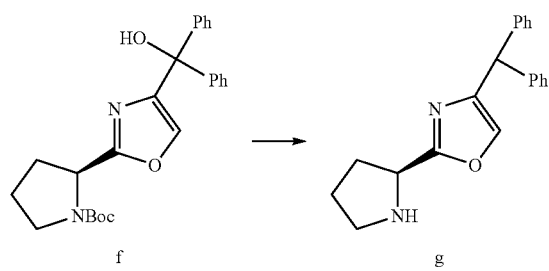 [SMILES: CC(C)(C)OC(=O)N1CCC[C@H]1c1nc(C(O)(c2ccccc2)c2ccccc2)co1 ; c1ccc(C(c2ccccc2)c2coc([C@@H]3CCCN3)n2)cc1]

Triethylsilane (20 μl) and TFA (1 mL) were added sequentially to a solution of alcohol f (50 mg, 0.1 mmol) and CH₂Cl₂ (1 mL). The resulting solution was allowed stand at rt for 1 h. The solvent was evaporated, and the residue partitioned between EtOAc (20 mL) and 1N NaOH (20 mL). The organic phase was washed with 1N NaOH (2×20 mL). The combined aqueous phases were extracted with EtOAc (1×20 mL), and the combined organic phases were washed with brine (1×20 mL) dried (Na₂SO₄), filtered, and concentrated to afford amine g as a colorless oil, contaminated with residual triethylsilane. This material was used directly in the next coupling.

Example 4

Synthesis of Methyl Ketones

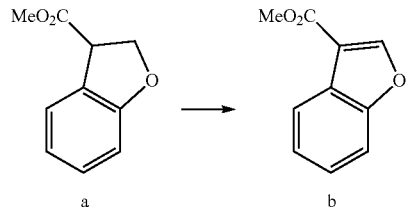 [SMILES: COC(=O)C1COc2ccccc21 ; COC(=O)c1coc2ccccc12]

A mixture of dihydrobezofuran a (Davies, H. M. L.; Grazini, M. V. A.; Aouad, E. *Org. Lett.* 2001, 3, 1475) (160 mg, 0.9 mmol) DDQ (300 mg) and CH₂Cl₂ (11 mL) was maintained at room temp. for 2 days. The solution was diluted with 50% ethyl acetate-hexanes and washed with 0.5 N NaOH (3×10 mL), brine (1×10 mL), dried (Na₂SO₄), filtered, and concentrated to afford 150 mg (93%) of bezofuran b.

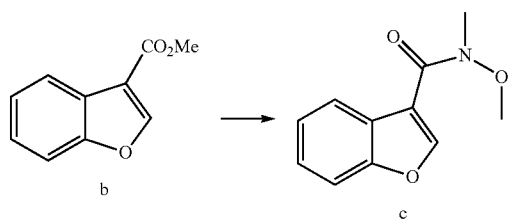

Isopropylmagnesium chloride (7.1 mL of a 2.0 M solution in THF, 14.2 mmol) was added dropwise to a mixture of benzofuran methyl ester b (500 mg, 2.84 mmol) and N,O-dimethyl hydroxyl amine hydrochloride (690 mg, 7.1 mmol) and THF (8 mL) maintained <-20° C. The mixture was allowed to warm to 0° C. over 20 min, then poured into 50 mL of saturated aqueous NH₄Cl. The aqueous phase was extracted with EtOAc (3×20 mL), the combined organic phases were washed with brine (1×50 mL), dried (Na₂SO₄), filtered, and concentrated to afford 577 mg (85%) of amide c, as a clear oil.

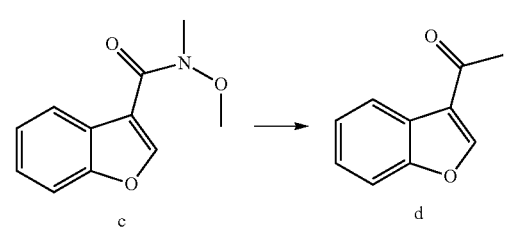

To a solution of amide c (660 mg, 3.22 mmol) and THF (6 mL) was added MeMgBr (3 mL of a 3.0 M solution in THF, 9 mmol) at 0° C. The solution was maintained at 0° C. for 30 min, then allowed to warm to 20° C. for 30 min, at which time a precipitate forms. The mixture was poured into 100 mL of saturated aqueous NH₄Cl. The aqueous phase was extracted with EtOAc (3×50 mL), the combined organic phases were washed with brine (1×50 mL), dried (Na$_2$SO$_4$), filtered, and concentrated to afford 460 mg (89%) of ketone d, as a clear oil.

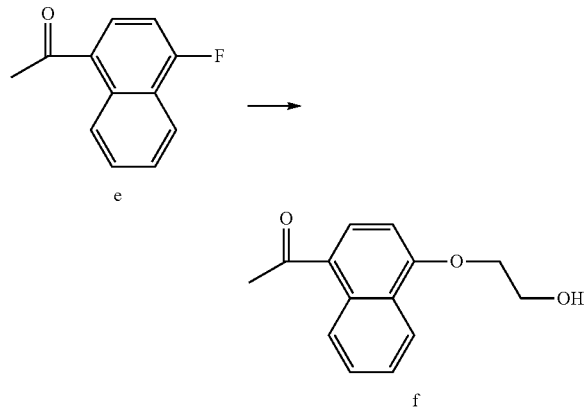

A mixture of potassium tert-butoxide (2.2 g, 17.5 mmol), fluoro ketone e (3.0 g, 15.9 mmol) and ethylene glycol (30 mL) was heated at 50° C. for 1 h, then 60° C. for 2 h. The mixture was then poured into 500 mL of saturated aqueous NH$_4$Cl. The aqueous phase was extracted with Et$_2$O (3×150 mL), the combined organic phases were washed with water (3×150 mL), brine (1×50 mL), dried (Na$_2$SO$_4$). The mixture was adsorbed onto Celite, and chromatographed (ISCO, 120 g silica column, 10-60% EtOAc-hexanes) to afford 2.23 g (61%) of the hydroxy ether f as a colorless solid.

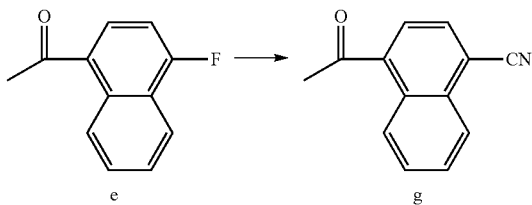

A mixture of potassium cyanide (6.9 g, 106 mmol), fluoro ketone e (2.0 g, 10.6 mmol) and DMSO (20 mL) was maintained at rt for 4 days, then heated at 50° C. for 1 day. The mixture was then poured into 500 mL of 1 N NaOH. The aqueous phase was extracted with Et$_2$O (3×150 mL), the combined organic phases were washed with water (3×150 mL), brine (1×50 mL), dried (Na$_2$SO$_4$). The mixture was adsorbed onto Celite, and chromatographed (ISCO, 120 g silica column, 0-20% EtOAc-hexanes) to afford 1.15 g (55%) of the nitrile g as a yellow solid.

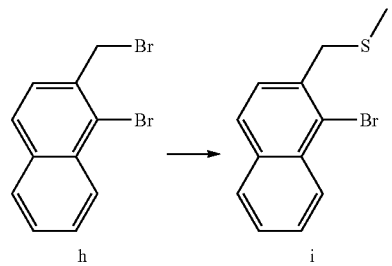

A mixture of dibromide h (2.33 g, 7.78 mmol), NaSMe (600 mg, 8.56 mmol), and EtOH (5 mL) was maintained at rt 18 h. The mixture was poured into 75 mL of 1 N NaOH and extracted with EtOAc (3×50 mL). The combined organic phases were washed with 1 N NaOH (1×50 mL), brine (3×50 mL), dried (Na$_2$SO$_4$), filtered and concentrated to afford 2.06 g (98%) of thioether i as a colorless oil.

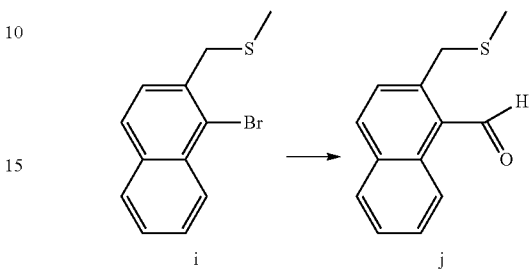

To a −78° C. solution of bromide i (500 mg, 1.87 mmol) and THF (15 mL) was added sec-BuLi (1.6 mL of 1.4 M solution in cyclohexane, 2.25 mmol) over 5 min. After 5 min at −78° C., the dark purple solution was quenched rapidly with DMF (0.5 mL) and the solution warmed to 0° C. and maintained at that temp. for 5 min. The solution was then poured into saturated aqueous NH$_4$Cl (50 mL). The aqueous phase was extracted with EtOAc (3×25 mL), the combined organic phases were washed brine (1×50 mL), dried (Na$_2$SO$_4$) and filtered. The mixture was adsorbed onto Celite, and chromatographed (ISCO, 12 g silica column, 0-10% EtOAc-hexanes) to afford 260 mg (64%) of aldehyde i as a clear oil.

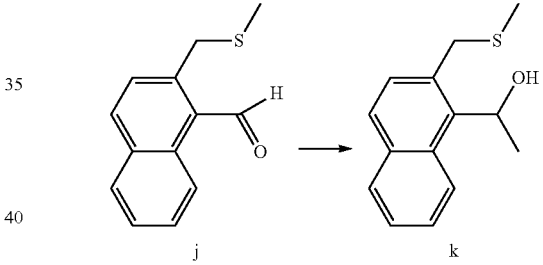

To a solution of aldehyde 1 (400 mg, 1.86 mmol) and THF (5 mL) was added MeMgCl (0.9 mL of a 3.0M solution in THF, 2.8 mmol) at 0° C. The solution was maintained at 0° C. for 30 min, then allowed to warm to 20° C. for 30 min. The mixture was poured into 50 mL of saturated aqueous NH$_4$Cl. The aqueous phase was extracted with EtOAc (3×25 mL), the combined organic phases were washed with brine (1×50 mL), dried (Na$_2$SO$_4$), filtered, and concentrated to afford crude alcohol k as a clear oil, which was used without further purification.

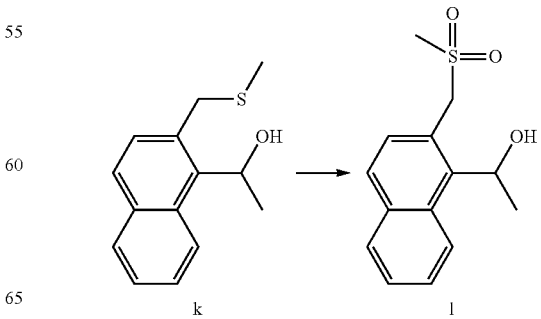

To a solution of crude sulfide k and MeOH (5 mL) at 0° C. was added a suspension of Oxone (1.3 g, 2.1 mmol) in water (5 mL) over 20 min. The mixture was allowed to reach room temp and then poured into 50 mL of saturated aqueous NH₄Cl. The aqueous phase was extracted with EtOAc (3×25 mL), the combined organic phases were washed with brine (1×50 mL), dried (Na₂SO₄), filtered, and concentrated. This residue was dissolved in MeOH (10 mL), cooled to 0° C., and to it was added a suspension of Oxone (2.6 g, 4.2 mmol) in water (10 mL) over 20 min. The mixture was stiffed at rt overnight then poured into 50 mL of saturated aqueous NH₄Cl. The aqueous phase was extracted with EtOAc (3×25 mL), the combined organic phases were washed with brine (1×50 mL), dried (Na₂SO₄), filtered, and concentrated to afford 550 mg (100% for two steps) of sulfone 1 as a clear oil.

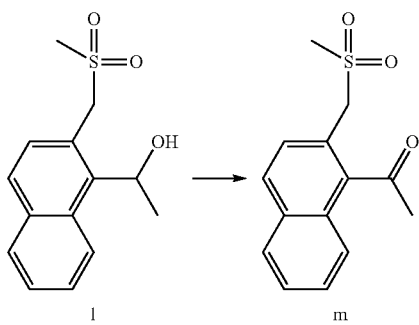 [SMILES: CC(O)c1c(CS(C)(=O)=O)ccc2ccccc12 ; CC(=O)c1c(CS(C)(=O)=O)ccc2ccccc12]

A mixture of alcohol 1 (550 mg, 2.1 mmol), Celite (680 mg), and PCC (500 mg, 2.31 mmol) was stirred vigorously at rt for 6 h. More PCC (200 mg) was added and the mixture was stirred overnight. The mixture was adsorbed onto more Celite (5 g) and chromatographed (ISCO, 12 g silica column 0-50% EtOAc-hexanes) to afford 380 mg (69%) of ketone m as a colorless solid.

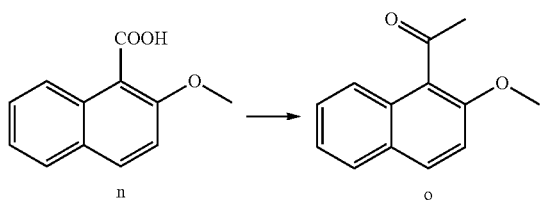

Thionyl chloride (26 mL, 365 mmol) was added to a mixture of 2-methoxy-1-naphthoic acid n (4.5 g, 22.3 mmol) and toluene (45 mL). The resulting mixture was heated at 75° C. for 3 h. The solvent was removed under reduced pressure, and the intermediate acid chloride was dried under high vacuum for 1 h. It was dissolved in THF (50 mL) and cooled to 0° C. under N₂. Dimethylzinc (45 mL of 1.0 M solution in heptane, 44.6 mmol) was added over 15 min. The reaction mixture was kept at 0° C. for 5 min, allowed to warm to room temperature. The reaction was quenched with slow addition of saturated NH₄Cl (200 mL). The aqueous phase was extracted with EtOAc (3×100 mL), and the combined organic phases were washed with brine (1×100 mL), dried (MgSO₄), filtered, and concentrated in vacuo. The crude product was adsorbed on to Celite and purified by ISCO CombiFlash 40 g column (5-15% ethyl acetate-hexane) to afford 1.96 g (44%) of ketone o as a white solid.

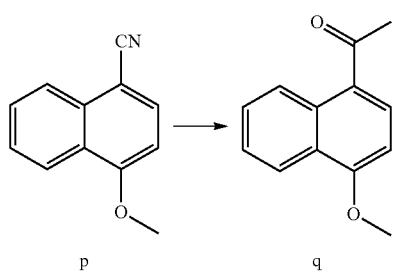

Following the general procedure of Caldwell (Ichinose, N.; Mizuno, K.; Otsuji, Y.; Caldwell, R. A.; Helms, A. M. *J. Org. Chem.* 1998, 63, 3176-84), to a solution of CH₃MgCl (3.4 mL of 3.0 M solution in THF, 10.0 mmol) in THF (20 mL) was added dropwise a solution of 4-methoxy-1-naphthalenecarbonitrile p (0.5 g, 2.7 mmol) in toluene (10 mL). After the addition, toluene (10 mL) was added to the mixture. The resulting solution was heated to reflux for 8 h. Aqueous AcOH (50%, 10 mL) was added, and the mixture was heated to reflux for 4 h. After cooling, the mixture was diluted with water, and the organic phase separated, dried (MgSO₄), filtered, and concentrated in vacuo to afford 0.5 g (93%) of ketone q as a yellow oil, which was used without further purification.

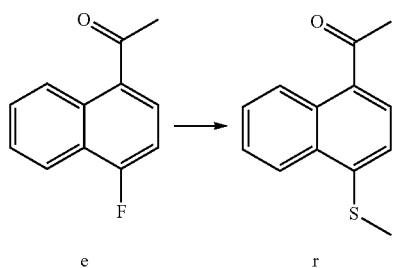

Following the general procedure of Boswell (Boswell, E. G.; Licause, J. F. *J. Org. Chem.* 1995, 60, 6592-94), to a solution of sodium thiomethoxide (0.41 g, 5.8 mmol) in anhydrous DMSO (8 mL) at 0° C. under N₂ was added dropwise a solution of 4-fluoro-1-acetylnaphthalene e (1.0 g, 5.3 mmol) in DMSO (8 mL). After stirring at room temperature for 1.5 h, the mixture was diluted with water, extracted with CH₂Cl₂ (3×20 mL), and the combined organic phases were dried (MgSO₄), filtered, and concentrated in vacuo to afford 1.0 g (88%) of sulfide r as a light yellow solid, which was carried on without further purification.

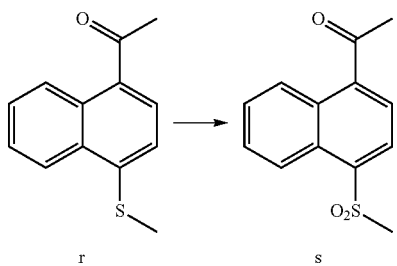 [SMILES: CSc1ccc(C(C)=O)c2ccccc12 ; CC(=O)c1ccc(S(C)(=O)=O)c2ccccc12]

Following the general procedure of Trost (Trost, B. M.; Curran, D. P. *Tetrahedron Lett.* 1981, 22, 1287-90), to a cold (0° C.) solution of sulfide r (2.3 g, 10.6 mmol) in methanol (50 mL) was added dropwise a solution of potassium hydrogen persulfate (Oxone, 22.8 g, 37.1 mmol) in water (75 mL) keeping the reaction temperature below 5° C. The resulting slurry was stirred at room temperature for 72 h, diluted with water and extracted with $CH_2Cl_2$ (2×100 mL). The combined organics were washed with brine, dried ($MgSO_4$), filtered, and concentrated to afford crude product. The residue was adsorbed on to Celite and purified by ISCO CombiFlash 40 g column (10-40% ethyl acetate-hexane) to afford 2.32 g (88%) of sulfone s as an off white solid.

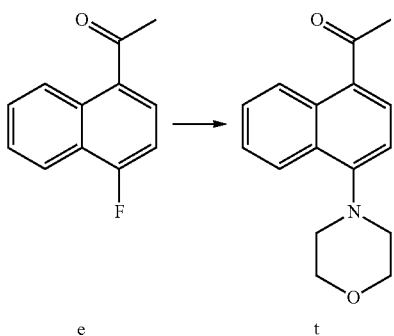 [SMILES: CC(=O)c1ccc(F)c2ccccc12 ; CC(=O)c1ccc(N2CCOCC2)c2ccccc12]

A mixture of 4-fluoro-1-acetylnaphthalene e (4.75 g, 25.2 mmol), morpholine (6.60 mL, 75.8 mmol), $K_2CO_3$ (5.21 g, 37.8 mmol), DMSO (30 mL), and water (12 mL) was heated at 90° C. for 8 h. The reaction mixture was diluted with water, extracted with $CH_2Cl_2$ (2×100 mL). The combined organic layers were washed with brine, dried ($MgSO_4$), filtered, and concentrated in vacuo to afford crude product. It was triturated with water, filtered, washed with water, dried to afford 6.40 g (99%) of morpholinyl ketone t as a yellow solid.

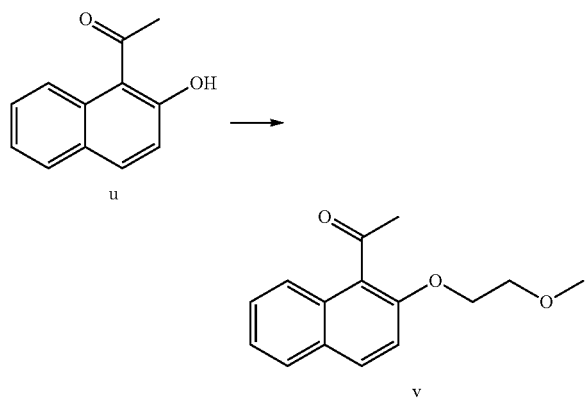

2'-Hydroxy-1'-acetonaphthone u (5.0 g, 26.9 mmol) and $K_2CO_3$ (11.1 g, 81.0 mmol) in acetone (150 mL) were stirred for 20 min. To this mixture was added bromoethyl methyl ether (3.8 mL, 39.5 mmol) and catalytic KI. The resulting mixture was heated to reflux for 72 h. After cooling, the solvent was removed in vacuo. The residue was dissolved in EtOAc, washed with 1 N aqueous NaOH, brine, dried ($MgSO_4$), filtered, and concentrated in vacuo. The crude product was adsorbed on to Celite and purified by ISCO CombiFlash 120 g column (5-25% ethyl acetate-hexane) to afford 3.21 g (49%) of ether v as an oil.

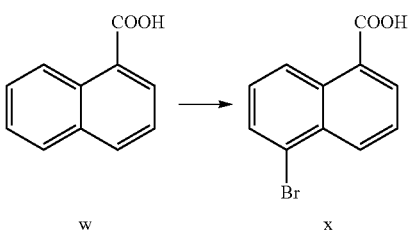 [SMILES: O=C(O)c1cccc2ccccc12 ; O=C(O)c1cccc2c(Br)cccc12]

Following the general procedure of Short (Short, W. F.; Wang, H. *J. Chem. Soc.* 1950, 991-4), to a three-necked round-bottomed flask equipped with a reflux condenser, a dropping funnel, and an aqueous NaOH trap was added 1-naphthoic acid w (10.0 g, 58.0 mmol) and AcOH (35 mL). This solution was heated at 110° C. and stirred during the addition of bromine (3.12 mL, 61.0 mmol). After the addition, the mixture was heated for another 1.5 h (A yellow solid precipitated during the heating), and then stirred at room temperature for 24 h. The mixture was poured into ice water. The solid was filtered, washed with water, and crystallized from acetic acid (250 mL) to afford 8.9 g (61%) of bromo acid x as a white solid.

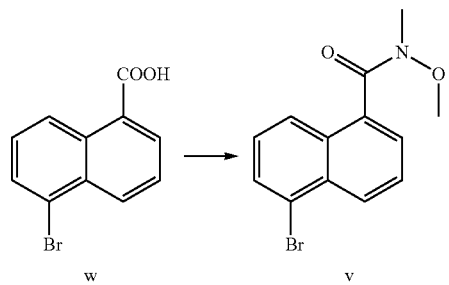 [SMILES: O=C(O)c1cccc2c(Br)cccc12 ; CON(C)C(=O)c1cccc2c(Br)cccc12]

A solution of bromo acid x (6.0 g, 23.9 mmol), N,O-dimethythydroxyl amine hydrochloride (2.33 g, 23.9 mmol), EDC (4.6 g, 23.9 mmol), and DIPEA (6.3 mL, 35.8 mmol) in DMF (35 mL) was stirred at room temperature for 4 h. The mixture was poured into water, extracted with $CH_2Cl_2$ (2×200 mL). The combined organic layers were washed with 0.5 N aqueous HCl, 0.5 N aqueous NaOH, dried ($MgSO_4$), filtered, and concentrated in vacuo. The crude product was adsorbed on to Celite and purified by ISCO CombiFlash 120 g column (2-10% ethyl acetate-$CH_2Cl_2$) to afford 4.6 g (65%) of amide y as an oil.

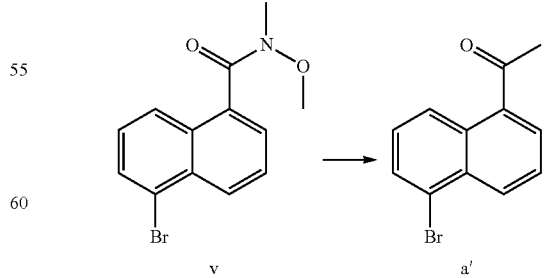

Methylmagnesium chloride (8.5 mL of 3 M solution in THF, 25.5 mmol) was added dropwise to a cold (0° C.) solution of amide z (2.5 g, 8.5 mmol) and THF (80 mL). The resulting solution was stirred at 0° C. for 1 h, then allowed to warm to room temperature. After 2.5 h, it was quenched by slow addition of aqueous AcOH (50%, 10 mL), diluted with water (100 mL), and separated. The aqueous layer was extracted with EtOAc (1×100 mL). The combined organic layers were washed with brine, dried (MgSO$_4$), filtered, and concentrated in vacuo to afford 1.9 g (90%) of ketone a' as a yellow solid.

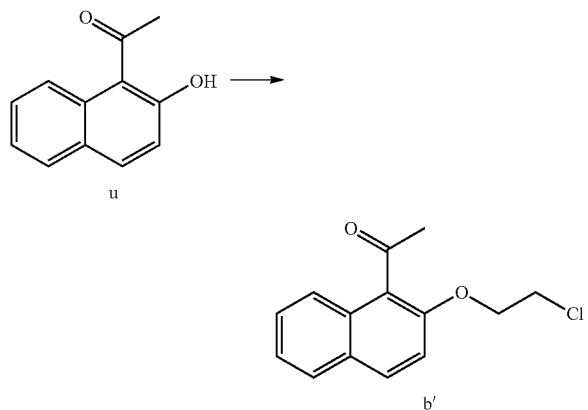 [SMILES: CC(=O)c1c(O)ccc2ccccc12 ; CC(=O)c1c(OCCCl)ccc2ccccc12]

A mixture of 2'-hydroxy-1'-acetonaphthone u (5.0 g, 26.9 mmol), K$_2$CO$_3$ (7.41 g, 53.7 mmol), and 1-bromo-2-chloroethane (4.4 mL, 53.7 mmol) in DMF (70 mL) was heated at 80° C. for 24 h. The cooled mixture was diluted with water, and extracted with CH$_2$Cl$_2$ (2×100 mL). The combined organic phases were washed with 0.5 N aqueous NaOH, brine, dried (MgSO$_4$), filtered, and concentrated to afford crude product. The residue was adsorbed on to Celite and purified by ISCO CombiFlash 40 g column (5-25% ethyl acetate-hexane) to afford 1.6 g (24%) of chloroethoxy ketone b' as a light yellow solid.

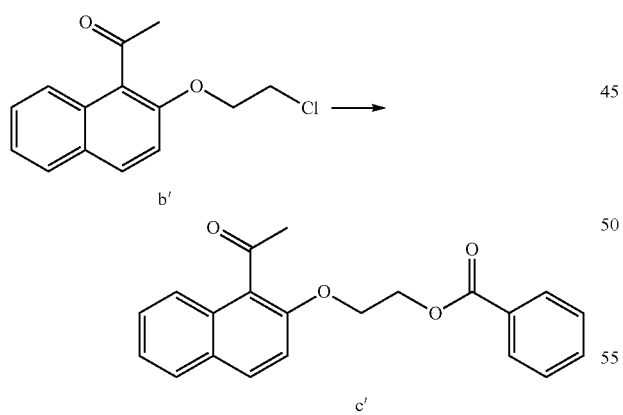

A mixture of chloroethoxy ketone b' (3.0 g, 12.1 mmol), benzoic acid (1.47 g, 12.1 mmol), and Cs$_2$CO$_3$ (4.73 g, 14.5 mmol) in DMF (25 mL) was heated at 50° C. for 16 h. Benzoic acid (0.735 g, 6.0 mmol) and Cs$_2$CO$_3$ (2.36 g, 7.2 mmol) were added, and the mixture heated at 80° C. for 24 h. The mixture was filtered, diluted with EtOAc (100 mL), washed with water, dried (MgSO$_4$), filtered, and concentrated in vacuo to afford 3.95 g (98%) of ketone c' as a yellow oil.

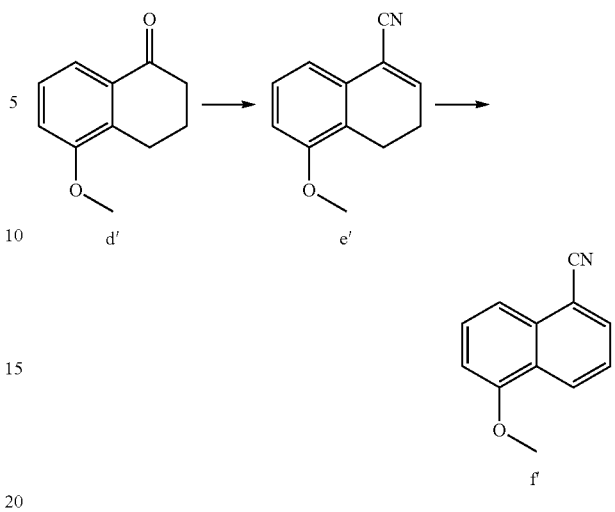

Following the general procedure of Oda (Oda, M.; Yamamuro, A.; Watabe, T. *Chem. Lett.* 1979, 1427-30), Trimethylsilyl cyanide (4.5 mL, 34.1 mmol) was added slowly into a mixture of 5-methoxy-1-tetralone d' (5.0 g, 28.4 mmol), catalytic ZnI$_2$ in toluene (12 mL). The resulting mixture was stirred at room temperature for 24 h. Pyridine (40 mL) and POCl$_3$ (8.0 mL, 85.2 mmol) were added, and the mixture was heated to reflux for 8 h. The cooled dark solution was poured into ice water (300 mL) and conc. HCl (10 mL) with stirring, extracted with EtOAc (3×400 mL). The combined organic layers were washed with brine, dried (MgSO$_4$), filtered, and concentrated to afford 4.78 g of crude unsaturated nitrile e' as a brown solid.

A mixture of the above unsaturated nitrile e' (4.78 g, 25.8 mmol) and DDQ (5.86 g, 25.8 mmol) in toluene (100 mL) was heated at 100° C. for 3.5 h. After cooling, the precipitate was removed by filtration, and washed with toluene. The combined toluene layers were washed with 0.5 N NaOH (2×100 mL), dried (MgSO$_4$), and concentrated in vacuo to afford 4.22 g (81%) of nitrile f' as a yellow solid, which was carried on without further purification.

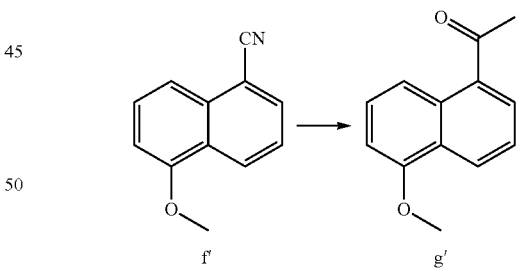

Following the general procedure for conversion of p to q, nitrile f' (2.20 g, 12.0 mmol) afforded 1.64 g (68%) of ketone g' as a brown oil.

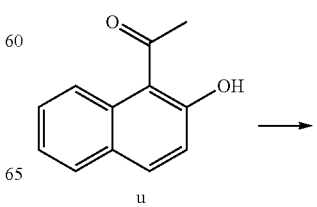

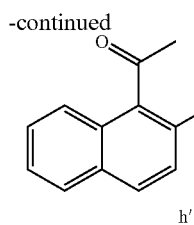

h'

(2-Chloroethoxy)trimethylsilane (8.70 mL, 53.8 mmol) was added to the mixture of 2'-hydroxy-1'-acetonaphthone u (5.0 g, 26.9 mmol), KOH (3.0 g, 53.8 mmol) in DMSO (60 mL) and water (20 mL). The resulting mixture was heated at 80° C. for 24 h. The mixture was diluted with water (400 mL). The crystalline precipitate was collected by filtration, washed with water, dried to afford 5.21 g (84%) of hydroxy ketone h' as a brown solid.

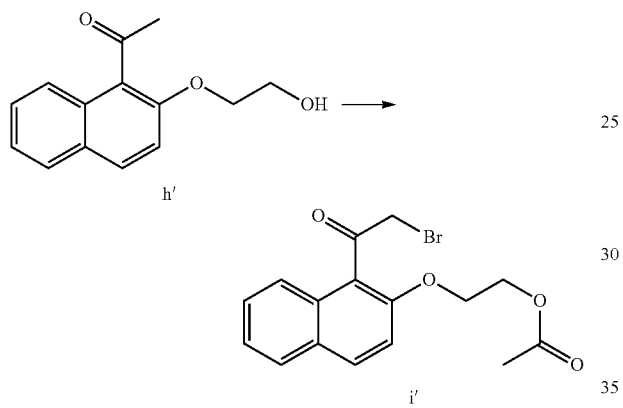

Bromine (610 µl, 11.9 mmol) was added over 10 min to a solution of hydroxy ketone h' (2.50 g, 10.9 mmol) in $CH_2Cl_2$ (30 mL) and AcOH (8.0 mL) at room temperature. After 2 h, it was quenched with 10% aqueous $Na_2S_2O_3$ (5 mL), diluted with $CH_2Cl_2$ (50 mL). The layers were separated and the aqueous layer was extracted with 50 mL of $CH_2Cl_2$. The combined organics were washed with 0.5 N aqueous NaOH until the aqueous washes are basic, dried ($MgSO_4$), filtered, and concentrated to afford 3.70 g (96%) of bromo ketone i' as a dark brown oil.

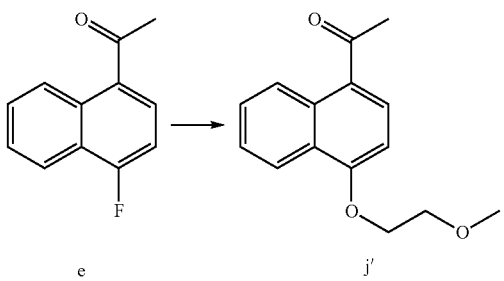 [SMILES: CC(=O)c1ccc(F)c2ccccc12 ; COCCOc1ccc(C(C)=O)c2ccccc12]

A mixture of 2-methoxyethanol (3.35 mL, 42.5 mmol) and potassium t-butoxide (4.76 g, 42.5 mmol) in THF (80 mL) was stirred at room temperature for 10 min. To this mixture was added dropwise a solution of 4-fluoro-1-acetylnaphthalene (4.0 g, 21.3 mmol) in THF (20 mL), and the mixture was stirred at room temperature for 24 h. The mixture was diluted with water (50 mL), and the phases separated. The organic layer was washed with 0.5 N NaOH, brine, dried ($MgSO_4$), filtered, and concentrated to afford 5.6 g (106%, excess wt. is solvent) of ketone has a brown liquid which solidified under high vacuum.

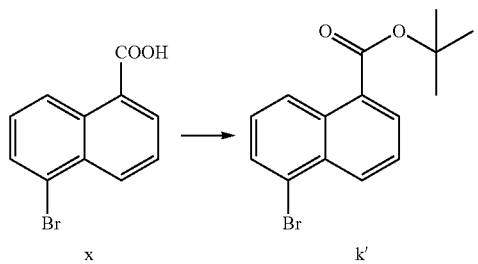 [SMILES: O=C(O)c1cccc2c(Br)cccc12 ; CC(C)(C)OC(=O)c1cccc2c(Br)cccc12]

Following the general procedure of Tagat (Tagat, J. R.; McCombie, S. W.; Nazareno, D. V.; Boyle, C. D.; Kozlowski, J. A.; Chackalamannil, S.; Josien, H.; Wang, Y.; Zhou, G. *J. Org. Chem.* 2002, 67, 1171-77), a suspension of the bromo acid x (3.0 g, 12.0 mmol) in toluene (18 mL) was heated at 80° C. To this reaction mixture was added dropwise N,N-dimethylformamide di-tert-butyl acetal (10.0 mL, 42 mmol), and the resulting mixture was heated for an additional 30 min. It was cooled to rt, washed with water, saturated aqueous $NaHCO_3$, brine, dried ($Na_2SO_4$), filtered, and concentrated in vacuo to afford 2.87 g (78%) of t-butyl ester k' as a yellow oil, which was carried on without further purification.

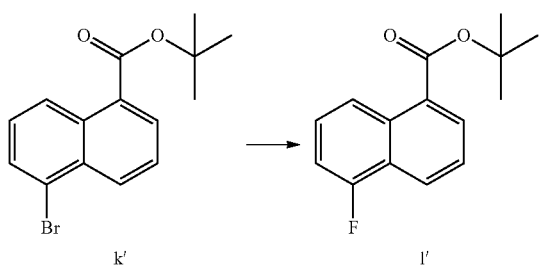 [SMILES: CC(C)(C)OC(=O)c1cccc2c(Br)cccc12 ; CC(C)(C)OC(=O)c1cccc2c(F)cccc12]

Following the general procedure of Tagat, a stirred solution of t-butyl ester k' (1.4 g, 4.5 mmol) in anhydrous THF (30 mL) was cooled to −78° C. under $N_2$. n-BuLi (3.65 mL of 1.6 M solution in hexane, 5.85 mmol) was added, and the resulting solution was stirred for 2 min, followed by addition of a solution of 7V-fluorobenzenesulfonimide (2.83 g, 9.0 mmol) in THF (10 mL). After stirring at −78° C. for 30 min, the reaction was quenched at −78° C. with saturated aqueous $NH_4Cl$. The aqueous layer was extracted with $Et_2O$ (2×50 mL), dried ($MgSO_4$), filtered, and concentrated in vacuo. The crude material was adsorbed on to Celite and purified by ISCO CombiFlash 40 g column (2-20%, EtOAc-hexane) to afford 0.57 g (52%) of fluoro compound l' as colorless liquid.

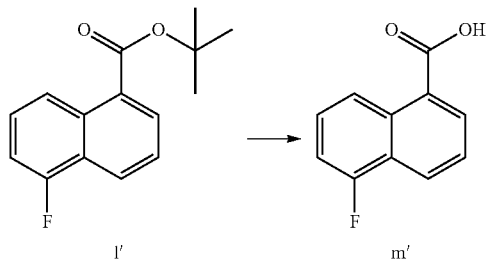 [SMILES: CC(C)(C)OC(=O)c1cccc2c(F)cccc12 ; O=C(O)c1cccc2c(F)cccc12]

Trifluoroacetic acid (3.85 mL, 50 mmol) was added to a stirred solution of fluoro compound l' (1.23 g, 5.0 mmol) in CH$_2$Cl$_2$ (50 mL) at rt. After stirring for 3 h, the solution was concentrated in vacuo to afford 0.95 g (100%) of fluoro acid m' as an oil, which was carried on.

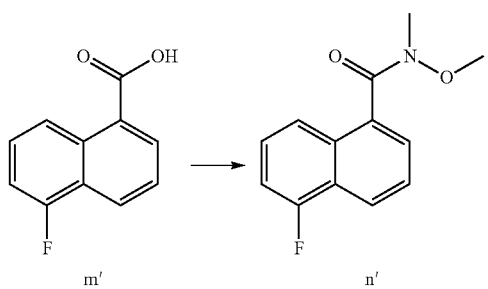 [SMILES: O=C(O)c1cccc2c(F)cccc12 ; CON(C)C(=O)c1cccc2c(F)cccc12]

A mixture of fluoro acid m' (820 mg, 4.3 mmol), N, O-dimethylhydroxyl amine hydrochloride (420 mg, 4.3 mmol), EDC (825 mg, 4.3 mmol), and DIPEA (750 µl, 4.3 mmol) in DMF (12 mL) was stirred at rt for 3 h. The mixture was diluted with EtOAc (50 mL), washed with 10% citric acid, 0.5 N NaOH, dried (MgSO$_4$), filtered, adsorbed on to Celite, and purified by ISCO CombiFlash 12 g column (2-10%, EtOAc-hexane) to afford 0.48 g (48%) of fluoro amide n' as an oil.

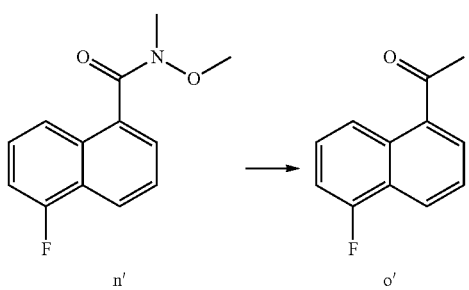 [SMILES: CON(C)C(=O)c1cccc2c(F)cccc12 ; CC(=O)c1cccc2c(F)cccc12]

To a solution of fluoro amide n' (1.07 g, 4.6 mmol) in THF at 0° C. was added dropwise a solution of CH$_3$MgCl (4.6 mL of 3 M solution in THF, 13.8 mmol). The resulting mixture was stirred at 0° C. for 1 h, then 2 h at rt. The mixture was quenched with 50% aqueous AcOH (10 mL), diluted with water (50 mL), EtOAc (50 mL), and separated. The aqueous layer was extracted with EtOAc (50 mL). The combined EtOAc layers were dried (MgSO$_4$), filtered, and concentrated to afford 0.77 g (89%) of fluoro ketone o' as an oil.

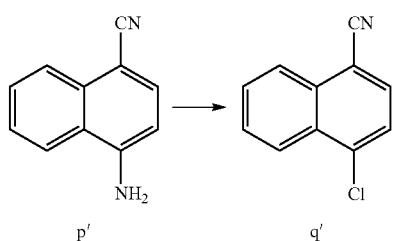 [SMILES: N#Cc1ccc(N)c2ccccc12 ; N#Cc1ccc(Cl)c2ccccc12]

Following the general procedure of Coudret (Hortholary, C.; Coudret, C. *J. Org. Chem.* 2003, 68, 2167-74), to a solution of 4-amino-1-naphthalenecarbonitrile p' (5.0 g, 29.7 mmol) in conc. HCl (50 mL) at 0° C. was carefully added sodium nitrite (3.07 g, 44.5 mmol). The mixture was stirred at 0° C. for 1 h, then transferred into an additional funnel, and added dropwise to an ice-cold solution of CuCl (5.3 g, 53.5 mmol) in water (150 mL). After addition, CH$_2$Cl$_2$ (80 mL) was added to the reaction mixture. The resulting mixture was allowed to warm to rt and was stirred for 4 h. The mixture was diluted with Cl$_2$Cl$_2$, and the phases separated. The aqueous phase was carefully extracted with CH$_2$Cl$_2$ (2×150 mL). The combined CH$_2$Cl$_2$ phases were washed once with saturated sodium thiosulfate, dried (MgSO$_4$), filtered, adsorbed on to Celite, and purified by ISCO CombiFlash 120 g column (2-12%, EtOAc-hexane) to afford 2.63 g (46%) of chloro compound q' as white solid.

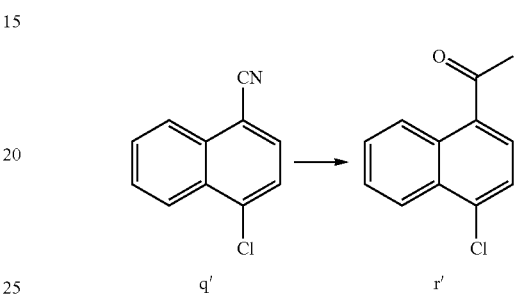

Following the general procedure for conversion of p to q, chloro compound q' (2.63 g, 14.1 mmol) afforded 2.1 g (74%) of chloro ketone r' as a yellow liquid.

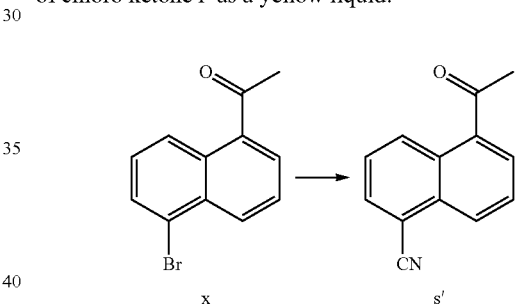

Following the procedure of Hallberg (Alterman, M.; Hallberg, A. *J. Org. Chem.* 2000, 68, 7984-89) a mixture of bromo ketone x (1.40 g, 5.62 mmol), Zn(CN)$_2$ (790 mg, 6.74 mmol), Pd(PPh$_3$)$_4$ (216 mg, 0.19 mmol) and DMF (8 mL) was heated in a microwave reactor (Emry's Optimizer) in a sealed heavy-walled tube at 180° C. for 5 min. After cooling, it was diluted with water (30 mL), extracted with EtOAc (50 mL), dried (MgSO$_4$), filtered, adsorbed on to Celite, and purified by ISCO CombiFlash 40 g column (5-20%, EtOAc-hexane) to afford 900 mg (83%) of nitrile ketone s' as white solid.

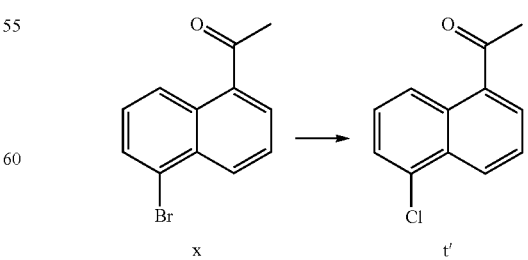

Following the procedure of Leadbeater (Arvela, R.; Leadbeater, N. E. *SynLett.* 2003, 8, 1145-48), a mixture of bromo ketone x (100 mg, 0.40 mmol), NiCl$_2$ (103 mg, 0.80 mmol) and DMF (2 mL) was heated in a microwave reactor (Emry's Optimizer) in a sealed heavy-walled tube at 200° C. for 8 min. After cooling, it was diluted with water (15 mL), extracted with EtOAc (20 mL), dried (MgSO$_4$), filtered, adsorbed on to Celite, and purified by ISCO CombiFlash 4 g column (5-15%, EtOAc-hexane) to afford 55 mg (68%) of chloro ketone t' as off white solid.

Example 5

Bromination of Methyl Ketones and Preparation of Thiazoles

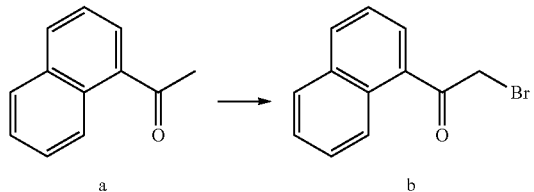

Bromine (260 µl, 5.07 mmol), was added over 20 min to a solution of ketone a (784 mg, 4.6 mmol) in CH$_2$Cl$_2$ (10 mL). The solution was maintained at rt for 1 h, then quenched with 10% aqueous Na$_2$S$_2$O$_3$ (10 mL) and stirred vigorously for 20 min. The layers were separated and the organic phase washed with saturated aqueous NaHCO$_3$ (1×10 mL), brine (1×10 mL), dried (Na$_2$SO$_4$), filtered, and concentrated to afford 1.15 g of bromo ketone b as a yellow oil. Analysis by $^1$H NMR indicates a 70:15:15 mixture of product to starting ketone and dibrominated material.

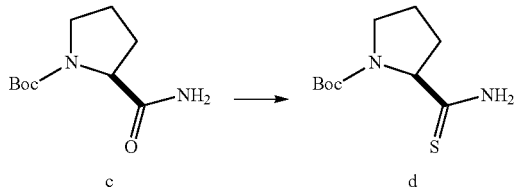 [SMILES: CC(C)(C)OC(=O)N1CCC[C@H]1C(N)=O ; CC(C)(C)OC(=O)N1CCC[C@H]1C(N)=S]

A particular procedure: A mixture of Boc-proline-amide c (8.4 g, 39.2 mmol), Lawesson's reagent (8.25 g, 20.4 mmol) and toluene was heated at 50° C. for 1 h (use of higher temperatures results in loss of enantiopurity). The mixture was then adsorbed onto Celite, and purified by chromatography (ISCO, 120 g silica column, gradient elution 10-70% EtOAc-hexanes) to afford 7.6 g (84%) of the thioamide d as a colorless solid.

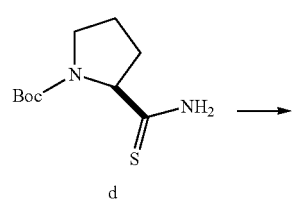

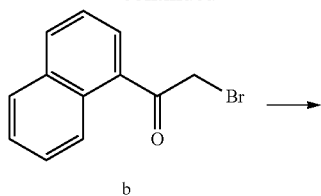

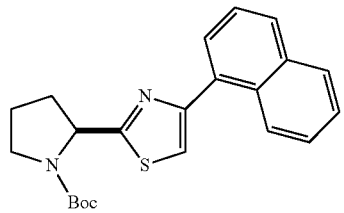

A particular procedure for thiazole formation: A mixture of thioamide d (7.81 g, 34 mmol), bromoketone b (7.05 g, 80% pure by $^1$H NMR, 22.6 mmol), pyridine (1.76 mL, 20.3 mmol) and ethanol (75 mL) was heated at 80° C. for 1 h. The ethanol was removed under reduced pressure, and the residue was adsorbed onto Celite. The residue was chromatographed (SiO$_2$, gradient elution 0-2.5-5% EtOAc/CH$_2$Cl$_2$) to afford 6.3 g (73%) of thiazole e as a colorless solid.

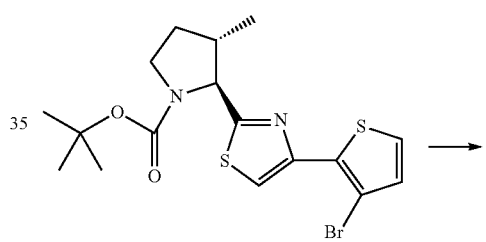

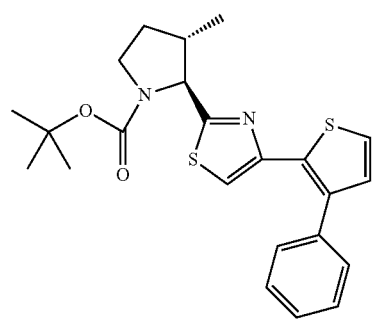

A mixture of bromide f (145 mg, 0.33 mmol), PhB(OH)$_2$ (107 mg, 0.88 mmol), K$_2$CO$_3$ (825 µl of 2.0 M aqueous solution, 1.65 mmol), Pd(PPh$_3$)$_4$ (15 mg, 0.13 mmol), and 20% EtOH-toluene (2.5 mL) was maintained at 80° C. for 3 h. The mixture was diluted with CH$_2$Cl$_2$ (10 mL), and washed with 1 N NaOH (2×5 mL). The combined aqueous layers were extracted with CH$_2$Cl$_2$ (1×10 mL). The combined organic phases were washed with brine (1×10 mL), dried (Na$_2$SO$_4$), filtered, adsorbed on to Celite, and purified by flash chromatography (SiO$_2$, 10-15-20% acetone-hexanes) to afford 74 mg (52%) of thiazole g as a colorless solid.

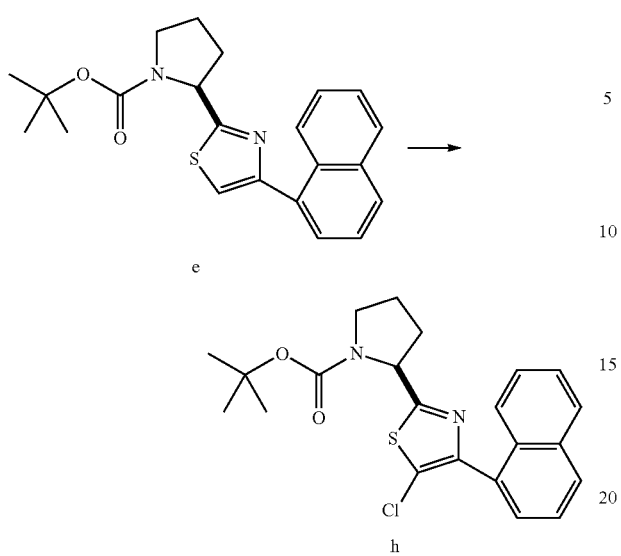

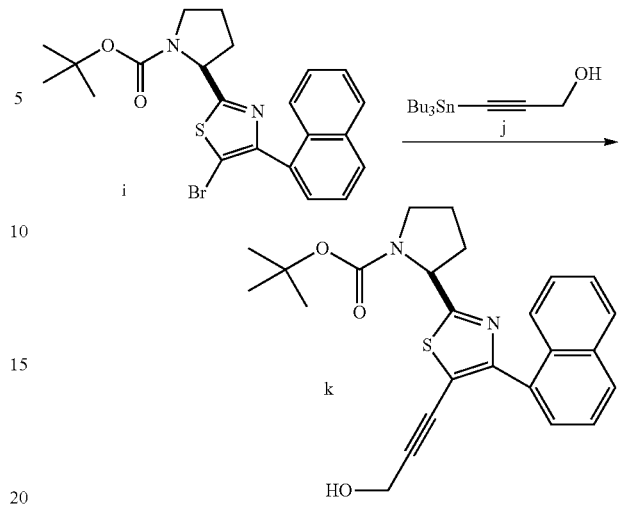

Thiazole e (70 mg, 0.18 mmol) in 1:1 dichloromethane: hexanes (1.5 mL), was treated with N-chlorosuccinimide (30 mg 0.22 mmol). The reaction mixture was stirred at rt for 2 h, at which point additional NCS (10 mg) was added and the mixture stirred overnight. Celite was added, and the dichloromethane was removed under reduced pressure. The product was purified by chromatography (ISCO, 12 g silica column, gradient elution 0-30% EtOAc/hexanes) to afford 70 mg (99%) of chlorothiazole h.

Following literature precedent ((1) Maguire, M. P.; Sheets, K. R.; McVety, K.; Spada, A. P.; Zilberstein, A. *J. Med. Chem.* 1994, 37, 2129-2137; (2) Moreno, I.; Tellitu, I.; Dominguez, E.; SanMartin, R.; *Eur. J. Org. Chem.* 2002, 2126-2135) a mixture of bromothiazole i, (280 mg, 0.61 mmol) and alkynylstannane j (Dabdoub, M. J.; Dabdoub, V. B.; Baroni, A. C. M. *J. Am. Chem. Soc.* 2001, 123, 9694-9695) (250 mg, 0.73 mmol), LiCl (approximately 50 mg, 120 mmol) and toluene (6 mL) was degassed with nitrogen for 30 min. Tetrakis(triphenylphosphine)palladium(0) (28 mg, 0.02 mmol), was added and the mixture was heated at 100° C. 3 h. After cooling, Celite was added to the mixture, and the solvents were removed under reduced pressure. The residue was purified by chromatography (ISCO, 12 g silica column, column was first flushed with $CH_2Cl_2$ for 5 minutes and then a gradient of 0-20% EtOAc/$CH_2Cl_2$ gradient over 10 minutes.) to afford 160 mg (60%) of alcohol k.

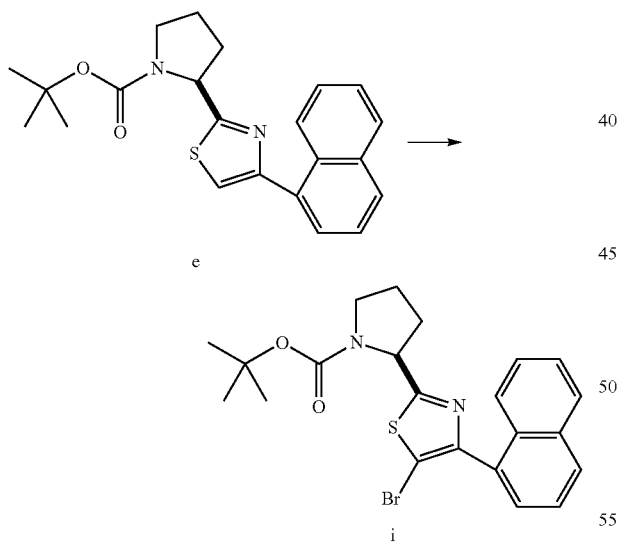

Thiazole e (120 mg, 0.31 mmol) in dichloromethane (1.5 mL), was treated with N-bromosuccinimide (65 mg 0.37 mmol). The reaction mixture was stirred at room temperature for 3 h. After this period, Celite was added, and the dichloromethane was removed under reduced pressure. The product was purified by chromatography (ISCO, 12 g silica column, column was first flushed with $CH_2Cl_2$ for 7 minutes and then a gradient of 0-9% EtOAc/$CH_2Cl_2$ gradient over 9 minutes.) to afford 128 mg (90%) of bromide i.

Following literature precedent (Neidlein, R.; Nussbaumer, T *Heterocycles*, 2000, 52, 349), bromide i (600 mg, 1.3 mmol), TMS-acetylene l (1.8 mL, 13 mmol) and TMG (0.6 mL, 5 mmol), were dissolved in dimethylacetamide (6 mL). This mixture was degassed with nitrogen for 30 min. Bis(triphenylphosphine)palladium dichloride (46 mg, 0.07 mmol) and copper(I) iodide (62 mg, 0.3 mmol) were added and the mixture was sealed and heated at 70-° C. for 30 minutes. The mixture was diluted with ½-saturated ammonium chloride and filtered through a pad of celite. The aqueous mixture was extracted with 70% diethyl ether in hexane (3×20 mL), dried (Na₂SO₄), filtered, adsorbed on to Celite, and chromatographed (ISCO, 40 g column and a solvent gradient of 0-11% ethyl acetate in hexane after flushing with hexane for 3 minutes). Terminal alkyne product 27 mg (5%) was isolated along with 200 mg of silyl derivative. The TMS group was removed from this material by treatment with potassium carbonate (200 mg) in methanol (5 mL) for 3 hours at rt. Celite and toluene (1 mL) were added to the mixture, and the solvents were removed under reduced pressure. The product was purified by chromatography (ISCO 40 g column, solvent gradient of 0-11% ethyl acetate/hexane after flushing with pure hexane for 3 minutes), to afford a further 110 mg of terminal alkyne m (26% combined).

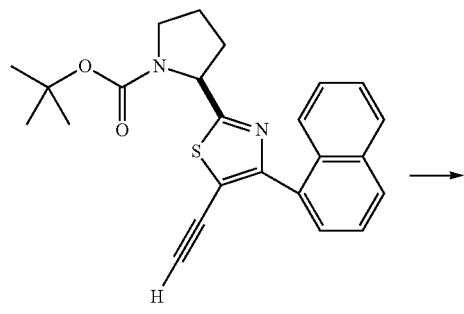

m

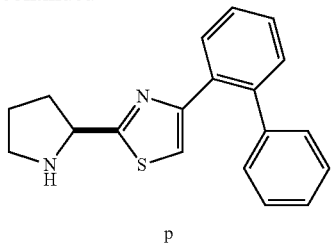

p

Typical Boc deprotection: Carbamate o (75 mg, 0.18 mmol) was treated with TFA (2 mL) and water (2 drops), in CH₂Cl₂ (2 mL) for 2 h. The volatiles were removed under reduced pressure, the residue dissolved in ethyl acetate (10 mL) and washed with 1 N NaOH (3×3 mL). The combined aqueous layers were extracted with ethyl acetate (1×2 mL). The combined organic phases were washed with brine (1×3 mL), dried (Na₂SO₄), filtered, and concentrated to provide quantitative yield of amine p.

Example 6

Linear Coupling Procedure

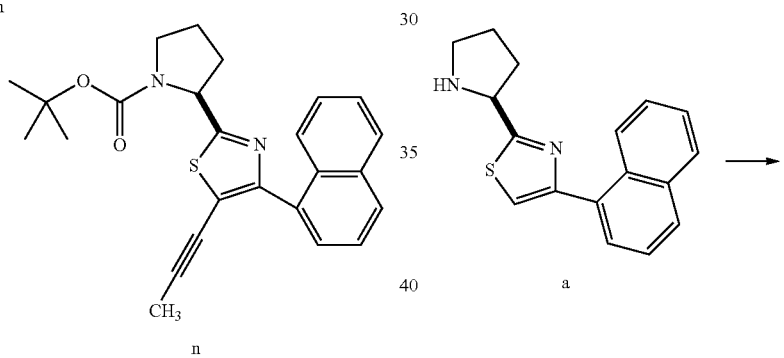

n                                                              a

Terminal alkyne m (50 mg, 0.12 mmol) was dissolved in THF (0.3 mL) and cooled to −78° C. LHMDS (0.15 mL of a 1.0 M solution of in THF, 0.15 mmol) was added dropwise and allowed to stir for 10 minutes. Methyl iodide (0.1 mL, excess) was added, the reaction was stirred for 10 minutes at −78° C. and then allowed to gradually warm to rt, over 45 minutes. Celite was then added to the reaction mixture, the solvents were evaporated under reduced pressure, and the residue purified by chromatography (ISCO, 12 g, column gradient elution 0-18% ethyl acetate in hexane) to afford 25 mg (63%) of the methyl alkyne n.

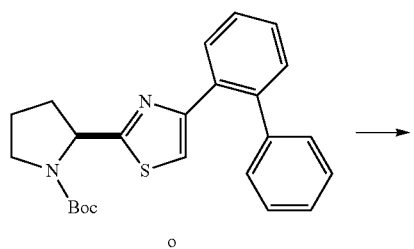

o

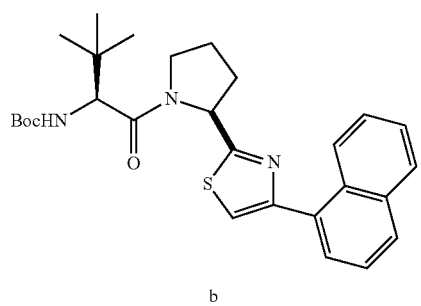

b

Typical HATU coupling: A mixture of amine a (169 mg, 0.59 mmol), N-Boc-t-butly glycine (150 mg, 0.65 mmol), HATU (450 mg, 1.18 mmol), DIPEA (200 μl, 1.18 mmol) and DMF (2 mL) was maintained at rt for 2 h. The solution was diluted with ethyl acetate (50 mL) and washed with 1 N HCl (3×10 mL), 1 N NaOH (3×5 mL), brine (1×10 mL), dried (Na₂SO₄), filtered, and concentrated. The residue was purified by flash chromatography (SiO-₂, 10-15-20% ethyl acetate-hexanes) to afford 286 mg (97%) of amide b as a colorless solid.

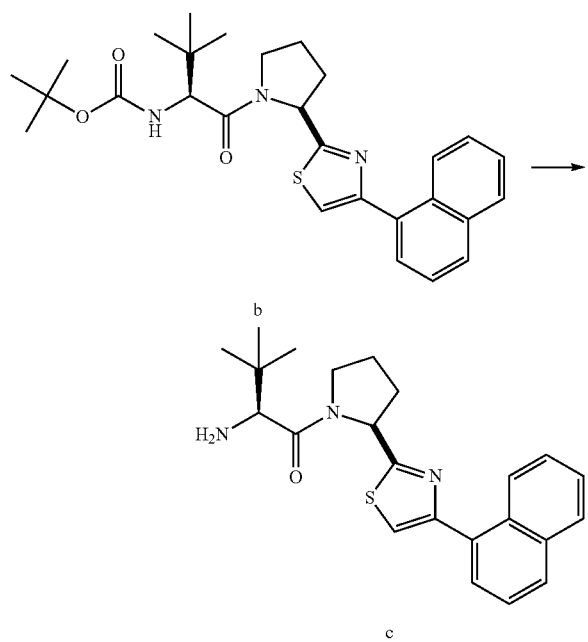

b

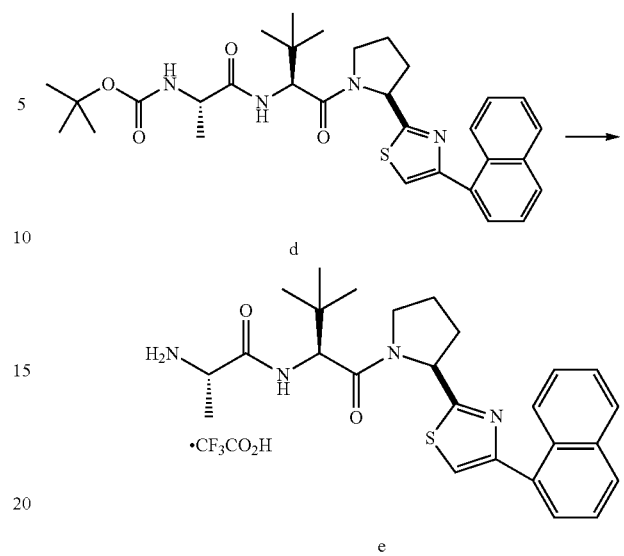

d

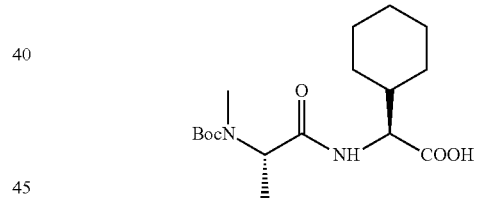

e

Following the general Boc deprotection procedure described above, Boc amine b (317 mg, 0.64 mmol) afforded a quantitative yield of amine c as a colorless solid.

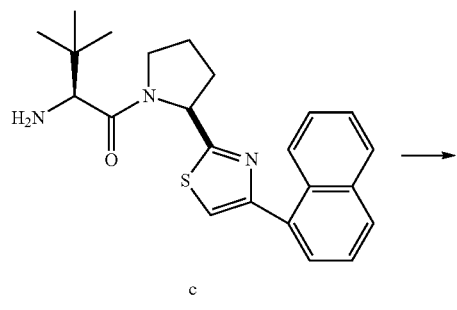

c

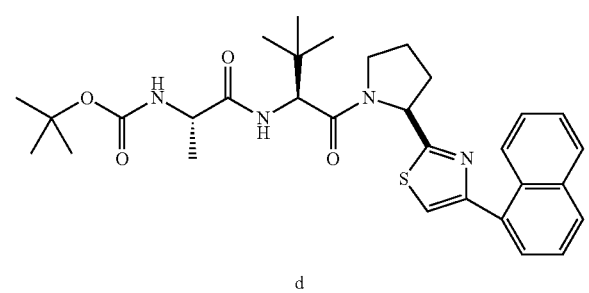

d

Typical EDC coupling: A solution of amine c (300 mg, 0.76 mmol), N-Boc-alanine (158 mg, 0.84 mmol), EDC (161 mg, 0.84 mmol), catalytic DMAP and MeCN (3 mL) was maintained at rt for 3 h. The solution was diluted with ethyl acetate (50 mL) and washed with 1 N HCl (3×10 mL), 1 N NaOH (3×5 mL), brine (1×10 mL), dried ($Na_2SO_4$), filtered, and concentrated to provide 453 mg of crude residue d, which was carried on directly:

Typical final Boc removal and purification: The crude residue d from above was treated with TFA (2 mL) and water (2 drops), in $CH_2Cl_2$ (2 mL) for 2 h. The volatiles were removed under reduced pressure. The residue was purified by reverse-phase HPLC ($C_{18}$, MeCN—$H_2O$, 0.1% TFA) and the solvents removed by lyophylization to provide 166 mg (38% for 2 steps) of amine e as a colorless powder.

Example 7

N-Boc-N-methyl-L-alanine-L-cyclohexylglycine

A solution of Fmoc-L-cyclohexylglycine (3.6 g, 9.6 mmol) dissolved in DCM (50 mL) and DIPEA (5.6 mL, 32 mmol) was added to 2-chlorotrityl chloride resin (5 g, 8 mmol) and gently agitated for 3 hours at room temperature. The resin was washed with DCM 4 times, DCM/MeOH/DIPEA (17:2:1) 3 times, DCM 3 times, and 2 times dimethylacetamide (DMA). The Fmoc group was removed by treating the resin with 20% piperidine/DMA (50 mL) for 15 minutes. The resin was washed with DMA 6 times. A solution of Boc-N-methylalanine (3.3 g, 16 mmol), HBTU (6.1 g, 16 mmol), and DIPEA (5.6 mL, 32 mmol) and DMA/DCM (1:1, 50 mL) was added to the resin and gently agitated for 2 hours at room temperature. The resin was washed with DMA 5 times, DCM 2 times, and dried under reduced pressure. The dipeptide was cleaved from the resin by gentle agitation with HOAc/TFE/DCM (1:1:3, 100 mL) for 2 hours at room temperature. The resin was removed by filtration and the solution concentrated. Residual AcOH was removed by azeotroping with hexanes (15 times volume). The solid residue was purified by reverse-phase HPLC ($C_{18}$, MeCN—$H_2O$, 0.1% TFA) and the solvents removed by lyophylization to provide 1.2 g (43%) of dipeptide N-Boc-N-methyl-L-alanine-L-cyclohexylglycine as a white powder.

Example 8

N-Boc-N-methyl-L-alanine-L-dehydropyranylglycine

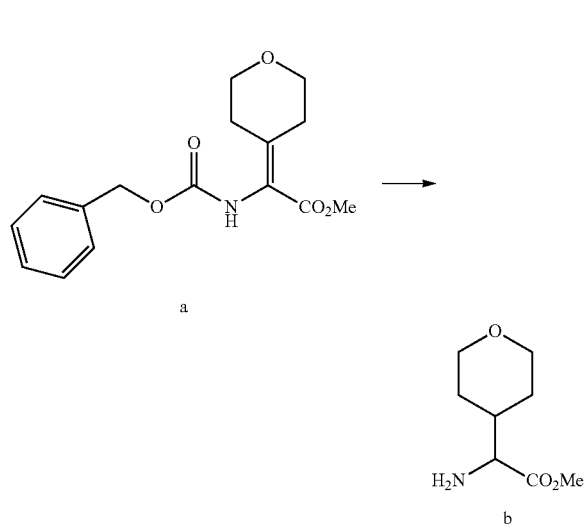

A mixture of N-Cbz-dehydropyranylglycine methyl ester a (Burk, M. J.; Gross, M. F.; Martinez, J. P. *J. Am Chem. Soc.* 1995, 117, 9375, and references therein) (5.2 g, 17 mmol), 5% Pd. C (500 mg), MeOH (75 mL) and THF (25 mL) was maintained under an atmosphere of $H_2$ for 24 h. The mixture was filtered through Celite and the Celite washed with MeOH, and concentrated under reduced pressure to afford a quantitative yield of amine b as a colorless oil, which was carried on directly.

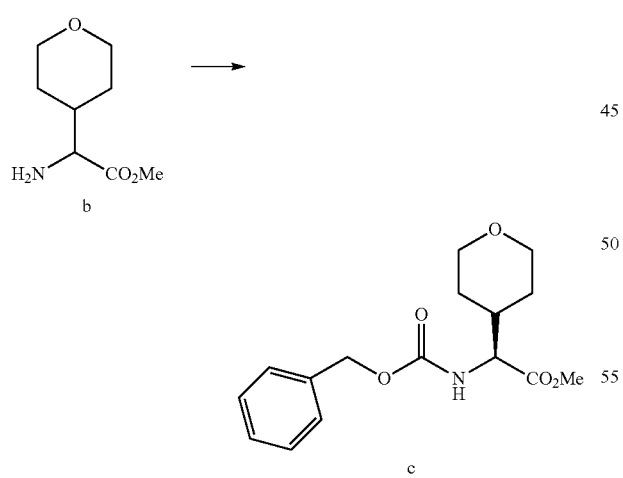

The amine b prepared above was combined with $CH_2Cl_2$ (40 mL), saturated aqueous $NaHCO_3$ (40 mL) and cooled to 0° C. Benzyloxy carbonyl chloride (3.0 mL) was then added dropwise and the mixture stirred vigorously overnight. The phases were separated and the aqueous phase extracted with $CH_2Cl_2$ (3×20 mL). The combined organic phases were washed with brine (1×50 mL), dried ($Na_2SO_4$), filtered, and adsorbed onto Celite and chromatographed (ISCO, 120 g silica column, gradient elution 5-55% EtOAc-hexanes) to afford 4.15 g (80%) of racemic Cbz-pyranylglycine methyl ester. The enantiomers were separated on a Chiracel OD column eluting with 10% EtOH-hexanes. The desired S-enantiomer c elutes first under these conditions.

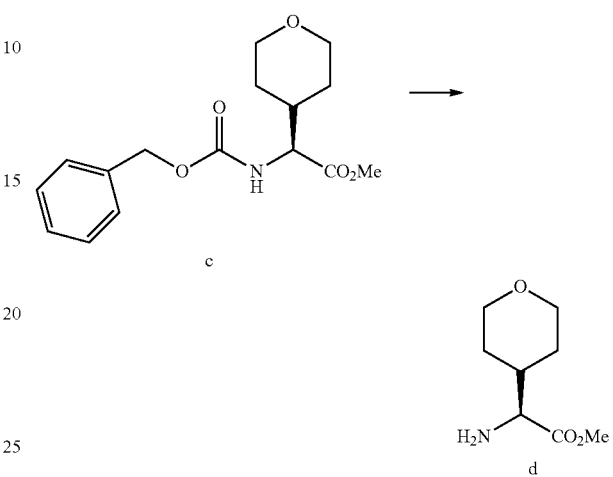

A mixture of (S)—N-Cbz-pyranyl glycine c methyl ester (2.4 g, 7.82 mmol) 10% Pd.C (700 mg), MeOH (80 mL) was maintained under 1 atmosphere of $H_2$ for 24 h. The mixture was filtered through Celite with MeOH, and concentrated under reduced pressure to afford 1.35 g (100%) of amine d as a colorless oil. Alternatively, pyranyl glycine can be synthesized in enantiopure form following the procedure of Ghosh (Ghosh, A. K.; Thompson, W. J.; Holloway, M. K.; McKee, S. P.; Duong, T. T.; Lee, H. Y.; Munson, P. M.; Smith, A. M.; Wai, J. M.; Darke, P. L.; Zugay, J. A.; Imini, E. A.; Schleif, W. A.; Huff, J. R.; Anderson, P. S. *J. Med. Chem.*, 1993, 36, 2300).

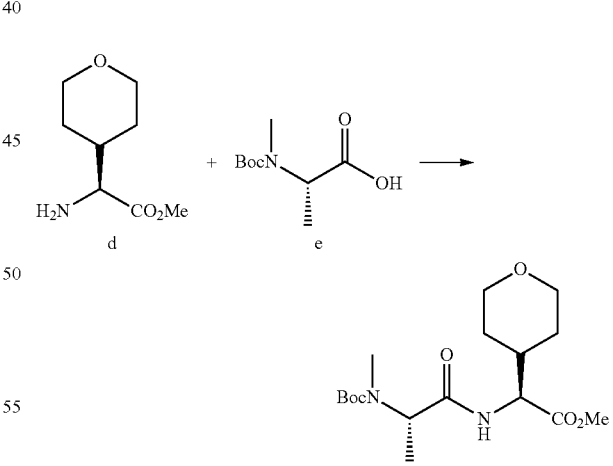

A mixture of amine d (1.35 g, 7.8 mmol), N-Boc-N-methyl alanine e (1.74 g, 8.6 mmol), EDC (1.65 g 8.8 mmol) and MeCN (50 mL) was maintained at rt overnight. The MeCN was removed under reduced pressure, and the residue diluted with EtOAc, washed with 0.5 N HCl (3×10 mL), 0.5 N NaOH (3×10 mL), dried ($MgSO_4$), filtered, and concentrated to provide 2.1 g (75%) of protected dipeptide f, as a clear oil.

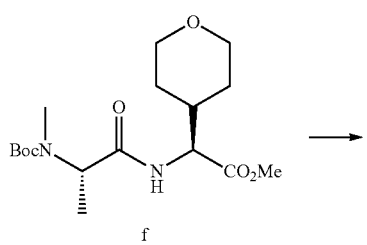

f

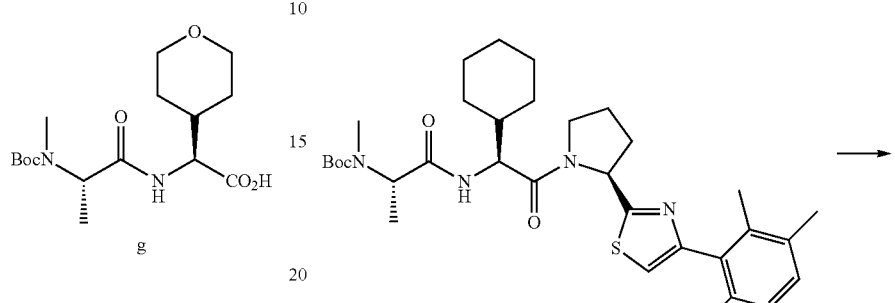

To a 0° C. solution of ester f (2.10 g, 5.86 mmol) and THF (50 mL) were added LiOH.H$_2$O (1.23 g, 29.3 mmol) and water (2 mL). The mixture was maintained at 0° C. for 2 h, then the cooling bath was removed and the mixture was stirred overnight. Most of the THF was then removed under reduced pressure and the residue was diluted with CH$_2$Cl$_2$, washed with 0.5 N HCl, dried (MgSO$_4$), filtered, and concentrated to provide 1.53 g (78%) of dipeptide N-Boc-N-methyl-L-alanine-L-dehydropyranylglycine g, as a colorless solid.

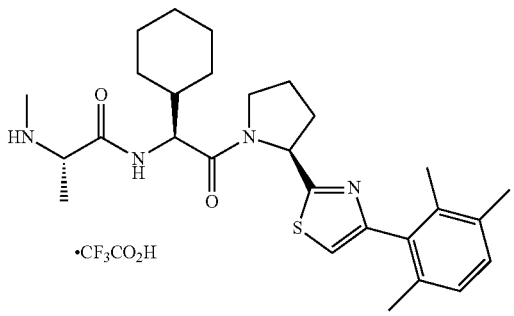

i

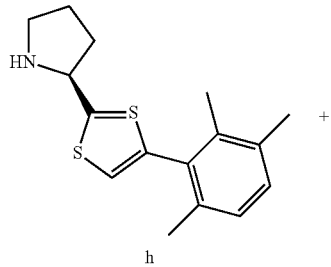

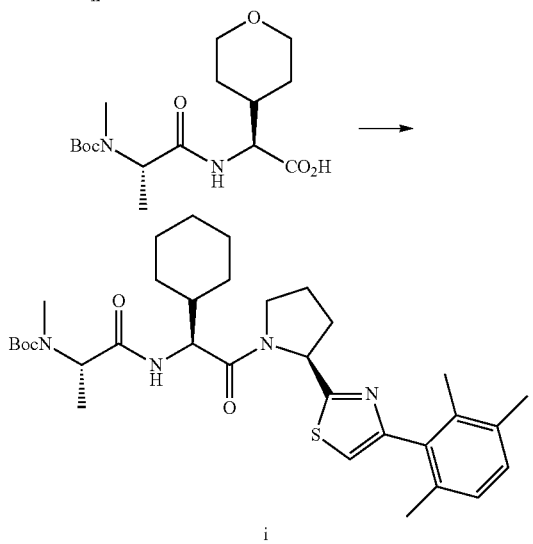

i

A particular procedure for convergent coupling: A mixture of amine h (69 mg, 0.26 mmol), dipeptide N-Boc-N-methyl-L-alanine-L-cyclohexylglycine from example 7 (60 mg, 0.23 mmol), HOAt (Carpino, L. A.; El-Faham, A. *Tetrahedron*, 1999, 55, 6813) (47 mg, 0.24 mmol), DIC (53 μl, 0.34 mmol) and CH$_2$Cl$_2$ (2 mL) was maintained at rt overnight. The mixture was adsorbed onto Celite and purified by chromatography (ISCO, 4 g silica column, gradient elution 5-50% EtOAc-hexanes) to afford 94 mg of the product i as a colorless solid contaminated with diisopropyl urea. The mixture was carried on directly to the next step.

The crude residue i from above was treated with TFA (2 mL) and water (2 drops), in CH$_2$Cl$_2$ (2 mL) for 2 h. The volatiles were removed under reduced pressure. The residue was purified by reverse-phase HPLC (C$_{18}$, MeCN—H$_2$O, 0.1% TFA) and the solvents removed by lyophylization to provide 77 mg (54% for 2 steps) of amine salt 1 as a colorless powder.

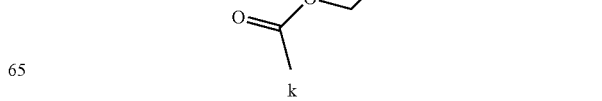

k

-continued

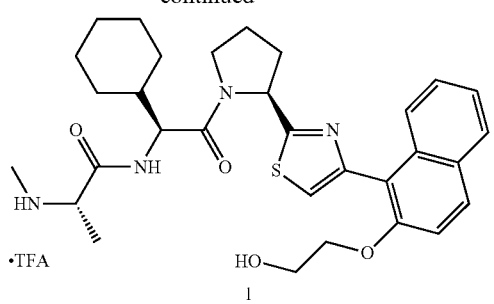

A mixture of the Acetate product k (228 mg, 0.32 mmol), K₂CO₃ (53 mg, 0.38 mmol) in aqueous methanol (1:2, v:v, 15 mL) was stirred at rt for 1 h. Methanol was removed in vacuo. The residue was diluted with water, extracted with CH₂Cl₂ (1×50 mL), and the organic phase dried (MgSO₄), and concentrated in vacuo to afford a crude product. Conversion to the amine salt 1 was accomplished in 18% yield (3 steps) following the general procedure.

Example 8

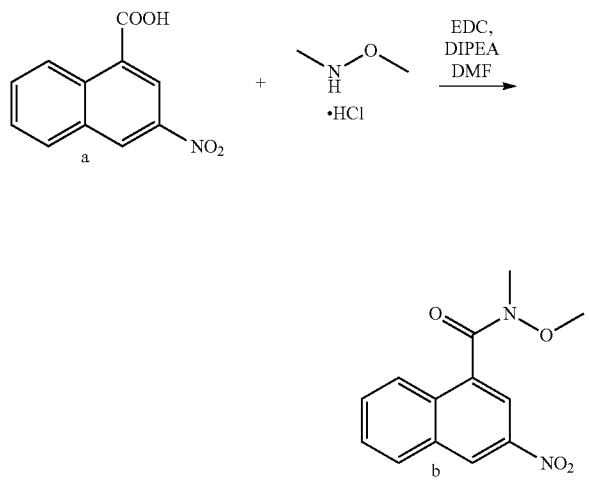

A mixture of acid a (1.5 g, 6.9 mmol) prepared according to the procedures of described in Kice et al. (*J. Org. Chem.* 1989, 54, 3596-3602), amine HCl salt (868 mg, 8.9 mmol), EDC (1.3 g, 6.9 mmol), and DIPEA (1.2 mL, 6.9 mmol) in DMF (17 mL) was stirred at RT for overnight. The mixture was diluted with EtOAc (50 mL), washed with 0.5 N HCl, 0.5 N NaOH, dried (MgSO₄), filtered, concentrated in vacuo to afford 1.3 g (74%) of amide b as a yellow solid, which was carried on without further purification.

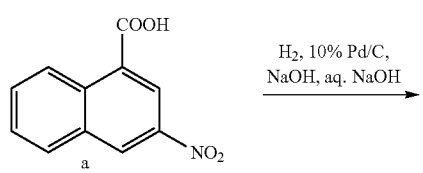

10% Pd/C (200 mg) was added into a solution of acid a (500 mg, 2.3 mmol), NaOH (92 mg, 2.3 mmol) in EtOH (25 mL) and water (5 mL) in a Parr reactor. This mixture was purged with N₂ for 10 min, then hydrogenated with a Parr hydrogenator at 50 psi at RT for 2.5 h. The resulting mixture was filtered through Celite, concentrated in vacuo to afford 50 mg (104%) of amine salt b as a greenish-brown solid.

Example 10

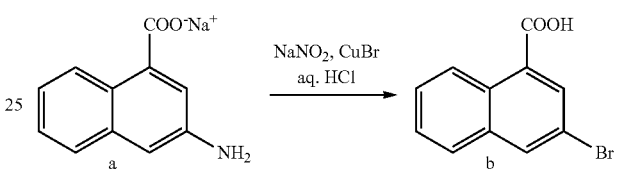

To a stirred mixture of the amine salt a (500 mg, 2.4 mmol) in 6N HCl (30 mL), cooled at 0° C., was added NaNO₂ (248 mg, 3.6 mmol) in one portion (caution was used due to elevated reaction temperature). After stirred at 0° C. for 1 h, this solution was added drop wise, via a dropping funnel, over 20 min to an ice-water cold solution of CuBr (618 mg, 4.3 mmol) in water (30 mL). Then dichloromethane (40 mL) was added to slowly to the reaction mixture (caution was used due to foaming). The resulting mixture was allowed to reach RT and was stirred for 4 h. It was diluted with CH₂Cl₂ (100 mL), separated, washed the aqueous layer with another portion of CH₂Cl₂ (100 mL). The combined CH₂Cl₂ were washed once with sat. aq. Na₂S₂O₃, dried (MgSO₄), and concentrated in vacuo. The crude product was adsorbed on to Celite and purified by ISCO CombiFlash 12 g column (20-100% ethyl acetate-hexane) to afford 175 mg (29%) of bromo acid b as a light yellow solid.

Example 11

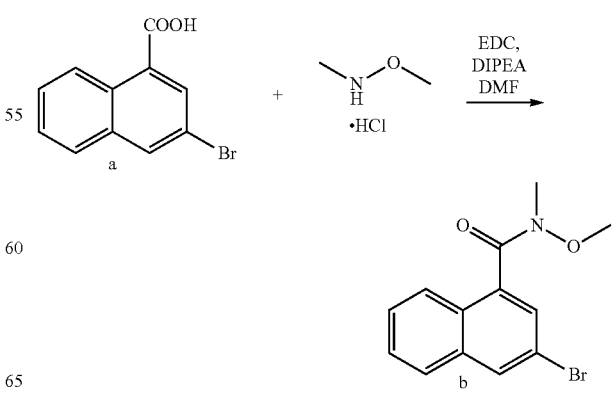

A mixture of bromo acid a (680 mg, 2.7 mmol), amine HCl salt (264 mg, 2.7 mmol), EDC (520 mg, 2.7 mmol), and DIPEA (472 µL, 2.7 mmol) in DMF (10 mL) was stirred at RT for overnight. The mixture was partition between water (50 mL) and EtOAc (100 mL), separated, washed the aqueous layer with another portion of EtOAc (100 mL). The combined organic were washed with 1N HCl (50 mL), 1N NaOH (50 mL), dried (MgSO₄), filtered, concentrated in vacuo. The crude product was adsorbed on to Celite and purified by ISCO CombiFlash 12 g column (10-50% ethyl acetate-hexane) to afford 300 mg (38%) of bromo amide b as a yellow oil.

Example 12

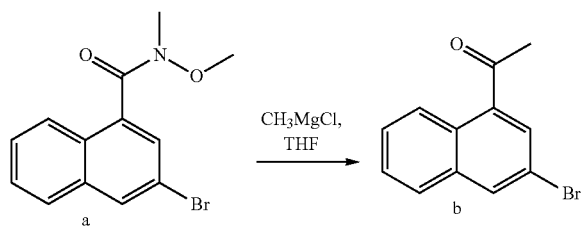 [SMILES: CON(C)C(=O)c1cc(Br)cc2ccccc12 ; CC(=O)c1cc(Br)cc2ccccc12]

To a solution of bromo amide a (300 mg, 1.0 mmol) in THF (8 mL) at 0° C. was added drop wise a solution of CH₃MgCl (2.0 mL of 3 M solution in THF, 6.0 mmol). The resulting mixture was stirred for 1 h, and then allowed to warm to RT for 2 h. The mixture was quenched with 50% aq. AcOH (4 mL), diluted with water (50 mL) and EtOAc (50 mL), separated. The aqueous layer was extracted with EtOAc (50 mL). The combined EtOAc were dried (MgSO₄), filtered, and concentrated. The crude product was adsorbed on to Celite and purified by ISCO CombiFlash 12 g column (2-10% ethyl acetate-hexane) to afford 150 mg (60%) of bromo ketone b as light yellow oil. Compound b may also be prepared employing the procedures described by Alvaro et al. (WO 2004099143) and Tsuno et al. (*Bull. Chem. Soc. of Japan* 1975, 48(11), 3347-55).

Example 13

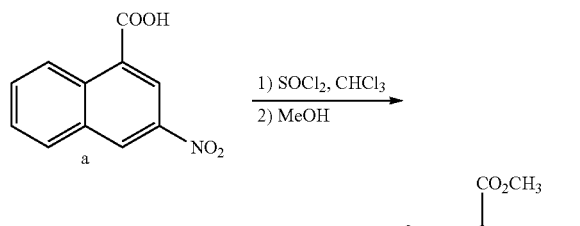

The starting acid a (6.6 g, 30.4 mmol) was treated with thionyl chloride (50 mL), CHCl₃ (50 mL), and 1 drop of DMF at 78° C. for 5 h. The resulting mixture was concentrated in vacuo, dried under high vacuum for overnight. The resulting yellow solid was cooled in an ice-water bath and MeOH (200 mL) was added slowly. This was then refluxed for 1 h. After cooled to RT, the resulting precipitate was collected by filtration, washed with cold MeOH, and dried to afford 5.0 g (71%) of ester b as a yellow solid.

Example 14

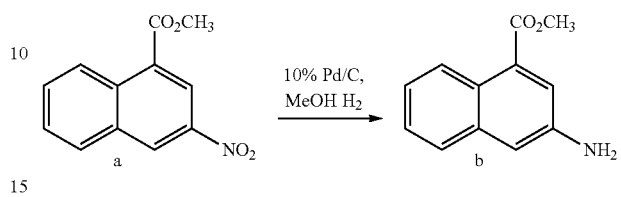

A suspension of ester a (5.0 g, 21.6 mmol) and 10% Pd/C (1.2 g) in MeOH (200 mL) was purged with N₂ for 5 min, then treated with a balloon of H₂ at RT until the reaction is completed (checked by LCMS). After purging the reaction mixture with N₂ for 10 mim, the mixture was filtered through Celite, washed with MeOH, concentrated in vacuo, and high vacuum dried to afford 4.2 g (97%) of amine b as a brown oil.

Example 15

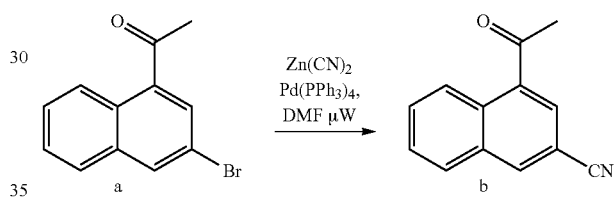

A mixture of bromo ketone a (285 mg, 1.1 mmol), Zn(CN)₂ (400 mg, 3.4 mmol), and Pd(PPh₃)₄ (88 mg, 0.076 mmol) in DMF (2 mL) was heated in a microwave at 200° C. for 600 sec. After cooled, diluted with water (10 mL), extracted with EtOAc (2×10 mL). The insoluble material was removed by filtration; the solvent was dried (MgSO₄), and concentrated. The crude product was adsorbed on to Celite and purified by ISCO CombiFlash 12 g column (5-20% ethyl acetate-hexane) to afford 147 mg (66%) of nitrile ketone b as a white solid. Compound a may also be prepared employing the procedures described by Alvaro et al. (WO 2004099143) and Tsuno et al. (*Bull. Chem. Soc. of Japan* 1975, 48(11), 3347-55).

Example 16

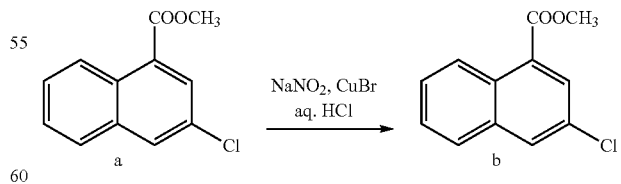

To a suspension of amine a (4.2 g, 20.9 mmol) in 6 N HCl (100 mL), cooled in ice-water bath, was added NaNO₂ (2.2 g, 31.4 mmol) in portions (caution was used due to elevated reaction temperature). After stirred at ice-water temperature for 1 h, this cold solution was added drop wise onto an ice-cold solution of CuBr (5.4 g, 37.6 mmol) in water (150 mL). After addition, CH$_2$Cl$_2$ (80 mL) was added slowly to the mixture. The reaction mixture was allowed to reach RT and was stirred for 4 h. It was diluted with more CH$_2$Cl$_2$ (50 mL). The phases were separated. The aqueous phase was extracted with CH$_2$Cl$_2$ (2×50 mL). The combined CH$_2$Cl$_2$ were washed with sat. sodium thiosulfate (100 mL), dried (MgSO$_4$), and concentrated. The crude product was adsorbed on to Celite and purified by ISCO CombiFlash 120 g column (1-8% ethyl acetate-hexane) to afford 3.1 (66%) of chloro ester b as a white solid.

Example 17

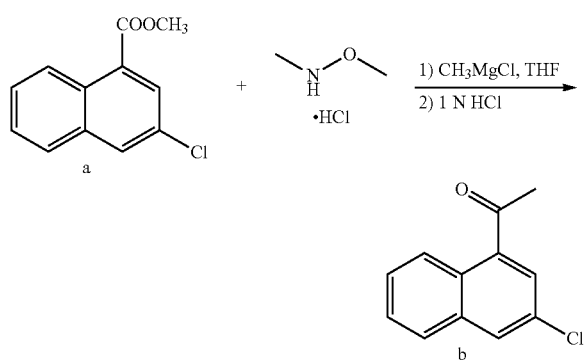

Following the general procedure of Williams et al. (*Tetrahedron Lett.* 1995, 36(31), 5461-5464), to a stirred suspension of ester a (1.5 g, 5.7 mmol) and amine (700 mg, 7.1 mmol) in THF (30 mL) at −5° C. under N$_2$ was added CH$_3$MgCl (16.1 mL of 3 M solution in THF, 48.4 mmol) over 20 min while keeping the temperature below 0° C. After 0.5 h at −5° C., the reaction mixture was allowed to warm to RT and stirred for overnight. The reaction was quenched with 1 N HCl, diluted with 1 N HCl (100 mL), heated the mixture at 35° C. for 3 h, then cooled, diluted with EtOAc (150 mL), dried (MgSO$_4$), and concentrated in vacuo. The crude product was adsorbed on to Celite and purified by ISCO CombiFlash 40 g column (1-10% ethyl acetate-hexane) to afford 900 mg (64%) of chloro ketone b as a clear liquid. Compound b may also be prepared employing the procedures described by Alvaro et al. (WO 2004099143) and Tsuno et al. (*Bull. Chem. Soc. of Japan* 1975, 48(11), 3347-55).

Example 18

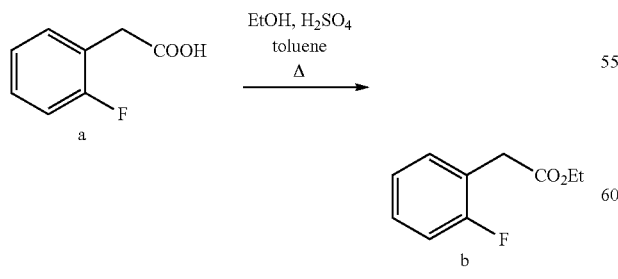

Concentrated sulfuric acid (2 mL) was added slowly to a stirred solution of 2-fluorophenylacetic acid a (10.0 g, 65.0 mmol) in toluene (100 mL) and EtOH (7.6 mL, 130 mmol).

The resulting mixture was heated at 100° C. for 1.5 h. It was concentrated in vacuo, diluted with EtOAc (200 mL), washed with 10% K$_2$CO$_3$ until the washes were basic, dried (MgSO$_4$), and concentrated in vacuo to afford 9.9 g (84%) of ester b as a light yellow oil.

Example 19

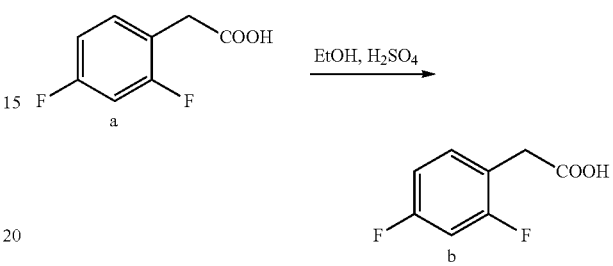

Concentrated sulfuric acid (3 mL) was added slowly to a stirred solution of 2,4 difluorophenylacetic acid a (10.0 g, 58.1 mmol) in EtOH (100 mL), stirred at RT for 2 d. It was concentrated, diluted with EtOAc (200 mL), washed with 10% K$_2$CO$_3$ until the washes were basic, dried (MgSO$_4$), and concentrated in vacuo to afford 11.1 g (95.5%) of difluoro ester b as a white solid.

Example 20

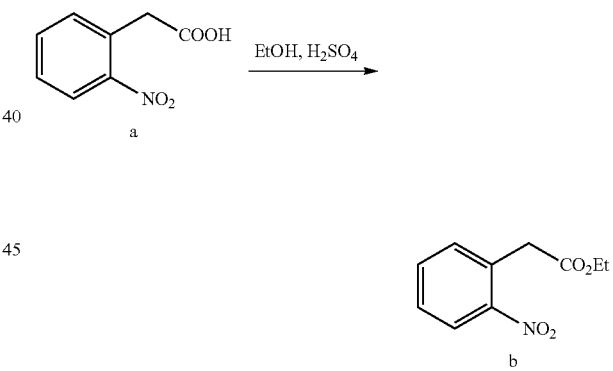

Following the procedure for preparing ester from example 19, 2-nitrophenylacetic acid a (10.0 g, 55.2 mmol) afforded 10.9 g (95%) of nitro ester b as a light yellow solid.

Example 21

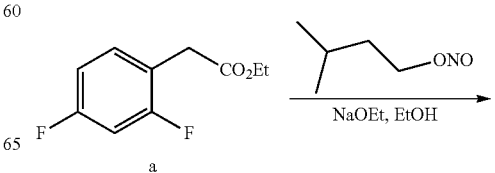

-continued

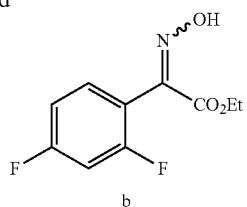

b

Following the general procedure described by Kemp et al. (*J. Am. Chem. Soc.* 1975, 97, 7305-7312), reaction of difluoro-ester a (4.0 g, 20.0 mmol), isoamyl-nitrite (3.2 mL, 24.0 mmol), and NaOEt (1.4 g, 20.0 mmol) in EtOH (40 mL), after purified by ISCO CombiFlash 80 g column (2-30% ethyl acetate-hexane) to afford 2.1 g (47%) of difluoro oxime b as a light yellow solid.

Example 22

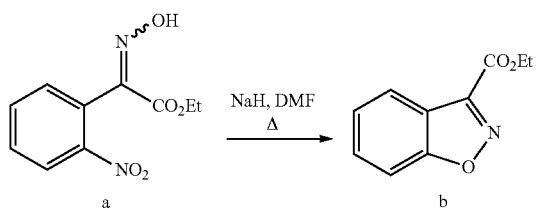 [SMILES: CCOC(=O)C(=NO)c1ccccc1[N+](=O)[O-] ; CCOC(=O)c1noc2ccccc12]

A solution of the nitro oxime a (5.0 g, 21.0 mmol) prepared according to the procedures described by Kemp et al. (*J. Am. Chem. Soc.* 1975, 97, 7305-7312) in DMF (30 mL) was added drop wise over 25 min to a vigorously stirred suspension of hexane-washed NaH (60% in mineral oil, 840 mg, 21.0 mmol) in DMF (40 mL) under $N_2$. The resulting dark colored solution was heated slowly to 130° C. for 8 h. It was diluted with water (200 mL), extracted with EtOAc (2×200 mL), washed the EtOAc with brine, dried (MgSO$_4$), and concentrated in vacuo. The crude product was adsorbed on to Celite and purified by ISCO CombiFlash 120 g column (1-10% ethyl acetate-hexane) to afford 1.6 g (41%) of benzisoxazole b as an off white solid.

Example 23

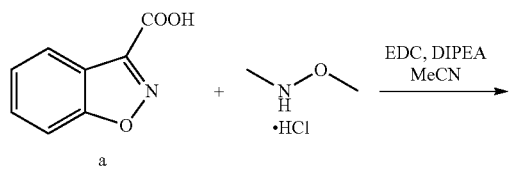

A mixture of benzisoxazole acid a (1.23 g, 7.5 mmol) prepared according to the procedures described by Kemp et al. (*J. Am. Chem. Soc.* 1975, 97, 7305-7312), amine HCl salt (736 mg, 7.5 mmol), EDC (1.44 g, 7.5 mmol), and DIPEA (1.2 mL, 6.7 mmol) in MeCN (50 mL) was stirred at RT for overnight. It was concentrated in vacuo, dissolved in EtOAc (200 mL), washed with 0.5 N HCl and water, dried (MgSO$_4$), and concentrated to afford 1.4 g (88%) of benzisoxazole amide b as an off white solid.

Example 24

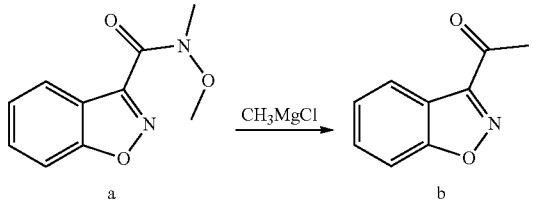

Following the procedure for preparing bromo ketone from example 12, to benzisoxazole amide a (1.2 g, 5.9 mmol) was added CH$_3$MgCl (6.0 mL of 3 M solution in THF, 17.8 mmol). The crude product was adsorbed on to Celite and purified by ISCO CombiFlash 40 g column (1-5% ethyl acetate-hexane) to afford 670 mg (71%) of benzisoxazole ketone b as a white crystalline. Compound b may also be prepared according to the procedures described by Smalley et al. (*Science of Synthesis* 2002, 11, 289-335) and Farooq et al. (WO 9614305).

Example 25

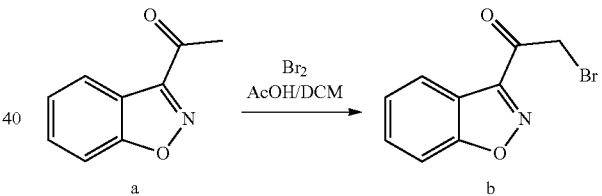

Bromine (184 μL, 3.6 mmol) was added drop wise to a solution of benzisoxazole ketone a (525 mg, 3.3 mmol) in AcOH (1.5 mL) and CH$_2$Cl$_2$ (6.0 mL). After 1 h at RT, LCMS indicated no reaction. Five drops of conc. HCl were added to the reaction mixture and stirred at RT for overnight. It was quenched with 10% Na$_2$S$_2$O$_3$, diluted with CH$_2$Cl$_2$ (100 mL), washed with 5% NaHCO$_3$, separated, dried (MgSO$_4$), and concentrated in vacuo to afford 820 mg (105%) of bromo ketone b as a brown oil.

Example 26

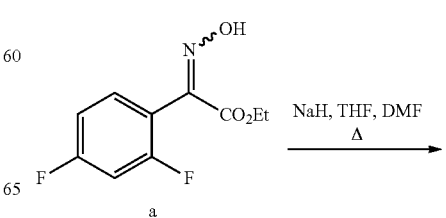

-continued

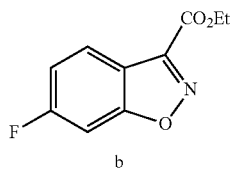
b

Following the general procedure of Strupczewski et al. (*J. Med. Chem.* 1985, 28, 761-769), to a suspension of NaH (60% in mineral oil, 37 mg, 0.92 mmol) in THF (3.0 mL) was added drop wise a solution of difluoro oxime a (140 mg, 0.61 mmol) in DMF (1.5 mL). The resulting mixture was heated at 70° C. for 4 h. It was cooled, poured onto water (30 mL), extracted with EtOAc (2×50 mL). The EtOAc was washed with water, dried ($MgSO_4$), and concentrated. The crude product was adsorbed on to Celite and purified by ISCO CombiFlash 12 g column (1-5% ethyl acetate-hexane) to afford 60 mg (47%) of benzisoxazole ester b as an off white solid.

Example 27

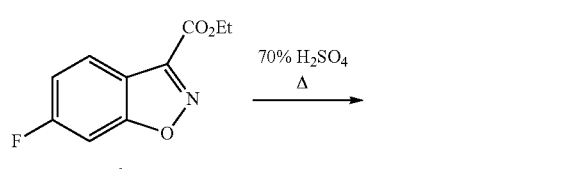

A suspension of benzisoxazole a (1.6 g, 7.8 mmol) in 70% $H_2SO_4$ (30 mL) was heated at 80° C. for 4 h. It was cooled, poured onto crushed ice. The solid was collected by filtration, washed with water, and dried to afford 1.3 g (89%) of benzisoxazole acid b as a white solid.

Example 28

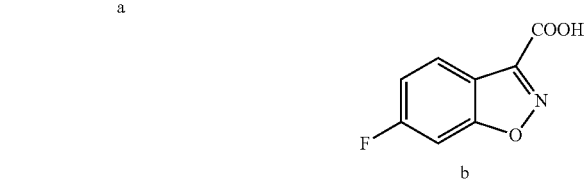

Following the procedure for preparing amide from example 23, benzisoxazole acid a (1.3 g, 7.0 mmol) afforded, after purified by ISCO CombiFlash 12 g column (2-15% ethyl acetate-hexane), 740 mg (47%) of benzisoxazole amide b as a white solid.

Example 29

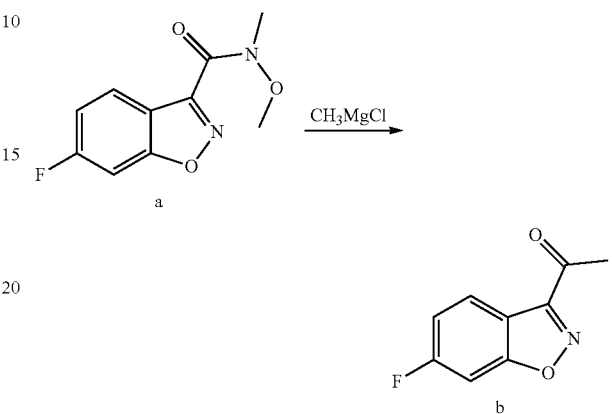

Following the procedure for preparing of ketone from example 24, benzisoxazole amide a (740 mg, 3.3 mmol) afforded 390 mg (66%) of benzisoxazole ketone b as an off white solid.

Example 30

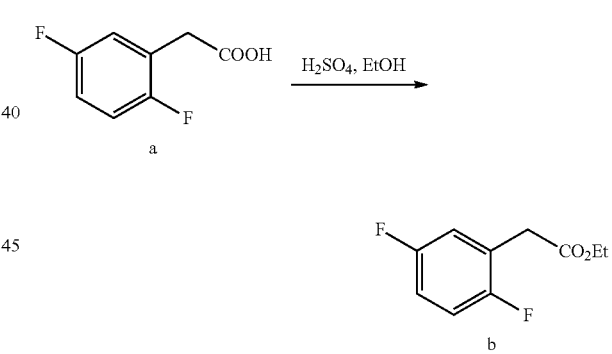

Following the procedure for preparing ester from example 19, 2,5-difluorophenylacetic acid a (9.56 g, 55.6 mmol) afforded 9.24 g (83%) of difluoro ester b as a clear liquid.

Example 31

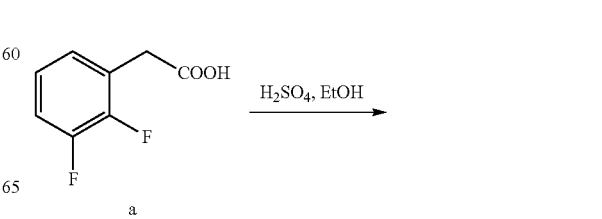

-continued

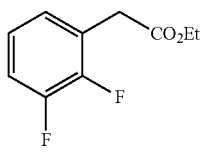
b

Following the procedure for preparing ester from example 19, 2,3-difluorophenylacetic acid a (10.0 g, 58.1 mmol) afforded 10.8 g (93%) of difluoro ester b as a clear liquid.

Example 32

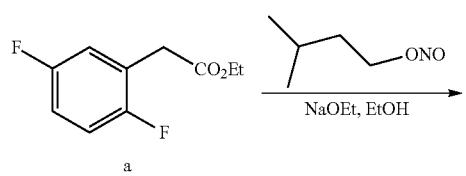

Following the procedure for preparing oxime from example 21, difluoro ester a (9.2 g, 46.0 mmol) afforded 5.57 g (53%) of difluoro oxime b as a white solid.

Example 33

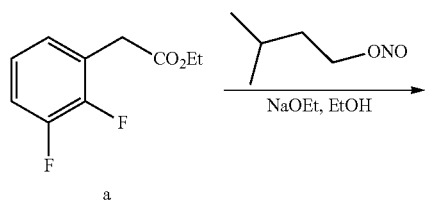

Following the procedure for preparing oxime from example 21, difluoro ester a (10.8 g, 54 mmol) afforded 4.9 g (40%) of difluoro oxime b as a white solid.

Example 34

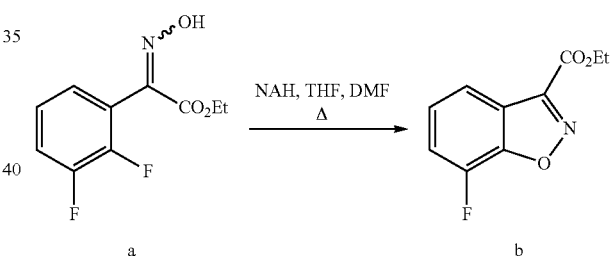

Following the procedure for preparing ester from example 26, difluoro oxime a (5.5 g, 24.0 mmol) afforded, after purified by ISCO CombiFlash 40 g column (1-5% ethyl acetate-hexane), 2.66 g (53%) of benzisoxazole ester b as an off white solid.

Example 35

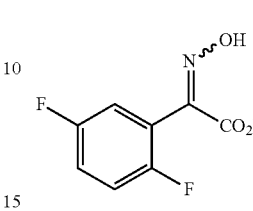

Following the procedure for preparing ester from example 26, difluoro oxime a (4.9 g, 21.4 mmol) afforded 2.9 g (65%) of benzisoxazole ester b as a light yellow crystalline.

Example 36

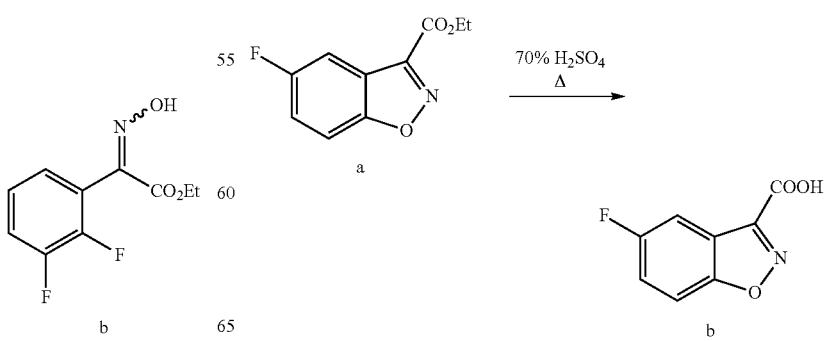

Following the procedure for preparing acid from example 27, benzisoxazole ester a (2.1 g, 10.0 mmol) afforded 1.92 g (86%) of benzisoxazole acid b as an off white solid.

Example 37

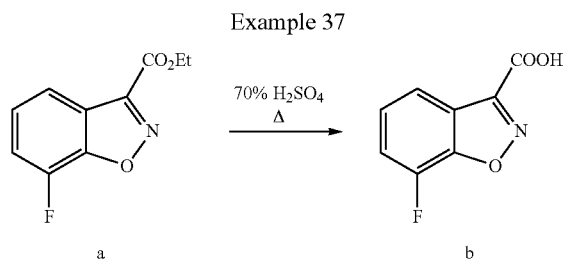

Following the procedure for preparing acid from example 27, benzisoxazole ester a (2.4 g, 11.5 mmol) afforded 1.92 g (76%) of benzisoxazole acid b as an off white solid.

Example 38

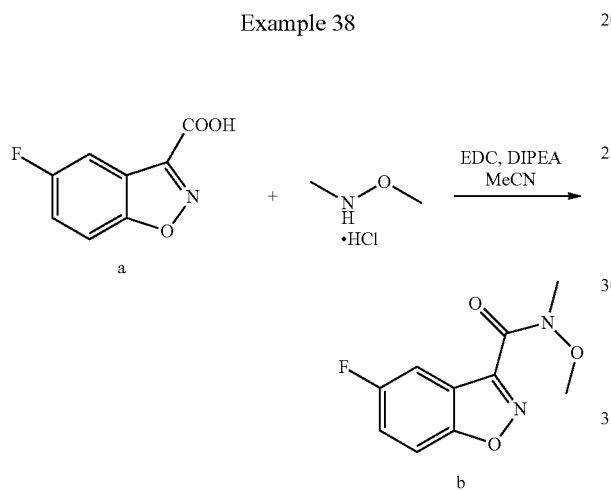

Following the procedure for preparing amide from example 23, benzisoxazole acid a (1.4 g, 7.73 mmol) afforded 1.95 g (83%) of benzisoxazole amide b as a yellow solid.

Example 39

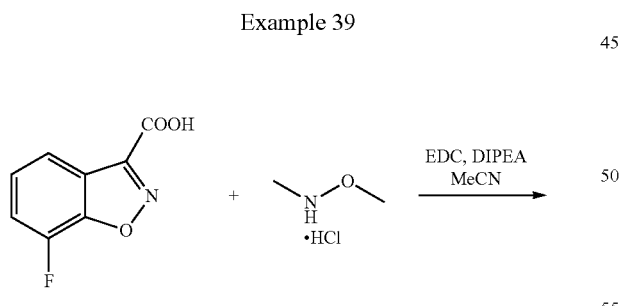

(Following the procedure for preparing amide from example 23, benzisoxazole acid a (1.9 g, 10.5 mmol) afforded 1.7 g (72%) of benzisoxazole amide b as a brown solid.

Example 40

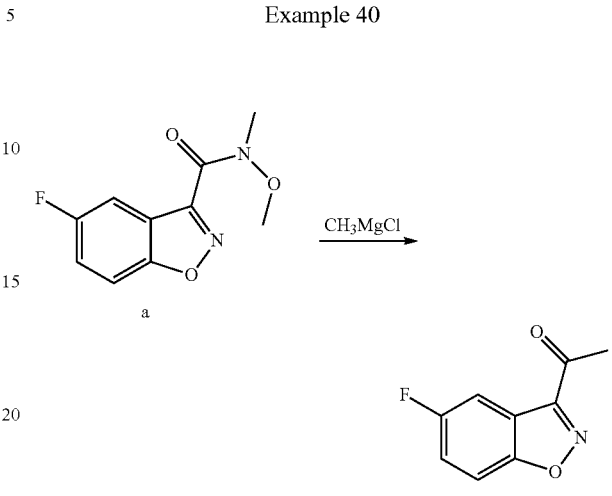

Following the procedure for preparing ketone from example 12, benzisoxazole amide a (1.95 g, 8.7 mmol) afforded 448 mg (30%) of benzisoxazole ketone b as a brown oil. Compound b may also be prepared according to the procedures described by Farooq et al. (WO 9614305).

Example 41

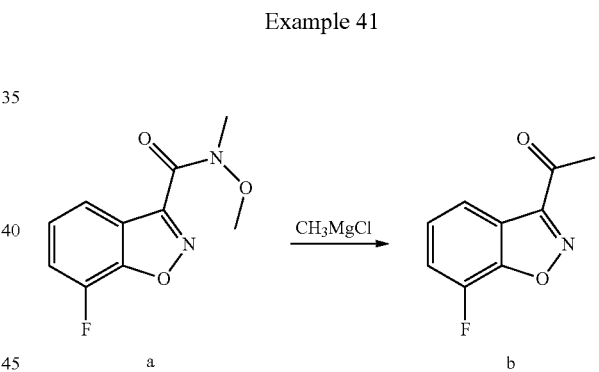

Following the procedure for preparing ketone from example 12, benzisoxazole amide a (1.70 g, 7.6 mmol) afforded 192 mg (14%) of benzisoxazole ketone b as a white crystalline solid.

Example 42

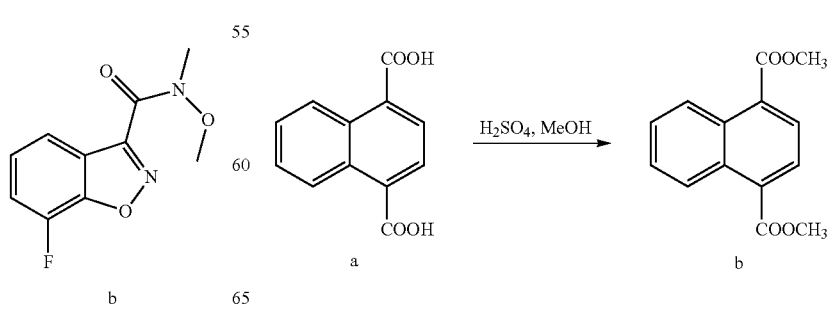

A suspension of 1,4-naphthalenedicarboxylic acid a (10.0 g, 46.3 mmol) in MeOH (70 mL) and $H_2SO_4$ (5 mL) was stirred at RT for 2 days, and then heated at 50° C. for 10 h. It was concentrated in vacuo, re-dissolved in $CH_2Cl_2$ (300 mL), washed with 10% $K_2CO_3$ (200 mL), dried ($MgSO_4$), and concentrated to give 6.6 g (60%) of di-ester b as yellow solid.

Example 43

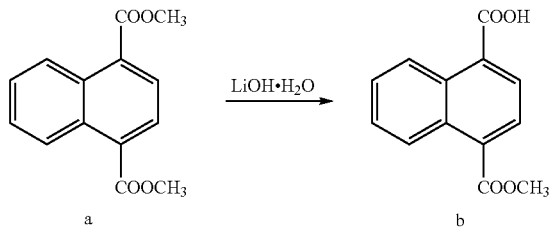

A mixture of the di-ester a (2.0 g, 8.2 mmol), LiOH (344 mg, 8.2 mmol) in THF (40 mL), water (5 mL), and MeOH (1 mL) was stirred at RT overnight. LCMS indicated some starting di-ester still remains un-reacted. Extra LiOH (84 mg, 2.0 mmol) was added to the reaction mixture. After 4 h, it was diluted with 0.5 N HCl (100 mL), extracted with EtOAc (100 mL), dried ($MgSO_4$), concentrated to afford 1.4 g (74%) of monoacid b as a light yellow solid.

Example 44

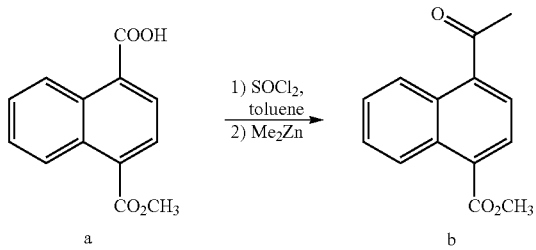

A mixture of monoacid a (1.4 g, 6.1 mmol) and $SOCl_2$ (9 mL) in toluene (15 mL) was heated at 75° C. for 4 h. The solvent was removed in vacuo, diluted with toluene (50 mL) and concentrated, and dried under high vacuum overnight. The residue was suspended in toluene (30 mL) and cooled in ice-water bath. $Me_2Zn$ (12 mL of 1 M solution in heptane, 12.0 mmol) was added slowly, stirred at RT for 3.5 h. The reaction was quenched with sat. $NH_4Cl$, diluted with water (100 mL), extracted with EtOAc (2×100 mL), dried ($MgSO_4$), and concentrated in vacuo. The crude product was adsorbed on to Celite and purified by ISCO CombiFlash 40 g column (1-10% ethyl acetate-hexane) to afford 890 mg (86%) of ketone ester b as an off white solid. Compound b may also be prepared according to the procedures described by Uehata et al. (JP 2003073357).

Example 45

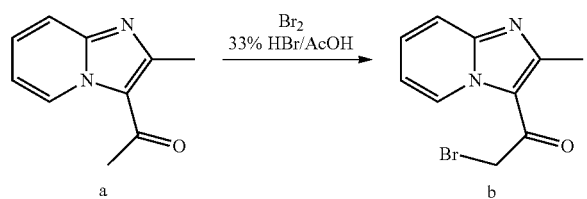

Bromine (1.49 g, 9.3 mmol) was added slowly to a stirred solution of ketone a (1.47 g, 8.5 mmol) prepared according to the procedures described by Berg et al. (WO 02066480) in 33% HBr/AcOH (20 mL) at RT. It was stirred for 1 h, diluted with ether (65 mL), and stirred vigorously for 1 h. The solid was collected by filtration, washed with ether, high vacuum dried to afford 2.88 g (100%) of bromo methyl ketone b as a yellow solid.

Example 46

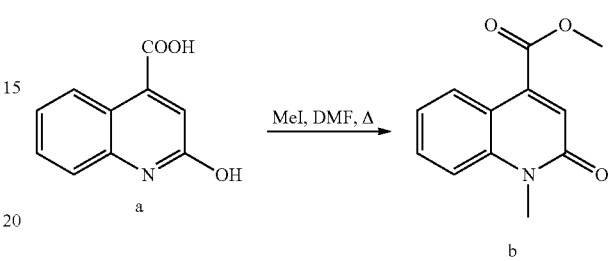

A mixture of 2-hydroxyquinoline-4-carboxylic acid a (6.25 g, 33.1 mmol), MeI (10.33 g, 72.7 mmol), and $K_2CO_3$ (10.0 g, 72.7 mmol) in DMF (110 mL) was heated at 80° C. for 16 h overnight. LCMS indicated incomplete reaction. Extra MeI (4.69 g, 33.1 mmol) was added to the reaction mixture and heated at 100° C. for 3 h. It was cooled, poured into ice water, and 10% $K_2CO_3$ (50 mL), extracted with EtOAc (2×150 mL). The combined EtOAc were washed with water, dried ($MgSO_4$), concentrated in vacuo. The crude product was adsorbed on to Celite and purified by ISCO CombiFlash 80 g column (2-50% ethyl acetate-hexane) to afford 4.68 g (65%) of dihydroquinoline ester b as an off white solid.

Example 47

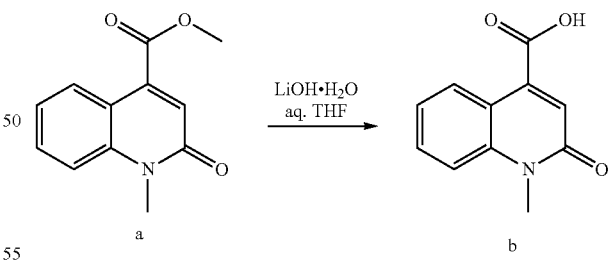

Lithium hydroxide (1.45 g, 34.5 mmol) was added to a solution of dihydroquinoline ester a (1.50 g, 6.91 mmol) in THF (40 mL), followed by water (10 mL). The mixture was stirred at RT for 16 h. It was concentrated in vacuo, diluted with EtOAc (100 mL) and 0.5 N HCl (100 mL). A white solid precipitated and was collected by filtration, washed with water. The EtOAc was separated, dried ($MgSO_4$), concentrated in vacuo to afford a white solid product. A combined yields of 1.41 g (100%) of dihydroquinoline acid b as a white solid, which was used with out further purification.

Example 48

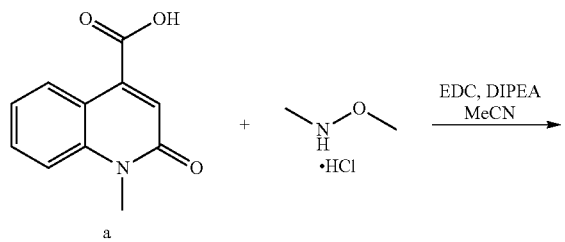

N,N-Diisopropylethylamine (1.37 g, 10.7 mmol) was added to a suspension of dihydroquinoline acid a (2.42 g, 11.9 mmol), amine (1.40 g, 14.3 mmol), and EDC (2.28 g, 11.9 mmol) in MeCN (80 mL), stirred at RT for 2 h. It was concentrated in vacuo, diluted with $CH_2Cl_2$ (100 mL), washed with 0.5 N HCl (50 mL) and 0.5 N NaOH (50 mL), dried ($MgSO_4$), concentrated to afford 1.98 g (67%) of dihydroquinoline amide b as a white solid, which was used with out further purification.

Example 49

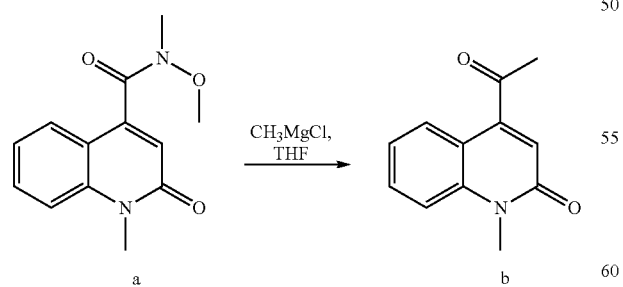

Following the procedure for preparing ketone from example 12, dihydroquinoline amide a (2.17 g, 8.82 mmol), $CH_3MgCl$ (8.82 mL of 3 M solution in THF, 26.5 mmol) afforded 766 mg (43%) of dihydroquinoline ketone b as a yellow solid. Compound b may also be prepared according to the procedures described by Fujita et al. (*Chem. & Pharm. Bull.* 2001, 49(7), 900-904 and *Chem. & Pharm. Bull.* 2001, 49(4), 407-412).

Example 50

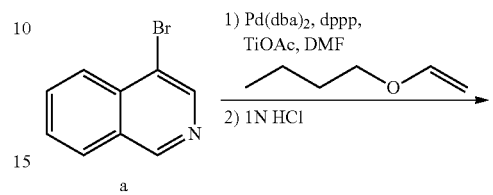

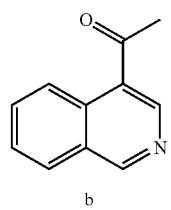

Following the general procedure of Legros et al. (*Tetrahedron* 2001, 57, 2507-2514), 4-bromoisoquinoline a (1.0 g, 4.8 mmol) afforded 707 mg (86%) of ketone b as a light yellow solid.

Example 51

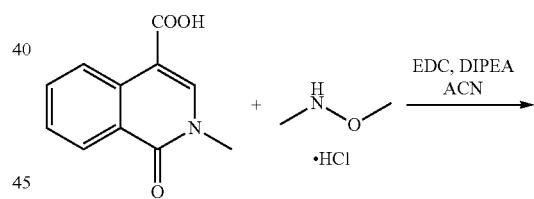

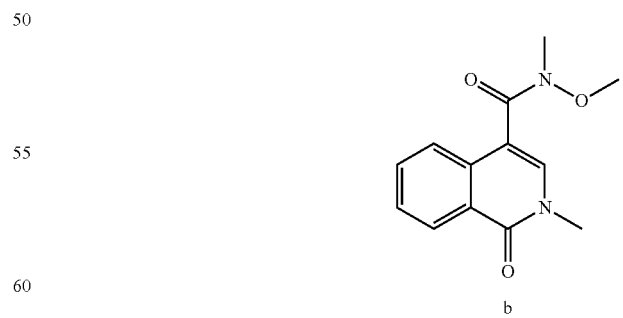

Following the procedure for preparing amide from example 48, dihydroisoquinoline acid a (1.25 g, 6.2 mmol) prepared according to the procedures described by Deady et al. (*J. Heterocyclic Chem.* 2001, 38, 1185) afforded 754 mg (50%) of dihydroisoquinoline amide b as a yellow gum.

Example 52

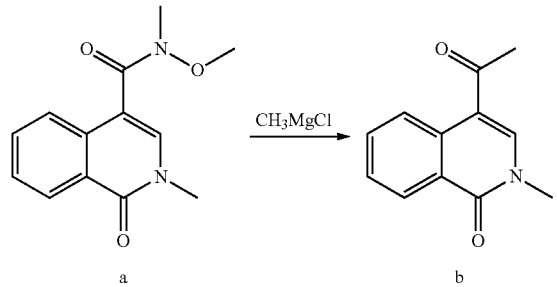

Following the procedure for preparing ketone from example 49, dihydroisoquinoline amide a (0.754 g, 3.06 mmol) afforded 510 mg (85%) of dihydroisoquinoline ketone b as a yellow solid. Compound b may also be prepared according to the procedures described by Alvarez et al. (*Science of Synthesis* 2005, 15, 839-906), Kimura et al. (*Chem. & Pharm. Bull.* 1983, 31(4), 1277-82), Tomisawa et al. (*Chem. & Pharm. Bull.* 1975, 23(3), 592-6) and Dyke et al. (*Tetrahedron* 1973, 29(23), 3881-8).

Example 53

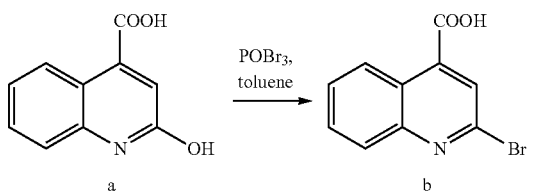 [SMILES: O=C(O)c1cc(O)nc2ccccc12 ; O=C(O)c1cc(Br)nc2ccccc12]

A mixture of 2-hydroxyquinoline-4-carboxylic acid a (4.0 g, 21.2 mmol), POBr₃ (25.0 g, 87.2 mmol) in toluene (40 mL) was heated at 100° C. for 3 h. It was cooled to RT, carefully poured onto crushed ice, extracted with EtOAc (2×250 mL), dried (MgSO₄), concentrated in vacuo. The residue was dissolved in 1 N NaOH (150 mL), extracted with EtOAc (2×100 mL). The aqueous layer was then acidified with 1 N HCl to pH 3. The white solid was collected by filtration, washed with water, dried to afford 3.0 g (56%) of bromo acid b as a white solid.

Example 54

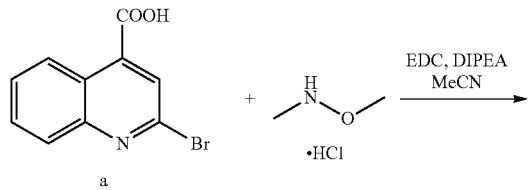

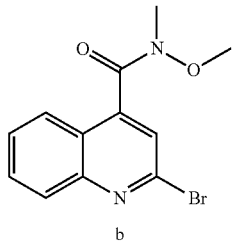

Following the procedure for preparing amide from example 48, bromo acid a (3.0 g, 11.9 mmol) afforded 2.67 g (77%) of bromo amide b as a white solid.

Example 55

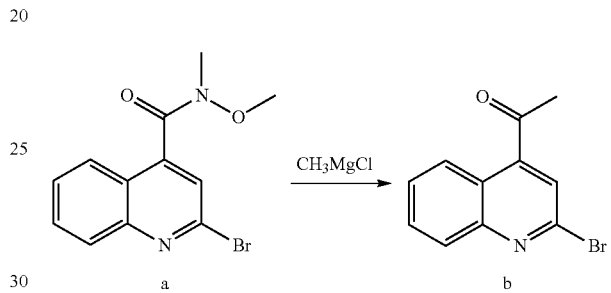

(46801-78) Following the procedure for preparing ketone from example 49, bromo amide a (1.0 g, 3.4 mmol) afforded 800 mg (94%) of bromo ketone b as an off white solid.

Example 56

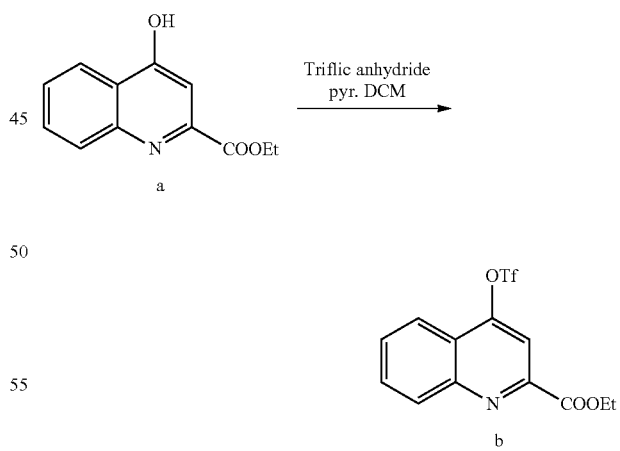

Trifluoromethane sulfonic anhydride (6.82 g, 24.2 mmol) was added drop wise onto to a mixture of ethyl-4-hydroxyquinoline carboxylate a (5.0 g, 23.0 mmol) and pyridine (1.95 mL, 24.2 mmol) in CH₂Cl₂ (100 mL) at ice water bath temperature under N₂. The mixture was stirred at RT overnight. It was diluted with CH₂Cl₂ (100 mL), washed with 0.5 N NaOH (100 mL), dried (MgSO₄), concentrated in vacuo. The crude product was adsorbed an to Celite and purified by ISCO CombiFlash 80 g column (2-15% ethyl acetate-hexane) to afford 7.4 g (93%) of triflate b as a white solid.

also be prepared according to the procedures described by Priestly et al. (*Bioorg. & Med. Chem.* 1996, 4(7), 1135-1147).

Example 57

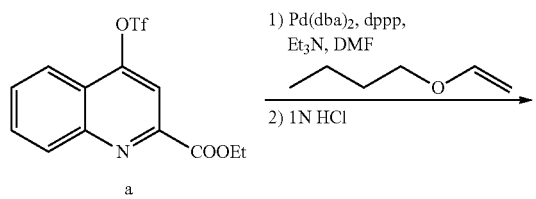

a

Example 59

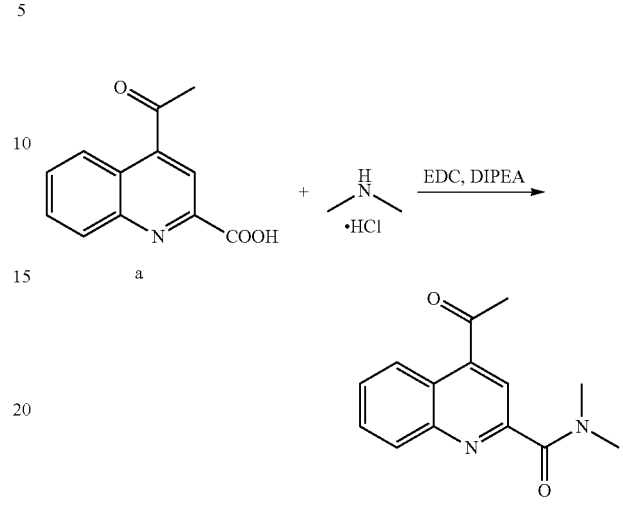

A mixture of the ketone acid a (1.30 g, 5.16 mmol), dimethylamine hydrochloride (480 mg, 5.93 mmol), EDC (1.14 g, 5.93 mmol), and DIPEA (765 mg, 5.93 mmol) in MeCN (30 mL) was stirred at RT overnight. Solvent was removed. The residue was dissolved in $CH_2Cl_2$ (100 mL), washed with 1 N HCl (50 mL) and 1 N NaOH (50 mL), dried ($MgSO_4$), and concentrated. The crude product was adsorbed on to Celite and purified by ISCO CombiFlash 40 g column (2-20% ethyl acetate-dichloromethane) to afford 656 mg (53%) of ketone amide b as a light yellow gum.

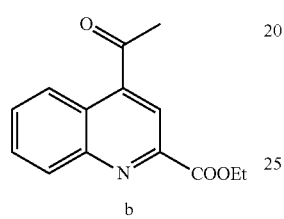

b

Following the general procedure of Legros et al. (*Tetrahedron* 2001, 57, 2507-2514), a mixture of triflate a (1.0 g, 2.86 mmol), bis(dibenzylideneacetone)palladium(0) (82 mg, 0.14 mmol), 1,3-bis(diphenylphosphino)propane (65 mg, 0.16 mmol), and $Et_3N$ (1.19 mL, 8.58 mmol) in DMF (10 mL) were stirred at RT for 15 min under $N_2$. n-Butyl vinyl ether (1.43 g, 14.3 mmol) in DMF (5 mL) was added and the resulting mixture was stirred at 80° C. for 24 h. It was cooled to RT, 1 N HCl (30 mL) were added slowly, stirred at RT for 24 h. The mixture was neutralized with 1 N NaOH and extracted with ether (2×100 mL), dried ($MgSO_4$), and concentrated. The crude product was adsorbed on to Celite and purified by ISCO CombiFlash 12 g column (2-20% ethyl acetate-hexane) to afford 460 mg (66%) of ketone b as a white solid.

Example 58

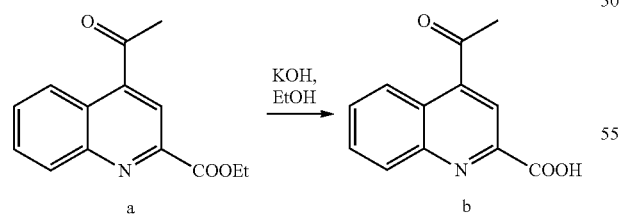

A mixture of ketone ester a (1.50 g, 6.17 mmol), KOH (640 mg, 11.35 mmol) in EtOH (30 mL) was stirred at RT overnight. The reaction mixture was diluted with water (150 mL), extracted with EtOAc (100 mL). The aqueous layer was then acidified with 1 N HCl, extracted with EtOAc (2×100 mL), dried ($MgSO_4$), concentrated in vacuo afforded 1.53 g (100%) of ketone acid b as a yellow solid. Compound b may

Example 60

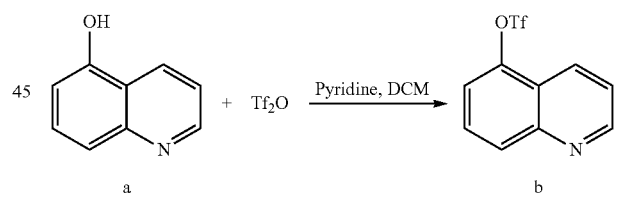

Following the procedure for preparing triflate from example 56, 5-hydroxyquinoline a (3.42 g, 23.6 mmol) afforded 6.0 g (92%) of triflate b as light yellow liquid.

Example 61

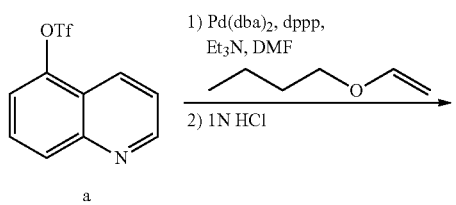

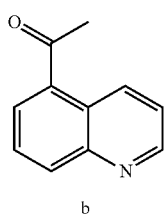
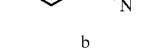

Following the procedure for preparing ketone from example 57, triflate a (6.0 g, 21.7 mmol) afforded 3.58 g (97%) of ketone b as a brown oil.

Example 62

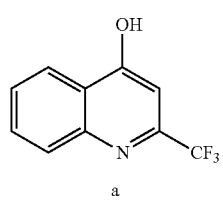

Following the procedure for preparing triflate from example 56, 2-(trifluoromethyl)-4-hydroxyquinoline a (6.87 g, 32.3 mmol) afforded 9.31 g (84%) of triflate b as a yellow solid.

Example 63

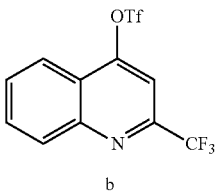

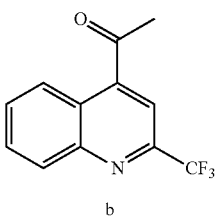

Following the procedure for preparing ketone from example 57, triflate a (7.35 g, 21.3 mmol) afforded 1.79 g (35%) of ketone b as a yellow solid.

Example 64

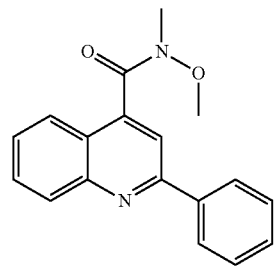

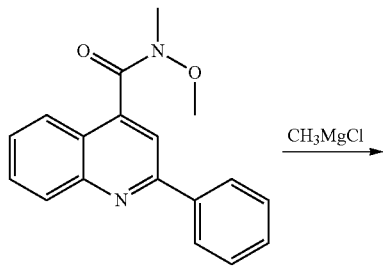

Following the procedure for preparing amide from example 59, 2-phenyl-4-quinolinecarboxylic acid a (5.0 g, 20.1 mmol) afforded 3.29 g (56%) of amide b as an off white solid.

Example 65

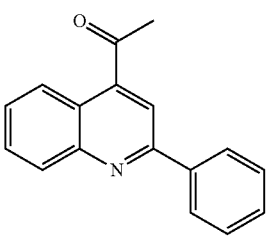

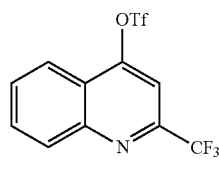

Following the procedure for preparing ketone from example 49, amide a (3.29 g, 11.26 mmol) afforded 3.29 g (118%) of ketone b as a yellow solid. Compound b may also be prepared according to the procedures described by Sato et al. (JP 2002371078), Wong et al (WO 9846572), Leardini et al. (*J. Chem. Soc., Chem. Communications* 1984, 20, 1320-1), Kaneko et al. (*Chem. & Pharm. Bull.* 1982, 30(1), 74-85), Schwenk et al. (*J. Org. Chem.* 1946, 11, 798-802) and Shivers et al (*J. Am. Chem. Soc.* 1947, 69, 119-23).

Example 66

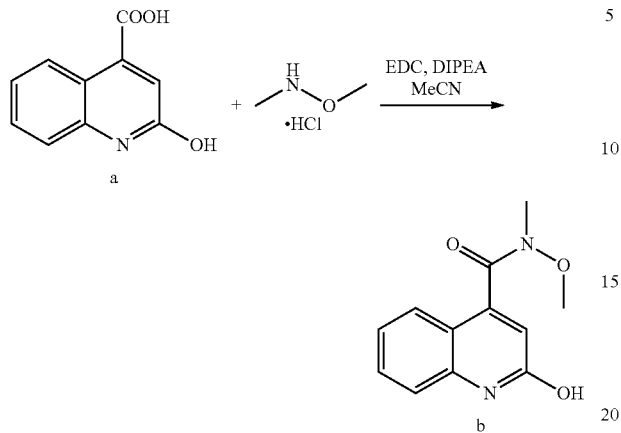

Following the procedure for preparing amide from example 59, 2-hydroxy-4-quinolinecarboxylic acid a (5.0 g, 26.4 mmol) afforded 1.88 g (30%) of amide b as a cream color solid.

Example 67

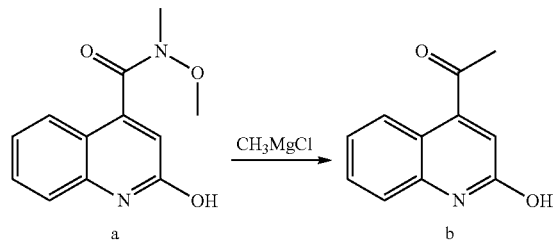

Following the procedure for preparing ketone from example 49, amide a (1.88 g, 8.1 mmol) afforded 993 mg (66%) of ketone b as a light yellow solid. Compound b may also be prepared according to the procedures described by Wetzel et al. (*J. Med. Chem.* 1973, 16(5), 528-32), Jones et al. (*J. Chem. Soc. [Section C]: Organic* 1967, 19, 1808-13) and Ochia et al. (*Chem. & Pharm. Bull.* 1963, 11, 137-8).

Example 68

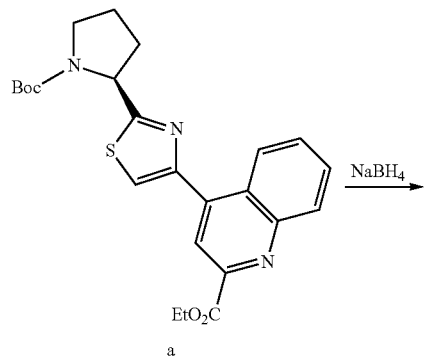

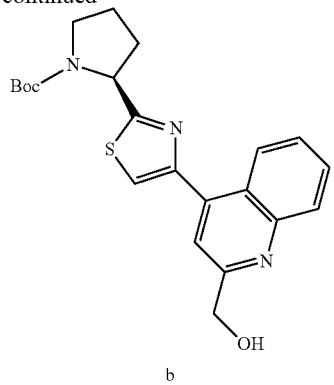

Boc-ester a (900 mg, 2.0 mmol) was dissolved in THF (20 mL) and MeOH (1 mL) at ice water bath temperature. NaBH$_4$ (300 mg, 8.0 mmol) was added and the mixture was stirred for 1 h then another 1 h at RT. Reaction was quenched with the addition of few drops of water, then diluted with more water (100 mL), extracted with EtOAc (2×100 mL), dried (MgSO$_4$), and concentrated in vacuo to afford 739 mg (90%) of alcohol b as a yellow foamy solid.

Example 69

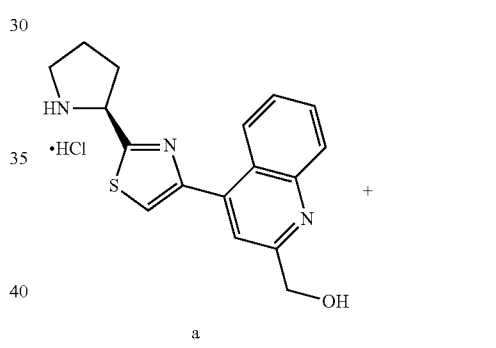

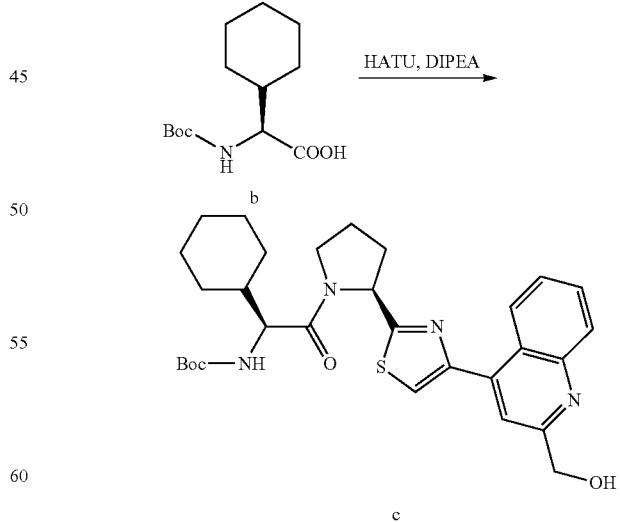

To the mixture of amine a (159 mg, 0.46 mmol), Boc-cyclohexyl-Gly-OH b (129 mg, 0.50 mmol), and HATU (350 mg, 0.92 mmol) in MeCN (4 mL) was added DIPEA (162 μL, The resulting mixture was stirred at RT for 2 h. LCMS indicated incomplete reaction. An extra equivalence of HATU (175 mg, 0.46 mmol) and DIPEA (81 μL, 0.46 mmol) were added and stirred for another 1 h. Solvent was removed in vacuo, diluted with CH₂Cl₂ (10 mL), washed with 0.5 N HCl (10 mL) and with water, dried (MgSO₄), and concentrated. The crude product was adsorbed on to Celite and purified by ISCO CombiFlash 12 g column (0-5% MeOH/CH₂Cl₂) to afford 187 mg (74%) of product c as a brown solid.

Example 70

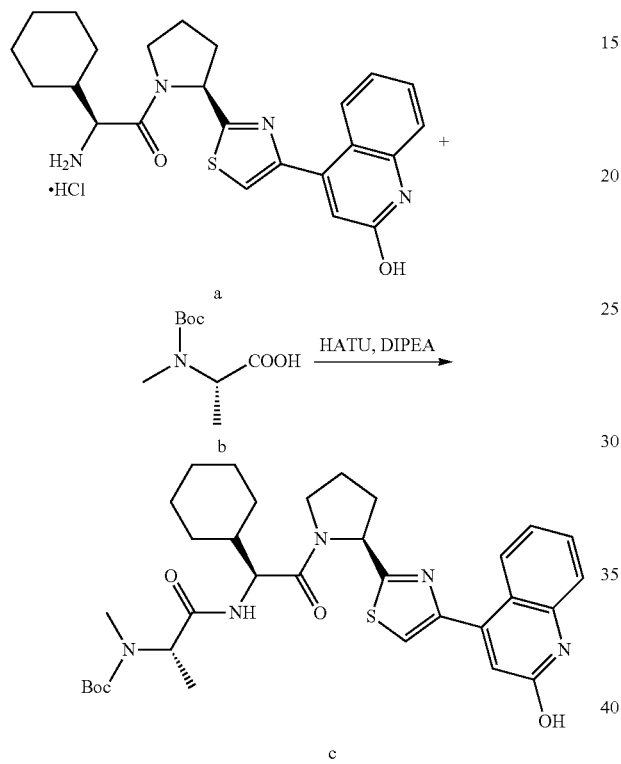

To the mixture of amine a (62 mg, 0.13 mmol), Boc-N-Me-Ala-OH b (27 mg, 0.13 mmol), and HATU (99 mg, 0.26 mmol) in MeCN (2 mL) was added DIPEA (46 μL, 0.26 mmol). The resulting mixture was stirred at RT for 2 h. Solvent was removed in vacuo, diluted with CH₂Cl₂ (10 mL), washed with 0.5 N HCl (10 mL) and with water, dried (MgSO₄), and concentrated to afford 69 mg (85%) of product c as a clear oil.

Example 71

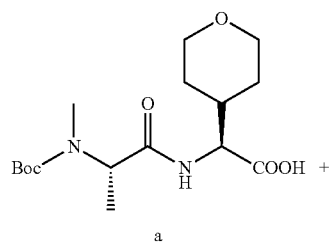

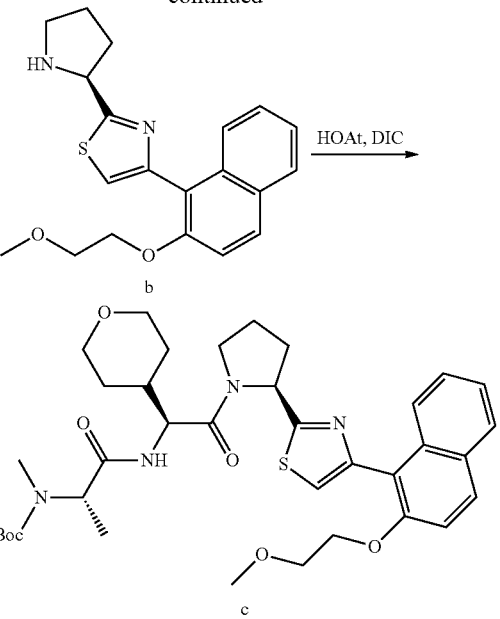

A mixture of di-peptide a (100 mg, 0.29 mmol), thiazole amine b (113 mg, 0.32 mmol), HOAt (59 mg, 0.435 mmol), and DIC (67 μL, 0.435 mmol) in CH₂Cl₂ (3 mL) was stirred at RT for overnight. The mixture was diluted with CH₂Cl₂ (10 mL), washed with 0.5 N HCl (10 mL) and 0.5 N NaOH (10 mL), dried (MgSO₄), and concentrated. The crude product was adsorbed on to Celite and purified by ISCO CombiFlash 12 g column (10-90% ethyl acetate-hexane) to afford 175 mg (89%) of product c as a clear oil.

Example 72

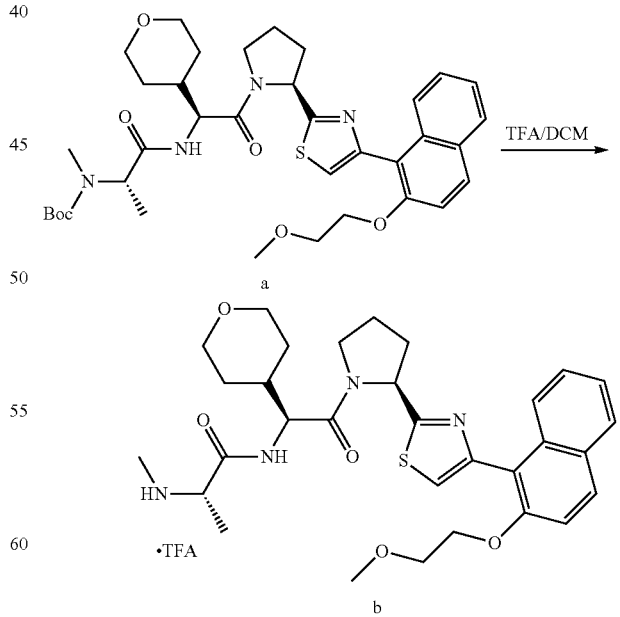

Boc-amine a (175 mg, 0.26 mmol) was treated with (1:1) TFA/CH₂Cl₂ (8 mL), catalytic toluene at RT for 1 h. Solvent was removed in vacuo. The residue was purified by reverse-phase HPLC (C$_{18}$, MeCN—H$_2$O, 0.1% TFA) and lyophilized to afford 98 mg (49%, in 2 steps) of desired product b as a hygroscopic white solid.

Example 73

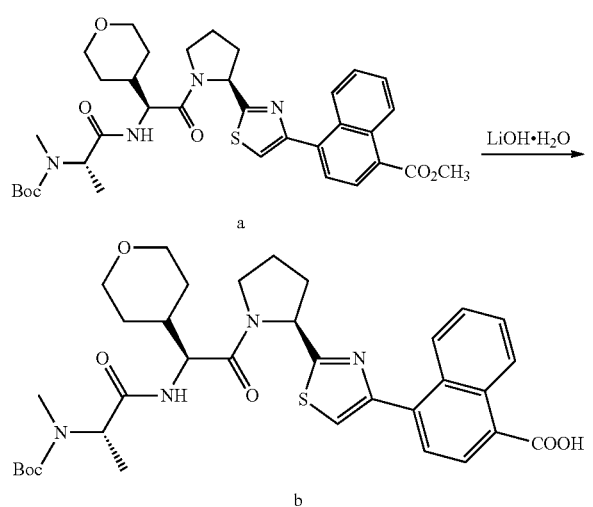

A mixture of the Boc-ester a (200 mg, 0.30 mmol), LiOH (200 mg, 0.30 mmol) in THF (2 mL), and water (25 µL) was stirred at RT for 1 h. MeOH (500 µL) was added and stirred at RT overnight. It was diluted with EtOAc (10 mL), washed with 0.5 N HCl (10 mL), dried (MgSO$_4$), concentrated in vacuo to afford 160 mg (82%) of Boc acid 187 as a white solid.

Example 74

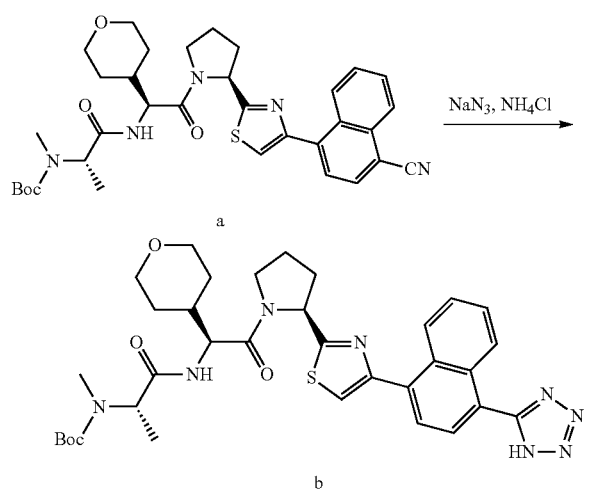

A mixture of the Boc nitrile a (200 mg, 0.31 mmol), NaN$_3$ (309 mg, 4.75 mmol), and NH$_4$Cl (252 mg, 4.75 mmol) in DMF (3 mL) was heated at 100° C. for 3.5 d. It was cooled to RT, diluted with water, extracted with EtOAc (2×50 mL), washed with brine, dried (MgSO$_4$), concentrated in vacuo. The crude product was adsorbed on to Celite and purified by ISCO CombiFlash 4 g column (10-90% ethyl acetate-hexane) to afford 37 mg of tetrazole # as a brown oil. More material was recovered by extracting the aqueous layer with CH$_2$Cl$_2$ to recover 65 mg of product. A combined 102 mg (49%) of tetrazole b was isolated.

Example 75

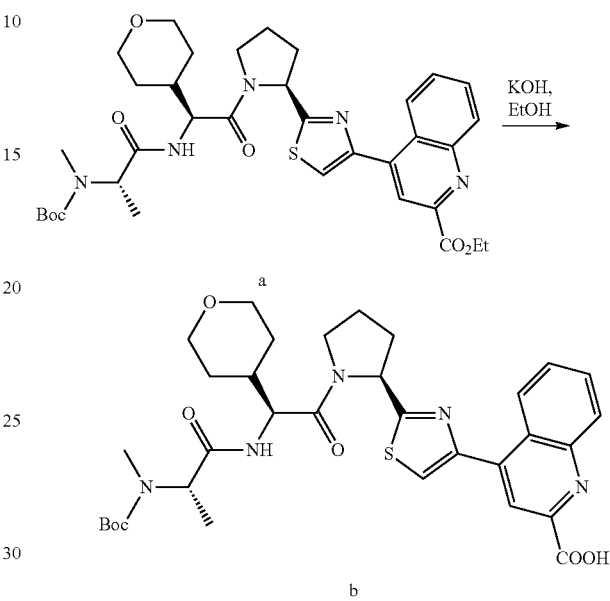

A mixture of the Boc ester a (135 mg, 0.20 mmol), KOH (14.5 mg, 0.26 mmol) in EtOH (4 mL) was stirred at RT for 2 h, then diluted with EtOAc (8 mL), acidified with 1 N HCl, separated, dried (MgSO$_4$), concentrated in vacuo, and high vacuum dried. The crude product b was carried on without further purification.

Example 76

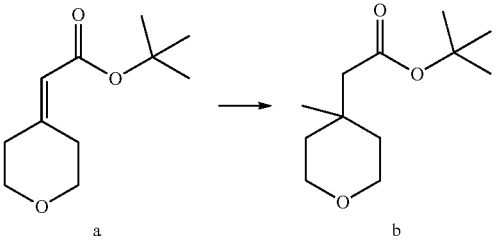

Following the general procedure of Yamamoto [Asao, N; Lee, S.; Yamamoto, Y. *Tetrahedron Letters,* 2003, 4265-4266.], MeLi (20 mL of 1.6M solution in ether, 30.2 mmol) was added to a 0° C. suspension of powdered CuI (2.90 g, 15.1 mmol) and ether (5 mL). The resulting grey solution was stirred vigorously for 10 min then concentrated under reduced pressure at 0° C. Dichloromethane (20 mL, pre-cooled to 0° C.) was added, then the suspension was cooled to −78° C. and TMSCl (1.9 mL, 15.1 mmol) was added followed quickly by a solution of ester 192 [WO 01168603] (1.0 g, 5.0 mmol) and CH$_2$Cl$_2$ (50 mL), the mixture was stirred vigorously at −78° C. for 30 min, then at 0° C. for 2 h. The mixture was then poured into 200 mL of 1:1 saturated NH₄Cl:NH₄OH. The layers were separated and the aqueous phase was extracted with CH₂Cl₂ (2×20 mL). The combined organic phases were washed with brine (1×20 mL), dried (Na₂SO₄), adsorbed onto Celite and purified by chromatography ISCO CombiFlash 12 g column, 0-8% ethyl acetate-hexanes to afford 783 mg (72%) of ester 193 as a clear oil.

Example 77

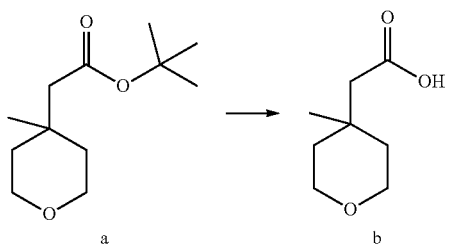

A solution of ester a (780 mg), CH₂Cl₂ (5 mL), and TFA (2 mL) was maintained at rt overnight. The solvents were removed under reduced pressure to afford quantitative yield acid b as a colorless oil which was used without further purification.

Example 78

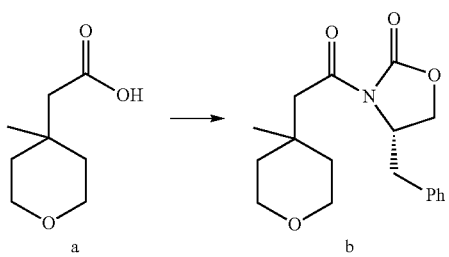 [SMILES: CC1(CC(=O)O)CCOCC1 ; CC1(CC(=O)N2C(=O)OC[C@@H]2Cc2ccccc2)CCOCC1]

Following the general procedure of Evans [Evans, D. A.; Britton, T. C.; Ellman, J. A.; Dorow, R. L. *J. Am. Chem. Soc.* 1990, 112, 4011-4030], pivaloyl chloride (3.2 mL, 26 mmol) was added to a −10° C. solution of acid a (3.72 g, 23.5 mmol), TEA (4.3 mL, 31 mmol) and THF (50 mL). The resulting white slurry was allowed to warm to −5° C. over 20 min with vigorous stirring. The mixture was then cooled to −78° C. and a solution of the lithium salt of (S)-4-benzyl-2-oxazolidinone (prepared from (S)-4-benzyl-2-oxazolidinone (7.5 g, 42.3 mmol), n-BuLi (26 mL of 1.6M solution in hexanes, 42.3 mmol) and THF (150 mL) at −78° C.) was added via cannula over 10 min. The mixture was maintained at −78° C. for 1 h, then quenched with saturated NH₄Cl (200 mL) and the THF removed under reduced pressure. The aqueous phase was extraced with EtOAc (3×50 mL). The combined organic phases were washed with brine (1×50 mL), dried (Na₂SO₄), adsorbed onto Celite and purified by chromatography ISCO CombiFlash 120 g column, 5-40% ethyl acetate-hexanes to afford 5.7 g (76%) of imide b as a clear oil.

Example 79

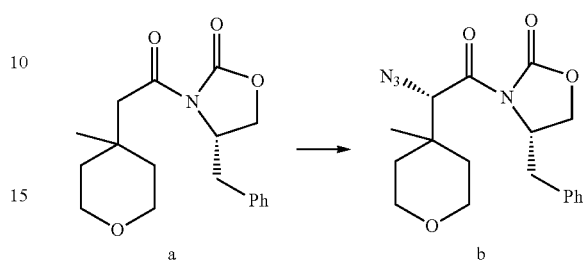

Following the general procedure of Evans [Evans, D. A.; Britton, T. C.; Ellman, J. A.; Dorow, R. L. *J. Am. Chem. Soc.* 1990, 112, 4011-4030], a cold (−78° C.) solution of imide a (5.7 g, 18 mmol) and THF (64 mL) was added to a cold (−78° C.) solution of KHMDS (20 mmol) and THF (120 mL) over 10 min. The colorless solution was maintained at −78° C. for 30 min., then a cold (−78° C.) solution of TrsylN₃ (6.9 g, 22.4 mmol) and THF (40 mL) was added via cannula over 5 min. Acetic acid (5.3 mL, 90 mmol) was added and the mixture was immediately brought to 30° C. and held there for 1 h. The reaction was quenched with brine (200 mL) and CH₂Cl₂ (200 mL). The phases were separated and the aqueous phase was extraced with CH₂Cl₂ (2×50 mL). The combined organic phases were washed with saturated NaHCO₃ (1×50 mL), dried (Na₂SO₄), adsorbed onto Celite and purified by chromatography ISCO CombiFlash 330 g column, 5-45% ethyl acetate-hexanes to afford 4.2 g (65%) of azo imide b as a colorless solid.

Example 80

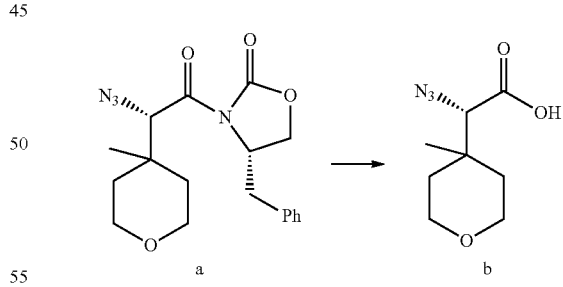

A mixture of azido-imide a (4.7 g, 13 mmol) LiOH.H₂O (660 mg, 15.6 mmol) THF (93 mL) and water (31 mL) was maintained at rt for 1 d. Further LiOH.H₂O (200 mg) was added, and the mixture stirred for 2 h. Solid NaHCO₃ (2.18 g) was added and the THF removed under reduced pressure. Following dilution with water (150 mL), the aqueous phase was washed with CH₂Cl₂ (3×50 mL) and the combined organic phases were extracted with saturated NaHCO₃ (1×50 mL). The combined aqueous phases were acidified with con. HCl to pH<2 and extracted with EtOAc (4×50 mL). The combined organic phases were dried (Na$_2$SO$_4$), and concentrated to yield 1.38 g (53%) of acid b as a colorless solid.

Example 81

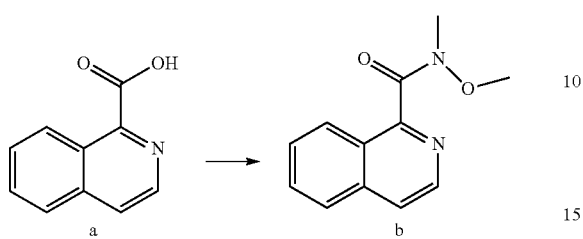

Isoquinoline carboxylic acid a (5.0 g, 28.9 mmol), N,O-dimethy-hydroxylamine hydrochloride (3.1 g, 31.8 mmol) EDC (6.1 g, 32 mmol), DIPEA (5.7 mL, 32 mmol) and MeCN (50 mL) were mixed together and stirred at rt overnight. The MeCN was removed under reduced pressure and the residue partitioned between water (200 mL) and EtOAc (200 mL). The phases were separated and the aqueous phase was extracted with EtOAc (2×50 mL). The combined organic phases were b as a colorless solid.

Example 82

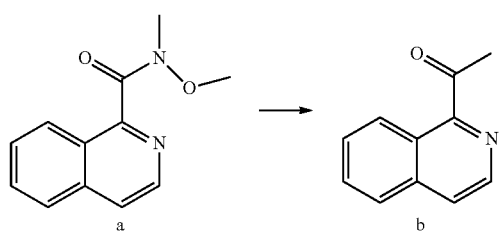 [SMILES: CON(C)C(=O)c1nccc2ccccc12 ; CC(=O)c1nccc2ccccc12]

Methyl magnesium chloride (12.3 mL of 3.0M THF) was added to a 0° C. solution of amide a (4.0 g, 18.5 mmol) and THF (40 mL). After 30 min at 0° C., the cooling bath was removed for 40 min. The reaction was poured into cold saturated NH$_4$Cl (200 mL), and extracted with EtOAc (3×50 mL). The combined organic phases were washed with water, brine, dried (Na$_2$SO$_4$), and concentrated to yield 3.15 g (100%) of ketone b as a colorless oil.

Example 83

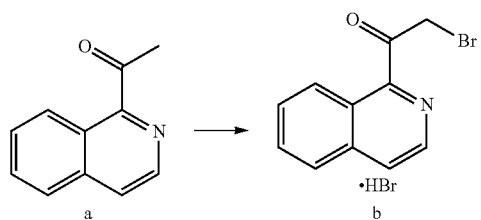

Following the general procedure of Barlin [Barlin, G. A.; Davies, L. P.; Ireland, S. J.; Ngu, M. M. L. *Aust. J. Chem.* 1989, 42, 1735-1748], Br$_2$ (150 µL, 2.92 mmol) was added in one portion to a solution of ketone a (500 mg, 2.92 mmol) and 33% HBr/AcOH (10 mL). After 1 h, ether (20 mL) was added, and the ppt was collected on filter paper, washed with ether, and dried under vacuum to afford 910 mg (94%) of bromide b as a yellow solid.

Example 84

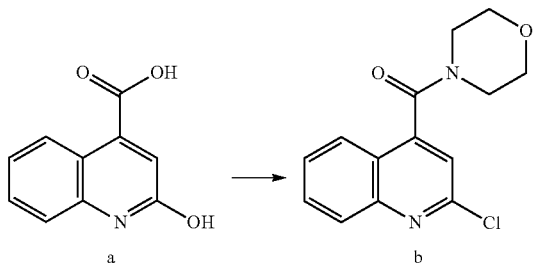 [SMILES: O=C(O)c1cc(O)nc2ccccc12 ; O=C(c1cc(Cl)nc2ccccc12)N1CCOCC1]

A mixture of 4-carboxy-2-hydroxyquinoline a (500 mg, 2.64 mmol) and POCl$_3$ (5 mL) was heated at 100° C. for 1 h. The solvent was removed under reduced pressure, and the residue was dissolved in CH$_2$Cl$_2$ (10 mL), and cooled to 0° C. Morpholine (1.0 mL, 13.2 mmol) was added dropwise, and the mixture was allowed to come to rt. The mixture was then re-cooled to 0° C. and more morpholine (1.0 mL, 13.2 mmol) was added dropwise, and the mixture was allowed to come to rt overnight. The mixture was then diluted with CH$_2$Cl$_2$ (50 mL), and washed with saturated NH$_4$Cl (3×20 mL). The combined aqueous phases were extracted with CH$_2$Cl$_2$ (1×20 mL), and the combined organic phases were dried (Na$_2$SO$_4$), adsorbed onto Celite and purified by chromatography ISCO CombiFlash 12 g column, 5-75% ethyl acetate-hexanes to afford 570 mg (78%) of amide b as a colorless solid.

Example 85

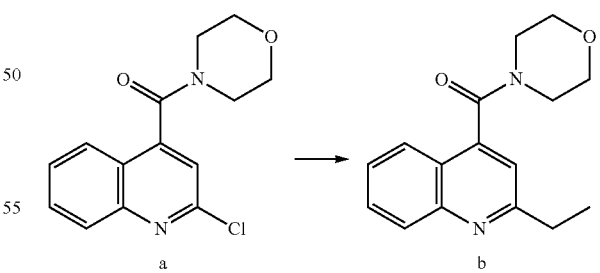

Diethyl zinc (2.3 mL, of 1.1M solution in toluene, 2.5 mmol) was added to a mixture of amide a (500 mg, 1.8 mmol), NiCl$_2$DPPP (100 mg, 0.18 mmol), and THF (5 mL) (caution was used due to exothermic reaction). The dark solution was then heated at 100° C. in a µW reactor for 15 min. The reaction was then quenched into saturated NH$_4$Cl (50 mL), and extracted with EtOAc (3×20 mL). The combined organic phases were dried (Na$_2$SO$_4$), adsorbed onto Celite and purified by chromatography ISCO CombiFlash 12 g column, 0-75% ethyl acetate-hexanes to afford 350 mg (71%) of amide b as a colorless solid.

Example 86

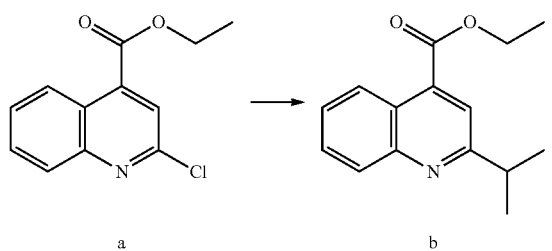 [SMILES: CCOC(=O)c1cc(Cl)nc2ccccc12 ; CCOC(=O)c1cc(C(C)C)nc2ccccc12]

Diisopropyl zinc (3 ml of 1.0M solution in toluene, 2.5 mmol) was added to a mixture of chloride a (500 mg, 1.8 mmol), NiCl$_2$DPPP (115 mg, 0.18 mmol), and THF (3 mL) The dark solution was then heated at 100° C. in a μW reactor for 15 min. The reaction was then quenched into saturated NH$_4$Cl (50 mL), and extracted with EtOAc (3×20 mL). The combined organic phases were dried (Na$_2$SO$_4$), adsorbed onto Celite and purified by chromatography ISCO Combi-Flash 12 g column, 0-15% ethyl acetate-hexanes to afford 383 mg (74%) of amide b as a colorless solid.

Example 87

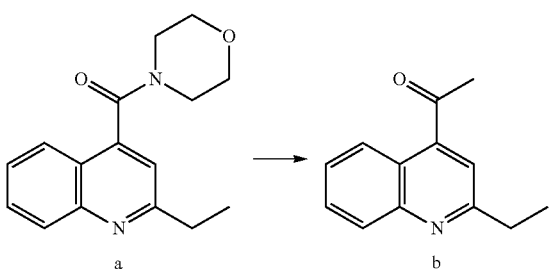 [SMILES: CCc1cc(C(=O)N2CCOCC2)c2ccccc2n1 ; CCc1cc(C(C)=O)c2ccccc2n1]

Methyl magnesium chloride (12.3 mL of 3.0M in THF, 37 mmol) was added to 0° C. solution of amide a (2.84 g, 10.51 mmol) and THF (20 mL). The solution was allowed to come to rt, then maintained at that temp. for 4 h. The reaction was quenched into cold saturated NH$_4$Cl (100 mL), extracted with EtOAc (3×50 mL). The combined organic phases were washed with brine (1×50 mL), dried (Na$_2$SO$_4$), adsorbed onto Celite and purified by chromatography ISCO CombiFlash 40 g column, 0-30% ethyl acetate-hexanes to afford 1.88 g (86%) of ketone b as a colorless oil.

Example 88

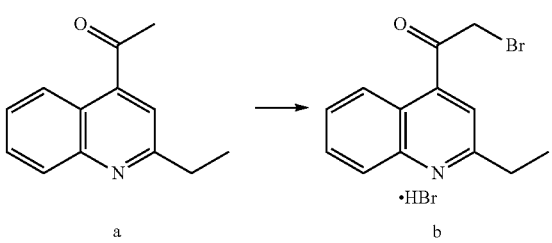 [SMILES: CCc1cc(C(C)=O)c2ccccc2n1 ; CCc1cc(C(=O)CBr)c2ccccc2n1 ; Br]

Following the general procedure of Barlin [Barlin, G. A.; Davies, L. P.; Ireland, S. J.; Ngu, M. M. L. *Aust. J. Chem.* 1989, 42, 1735-1748], Br$_2$ (640 μL, 2.92 mmol) was added in one portion to a solution of ketone a (2.27 g, 11.4 mmol) and 33% HBr/AcOH (40 mL). After 1 h, ether (50 mL) was added, and the ppt was collected on filter paper, washed with ether, and dried under vacuum to afford 3.88 g (94%) of bromide b as a yellow solid.

Example 89

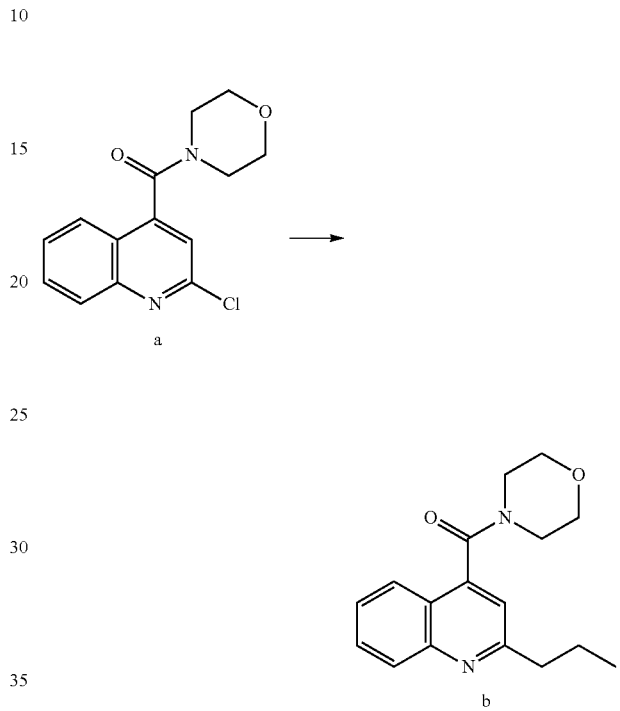

Following the general procedure of Rieke [Zhu, L.; Wehmeyer, R. M.; Rieke, R. D. *J. Org. Chem.* 1991, 56, 1445-1453], propyl zinc bromide (4.0 mL of 0.5M solution in THF, 2.0 mmol) was added to a mixture of chloride a (500 mg, 1.81 mmol), Pd(PPh$_3$)$_4$ (100 mg, 0.09 mmol) and THF (3 mL). The resulting solution was heated at 70° C. in a μW reactor for 15 min. The reaction was then quenched into saturated NH$_4$Cl (50 mL), and extracted with EtOAc (3×20 mL). The combined organic phases were dried (Na$_2$SO$_4$), adsorbed onto Celite and purified by chromatography ISCO CombiFlash 12 g column, 0-75% ethyl acetate-hexanes to afford 400 mg (77%) of amide b as a colorless solid.

Example 90

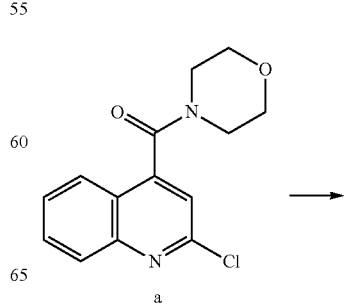

-continued

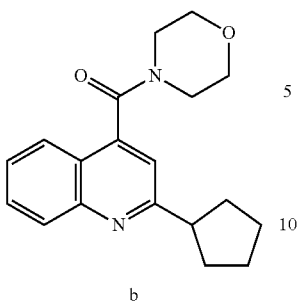

b

Following the general procedure of Rieke [Zhu, L.; Wehmeyer, R. M.; Rieke, R. D. *J. Org. Chem.* 1991, 56, 1445-1453], cyclopently zinc bromide (4.0 mL of 0.5M solution in THF, 2.0 mmol) was added to a mixture of chloride a (500 mg, 1.81 mmol), Pd(PPh$_3$)$_4$ (100 mg, 0.09 mmol) and THF (3 mL). The resulting solution was heated at 70° C. in a µW reactor for 15 min. The reaction was then quenched into saturated NH$_4$Cl (50 mL), and extracted with EtOAc (3×20 mL). The combined organic phases were dried (Na$_2$SO$_4$), adsorbed onto Celite and purified by chromatography ISCO CombiFlash 12 g column, 0-75% ethyl acetate-hexanes to afford 333 mg (59%) of amide b as a colorless solid.

Example 91

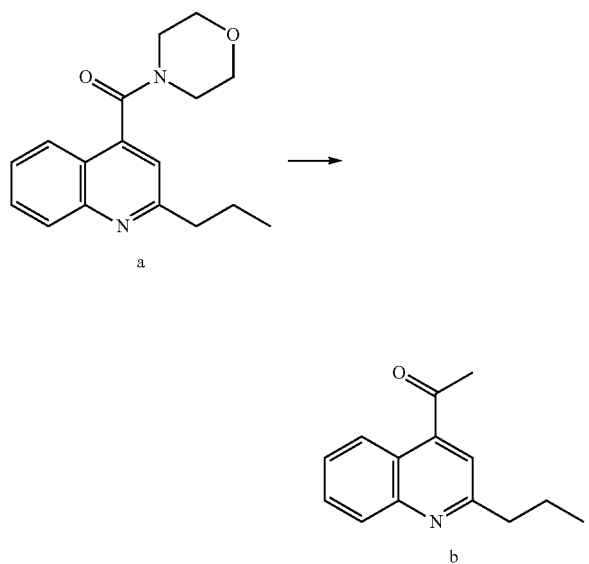

Methyl magnesium chloride (7.3 mL of 3.0M in THF, 22 mmol) was added to 0° C. solution of amide a (1.77 g, 6.2 mmol) and THF (15 mL). The solution was allowed to come to rt, then maintained at that temp. for 4 h. The reaction was quenched into cold saturated NH$_4$Cl (100 mL), extracted with EtOAc (3×50 mL). The combined organic phases were washed with brine (1×50 mL), dried (Na$_2$SO$_4$), adsorbed onto Celite and purified by chromatography ISCO CombiFlash 40 g column, 0-30% ethyl acetate-hexanes to afford 1.14 g (85%) of ketone b as a colorless oil.

Example 92

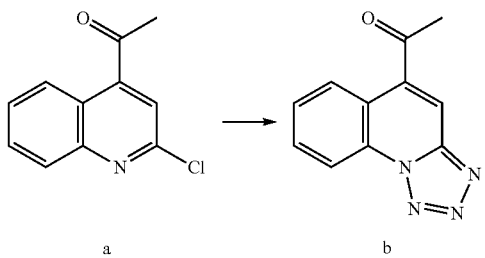 [SMILES: CC(=O)c1cc(Cl)nc2ccccc12 ; CC(=O)c1cc2nnnn2c2ccccc12]

Following the general procedure of Angibaud [Angibaud, P; et. al, *Bioorg. Med. Chem. Lett.* 2003, 13, 4365-4369], a mixture of chloride a (1.0 g, 5.0 mmol) NaN$_3$ (1.6 g, 25 mmol) DMF (10 mL) and water (1.0 mL) was heated at heated at 120° C. in a µW reactor for 2 h. The reaction was then quenched into water (50 mL), and extracted with EtOAc (3×20 mL). The combined organic phases were dried (Na$_2$SO$_4$), adsorbed onto Celite and purified by chromatography ISCO CombiFlash 40 g column, 0-50% ethyl acetate-hexanes to afford 300 mg (28%) of tetrazole b as a yellow solid.

Example 93

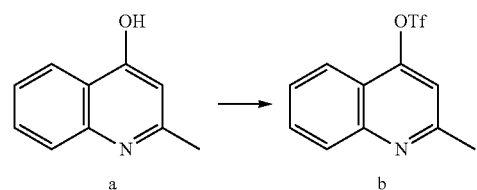 [SMILES: Cc1cc(O)c2ccccc2n1 ; Cc1cc(OS(=O)(=O)C(F)(F)F)c2ccccc2n1]

Trifluoromethane sulfonic anhydride (5.0 g, 17.7 mmol) was added drop wise to a mixture of 2-methyl-4-hydroxyquinoline a (2.56 g, 16.1 mmol) and pyridine (1.54 mL, 17.7 mmol) in CH$_2$Cl$_2$ (25 mL) at ice water bath temperature under N$_2$. The mixture was allowed to warm to 10° C. It was diluted with CH$_2$Cl$_2$ (100 mL), washed with saturated NaHCO$_3$ (3×50 mL), dried (Na$_2$SO$_4$), adsorbed on to Celite and purified by ISCO CombiFlash 40 g column (0-30% ethyl acetate-hexane) to afford 2.57 g (54%) of triflate b as a dark oil.

Example 94

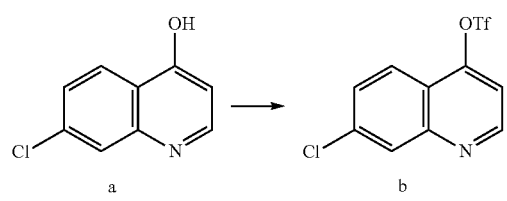 [SMILES: Oc1ccnc2cc(Cl)ccc12 ; O=S(=O)(Oc1ccnc2cc(Cl)ccc12)C(F)(F)F]

Following the general triflation procedure, 7-chloro-4-hydroxyquinoline a (10.0 g, 35.4 mmol) afforded 7.5 g (68%) of triflate b as a colorless solid.

Example 95

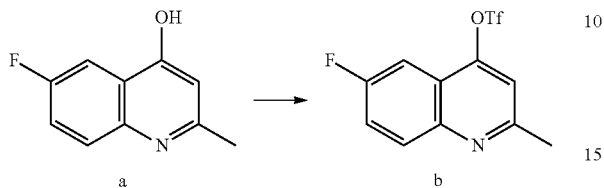

Following the general triflation procedure 6-flouro-4-hydroxyquinoline a (5.0 g, 28.2 mmol) afforded 6.6 g (75%) of triflate b as a colorless solid.

Example 96

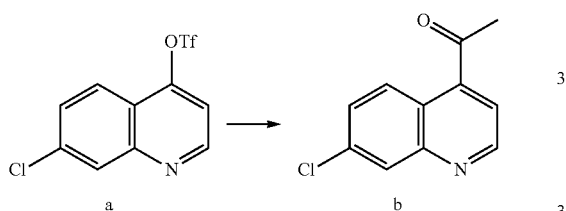

Following the general procedure of Legros [*Tetrahedron* 2001, 57, 2507-2514], a mixture of triflate a (7.5 g, 24.1 mmol), bis(dibenzylideneacetone)palladium(0) (690 mg, 1.2 mmol), 1,3-bis(diphenylphosphino)propane (546 mg, 1.33 mmol), and $Et_3N$ (10 mL, 72.3 mmol) in DMF (50 mL) were stirred at RT for 15 min under $N_2$. n-Butyl vinyl ether (15 mL, 120 mmol) in DMF (15 mL) was added and the resulting mixture was stirred at 80° C. for 24 h. It was cooled to RT, 1 N HCl (150 mL) were added slowly, stirred at RT for 24 h. The mixture was neutralized with 1 N NaOH and extracted with ether (3×100 mL), dried ($MgSO_4$), and concentrated. The crude product was adsorbed on to Celite and purified by ISCO CombiFlash 120 g column (5-30% ethyl acetate-hexane) to afford 1.62 g (32%) of ketone b as a white solid.

Example 97

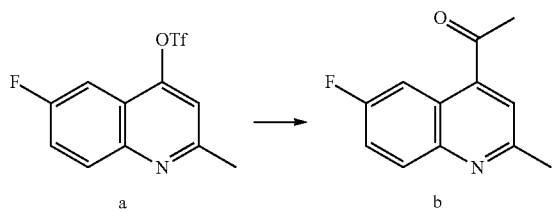 [SMILES: Cc1cc(OS(=O)(=O)C(F)(F)F)c2cc(F)ccc2n1 ; CC(=O)c1cc(C)nc2ccc(F)cc12]

Following the general procedure for preparing ketone from example 96, 6.56 g of triflate a afforded 3.14 g (73%) of ketone b as a colorless solid.

Example 98

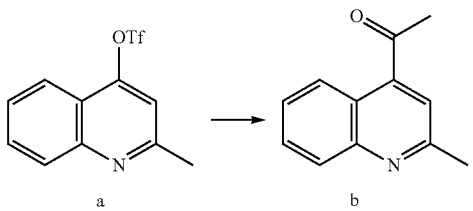 [SMILES: Cc1cc(OS(=O)(=O)C(F)(F)F)c2ccccc2n1 ; CC(=O)c1cc(C)nc2ccccc12]

Following the general procedure for preparing ketone from example 96, 2.57 g of triflate a afforded 820 mg (50%) of ketone b as a colorless solid.

Example 99

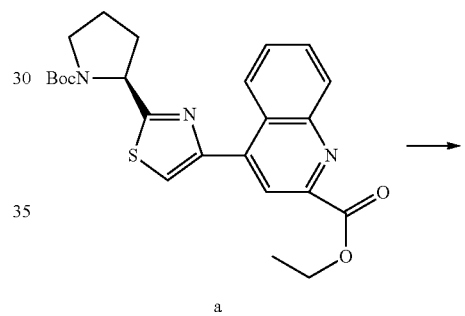

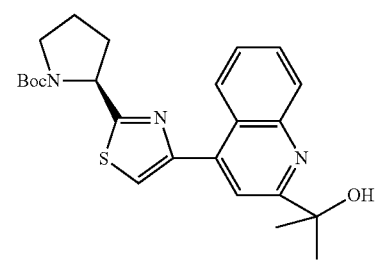

Methyl magnesium chloride (0.5 mL of 3.0M in THF, 1.5 mmol) was added to 0° C. solution of ester a (230 mg, 0.5 mmol) and THF (5 mL). The solution was maintained at 0° C. for 2 h. The reaction was quenched into cold saturated $NH_4Cl$ (50 mL), extracted with EtOAc (3×20 mL). The combined organic phases were washed with brine (1×50 mL), dried ($Na_2SO_4$), adsorbed onto Celite and purified by chromatography ISCO CombiFlash 12 g column, 0-50% ethyl acetate-hexanes to afford 135 mg (61%) of alcohol b as a colorless oil

Example 100

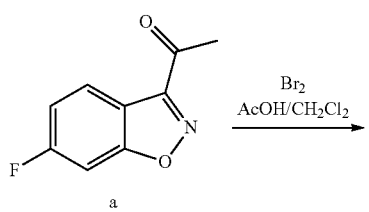

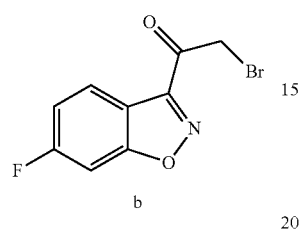

Bromine (122 μL, 2.4 mmol) was added to the solution of benzisoxazole ketone a (390 mg, 2.2 mmol) in AcOH (1.5 mL) and CH$_2$Cl$_2$ (6 mL). After 1 h at RT, LCMS indicated no reaction. Four drops of conc. HCl were added to the reaction mixture and stirred at RT overnight. It was quenched with 10% Na$_2$S$_2$O$_3$, diluted with CH$_2$Cl$_2$ (100 mL) and water, separated, washed the organic layer with 5% NaHCO$_3$, dried (MgSO$_4$), and concentrated to afford 537 mg (95%) of bromo ketone b as an off white solid.

Example 101

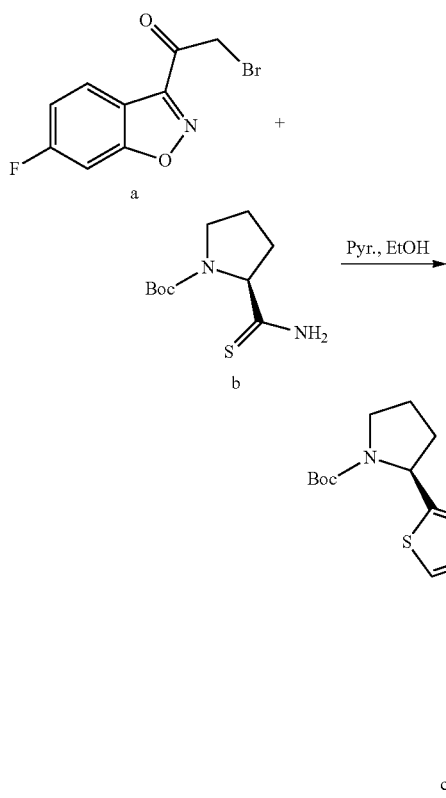

A mixture of bromo ketone a (537 mg, 2.1 mmol), thioamide b (718 mg, 3.1 mmol), and pyridine (153 μL, 1.9 mol) in EtOH (15 mL) was heated at 70° C. for 1 h. It was concentrated in vacuo. The crude product was adsorbed on to Celite and purified by ISCO CombiFlash 40 g column (3-30% ethyl acetate-hexane) to afford 190 mg (23%) of thiazole c as a light yellow gum.

Example 102

Tetrahydropyranylglycine

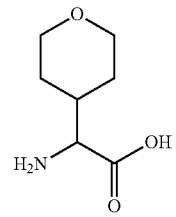

Tetrahydropyranylglycine was purchased from NovaBiochem, or synthesized according to the literature: Ghosh, A. K.; Thompson, W. J.; holloway, M. K.; McKee, S. P.; Duong, T. T.; Lee, H. Y.; Munson, P. M.; Smith, A. M.; Wai, J. M; Darke, P. L.; Zugay, J. A.; Emini, E. A.; Schleife, W. A.; Huff, J. R.; Anderson, P. S. *J. Med. Chem,* 1993, 36, 2300-2310.

Example 103

Piperidinylglycine

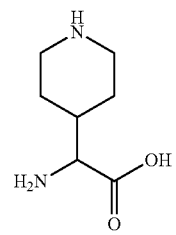

Piperidinylglycine was synthesized according to the procedures described by Shieh et al. (*Tetrahedron: Asymmetry,* 2001, 12, 2421-2425.

Example 104

4,4-difluorocyclohexylglycine

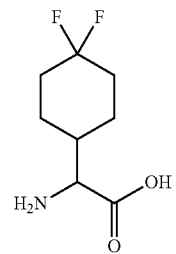

4,4-difluorocyclohexylglycine was made according to the procedures described in US 2003/0216325.

Example 105

Boc (S)-2-amino-2-(4-hydroxycyclohexyl)acetic acid

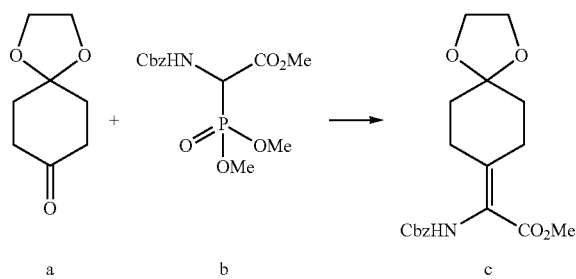 [SMILES: O=C1CCC2(CC1)OCCO2 ; COC(=O)C(NC(=O)OCc1ccccc1)P(=O)(OC)OC ; COC(=O)C(NC(=O)OCc1ccccc1)=C1CCC2(CC1)OCCO2]

a          b                    c

Following the procedure described by Sheih et al. (*Tetrahedron: Asymmetry*, 2001, 12, 2421-2425), a solution of ketone a (8.4 g) and EtOAc (30 mL) was added to a solution of N-Cbz-phosphonoglycine methyl ester b, TMG (4.5 mL) and EtOAc (30 mL). The solution was maintained at rt for 48 h, then washed with 1N HCl (3×50 mL), brine (1×50 mL) dried (Na$_2$SO$_4$), filtered, and concentrated. The residue was adsorbed onto Celite, and purified by chromatography, then further purified by re-crystallization from EtOAc/hexanes to afford 5.2 g of product c.

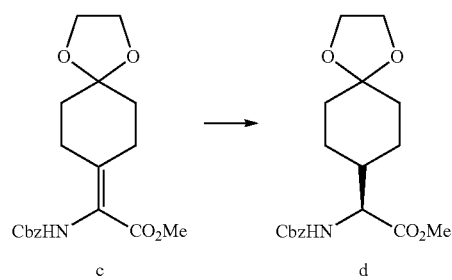 [SMILES: COC(=O)C(NC(=O)OCc1ccccc1)=C1CCC2(CC1)OCCO2 ; COC(=O)[C@@H](NC(=O)OCc1ccccc1)C1CCC2(CC1)OCCO2]

c                    d

Following the procedure described by Sheih, (*Tetrahedron: Asymmetry*, 2001, 12, 2421-2425), a solution of eneamide c (5.0 g), (S,S)-Me-BPE-Rh(I) (1.5 g, Strem Chemicals, Newburyport, Mass.), and MeOH (100 mL) was shaken vigorously under 70 psi of H$_2$ for 48 h. The solvent was removed under reduced pressure. The residue was taken up in EtOAc, and filtered through SiO$_2$ with more EtOAc. The solvent was removed under reduced pressure to afford 4.0 g of product d as a colorless solid.

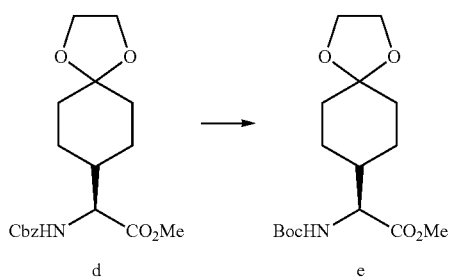 [SMILES: COC(=O)[C@@H](NC(=O)OCc1ccccc1)C1CCC2(CC1)OCCO2 ; COC(=O)[C@@H](NC(=O)OC(C)(C)C)C1CCC2(CC1)OCCO2]

d                    e

A mixture of Cbz-carbamate d, (4.0 g) Boc$_2$O, (2.9 g), 20% Pd(OH)$_2$—C (1.0 g) and MeOH (30 mL) was maintained under an atmosphere of H$_2$ for 6 h. The mixture was filtered through Celite with MeOH. The solvent was removed under reduced pressure to afford 4.5 g of residue e, which was taken on directly.

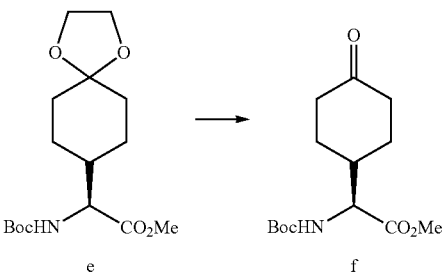 [SMILES: COC(=O)[C@@H](NC(=O)OC(C)(C)C)C1CCC2(CC1)OCCO2 ; COC(=O)[C@@H](NC(=O)OC(C)(C)C)C1CCC(=O)CC1]

e                    f

The residue e from above was dissolved in H$_2$O (10 mL), AcOH (30 mL), THF (5 mL), and dichloroacetic acid (3 mL) and maintained at rt overnight. Water (5 mL) was added and the solution and maintained until hyrolysis was complete, as monitored by HPLC-MS. Solid Na$_2$CO$_3$ was added cautiously until gas evolution ceased, the mixture was diluted with aq NaHCO$_3$, and extracted with 10% EtOAc/DCM. The combined organic phases were washed once with brine, dried (Na$_2$SO$_4$), filtered, and concentrated. The residue was purified by chromatography to afford 2.9 g of product f.

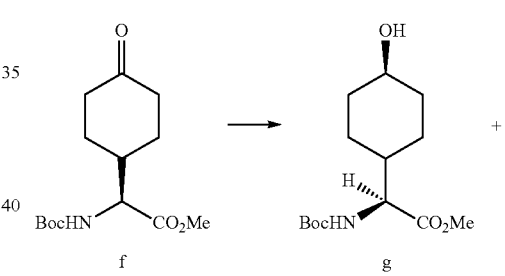

f                    g

h

A mixture of ketone f (1.5 g) MeOH (50 ml) was treated with NaBH4 (290 mg) at 0° C. for 20 min. The mixture was acidified to ~pH1 with 10% aq citric acid and the MeOH was removed under reduced pressure. The residue was diluted with water and extraced with 20% EtOAc/DCM. The combined organic phases were washed once with brine, dried (Na$_2$SO$_4$), filtered, and concentrated. The residue was purified by chromatography to afford 1.17 g of product g and 0.23 g of product h.

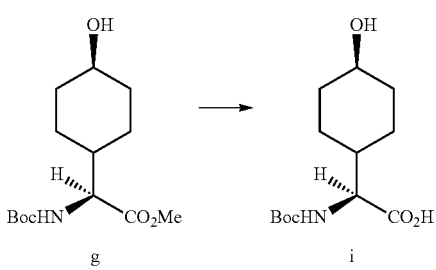

A mixture of ester g (1.17 g) LiOH.H2O (160 mg), THF (3 mL) and water (4.5 mL) was stirred vigorously at rt overnight. The mixture was diluted with brine and exhaustively extraced with EtOAc. The combined organic phases were washed once with brine, dried (Na$_2$SO$_4$), filtered, and concentrated to afford acid i (525 mg).

Example 106

N-Boc-N-cyclopropylmethyl-L-alanine

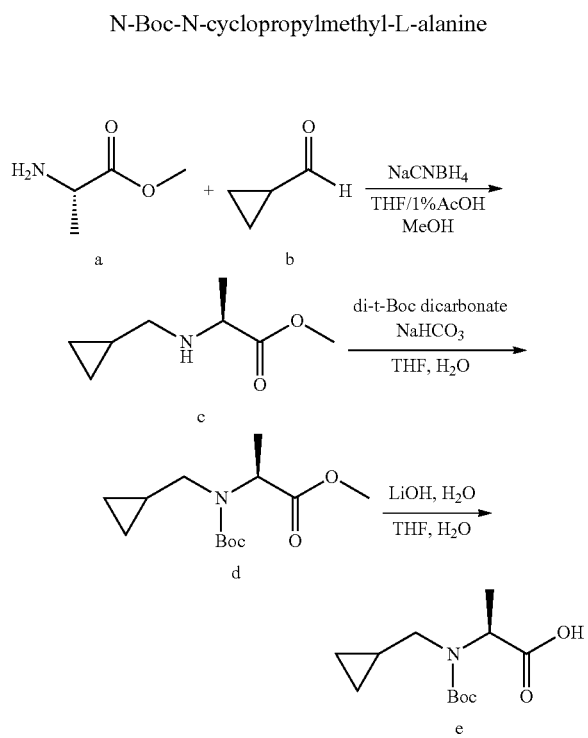

L-alanine methyl ester hydrochloride a (5 g, 35.8 mmol) and cyclopropanecarboxaldehyde b (2.67 ml, 35.8 mmol) were suspended in 50 ml THF w/1% AcOH. Addition of 5 ml of CH$_3$OH made the cloudy solution turned to clear. NaCNBH$_4$ (2.25 g, 35.8 mmol) was added and the reaction mixture stirred overnight. The reaction was quenched by addition of 1N aq. NaOH, extracted by EtOAc twice, organic layers were dried over Na$_2$SO$_4$ and concentrated to dryness. The crude material was purified by chromatography using 30% EtOAc/hexane (stained by ninhydrin) to obtain the compound c (1 g, 18%). The compound c (1 g, 6.37 mmol) and di-t-bocdicarbonate (2.1 g, 9.55 mmol) were diluted in THF (20 ml) and H$_2$O (20 ml), NaHCO$_3$ (1.3 g, 15.9 mmol) was added. The reaction mixture stirred overnight for completion. THF was removed under reduced pressure, and the aqueous layer was extracted by EtOAc 3 times. Combined organic layers were washed by 1N NaOH, sat, NH$_4$Cl followed by brine, the concentrated to dryness. The Boc-protected compound d (1.39 g, 5.40 mmol) was stirred with LiOH.H$_2$O (1.14 g, 27 mmol) in THF (20 ml) and H$_2$O (20 ml) overnight at room temperature. THF was stripped off, and the aqueous layer was adjusted to pH=4 by adding 10% citric acid, then extracted by EtOAc 3 times. Combined organic layers were washed by brine and concentrated. The crude was purified by reverse phase C-18 column eluted by 0%-50% acetonitrile/H$_2$O to give pure compound e as a white solid (794 mg).

Example 107

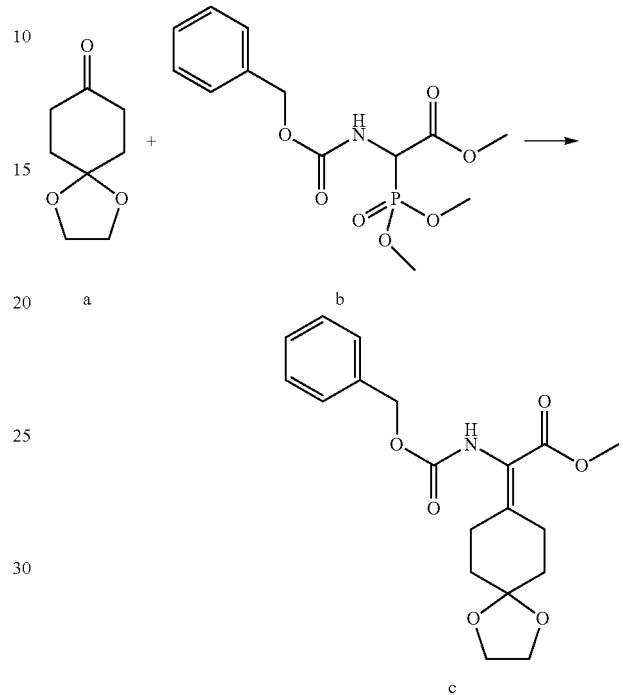

Phosphonate b (7.2 g, 21 mmol) was dissolved in THF (25 mL) at room temperature, and TMG (3.6 mL, 29 mmol, 1.3 equiv) was added dropwise. The mixture was stirred for 15 min at room temp. Commercially available ketone a (6.7 g, 43 mmol) was dissolved in THF (25 mL) and added dropwise to the mixture of phosphonate and base. The reaction was stirred for 24 h at room temperature and quenched by adding approx 200 mL of 1 N HCl. Organic products were quickly extracted into 80% ethyl acetate-hexanes (400 mL total). The combined organic phases were dried (Na$_2$SO$_4$), adsorbed onto Celite and purified twice by chromatography ISCO CombiFlash 120 g column, 0-55% ethyl acetate-hexanes over 20 min, followed by 55% ethyl acetate-hexanes for 5 min, to afford 3.83 g (10.6 mmol, 50%) of the product amino ester c as a white solid.

Example 108

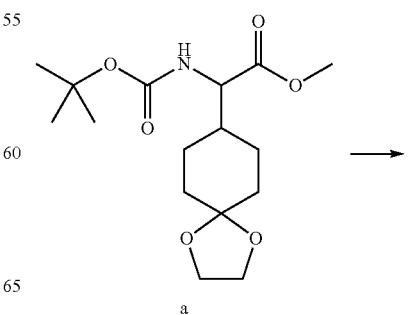

-continued

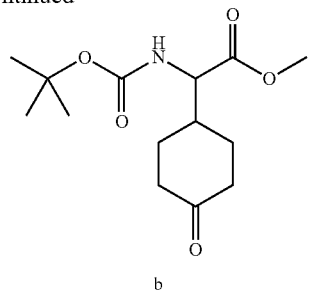

b

Ketal a (1.56 g, 4.73 mmol) was dissolved in 6 mL of THF. To this solution was added deionized water (15 mL), glacial acetic acid (6 mL), and dichloroacetic acid (1 mL). The mixture was stirred overnight at room temperature. Aqueous 1 N sodium hydroxide (approx. 100 mL) was added, and crude product was extracted into dichloromethane (approx. 200 mL). The organic product was adsorbed onto Celite by evaporation of the solvent, and purified by chromatography ISCO CombiFlash 80 g column with a solvent gradient of 0-40% ethyl acetate-hexanes over 20 min to afford 452 mg (1.58 mmol, 33%) of ketone b.

Example 109

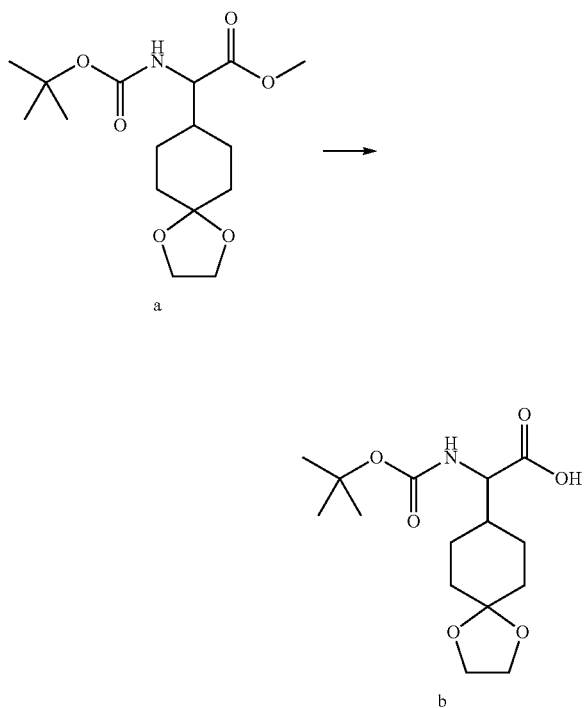 [SMILES: COC(=O)C(NC(=O)OC(C)(C)C)C1CCC2(CC1)OCCO2 ; CC(C)(C)OC(=O)NC(C(=O)O)C1CCC2(CC1)OCCO2]

Ester a (184 mg, 0.55 mmol) was dissolved in 2 mL of THF. Deionized water was added (1 mL), followed by lithium hydroxide monohydrate (42 mg, 1.0 mmol). The mixture was stirred at room temperature overnight, then acidified using aqueous 1 N HCl and extracted into dichloromethane. Drying (Na$_2$SO$_4$), filtration and evaporation of the solvent yielded 175 mg (quantitative yield) of the carboxylic acid b.

Example 110

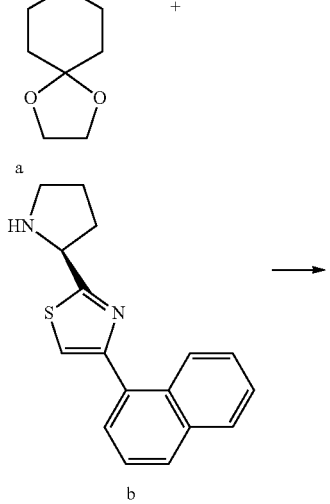

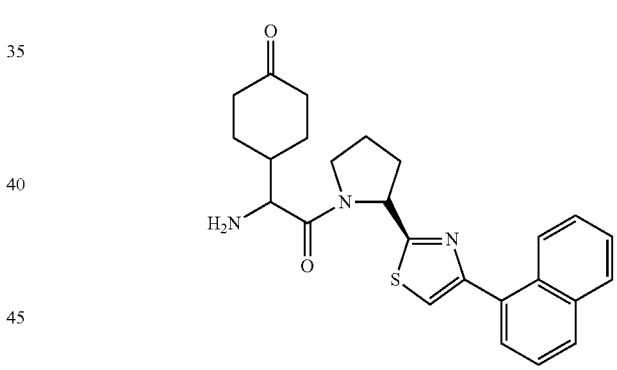

c

A small vial was charged with amine b (130 mg, 0.46 mmol), acid a (175 mg, 0.55 mmol) and EDC. HCl (135 mg, 0.70 mmol). The mixture was dissolved in dichloromethane (3 mL) and stirred overnight at room temperature. Celite was added to the reaction, and solvent was removed under reduced pressure. Crude product was purified by chromatography ISCO CombiFlash 40 g column with a solvent gradient of 0-45% ethyl acetate-hexanes over 10 min followed by 45% ethyl acetate-hexanes for 5 min. The BOC-protected amine obtained from this coupling reaction was dissolved in dichloromethane (2 mL), deionized water (0.5 mL) and trifluoroacetic acid (1 mL) and allowed to stir for 3 h at room temperature. Organic solvents were removed under reduced pressure, the aqueous layer was made basic using a small amount of 1 N NaOH, and product was extracted into dichloromethane. Removal of organic solvent yielded 110 mg (0.25 mmol, 45% amine #) of the free amine #.

Example 111

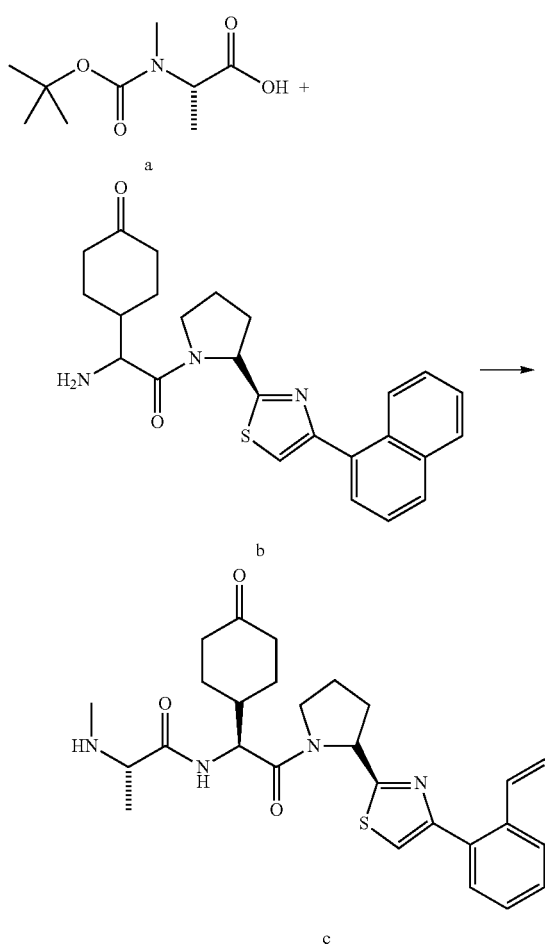

Standard EDC coupling procedure was performed using amine b (110 mg, 0.25 mmol) L-BOC-N-methylalanine a (72 mg, 0.35 mmol) and EDC (67 mg, 0.35 mmol). BOC-protected final product was purified by chromatography ISCO CombiFlash 12 g column with a solvent gradient of 5-55% ethyl acetate-dichloromethane over 15 min followed by 55% ethyl acetate-dichloromethane for 4 min. BOC-deprotection was performed using 2:1 DCM:TFA with few drops of water. Final product c (54 mg, 66%) was purified by reverse-phase HPLC C$_{18}$ column with a solvent gradient of 5-50% acetonitrile-water over 20 min.

Example 112

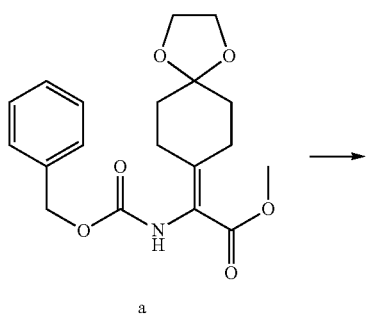

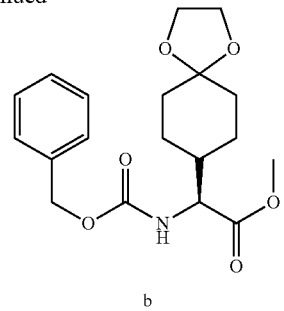

Following the general procedure of Burk [Burk, M. J.; Gross, M. F.; Martinez, J. P. *J. Am. Chem. Soc.* 1995, 117, 9375-9376.], 5.0 g (13.8 mmol) of alkene a, 100 mL of dry methanol, and [(S,S)-Me-BPE-Rh(COD)]$^+$OTf$^-$ (1.5 g, 2.4 mmol) were mixed in a Parr shaker flask purged with nitrogen. Parr shaker was evacuated and subsequently charged to 70 psi of hydrogen gas for 32 hours. Methanol was removed under reduced pressure, and crude product was filtered through a small plug of silica gel using ethyl acetate. Evaporation of the solvent gave 4.0 g (11 mmol, 80%) of product b with >98% yield.

Example 113

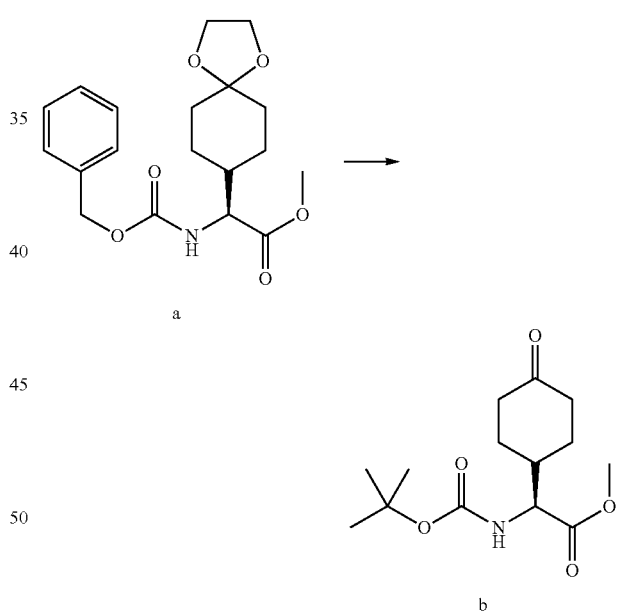

Z-protected amino ester a (4.0 g, 11 mmol) was dissolved in methanol (30 mL). To this solution was added BOC-anhydride (2.9 g, 13.5 mmol), followed by 20% Pd(OH)$_2$.C (1.0 g). All air was removed from the reaction flask by house vacuum, and the mixture was stirred vigorously for 5 min. The flask was then filled with hydrogen gas and allowed to stir vigorously at room temperature for 6 h. After evacuating the hydrogen atmosphere, the mixture was filtered through Celite using methanol, and crude product was obtained by evaporation of the solvent.

The product BOC-protected amine b was dissolved in 5 mL of THF. The following solvents were then added sequentially:

deionized water (15 mL), glacial acetic acid (30 mL), and dichloroacetic acid (3 mL). The mixture was stirred overnight at room temperature, and the reaction was quenched by slowly adding solid sodium carbonate with vigorous stirring until the release of gas was no longer visible. Crude product was extracted into 10% ethyl acetate-dichloromethane. The product was adsorbed onto Celite by evaporation of the solvents, and purified by chromatography ISCO CombiFlash 120 g column with a solvent gradient of 0-36% ethyl acetate-hexanes over 20 min followed by flushing with 36% ethyl acetate-hexanes for 5 min to afford 2.86 g (10.0 mmol, 91%) of ketone b.

Example 114

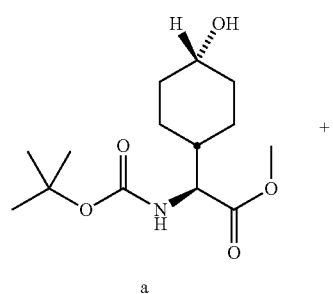

a

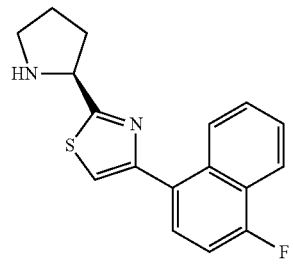

b

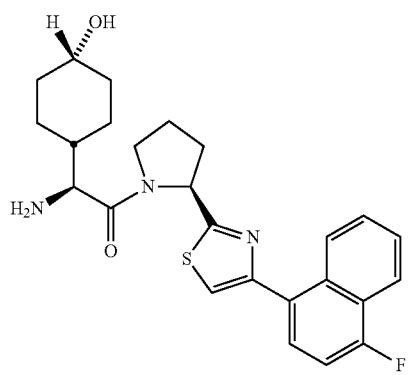

c

Standard EDC coupling was performed using amine b (46 mg, 0.15 mmol), carboxylic acid a, (42 mg, 0.15 mmol syn-diastereomer) and EDC (33 mg, 0.17 mmol). BOC-protected final product was purified by chromatography ISCO Combi-Flash stacker 2×4 g column with a solvent gradient of 0-28% ethyl acetate-dichloromethane over 15 min, followed by 28% ethyl acetate-dichloromethane for 3 min. Standard BOC-deprotection was performed using 2:1 DCM:TFA with few drops of water. The TFA salt was treated with base (aqueous 1 N NaOH) and extracted into dichloromethane.

Example 115

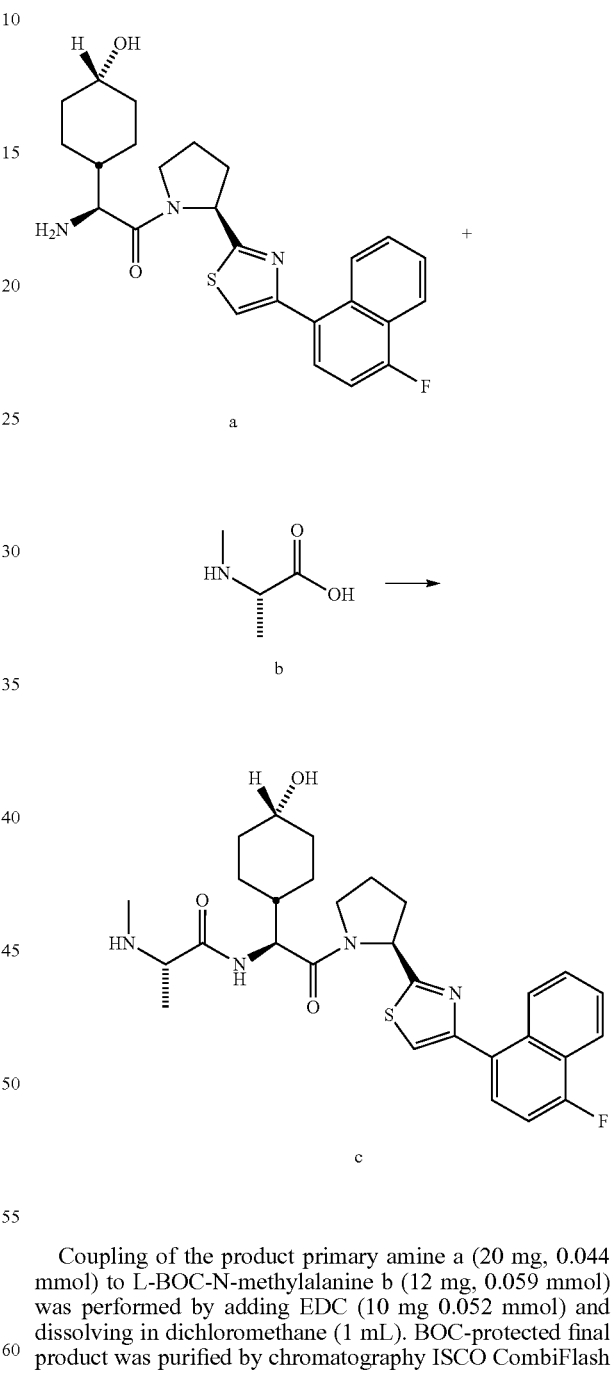

Coupling of the product primary amine a (20 mg, 0.044 mmol) to L-BOC-N-methylalanine b (12 mg, 0.059 mmol) was performed by adding EDC (10 mg 0.052 mmol) and dissolving in dichloromethane (1 mL). BOC-protected final product was purified by chromatography ISCO CombiFlash stacker 2×12 g column with a solvent gradient of 0-70% ethyl acetate-dichloromethane over 20 min followed by 70% ethyl acetate-dichloromethane for 5 min. BOC-deprotection was performed using 2:1 DCM:TFA with few drops of water. Final product c was purified by reverse-phase HPLC $C_{18}$ column with a gradient of 5-50% acetonitrile-water over 20 min. Yield of product anti-diastereomer c was 22 mg.

Example 116

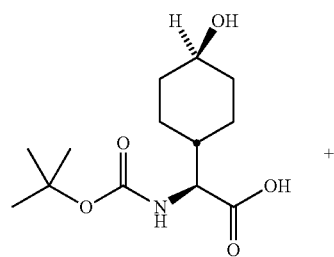

a

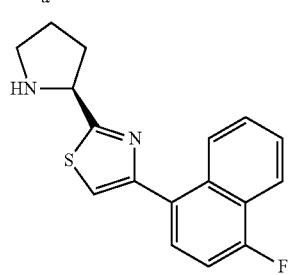

b

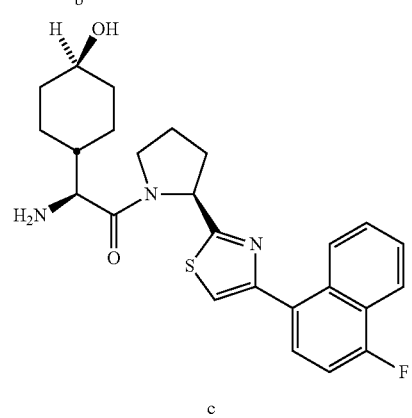

c

Standard EDC coupling was performed using amine b (110 mg, 0.38 mmol), carboxylic acid a, (105 mg, 0.38 mmol) and EDC (86 mg, 0.45 mmol). BOC-protected final product was purified by chromatography ISCO CombiFlash stacker 2×4 g column with a solvent gradient of 0-28% ethyl acetate-dichloromethane over 15 min, followed by 28% ethyl acetate-dichloromethane for 3 min. Standard BOC-deprotection was performed using 2:1 DCM:TFA with few drops of water. The TFA salt was treated with base (aqueous 1 N NaOH) and extracted into dichloromethane.

Example 117

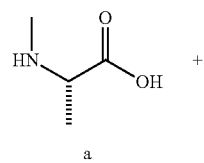

a

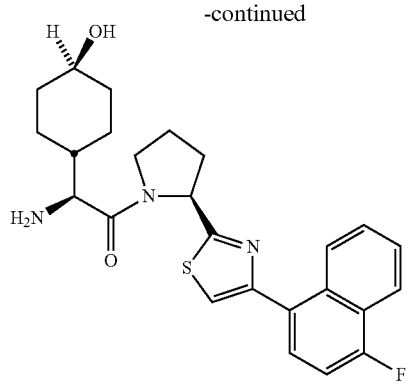

b

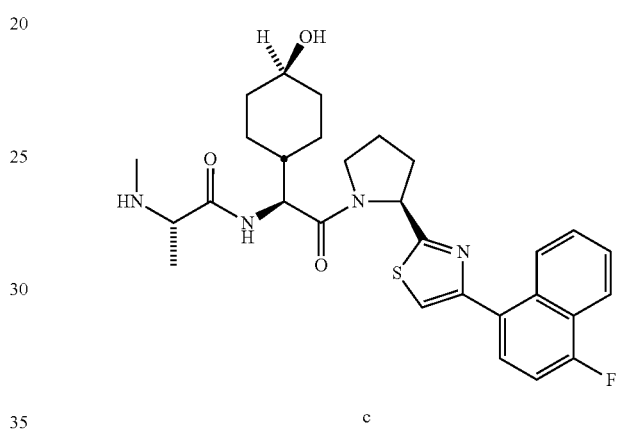

c

Coupling of the product primary amine b (170 mg, 0.35 mmol) to L-BOC-N-methylalanine a (81 mg, 0.40 mmol) was performed by adding EDC (77 mg 0.40 mmol) and dissolving in dichloromethane (2 mL). BOC-protected final product was purified by chromatography ISCO CombiFlash stacker 2×12 g column with a solvent gradient of 0-70% ethyl acetate-dichloromethane over 20 min followed by 70% ethyl acetate-dichloromethane for 5 min. Standard BOC-deprotection was performed using 2:1 DCM:TFA with few drops of water. Final product c was purified by reverse-phase HPLC $C_{18}$ column with a solvent gradient of 5-50% acetonitrile-water over 20 min. Yield of anti-diastereomer product c was 106 mg.

Example 118

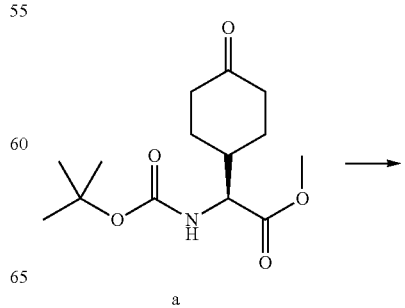

a

-continued

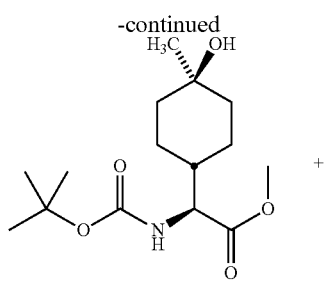

b

Ketone a (1.45 g, 5.3 mmol), was dissolved in dry diethyl ether (20 mL) and cooled to −78° C. Methyllithium (1.6 M in Et₂O, 9.5 mL, 15 mmol) was added dropwise to the reaction mixture and stirred vigorously at the reduced temperature for 1 h. The reaction was quenched by pouring the cold mixture into saturated aqueous ammonium chloride and extracting the organics into dichloromethane. The organic layer was dried (Na₂SO₄), filtered, adsorbed onto Celite and purified by chromatography ISCO CombiFlash 120 g column, 0-50% ethyl acetate-hexanes over 25 min, followed by flushing 50% ethyl acetate-hexanes for 3 min, and 90% ethyl acetate-hexanes for 3 min. This purification afforded 344 mg (1.1 mmol, 42%) of the syn-diastereomer c and 299 mg (0.99 mmol, 37%) of the anti-diastereomer b.

Example 119

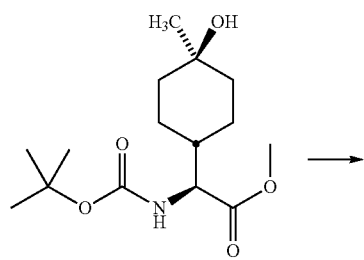

a

Hydrolysis of the methyl ester a (300 mg, 0.99 mmol) was carried out by dissolving in THF (0.8 mL), adding deionized water (1.2 mL) and LiOH.H₂O (47 mg, 1.1 mmol). The mixture was stirred at room temperature for 2 h, then reacidified using aqueous 1 N HCl and extracted into 90% ethyl acetate-dichloromethane. Brine was added to the aqueous acid layer to aid in the extraction. Drying (Na₂SO₄), filtration, and evaporation of the solvent yielded the carboxylic acid b (79 mg, 0.28 mmol).

Example 120

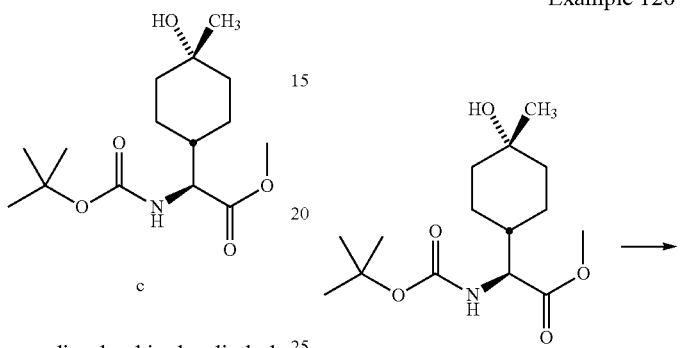

Hydrolysis of the methyl ester a (340 mg, 1.1 mmol) was carried out by dissolving in THF (0.9 mL), adding deionized water (1.4 mL) and LiOH.H₂O (50 mg, 1.2 mmol). The mixture was stirred at room temperature for 2 h, then reacidified using aqueous 1 N HCl and extracted into 90% ethyl acetate-dichloromethane. Brine was added to the aqueous acid layer to aid in the extraction. Drying (Na₂SO₄), filtration, and evaporation of the solvent yielded the carboxylic acid b (254 mg, 0.88 mmol), clean enough to use in the next step without purification.

Example 121

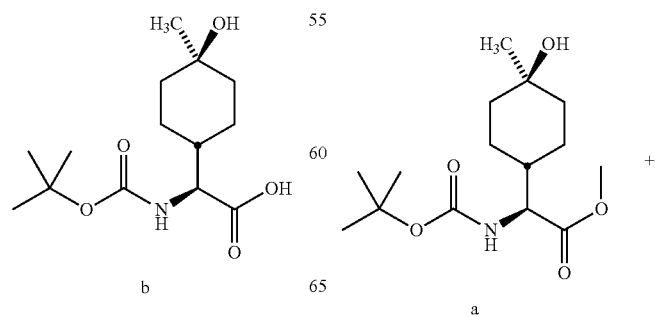

-continued

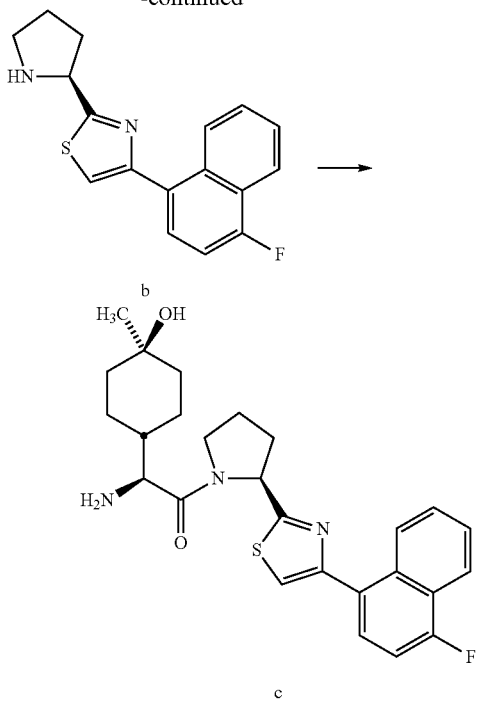

Standard EDC coupling was performed using amine b (62 mg, 0.21 mmol), the carboxylic acid a, (32 mg, 0.11 mmol) and EDC (21 mg, 0.11 mmol). BOC-protected final product was purified by chromatography ISCO CombiFlash 12 g column with a solvent gradient of 0-40% ethyl acetate-dichloromethane over 22 min, followed by 67% ethyl acetate-dichloromethane for 3 min. Standard BOC-deprotection was performed using 2:1 DCM:TFA with few drops of water. The TFA salt was treated with base (aqueous 1 N NaOH) and extracted into ethyl acetate with 10% dichloromethane.

Example 122

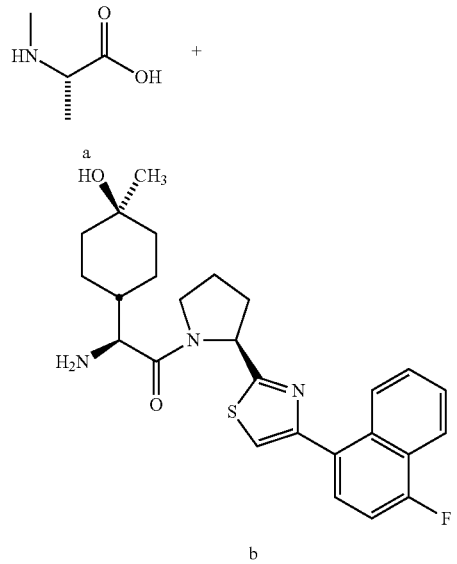

-continued

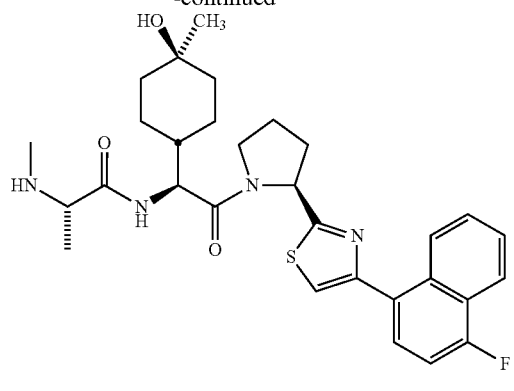

Coupling of the primary amine b (47 mg, 0.1 mmol) to L-BOC-N-methylalanine a (65 mg, 0.30 mmol) was performed by adding EDC (61 mg, 0.32 mmol) and dissolving in dichloromethane (2 mL). BOC-protected final product was purified by chromatography ISCO CombiFlash 12 g column with a solvent gradient of 5-65% ethyl acetate-dichloromethane over 25 min. Standard BOC-deprotection was performed using 2:1 DCM:TFA+few drops of water. Final product c was purified by reverse-phase HPLC $C_{18}$ column with a solvent gradient of 5-50% acetonitrile-water over 20 min. Yield of anti-diastereomer product c was 22 mg (31% from proline amine starting material).

Example 123

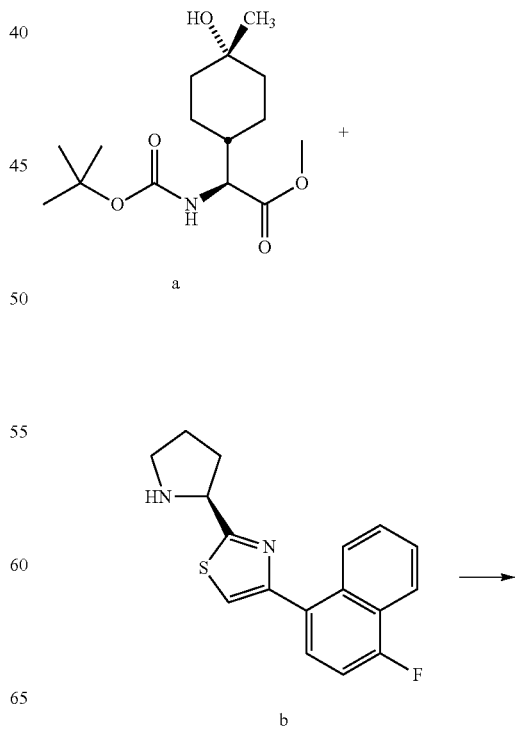

-continued

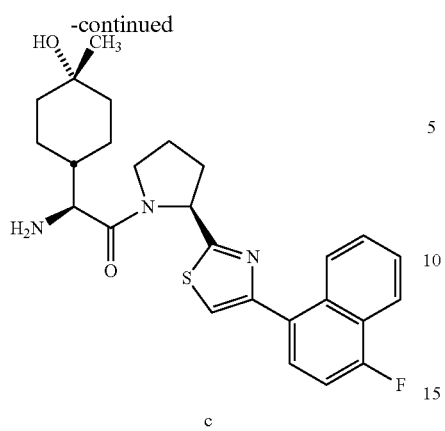

c

Standard EDC coupling was performed using amine b (82 mg, 0.27 mmol), the carboxylic acid a, (95 mg, 0.33 mmol) and EDC (65 mg, 0.34 mmol). BOC-protected final product was purified by chromatography ISCO CombiFlash 12 g column with a solvent gradient of 0-40% ethyl acetate-dichloromethane over 22 min, followed by 67% ethyl acetate-dichloromethane for 3 min. Standard BOC-deprotection was performed using 2:1 DCM:TFA with few drops of water. The TFA salt was treated with base (aqueous 1 N NaOH) and extracted into ethyl acetate with 10% dichloromethane.

Example 124

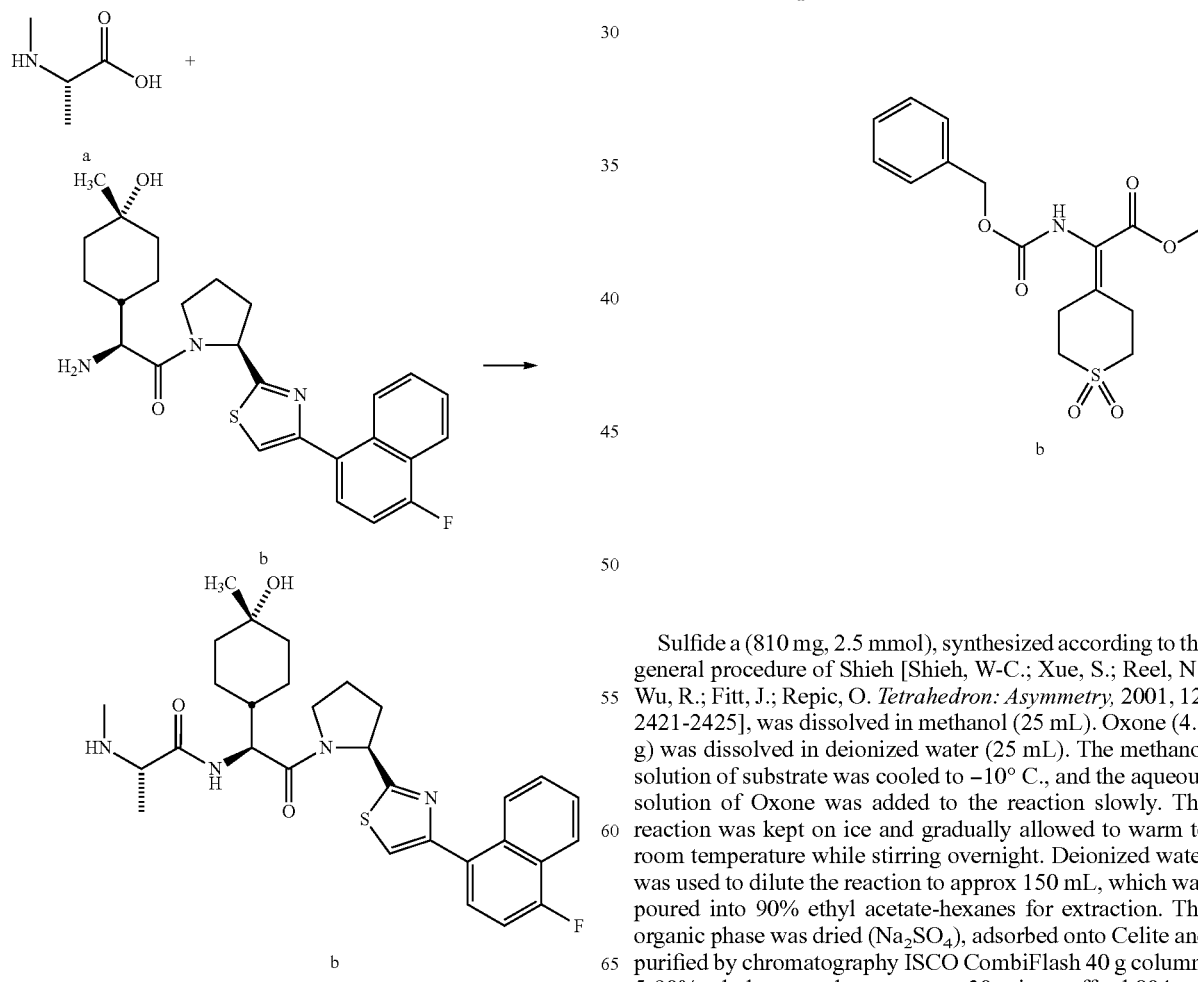

Coupling of the product primary amine b (70 mg, 0.15 mmol) to L-BOC-N-methylalanine a (37 mg, 0.18 mmol) was accomplished by adding EDC (36 mg 0.19 mmol) and dissolving in dichloromethane (2 mL). BOC-protected final product was purified by chromatography ISCO CombiFlash 12 g column with a solvent gradient of 1-51% ethyl acetate-dichloromethane over 20 min followed by 51% ethyl acetate-dichloromethane for 3 min. Standard BOC-deprotection was performed using 2:1 DCM:TFA+few drops of water. Final product b was purified by reverse-phase HPLC $C_{18}$ column with a solvent gradient of 5-50% acetonitrile-water over 20 min. Yield of product b was 49 mg.

Example 125

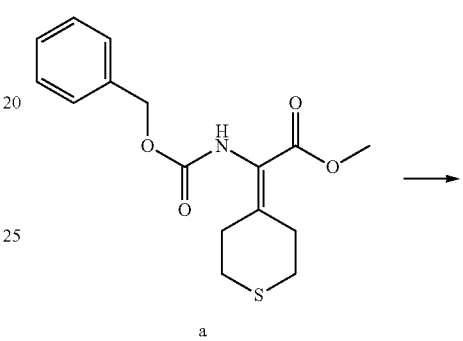

Sulfide a (810 mg, 2.5 mmol), synthesized according to the general procedure of Shieh [Shieh, W-C.; Xue, S.; Reel, N.; Wu, R.; Fitt, J.; Repic, O. *Tetrahedron: Asymmetry*, 2001, 12, 2421-2425], was dissolved in methanol (25 mL). Oxone (4.5 g) was dissolved in deionized water (25 mL). The methanol solution of substrate was cooled to −10° C., and the aqueous solution of Oxone was added to the reaction slowly. The reaction was kept on ice and gradually allowed to warm to room temperature while stirring overnight. Deionized water was used to dilute the reaction to approx 150 mL, which was poured into 90% ethyl acetate-hexanes for extraction. The organic phase was dried ($Na_2SO_4$), adsorbed onto Celite and purified by chromatography ISCO CombiFlash 40 g column, 5-90% ethyl acetate-hexanes over 30 min to afford 804 mg (2.27 mmol, 91%) of the product sulfone b.

Example 126

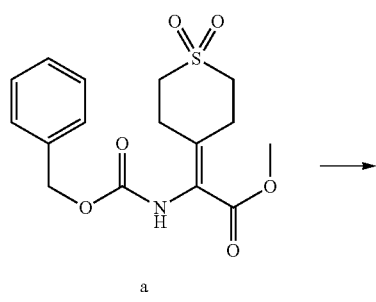

a

Following the general procedure of Burk [Burk, M. J.; Gross, M. F.; Martinez, J. P. *J. Am. Chem. Soc.* 1995, 117, 9375-9376.], alkene a (774 mg 2.19 mmol), dry methanol (40 mL), and [(S,S)-Me-BPE-Rh(COD)]⁺OTf⁻ (500 mg, 0.8 mmol) were mixed in a Parr shaker flask purged with nitrogen. Parr shaker was evacuated and subsequently charged to 60 psi of hydrogen gas and shaken vigorously overnight. Methanol was removed under reduced pressure, and crude product was filtered through a small plug of silica gel using ethyl acetate. Evaporation of the solvent yielded 730 mg (2.0 mmol, 94%) of product b with >98% yield.

Example 127

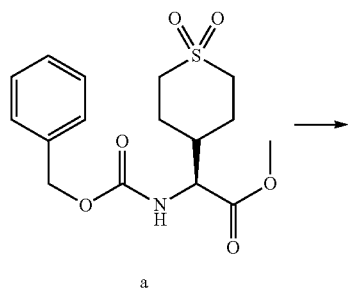

a

Z-protected amino ester a (804 mg, 2.27 mmol) was dissolved in methanol (16 mL). To this solution was added BOC-anhydride (1.5 g, 6.8 mmol), followed by 20% Pd(OH)$_2$.C (250 mg). All air was removed from the reaction flask by house vacuum, and the mixture was stirred vigorously for 5 min. The flask was then filled with hydrogen gas and allowed to stir vigorously at room temperature for 6 h. After evacuating the hydrogen atmosphere, the mixture was filtered through Celite using methanol, and crude product b was obtained by evaporation of the solvent (508 mg, 1.56 mmol, 70% yield).

Example 128

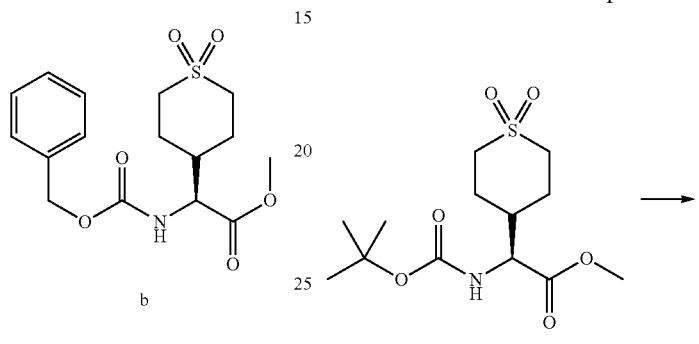

Ester a (508 mg, 1.56 mmol) was dissolved in 8 mL of THF. Deionized water (4 mL) was added, followed by LiOH.H$_2$O (120 mg, 2.8 mmol). The mixture was stirred at room temperature overnight, acidified using aqueous 1 N HCl and extracted into ethyl acetate. Drying (Na$_2$SO$_4$), filtration and evaporation of the solvent yielded 372 mg (1.21 mmol, 78% yield) of the carboxylic acid b, clean enough to use in the next step without purification.

Example 129

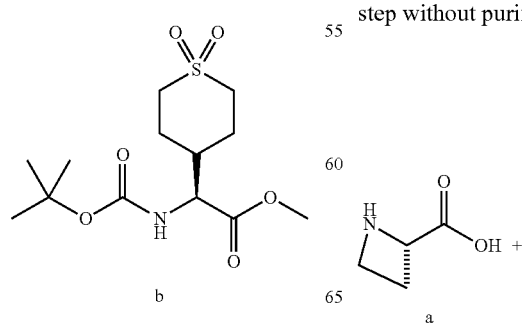

a

-continued

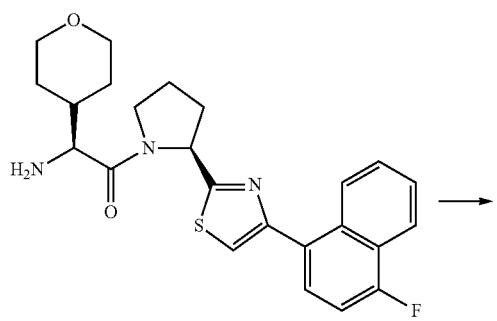

b

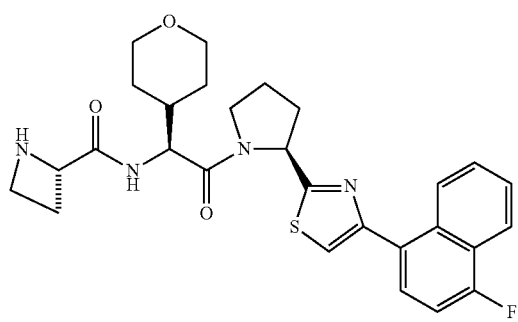

c

Standard EDC coupling was performed using amine b (100 mg, 0.2 mmol), the carboxylic acid a, (58 mg, 0.29 mmol) and EDC (56 mg, 0.29 mmol). BOC-protected final product was purified by chromatography ISCO CombiFlash 12 g column with a solvent gradient of 0-65% ethyl acetate-dichloromethane over 15 min. Standard BOC-deprotection was performed using 2:1 DCM:TFA with few drops of water. Final product c was purified by reverse-phase HPLC $C_{18}$ column with a solvent gradient of 5-50% acetonitrile-water over 18 min. Yield of product c was 132 mg.

Example 130

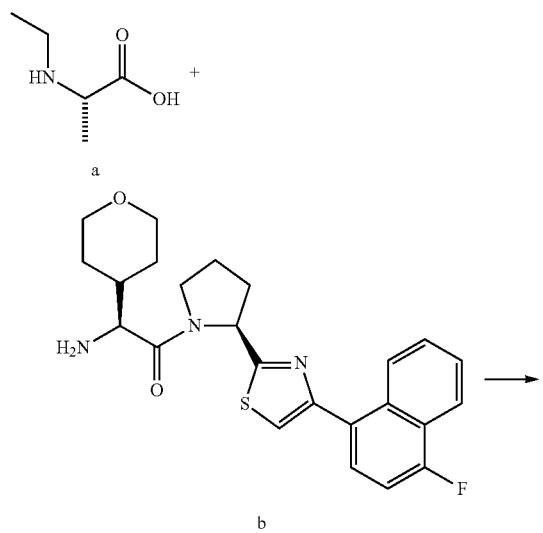

-continued

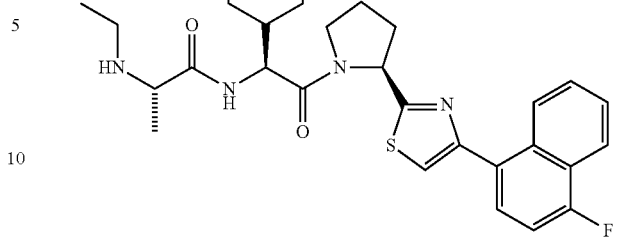

c

Standard EDC coupling was performed using amine b (130 mg, 0.3 mmol), the carboxylic acid a, (60 mg, 0.28 mmol) and EDC (60 mg, 0.3 mmol). BOC-protected final product was purified by chromatography ISCO CombiFlash 12 g column with a solvent gradient of 0-65% ethyl acetate-dichloromethane over 15 min. Standard BOC-deprotection was performed using 2:1 DCM:TFA with few drops of water. Final product c was purified by reverse-phase HPLC $C_{18}$ column with a solvent gradient of 5-50% acetonitrile-water over 18 min. Yield of product c was 78 mg.

Example 131

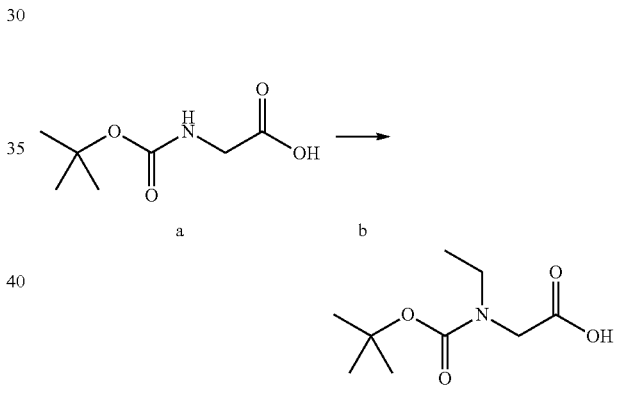

Following the general procedure of Grigg [Blaney, P.; Grigg, R.; Rankovic, Z.; Thornton-Pett, M.; Xu, J. *Tetrahedron*, 2002, 58, 1719-1737] a roundbottom flask was charged with sodium hydride (480 mg 60% dispersion in oil, 12.0 mmol, 4.0 equiv) and purged with nitrogen for 15 min. THF (6.0 mL) was added to the flask, and the suspension was cooled to 0° C. using an ice water bath. A separate flask was charged with BOC-glycine a (525 mg, 3.0 mmol), dry THF (6.0 mL) and ethyl iodide (1.0 mL, 12 mmol, 4 equiv). This mixture was added dropwise to the NaH suspension in THF, with vigorous stirring at 0° C. After 1 h of stirring, the reaction was warmed to room temperature and allowed to stir overnight. The reaction was again cooled to 0° C., and methanol (4 mL) was added very slowly to quench the excess hydride. Deionized water was added to dilute the mixture, and methanol was removed under reduced pressure. Impurities were extracted into 90% ethyl acetate-hexanes, the aqueous layer was then acidified by adding solid citric acid until the pH reached 2-3. The product was extracted into 90% ethyl acetate-hexanes. This organic layer was dried ($Na_2SO_4$) and

Example 132

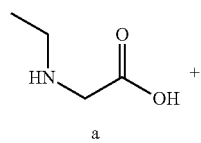

a

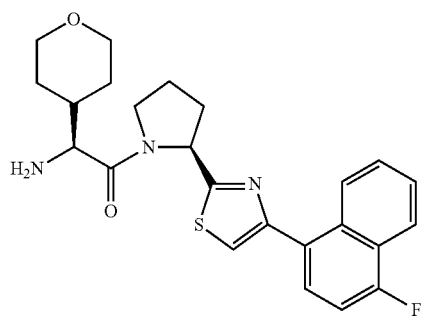

b

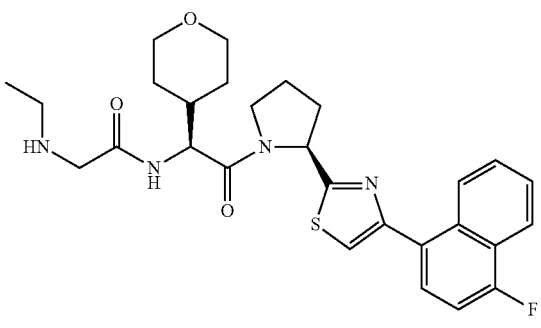

c

Standard EDC coupling was performed using amine b (70 mg, 0.16 mmol), the carboxylic acid a, (49 mg, 0.24 mmol) and EDC (46 mg, 0.24 mmol). BOC-protected final product was purified by chromatography ISCO CombiFlash 12 g column with a solvent gradient of 0-55% ethyl acetate-dichloromethane over 15 min. Standard BOC-deprotection was performed using 2:1 DCM:TFA with few drops of water. Final product c was purified by reverse-phase HPLC $C_{18}$ column with a solvent gradient of 5-50% acetonitrile-water over 18 min. Yield of product c was 82 mg.

Example 133

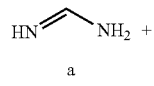

a

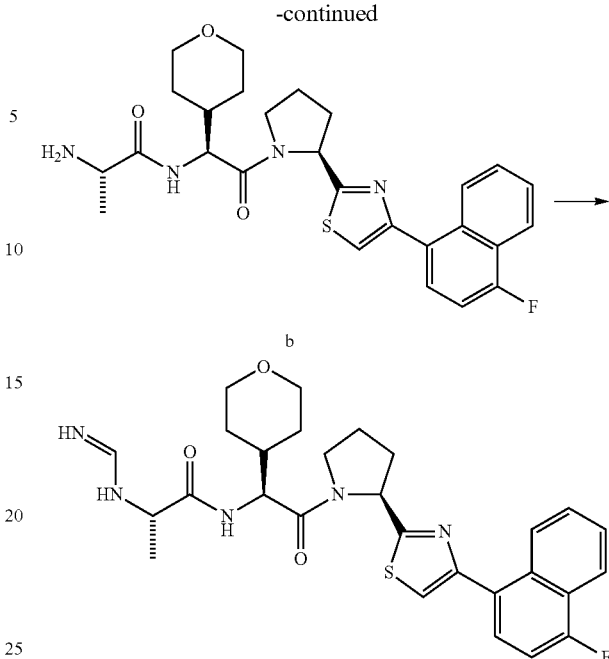

The free primary amine b (35 mg, 0.056 mmol), anhydrous potassium carbonate (70 mg, 0.5 mmol) and formamidine hydrochloride a (30 mg, 0.37 mmol) were mixed together in a vial and dissolved in methanol (1.2 mL). The mixture was stirred at room temperature for 1.5 hr. Glacial acetic acid was added until gas release was no longer visible, and the mixture was filtered. Reverse-phase HPLC, using a $C_{18}$ column and a solvent gradient of 5-50% acetonitrile-water over 25 min with 0.1% TFA, separated the desired product c, affording 8.2 mg (0.015 mmol, 27% yield) of the TFA salt after lyophilization.

Example 134

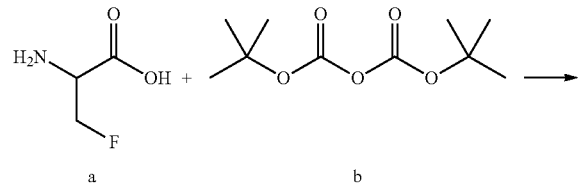

a b

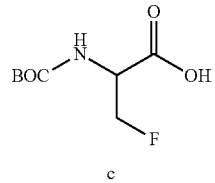

c

A mixture of unprotected amino acid a (775 mg, 7.24 mmol) and sodium carbonate (1.69 g, 16.0 mmol) was dissolved in a 1:1 solution of deionized water and THF (15 mL each). To this mixture was added BOC-anhydride b (1.73 g, 7.96 mmol). The mixture was stirred at room temperature overnight, and THF was removed under reduced pressure. The mixture was then acidified to pH 2-3 with saturated aqueous citric acid, and product was extracted into 10% ethyl acetate-dichloromethane. The organic layer was dried ($Na_2SO_4$), filtered and concentrated under reduced pressure to afford clean BOC-protected amino acid c (1.40 g, 6.7 mmol, 93%) to be used without further purification.

Example 135

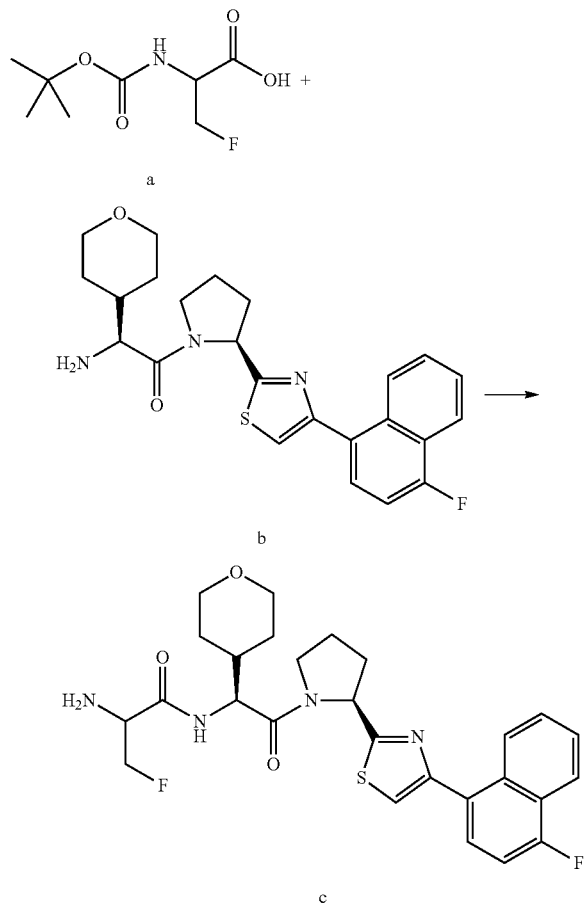

Standard EDC coupling was performed using amine b (64 mg, 0.14 mmol), the carboxylic acid a, (41 mg, 0.2 mmol) and EDC (38 mg, 0.2 mmol). BOC-protected final product was purified by chromatography ISCO CombiFlash 12 g column with a solvent gradient of 0-55% ethyl acetate-dichloromethane over 10 min, followed by a steady flow of 55% ethyl acetate-dichloromethane for 3 min. Standard BOC-deprotection was performed using 2:1 DCM:TFA+few drops of water. Final product c was purified by reverse-phase HPLC $C_{18}$ column with a solvent gradient of 5-50% acetonitrile-water over 18 min. Yield of product c was 70.2 mg.

Example 136

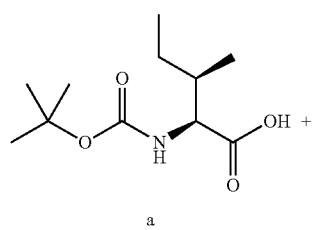

-continued

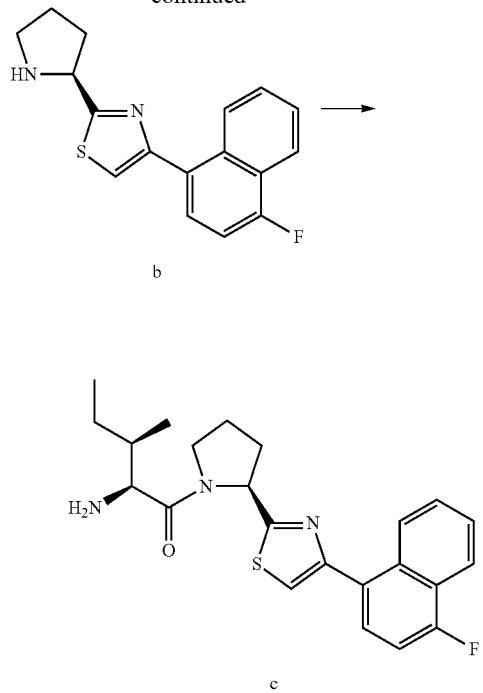

Standard EDC coupling was performed using amine hydrochloride b (250 mg, 0.67 mmol), the carboxylic acid a, (187 mg, 0.81 mmol), DIPEA (0.35 mL, 2.0 mmol) and EDC (157 mg, 0.81 mmol). Reaction was stirred at room temperature for 48 h. BOC-protected final product was purified by chromatography ISCO CombiFlash 12 g column with a solvent gradient of 0-25% ethyl acetate-hexanes over 10 min, followed by a steady flow of 26% ethyl acetate-hexanes for 3 min. Standard BOC-deprotection was performed using HCl in dioxane (4.0 M, 3.0 mL).

To the primary amine hydrochloride c (170 mg, 0.38 mmol) and L-BOC-N-methylalanine (91 mg, 0.45 mmol), was added dichloromethane (2 mL), DIPEA (0.20 mL, 1.1 mmol) and EDC (86 mg, 0.45 mmol), stirring at room temperature for 24 h. BOC-protected final product was purified by chromatography ISCO CombiFlash 12 g column with a solvent gradient of 0.5-52% ethyl acetate-hexanes over 13 min followed by 52% ethyl acetate-hexanes for 3 min. Standard BOC-deprotection was performed using 2:1 DCM:TFA with few drops of water. Final product was purified by reverse-phase HPLC $C_{18}$ column with a solvent gradient of 5-60% acetonitrile-water over 20 min. Yield of final product was 90 mg.

Example 137

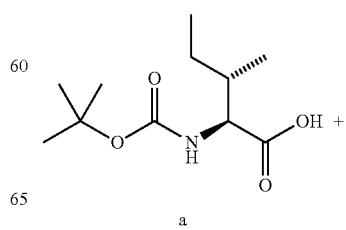

-continued

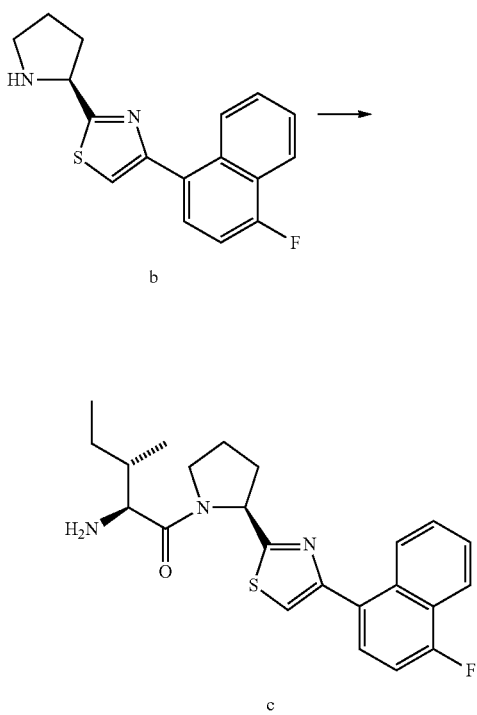

b c

Standard EDC coupling was performed using amine hydrochloride # (250 mg, 0.67 mmol), the carboxylic acid a, (187 mg, 0.81 mmol), DIPEA (0.350 mL, 2.0 mmol) and EDC (157 mg, 0.81 mmol). Reaction was stirred at room temperature for 3 h. BOC-protected final product was purified by chromatography ISCO CombiFlash 12 g column with a solvent gradient of 0-25% ethyl acetate-hexanes over 10 min, followed by a steady flow of 26% ethyl acetate-hexanes for 3 min. Standard BOC-deprotection was performed using HCl in dioxane (4.0 M, 3.0 mL).

To the primary amine hydrochloride (160 mg, 0.35 mmol) and L-BOC-N-methylalanine (91 mg, 0.45 mmol), was added dichloromethane (2 mL), DIPEA (0.200 mL, 1.1 mmol) and EDC (86 mg, 0.45 mmol), stirring at room temperature for 24 h. BOC-protected final product was purified by chromatography ISCO CombiFlash 12 g column with a solvent gradient of 0.5-52% ethyl acetate-hexanes over 13 min followed by 52% ethyl acetate-hexanes for 3 min. Standard BOC-deprotection was performed using 2:1 DCM:TFA with few drops of water. Final product was purified by reverse-phase HPLC $C_{18}$ column with a solvent gradient of 5-60% acetonitrile-water over 20 min. Yield of product c was 79 mg.

Example 138

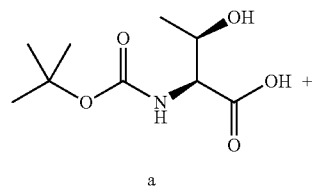

a

-continued

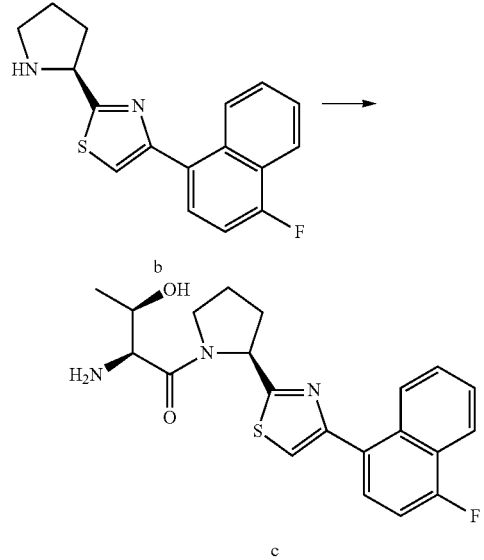

b c

EDC coupling was performed using amine hydrochloride b (230 mg, 0.61 mmol), the carboxylic acid a, (165 mg, 0.75 mmol), DIPEA (0.350 mL, 2.0 mmol) and EDC (157 mg, 0.81 mmol). Reaction was stirred at room temperature for 3 h, LC/MS indicated only half complete. More carboxylic acid (160 mg) and EDC (150 mg) was added to the reaction, and the mixture was stirred overnight at room temperature. BOC-protected final product was purified by chromatography ISCO CombiFlash 40 g column with a solvent gradient of 0-55% ethyl acetate-hexanes over 17 min, followed by a steady flow of 56% ethyl acetate-hexanes for 5 min. Standard BOC-deprotection was performed using 2:1 DCM:TFA+few drops of water. Coupling of the product primary amine c (199 mg, 0.5 mmol) to L-BOC-N-methylalanine (140 mg, 0.7 mmol) was performed with EDC (135 mg, 0.7 mmol) and dichloromethane (3 mL). BOC-protected final product was purified by chromatography ISCO CombiFlash 12 g column with a solvent gradient of 0-40% ethyl acetate-dichloromethane over 15 min followed by 40% ethyl acetate-dichloromethane for 3 min. Standard BOC-deprotection was performed using 2:1 DCM:TFA with few drops of water. Final product was purified by reverse-phase HPLC $C_{18}$ column with a solvent gradient of 5-50% acetonitrile-water over 20 min. Yield of final product was 178 mg.

Example 139

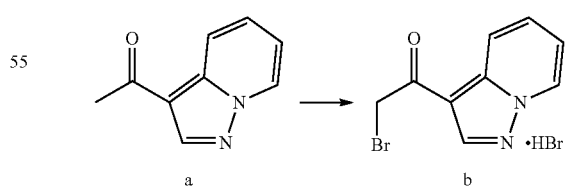

a b

Methyl ketone a (480 mg, 3.0 mmol), synthesized according to the general procedure of Miki [Miki, Y.; Nakamura, N.; Hachiken, H.; Takemura, S. *J. Heterocyclic Chem.*, 1989, 26, 1739-1745], was suspended in 33% HBr in acetic acid (6 mL). Elemental bromine was added in six portions (6×0.025 mL, 0.15 mL total, 3.0 mmol) with vigorous stirring at room temperature. The reaction appeared to have a light color after 10 min of stirring, when diethyl ether was added (10 mL). Stirring at room temperature was continued for 30 min. The mixture was filtered through a frit, and the solids left behind were rinsed with 20 mL of ether, transferred to a vial, and dried under high vacuum. The solid afforded (840 mg) was a mixture of desired product b and the HBr salt of the starting material, used without further purification in the thiazole-forming step.

Example 140

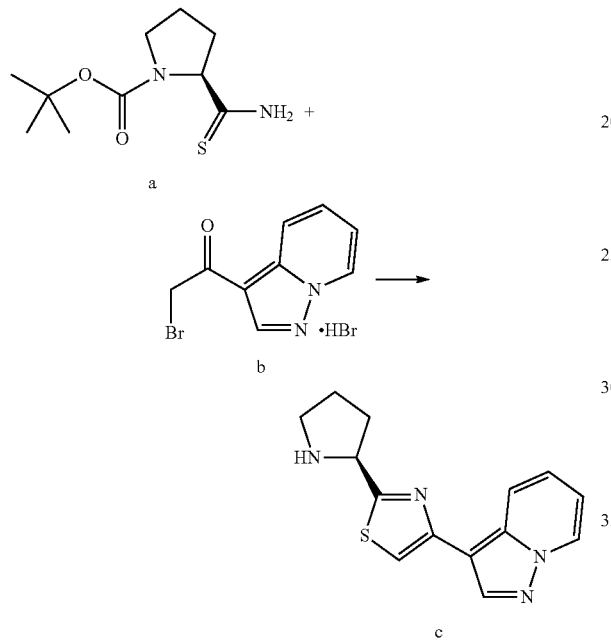

Thioamide a (2.26 mg, 9.8 mmol) was added to the mixture of bromomethyl ketone b and methyl ketone (1.44 g) in a roundbottom flask. Ethanol (30 mL) was added, dissolving the thioamide and suspending the salts. Pyridine was then added dropwise (0.4 mL, 5.0 mmol) and the mixture was stirred at room temperature for 5 min. The reaction flask was then heated to 70° C. in an oil bath, with vigorous stirring. After 10 min, the suspension of salts was no longer visible and the reaction was homogeneous. The reaction was allowed to cool to room temperature for 45 min, and Celite was added along with toluene (20 mL). Solvents were removed under reduced pressure. The crude product adsorbed onto Celite was purified by chromatography ISCO CombiFlash 120 g column, 0-30% ethyl acetate-dichloromethane over 20 min, followed by a gradient of 30-70% ethyl acetate-dichloromethane over 5 min, to afford 518 mg (1.4 mmol, 47%) of the product thiazole. Removal of BOC from the proline amine was accomplished by dissolving the substrate in 2:1 DCM:TFA with few drops of water, following the standard procedure. Free base was obtained by treating the TFA salt with 1 N aqueous sodium hydroxide and extracting the amine into dichloromethane. Drying of the organic layer (Na$_2$SO$_4$), filtering and removing the solvent under reduced pressure afforded 356 mg (1.3 mmol, 93%) of free amine c.

Example 141

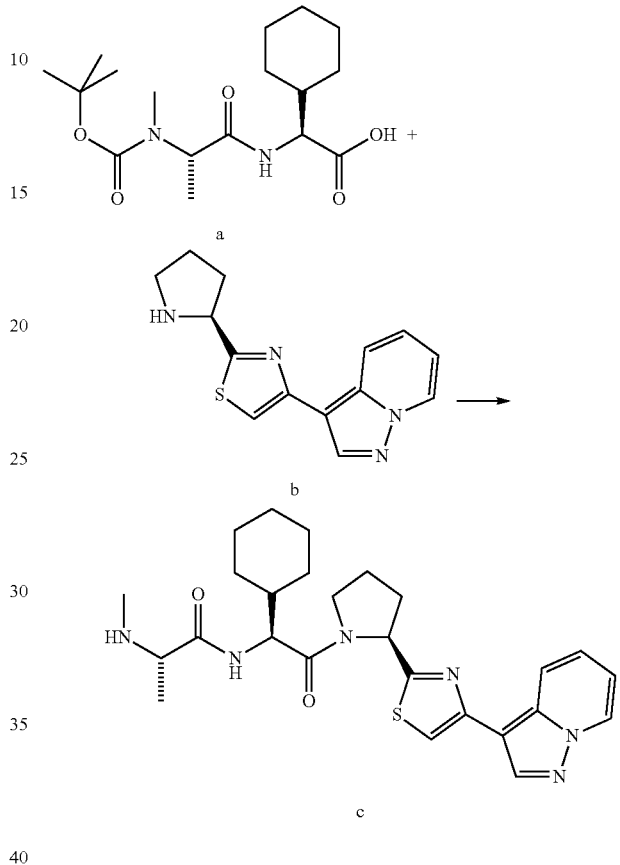

HOAt, DIC procedure was used to couple the above dipeptide to amine. Secondary amine b (65 mg, 0.25 mmol), carboxylic acid a, (97 mg, 0.28 mmol) HOAt (53 mg, 0.4 mmol) and DIC (50 mg, 0.4 mmol). BOC-protected final product was purified by chromatography ISCO CombiFlash 12 g column with a solvent gradient of 0-65% ethyl acetate-dichloromethane over 15 min. Standard BOC-deprotection was performed using 2:1 DCM:TFA+few drops of water. Final product c was purified by reverse-phase HPLC C$_{18}$ column with a solvent gradient of 5-50% acetonitrile-water over 18 min. Yield of product c was 98 mg.

Example 142

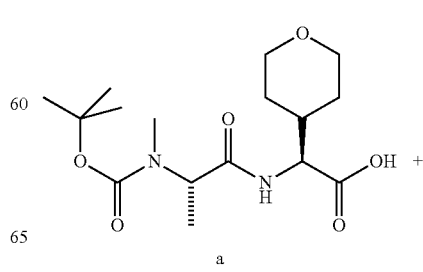

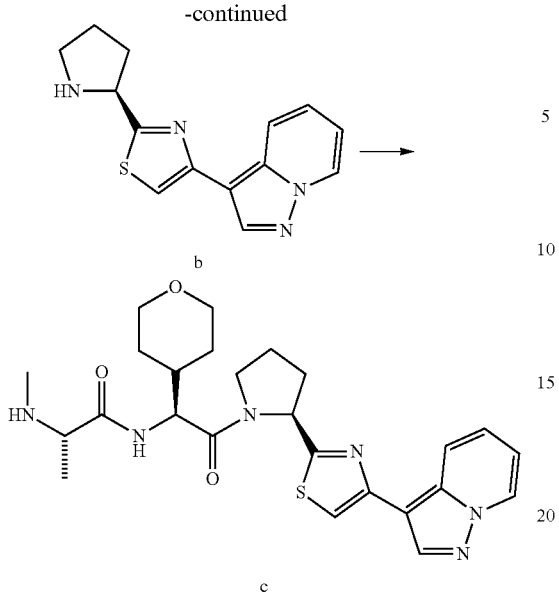

HOAt, DIC procedure was used to couple the above dipeptide to amine. Secondary amine b (50 mg, 0.2 mmol), carboxylic acid a, (72 mg, 0.21 mmol) HOAt (40 mg, 0.3 mmol) and DIC (38 mg, 0.3 mmol). BOC-protected final product was purified by chromatography ISCO CombiFlash 12 g column with a solvent gradient of 10-85% ethyl acetate-dichloromethane over 20 min. Standard BOC-deprotection was performed using 2:1 DCM:TFA+few drops of water. Final product c was purified by reverse-phase HPLC $C_{18}$ column with a solvent gradient of 3-40% acetonitrile-water over 20 min. Yield of final product c was 25 mg.

Example 143

A mixture of unprotected amino acid a (1.1 g, 10 mmol) and sodium carbonate (850 mg, 10 mmol) was dissolved in a 1:1 solution of deionized water and THF (13 mL each). To this mixture was added FMOC-OSu b (6×550 mg, total 3.3 g, 9.8 mmol) over a period of 1 h. After each addition of FMOC-OSu was added 2-3 mL of 1 M aqueous sodium bicarbonate to keep the reaction mixture at basic pH. The mixture was stirred at room temperature overnight, and THF was removed under reduced pressure. The mixture was then diluted with deionized water, poured into ethyl acetate in a separatory funnel, and made acidic by the addition of 6 N HCl. After extracting into ethyl acetate, the organic layer was washed with deionized water, followed by brine. The organic layer was dried ($Na_2SO_4$), filtered and concentrated under reduced pressure to afford clean FMOC-protected amino acid c (1.05 g, 3.19 mmol, 32%) to be used without further purification.

Example 144

Following the general procedure of Freidinger [Freidinger, R. M.; Hinkle, J. S.; Perlow, D. S.; Arison, B. H. *J. Org. Chem.*, 1983, 48, 77-81], the FMOC-protected primary amine a (1.04 g, 3.17 mmol) was dissolved in toluene (60 mL). Paraformaldehyde (630 mg) was added, followed by a catalytic amount of p-toluenesulfonic acid (70 mg, 0.37 mmol). The mixture was vigorously stirred at reflux temperature for 45 min, collecting any generated water in a Dean Stark trap. The reaction mixture was then allowed to cool to room temperature, and washed with saturated aqueous sodium bicarbonate (2×30 mL). The organic layer was dried ($Na_2SO_4$), filtered, and concentrated under reduced pressure to afford 910 mg (2.7 mmol) of oxazolidinone b. The oxazolidinone (337 mg, 0.99 mmol) was dissolved in dichloromethane (20 mL). To this solution was added anhydrous aluminum trichloride (260 mg, 2.0 mmol), followed by triethylsilane (0.32 mL, 2.0 mmol). The reaction mixture was stirred for 5 h at room temperature and then quenched with 20 mL of 1 N aqueous HCl. The product carboxylic acid was extracted into 25% ethyl acetate-dichloromethane and washed with 1 N aqueous HCl (20 mL) followed by brine. The organic layer was dried ($Na_2SO_4$) and filtered. Celite was added, and the solvent was removed under reduced pressure. The crude product adsorbed onto Celite was purified by chromatography ISCO CombiFlash 40 g column, 1-55% ethyl acetate-dichloromethane over 25 min, to afford 272 mg (0.79 mmol, 25% yield from FMOC-primary amine) of the FMOC protected N-methyl amino acid c.

Example 145

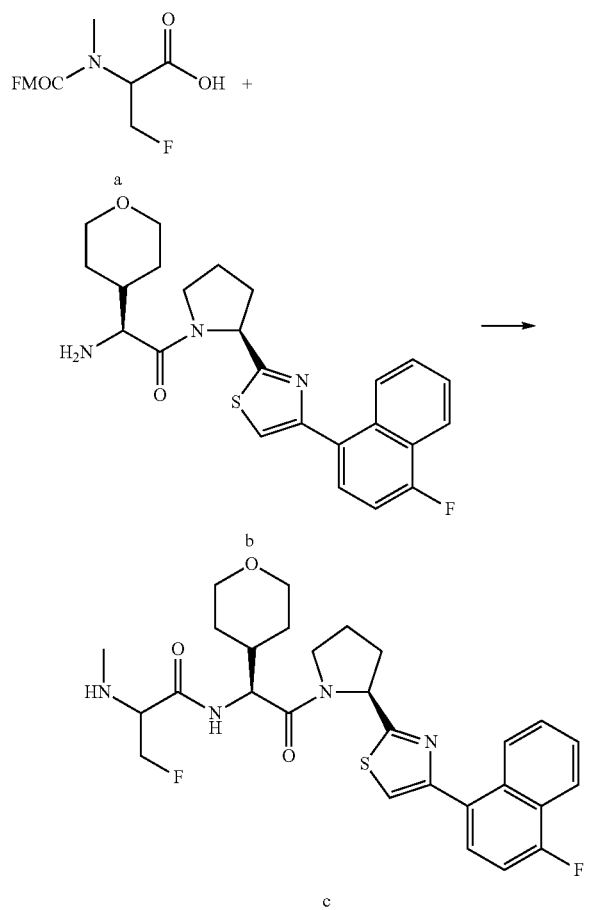

Standard EDC coupling was performed using amine # (140 mg, 0.4 mmol), the crude carboxylic acid a, (176 mg, 0.4 mmol) and EDC (80 mg, 0.4 mmol). BOC-protected final product was purified by chromatography ISCO CombiFlash 40 g column with a solvent gradient of 1-40% ethyl acetate-dichloromethane over 20 min. The desired BOC-protected product was split into two portions for removing the FMOC group. The first portion (50 mg, 0.065 mmol) was dissolved in dichloromethane (1.0 mL), treated with piperidine (0.10 mL, 1.0 mmol), and allowed to stir at room temperature for 2 h. The second portion (100 mg, 0.13 mmol) was dissolved in 20% piperidine in DMF (1.0 mL) and allowed to stir at room temperature overnight. Both reactions were quenched by adding few drops of TFA. Final product was purified by reverse-phase HPLC $C_{18}$ column with a solvent gradient of 3-40% acetonitrile-water over 20 min. Combined yield of final product c was 55 mg.

Example 146

IAP Inhibition Assays

In the following experiments was used a chimeric BIR domain referred to as MLXBIR3SG in which 11 of 110 residues correspond to those found in XIAP-BIR3, while the remainder correspond to ML-IAP-BIR. The chimeric protein MLXBIR3SG was shown to bind and inhibit caspase-9 significantly better than either of the native BIR domains, but bound Smac-based peptides and mature Smac with affinities similar to those of native ML-IAP-BIR. The improved caspase-9 inhibition of the chimeric BIR domain MLXBIR3SG has been correlated with increased inhibition of doxorubicin-induced apoptosis when transfected into MCF7 cells.

MLXBIR3SG Sequence:

(SEQ ID NO.: 1)
MGSSHHHHHHSSGLVPRGSHMLETEEEEEGAGATLSRGPAFPGMGSEEL

RLASFYDWPLTAEVPPELLAAAGFFHTGHQDKVRCFFCYGGLQSWKRGDD

PWTEHAKWFPGCQFLLRSKGQEYINNIHLTHSL

TR-FRET Peptide Binding Assay

Time-Resolved Fluorescence Resonance Energy Transfer competition experiments were performed on the Wallac Victor2 Multilabeled Counter Reader (Perkin Elmer Life and Analytical Sciences, Inc.) according to the procedures of Kolb et al (Journal of Biomolecular Screening, 1996, 1(4): 203). A reagent cocktail containing 300 nM his-tagged MLXBIR3SG; 200 nM biotinylated SMAC peptide (AVPI); 5 μg/mL anti-his allophycocyanin (XL665) (CISBio International); and 200 ng/mL streptavidin-europium (Perkin Elmer) was prepared in reagent buffer (50 mM Tris [pH 7.2], 120 mM NaCl, 0.1% bovine globulins, 5 mM DTT and 0.05% octylglucoside). (Alternatively, this cocktail can be made using europium-labeled anti-His (Perkin Elmer) and streptavidin-allophycocyanin (Perkin Elmer) at concentrations of 6.5 nM and 25 nM, respectively). The reagent cocktail was incubated at room temperature for 30 minutes. After incubation, the cocktail was added to 1:3 serial dilutions of an antagonist compound (starting concentration of 50 μM) in 384-well black FIA plates (Greiner Bio-One, Inc.). After a 90 minute incubation at room temperature, the fluorescence was read with filters for the excitation of europium (340 nm) and for the emission wavelengths of europium (615 nm) and a allophycocyanin (665 nm). Antagonist data were calculated as a ratio of the emission signal of allophycocyanin at 665 nm to that of the emission of europium at 615 nm (these ratios were multiplied by a factor of 10,000 for ease of data manipulation). The resulting values were plotted as a function of antagonist concentration and fit to a 4-parameter equation using Kaleidograph software (Synergy Software, Reading, Pa.). Indications of antagonist potency were determined from the IC50 values. Compounds of the invention that were tested in this assay exhibited IC50 values of less than 200 μM indicating IAP inhibitory activity.

Fluorescence Polarization Peptide Binding Assay

Polarization experiments were performed on an Analyst HT 96-384 (Molecular Devices Corp.) according to the procedure of Keating, S. M., Marsters, J, Beresini, M., Ladner, C., Zioncheck, K., Clark, K., Arellano, F., and Bodary., S. (2000) in *Proceedings of SPIE: In Vitro Diagnostic Instrumentation* (Cohn, G. E., Ed.) pp 128-137, Bellingham, Wash. Samples for fluorescence polarization affinity measurements were prepared by addition of 1:2 serial dilutions starting at a final concentration of 5 μM of MLXBIR3SG in polarization buffer (50 mM Tris [pH 7.2], 120 mM NaCl, 1% bovine globulins 5 mM DTT and 0.05% octylglucoside) to 5-carboxyflourescein-conjugated AVPdi-Phe-$NH_2$ (AVP-diPhe-FAM) at 5 nM final concentration.

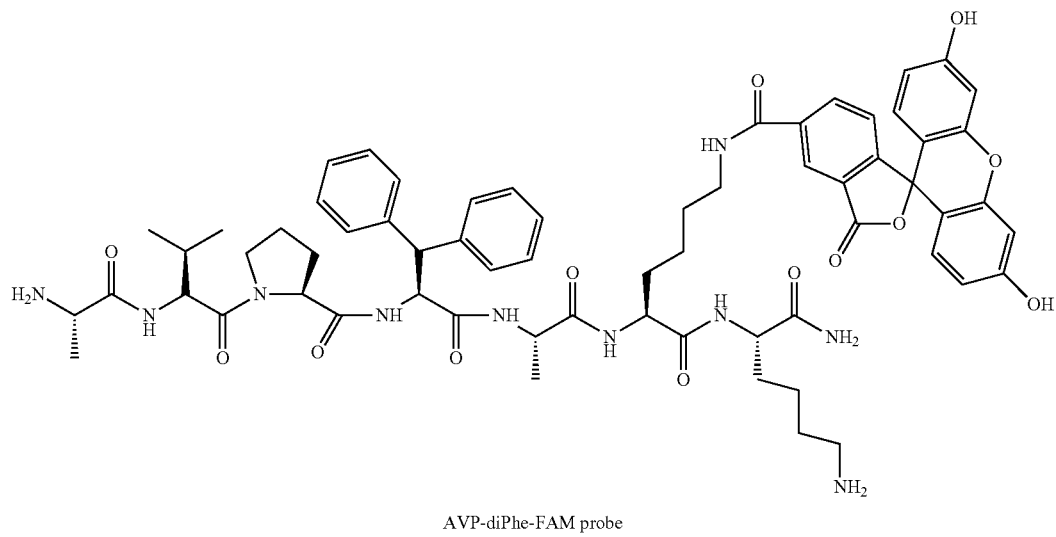

AVP-diPhe-FAM probe

The reactions were read after an incubation time of 10 minutes at room temperature with standard cut-off filters for the fluorescein fluorophore ($\lambda_{ex}$=485 nm; $\lambda_{em}$=530 nm) in 96-well black HE96 plates (Molecular Devices Corp.). Fluorescence values were plotted as a function of the protein concentration, and the IC50s were obtained by fitting the data to a 4-parameter equation using Kaleidograph software (Synergy software, Reading, Pa.). Competition experiments were performed by addition of the MLXBIR3SG at 30 nM to wells containing 5 nM of the AVP-diPhe-FAM probe as well as 1:3 serial dilutions of antagonist compounds starting at a concentration of 300 μM in the polarization buffer. Samples were read after a 10-minute incubation. Fluorescence polarization values were plotted as a function of the antagonist concentration, and the $IC_{50}$ values were obtained by fitting the data to a 4-parameter equation using Kaleidograph software (Synergy software, Reading, Pa.) Inhibition constants ($K_i$) for the antagonists were determined from the $IC_{50}$ values. Compounds of the invention that were tested in this assay exhibited a Ki or less than 100 μM.

We claim:
1. A method of inducing apoptosis in a cell comprising introducing into said cell a compound of Formula I:

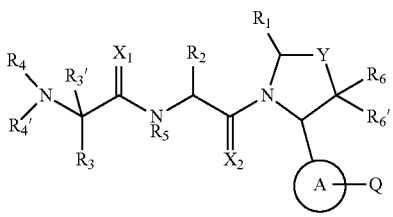

wherein
A is thiazole;
ring A and Q together are selected from the group consisting of:

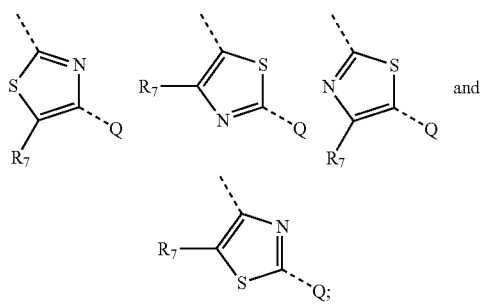

Q is (a) alkyl, wherein one or more $CH_2$ groups of an alkyl is optionally replaced with —O—, —S—, —S(O)—, —S(O)$_2$—, —N(R$_8$)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, or —NR$_8$—C(NH)—; and the alkyl is optionally substituted with one or more halogen, cyano, nitro, optionally substituted carbocycle, or optionally substituted heterocycle; or (b) a carbocycle or heterocycle optionally substituted with one or more halogen, nitro, cyano, oxo, alkyl, carbocycle, or heterocycle;

wherein one or more $CH_2$ groups of the alkyl substituent on Q is optionally replaced with —O—, —S—, —S(O)—, —S(O)$_2$—, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, —NR$_8$—C(NH)—, —C(O)—O— or —O—C(O)—, and the alkyl is optionally substituted with one or more halogen, cyano, nitro, an optionally substituted carbocycle, or an optionally substituted heterocycle; and wherein the carbocycle or heterocycle substituents on Q are optionally substituted with one or more hydroxyl, alkoxy, acyl, halogen, mercapto, oxo, carboxyl, halo-substituted alkyl, amino, cyano, nitro, amidino, guanidino, carbocycle, or heterocycle;

$X_1$ and $X_2$ are each independently O or S;
Y is $CH_2$;
$R_1$ is H, or $R_1$ and $R_2$ together form a 5-8 member ring;
$R_2$ is alkyl, a carbocycle, carbocyclylalkyl, a heterocycle, or heterocyclylalkyl, each optionally substituted with halogen, hydroxyl, oxo, thione, mercapto, carboxyl, alkyl, haloalkyl, alkoxy, alkylthio, sulfonyl, amino, or nitro;

$R_3$ is H or alkyl optionally substituted with halogen or hydroxyl; or $R_3$ and $R_4$ together form a 3-6 member heterocycle;

$R_3'$ is H, or $R_3$ and $R_3'$ together form a 3-6 member carbocycle;

$R_4$ is H, hydroxyl, amino, alkyl, carbocycle, carbocycloalkyl, carbocycloalkyloxy, carbocycloalkyloxycarbonyl, heterocycle, heterocycloalkyl, heterocycloalkyloxy or heterocycloalkyloxycarbonyl; wherein each alkyl, carbocycloalkyl, carbocycloalkyloxy, carbocycloalkyloxycarbonyl, heterocycle, heterocycloalkyl, heterocycloalkyloxy and heterocycloalkyloxycarbonyl is optionally substituted with halogen, hydroxyl, mercapto, carboxyl, alkyl, alkoxy, amino, imino, or nitro; or $R_4$ and $R_4'$ together form a heterocycle;

$R_4'$ is H;
$R_5$ is H or alkyl;
$R_6$ and $R_6'$ are each independently H, alkyl, aryl or aralkyl;
$R_7$ in each instance is independently H, cyano, hydroxyl, mercapto, halogen, nitro, carboxyl, amidino, guanidino, alkyl, a carbocycle, a heterocycle, or —U—V;
wherein U is —O—, —S—, —S(O)—, —S(O)$_2$—, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, —NR$_8$—C(NH)—, —C(O)—O—, or —O—C(O)—; and V is alkyl, a carbocycle, or a heterocycle;
and wherein one or more $CH_2$ groups of an alkyl is optionally replaced with —O—, —S—, —S(O)—, —S(O)$_2$—, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, —NR$_8$—C(NH)—, —C(O)—O—, or —O—C(O)—; and an alkyl, carbocycle, and heterocycle is optionally substituted with hydroxyl, alkoxy, acyl, halogen, mercapto, oxo, carboxyl, halo-substituted alkyl, amino, cyano, nitro, amidino, guanidino, an optionally substituted carbocycle, or an optionally substituted heterocycle;

$R_8$ is H, alkyl, a carbocycle, or a heterocycle; wherein one or more $CH_2$ groups of said alkyl is optionally replaced with —O—, —S—, —S(O)—, —S(O)$_2$—, or —C(O)—; and said alkyl, carbocycle, and heterocycle is optionally substituted with hydroxyl, alkoxy, acyl, halogen, mercapto, oxo (=O), carboxyl, acyl, halo-substituted alkyl, amino, cyano, nitro, amidino, guanidino, an optionally substituted carbocycle, or an optionally substituted heterocycle;

wherein each alkyl is independently a branched or unbranched, saturated or unsaturated aliphatic hydrocarbon group, having up to 12 carbon atoms;
or a salt thereof.

2. A method of sensitizing a cell to an apoptotic signal comprising introducing into said cell a compound of Formula I:

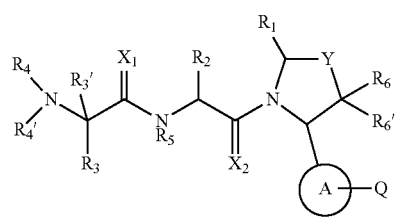

wherein
A is thiazole;
ring A and Q together are selected from the group consisting of:

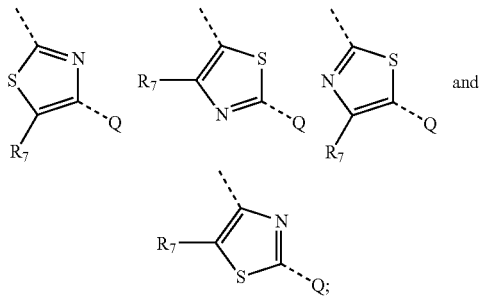

and

Q is (a) alkyl, wherein one or more CH$_2$ groups of an alkyl is optionally replaced with —O—, —S—, —S(O)—, —S(O)$_2$—, —N(R$_8$)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, or —NR$_8$—C(NH)—; and the alkyl is optionally substituted with one or more halogen, cyano, nitro, optionally substituted carbocycle, or optionally substituted heterocycle; or
(b) a carbocycle or heterocycle optionally substituted with one or more halogen, nitro, cyano, oxo, alkyl, carbocycle, or heterocycle;
wherein one or more CH$_2$ groups of the alkyl substituent on Q is optionally replaced with —O—, —S—, —S(O)—, —S(O)$_2$—, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, —NR$_8$—C(NH)—, —C(O)—O—, or —O—C(O)—, and the alkyl is optionally substituted with one or more halogen, cyano, nitro, an optionally substituted carbocycle, or an optionally substituted heterocycle; and
wherein the carbocycle or heterocycle substituents on Q are optionally substituted with one or more hydroxyl, alkoxy, acyl, halogen, mercapto, oxo, carboxyl, halo-substituted alkyl, amino, cyano, nitro, amidino, guanidino, carbocycle, or heterocycle;
X$_1$ and X$_2$ are each independently O or S;
Y is CH$_2$;
R$_1$ is H, or R$_1$ and R$_2$ together form a 5-8 member ring;
R$_2$ is alkyl, a carbocycle, carbocyclylalkyl, a heterocycle, or heterocyclylalkyl, each optionally substituted with halogen, hydroxyl, oxo, thione, mercapto, carboxyl, alkyl, haloalkyl, alkoxy, alkylthio, sulfonyl, amino, or nitro;
R$_3$ is H or alkyl optionally substituted with halogen or hydroxyl; or R$_3$ and R$_4$ together form a 3-6 member heterocycle;
R$_3$' is H, or R$_3$ and R$_3$' together form a 3-6 member carbocycle;
R$_4$ is H, hydroxyl, amino, alkyl, carbocycle, carbocycloalkyl, carbocycloalkyloxy, carbocycloalkyloxycarbonyl, heterocycle, heterocycloalkyl, heterocycloalkyloxy or heterocycloalkyloxycarbonyl; wherein each alkyl, carbocycloalkyl, carbocycloalkyloxy, carbocycloalkyloxycarbonyl, heterocycle, heterocycloalkyl, heterocycloalkyloxy, and heterocycloalkyloxycarbonyl is optionally substituted with halogen, hydroxyl, mercapto, carboxyl, alkyl, alkoxy, amino, imino, or nitro; or R$_4$ and R$_4$' together form a heterocycle;

R$_4$' is H;
R$_5$ is H or alkyl;
R$_6$ and R$_6$' are each independently H, alkyl, aryl or aralkyl;
R$_7$ in each instance is independently H, cyano, hydroxyl, mercapto, halogen, nitro, carboxyl, amidino, guanidino, alkyl, a carbocycle, a heterocycle, or —U—V;
wherein U is —O—, —S—, —S(O)—, —S(O)$_2$—, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, —NR$_8$—C(NH)—, —C(O)—O—, or —O—C(O)—; and
V is alkyl, a carbocycle, or a heterocycle;
and wherein one or more CH$_2$ groups of an alkyl is optionally replaced with —O—, —S—, —S(O)—, —S(O)$_2$—, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, —NR$_8$—C(NH)—, —C(O)—O—, or —O—C(O)—; and an alkyl, carbocycle, and heterocycle is optionally substituted with hydroxyl, alkoxy, acyl, halogen, mercapto, oxo, carboxyl, halo-substituted alkyl, amino, cyano, nitro, amidino, guanidino, an optionally substituted carbocycle, or an optionally substituted heterocycle;
R$_8$ is H, alkyl, a carbocycle, or a heterocycle; wherein one or more CH$_2$ groups of said alkyl is optionally replaced with —O—, —S—, —S(O)—, —S(O)$_2$—, or —C(O)—; and said alkyl, carbocycle, and heterocycle is optionally substituted with hydroxyl, alkoxy, acyl, halogen, mercapto, oxo (=O), carboxyl, acyl, halo-substituted alkyl, amino, cyano, nitro, amidino, guanidino, an optionally substituted carbocycle, or an optionally substituted heterocycle;
wherein each alkyl is independently a branched or unbranched, saturated or unsaturated aliphatic hydrocarbon group, having up to 12 carbon atoms;
or a salt thereof.

3. The method of claim 2, wherein said apoptotic signal is induced by contacting said cell with cytarabine, fludarabine, 5-fluoro-2'-deoxyuridine, gemcitabine, methotrexate, bleomycin, cisplatin, cyclophosphamide, adriamycin (doxorubicin), mitoxantrone, camptothecin, topotecan, colcemid, colchicine, paclitaxel, vinblastine, vincristine, tamoxifen, finasterid, taxotere, mitomycin C, or Apo2L/TRAIL, or with radiation.

4. A method for inhibiting the binding of an IAP protein to a caspase protein comprising contacting said IAP protein with a compound of Formula I:

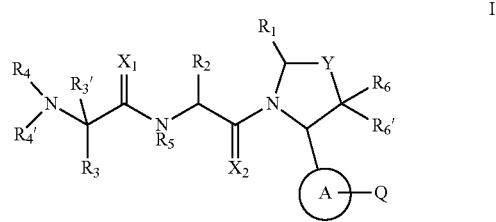

I wherein
A is thiazole;
ring A and Q together are selected from the group consisting of:

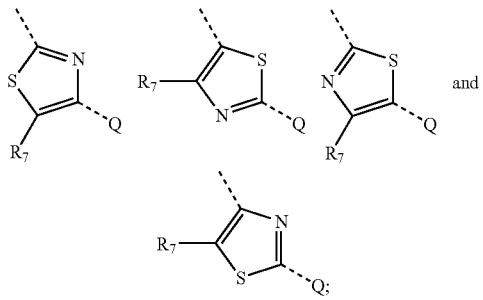

Q is (a) alkyl, wherein one or more CH$_2$ groups of an alkyl is optionally replaced with —O—, —S—, —S(O)—, —S(O)$_2$—, —N(R$_8$)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, or —NR$_8$—C(NH)—; and the alkyl is optionally substituted with one or more halogen, cyano, nitro, optionally substituted carbocycle, or optionally substituted heterocycle; or (b) a carbocycle or heterocycle optionally substituted with one or more halogen, nitro, cyano, oxo, alkyl, carbocycle, or heterocycle;

wherein one or more CH$_2$ groups of the alkyl substituent on Q is optionally replaced with —O—, —S—, —S(O)—, —S(O)$_2$—, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, —NR$_8$—C(NH)—, —C(O)—O—, or —O—C(O)—, and the alkyl is optionally substituted with one or more halogen, cyano, nitro, an optionally substituted carbocycle, or an optionally substituted heterocycle; and wherein the carbocycle or heterocycle substituents on Q are optionally substituted with one or more hydroxyl, alkoxy, acyl, halogen, mercapto, oxo, carboxyl, halo-substituted alkyl, amino, cyano, nitro, amidino, guanidino, carbocycle, or heterocycle;

X$_1$ and X$_2$ are each independently O or S;
Y is CH$_2$;
R$_1$ is H, or R$_1$ and R$_2$ together form a 5-8 member ring;
R$_2$ is alkyl, a carbocycle, carbocyclylalkyl, a heterocycle, or heterocyclylalkyl, each optionally substituted with halogen, hydroxyl, oxo, thione, mercapto, carboxyl, alkyl, haloalkyl, alkoxy, alkylthio, sulfonyl, amino, or nitro;

R$_3$ is H or alkyl optionally substituted with halogen or hydroxyl; or R$_3$ and R$_4$ together form a 3-6 member heterocycle;
R$_3$' is H, or R$_3$ and R$_3$' together form a 3-6 member carbocycle;
R$_4$ is H, hydroxyl, amino, alkyl, carbocycle, carbocycloalkyl, carbocycloalkyloxy, carbocycloalkyloxycarbonyl, heterocycle, heterocycloalkyl, heterocycloalkyloxy or heterocycloalkyloxycarbonyl; wherein each alkyl, carbocycloalkyl, carbocycloalkyloxy, carbocycloalkyloxycarbonyl, heterocycle, heterocycloalkyl, heterocycloalkyloxy, and heterocycloalkyloxycarbonyl is optionally substituted with halogen, hydroxyl, mercapto, carboxyl, alkyl, alkoxy, amino, imino, or nitro; or R$_4$ and R$_4$' together form a heterocycle;
R$_4$' is H;
R$_5$ is H or alkyl;
R$_6$ and R$_6$' are each independently H, alkyl, aryl, or aralkyl;
R$_7$ in each instance is independently H, cyano, hydroxyl, mercapto, halogen, nitro, carboxyl, amidino, guanidino, alkyl, a carbocycle, a heterocycle, or —U—V;
wherein U is —O—, —S—, —S(O)—, —S(O)$_2$—, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, —NR$_8$—C(NH)—, —C(O)—O—, or —O—C(O)—; and
V is alkyl, a carbocycle, or a heterocycle;
and wherein one or more CH$_2$ groups of an alkyl is optionally replaced with —O—, —S—, —S(O)—, —S(O)$_2$—, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)NR$_8$—, —NR$_8$—C(NH)—, —C(O)—O—, or —O—C(O)—; and an alkyl, carbocycle, and heterocycle is optionally substituted with hydroxyl, alkoxy, acyl, halogen, mercapto, oxo, carboxyl, halo-substituted alkyl, amino, cyano, nitro, amidino, guanidino, an optionally substituted carbocycle, or an optionally substituted heterocycle;
R$_8$ is H, alkyl, a carbocycle, or a heterocycle; wherein one or more CH$_2$ groups of said alkyl is optionally replaced with —O—, —S—, —S(O)—, —S(O)$_2$—, or —C(O)—; and said alkyl, carbocycle, and heterocycle is optionally substituted with hydroxyl, alkoxy, acyl, halogen, mercapto, oxo (=O), carboxyl, acyl, halo-substituted alkyl, amino, cyano, nitro, amidino, guanidino, an optionally substituted carbocycle, or an optionally substituted heterocycle;
wherein each alkyl is independently a branched or unbranched, saturated or unsaturated aliphatic hydrocarbon group, having up to 12 carbon atoms;
or a salt thereof.

* * * * *